US011053205B2

(12) United States Patent
Huigens, III et al.

(10) Patent No.: US 11,053,205 B2
(45) Date of Patent: Jul. 6, 2021

(54) PHENAZINE DERIVATIVES AS ANTIMICROBIAL AGENTS

(71) Applicant: University of Florida Research Foundation, Incorporated, Gainesville, FL (US)

(72) Inventors: Robert William Huigens, III, Williston, FL (US); Aaron Garrison, Gainesville, FL (US); Yasmeen Abouelhassan, Gainesville, FL (US); Hongfen Yang, Gainesville, FL (US); Gena Burch, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/486,694

(22) PCT Filed: Feb. 17, 2018

(86) PCT No.: PCT/US2018/018538
§ 371 (c)(1),
(2) Date: Aug. 16, 2019

(87) PCT Pub. No.: WO2018/152436
PCT Pub. Date: Aug. 23, 2018

(65) Prior Publication Data
US 2020/0010432 A1  Jan. 9, 2020

Related U.S. Application Data

(60) Provisional application No. 62/477,509, filed on Mar. 28, 2017, provisional application No. 62/460,282, filed on Feb. 17, 2017.

(51) Int. Cl.
| | |
|---|---|
| *A61K 31/498* | (2006.01) |
| *C07D 241/46* | (2006.01) |
| *A61P 31/06* | (2006.01) |
| *C07D 403/06* | (2006.01) |
| *C07D 501/16* | (2006.01) |
| *C07H 17/02* | (2006.01) |
| *A61K 45/06* | (2006.01) |

(52) U.S. Cl.
CPC ............ *C07D 241/46* (2013.01); *A61P 31/06* (2018.01); *C07D 403/06* (2013.01); *C07D 501/16* (2013.01); *C07H 17/02* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,609,153 | A | 9/1971 | Cook et al. |
| 9,856,225 | B2 | 1/2018 | Huigens, III et al. |
| 2005/0165044 | A1 | 7/2005 | Boykin et al. |
| 2008/0121873 | A1 | 5/2008 | Katakura et al. |
| 2010/0160346 | A1 | 6/2010 | Barnham et al. |
| 2014/0336221 | A1 | 11/2014 | Pegan et al. |
| 2016/0355487 | A1 | 12/2016 | Huigens et al. |
| 2018/0312473 | A1 | 11/2018 | Huigens et al. |

FOREIGN PATENT DOCUMENTS

| | | |
|---|---|---|
| GB | 1206866 A | 9/1970 |
| WO | WO-2015100331 A2 * 7/2015 ........... C07D 241/38 |
| WO | WO 2017/011730 A2 | 1/2017 |

OTHER PUBLICATIONS

Conda-Sheridan et al. J. Med. Chem. (2010), vol. 53, pp. 8688-8699.*
U.S. Appl. No. 15/107,531, filed Jun. 23, 2016, Huigens et al.
U.S. Appl. No. 15/744,319, filed Jan. 12, 2018, Huigens et al.
PCT/US2014/072165, Jul. 13, 2015, International Search Report and Written Opinion.
PCT/US2014/072165, Jul. 7, 2016, International Preliminary Report on Patentability.
PCT/US2016/042439, Sep. 20, 2016, Invitation to Pay Additional Fees.
PCT/US2016/042439, Jan. 5, 2017, International Search Report and Written Opinion.
PCT/US2016/042439, Jan. 25, 2018, International Preliminary Report on Patentability.
PCT/US2018/018538, May 4, 2018, International Search Report and Written Opinion.
PCT/US2018/018538, Aug. 29, 2019, International Preliminary Report on Patentability.
International Search Report and Written Opinion for PCT/US2014/072165, dated Jul. 13, 2015.
International Preliminary Report on Patentability for PCT/US2014/072165, dated Jul. 7, 2016.

(Continued)

*Primary Examiner* — Patrick T Lewis
(74) *Attorney, Agent, or Firm* — Wolf, Greenfield & Sacks, P.C.

(57) ABSTRACT

The present invention provides novel phenazine derivatives, such as compounds of Formula (I) (e.g., Formulae (II)-(XIX)), and pharmaceutically acceptable salts thereof. The compounds of the invention are expected to be antimicrobial agents and may act by a microbial warfare strategy (e.g., a reactive oxygen species (ROS)-based competition strategy). The present invention also provides pharmaceutical compositions, kits, uses, and methods that involve the compounds of the invention and may be useful in preventing or treating a microbial infection (e.g., a bacterial infection or mycobacterial infection) in a subject, inhibiting the growth and/or reproduction of a microorganism (e.g., a bacterium or mycobacterium), killing a microorganism (e.g., a bacterium or mycobacterium), inhibiting the formation and/or growth of a biofilm, reducing or clearing a biofilm, and/or disinfecting a surface.

37 Claims, 32 Drawing Sheets

(56) References Cited

OTHER PUBLICATIONS

Invitation to Pay Additional Fees for PCT/US2016/042439, mailed Sep. 20, 2016.
International Search Report and Written Opinion for PCT/US2016/042439, dated Jan. 5, 2017.
International Preliminary Report on Patentability for PCT/US2016/042439, dated Jan. 25, 2018.
International Search Report and Written Opinion for PCT/US2018/018538, dated May 4, 2018.
International Preliminary Report on Patentability for PCT/US2018/018538, dated Aug. 29, 2019.
[No Author Listed] Clinical and Laboratory Standards Institute. 2009. Methods for dilution antimicrobial susceptibility tests for bacteria that grow aerobically; approved standard, 8th edition (A17-A18), Clinical and Laboratory Standard, Wayne, PA, 2009.
[No Author Listed], CID 66651970. Compound Summary. Nov. 30, 2012. http://pubchem.ncbi.nlm.nih.gov/compound/66651970. [last accessed Mar. 31, 2015]. 4 pages.
Abouelhassan et al., A Phytochemical-Halogenated Quinoline Combination Therapy Strategy for the Treatment of Pathogenic Bacteria. ChemMedChem. Jul. 2015;10(7):1157-62. doi: 10.1002/cmdc.201500179. Epub May 15, 2015.
Abouelhassan et al., Discovery of quinoline small molecules with potent dispersal activity against methicillin-resistant *Staphylococcus aureus* and *Staphylococcus epidermidis* biofilms using a scaffold hopping strategy. Bioorg Med Chem Lett. Nov. 1, 2014;24(21):5076-80. doi: 10.1016/j.bmcl.2014.09.009. Epub Sep. 15, 2014.
Balaban et al., Bacterial persistence as a phenotypic switch. Science. Sep. 10, 2004;305(5690):1622-5. Epub Aug. 12, 2004.
Basak et al., Halogenated quinolines discovered through reductive amination with potent eradication activities against MRSA, MRSE and VRE biofilms. Org. Biomol. Chem., 2015;13:10290-10294. DOI: 10.1039/C5OB01883H.
Bjarnsholt et al., The role of bacterial biofilms in chronic infections. APMIS 2013; 121 (Suppl. 136): 1-54.
Borrero et al., Phenazine antibiotic inspired discovery of potent bromophenazine antibacterial agents against *Staphylococcus aureus* and *Staphylococcus epidermidis*. Org. Biomol. Chem., 2014;12:881-886. DOI: 10.1039/C3OB42416B.
Brackman et al., Quorum sensing inhibitors as anti-biofilm agents. Curr Pharm Des. 2015;21(1):5-11.
Breitmaier et al., Carbon-13 nuclear magnetic resonance chemical shifts of substituted phenazines. J. Org. Chem., 1976;41(12):2104-2108. DOI: 10.1021/jo00874a008.
Briard et al., QSAR Accelerated Discovery of Potent Ice Recrystallization Inhibitors. Scientific Reports 2016;6(Article No. 26403). doi:10.1038/srep26403.
Brown et al., New Targets and Screening Approaches in Antimicrobial Drug Discovery. Chem. Rev., 2005;105(2):759-774. DOI: 10.1021/cr030116o.
Camilli et al., Bacterial Small-Molecule Signaling Pathways. Science. Feb. 24, 2006;311(5764):1113-6.
Ceri et al., The Calgary Biofilm Device: new technology for rapid determination of antibiotic susceptibilities of bacterial biofilms. J Clin Microbiol. Jun. 1999;37(6):1771-6.
Chambers et al., Waves of resistance: *Staphylococcus aureus* in the antibiotic era. Nat Rev Microbiol. Sep. 2009;7(9):629-41. doi: 10.1038/nrmicro2200.
Clatworthy et al., Targeting virulence: a new paradigm for antimicrobial therapy. Nat Chem Biol. Sep. 2007;3(9):541-8.
Conlon et al., *Staphylococcus aureus* chronic and relapsing infections: Evidence of a role for persister cells: An investigation of persister cells, their formation and their role in *S. aureus* disease. Bioessays. Oct. 2014;36(10):991-6. doi: 10.1002/bies.201400080. Epub Aug. 6, 2014.
Deraeve et al., Bis-8-hydroxyquinoline ligands as potential anti-Alzheimer agents. New J. Chem., 2007;31:193-195. DOI: 10.1039/B616085A.

Di Vaira et al., Clioquinol, a Drug for Alzheimer's Disease Specifically Interfering with Brain Metal Metabolism: Structural Characterization of Its Zinc(II) and Copper(II) Complexes. Inorg. Chem., 2004;43(13):3795-3797. DOI: 10.1021/ic0494051.
Donlan et al., Biofilms: survival mechanisms of clinically relevant microorganisms. Clin Microbiol Rev. Apr. 2002;15(2):167-93.
Emmanuvel et al., NaIO4/LiBr-mediated Diastereoselective Dihydroxylation of Olefins: A Catalytic Approach to the Prevost-Woodward Reaction. Org. Lett., 2005;7(22):5071-5074. DOI: 10.1021/ol052080n.
Eun et al., DCAP: A Broad-Spectrum Antibiotic That Targets the Cytoplasmic Membrane of Bacteria. J. Am. Chem. Soc., 2012;134(28):11322-11325. DOI: 10.1021/ja302542j.
Evangelopoulos et al., Improving the Tuberculosis Drug Development Pipeline. Chem Biol Drug Des, 86: 951-960. doi:10.1111/cbdd.12549.
Fletcher et al., Draining the moat: disrupting bacterial biofilms with natural products. Tetrahedron 2014;70(37):6373-6383.
Garrison et al., Bromophenazine derivatives with potent inhibition, dispersion and eradication activities against *Staphylococcus aureus* biofilms. RSC Adv., 2015;5:1120-1124. DOI: 10.1039/C4RA08728C.
Garrison et al., Halogenated Phenazines that Potently Eradicate Biofilms, MRSA Persister Cells in Non-Biofilm Cultures, and *Mycobacterium tuberculosis*. Angew. Chem. Int. Ed., 54:14819-14823. doi:10.1002/anie.201508155.
Gershon et al., Antimicrobial Activity of 8-Quinolinol, Its Salts with Salicylic Acid and 3-Hydroxy-2-Naphthoic Acid, and the Respective Copper (II) Chelates in Liquid Culture. Appl. Environ. Microbiol. Jan. 1963;11(1):62-65.
Guttenberger et al., Recent developments in the isolation, biological function, biosynthesis, and synthesis of phenazine natural products. Bioorganic & medicinal chemistry, 2017;25:6149-6166. DOI: 10.1016/j.bmc.2017.01.002.
Hall-Stoodley et al., Bacterial biofilms: from the natural environment to infectious diseases. Nat Rev Microbiol. Feb. 2004;2(2):95-108.
Harbarth et al., Antibiotic research and development: business as usual? J Antimicrob Chemother. 2015;70(6):1604-7. doi: 10.1093/jac/dkv020. Epub Feb. 10, 2015.
Harrison et al., Copper and Quaternary Ammonium Cations Exert Synergistic Bactericidal and Antibiofilm Activity against Pseudomonas aeruginosa. Antimicrob. Agents Chemother. Aug. 2008;52(8):2870-2881.
Harrison et al., Microtiter susceptibility testing of microbes growing on peg lids: a miniaturized biofilm model for high-throughput screening. Nat Protoc. Jul. 2010;5(7):1236-54. doi: 10.1038/nprot.2010.71. Epub Jun. 10, 2010.
Hassan et al., Mechanism of the antibiotic action pyocyanine. J Bacteriol. Jan. 1980;141(1):156-63.
Hentzer et al., Attenuation of Pseudomonas aeruginosa virulence by quorum sensing inhibitors. EMBO J. Aug. 1, 2003;22(15):3803-15.
Hoque et al., Membrane Active Small Molecules Show Selective Broad Spectrum Antibacterial Activity with No Detectable Resistance and Eradicate Biofilms. J. Med. Chem., 2015;58(14):5486-5500. DOI: 10.1021/acs.jmedchem.5b00443.
Hoque et al., Selective and broad spectrum amphiphilic small molecules to combat bacterial resistance and eradicate biofilms. Chem. Commun., 2015;51:13670-13673. DOI: 10.1039/C5CC05159B.
Hughes et al., Antibacterials from the sea. Chemistry. Nov. 8, 2010;16(42):12512-25. doi: 10.1002/chem.201001279.
Jennings et al., Biofilm-eradicating properties of quaternary ammonium amphiphiles: simple mimics of antimicrobial peptides. Chembiochem. Oct. 13, 2014;15(15):2211-5. doi: 10.1002/cbic.201402254. Epub Aug. 21, 2014.
Jordan et al., Tamoxifen: a most unlikely pioneering medicine. Nat Rev Drug Discov. Mar. 2003;2(3):205-13.
Keren et al., Persister cells and tolerance to antimicrobials. FEMS Microbiol Lett. Jan. 15, 2004;230(1):13-8.

(56) References Cited

OTHER PUBLICATIONS

Kostakioti et al., Bacterial biofilms: development, dispersal, and therapeutic strategies in the dawn of the postantibiotic era. Cold Spring Harb Perspect Med. Apr. 1, 2013;3(4):a010306. doi: 10.1101/cshperspect.a010306.
Kwan et al., Lyngbyoic acid, a "tagged" fatty acid from a marine cyanobacterium, disrupts quorum sensing in Pseudomonas aeruginosa. Mol Biosyst. Apr. 2011;7(4):1205-1216. doi: 10.1039/c0mb00180e.
Laursen et al., Phenazine Natural Products: Biosynthesis, Synthetic Analogues, and Biological Activity. Chem. Rev., 2004;104(3):1663-1686. DOI: 10.1021/cr020473j.
Lechner et al., *Staphylococcus aureus* persisters tolerant to bactericidal antibiotics. J Mol Microbiol Biotechnol. 2012;22(4):235-44. doi: 10.1159/000342449. Epub Sep. 14, 2012.
Lewis et al., Persister cells, dormancy and infectious disease. Nat Rev Microbiol. Jan. 2007;5(1):48-56. Epub Dec. 4, 2006.
Lewis et al., Persister Cells. Annual Review of Microbiology Oct. 2010;64:357-372. https://doi.org/10.1146/annurev.micro.112408.134306.
Lewis et al., Platforms for antibiotic discovery. Nat Rev Drug Discov. May 2013;12(5):371-87. doi: 10.1038/nrd3975.
Machan et al., Interaction between Pseudomonas aeruginosa and *Staphylococcus aureus*: description of an anti-staphylococcal substance. J Med Microbiol. Apr. 1991;34(4):213-7.
Marler et al., Cancer Chemopreventive Potential of Aromathecins and Phenazines, Novel Natural Product Derivatives. Anticancer Research Dec. 2010;30(12):4873-4882.
McCune et al., Microbial Persistence. Journal of Experimental Medicine Mar. 1966;123(3):469-486. DOI: 10.1084/jem.123.3.469.
Mitchell et al., Scaffold-Hopping of Multicationic Amphiphiles Yields Three New Classes of Antimicrobials. ChemBioChem 2015;16:2299. https://doi.org/10.1002/cbic.201500381.
Navarro et al Image-Based 384-Well High-Throughput Screening Method for the Discovery of Skyllamycins A to C as Biofilm Inhibitors and Inducers of Biofilm Detachment in Pseudomonas aeruginosa. Antimicrob. Agents Chemother. Feb. 2014;58(2):1092-1099.
Ng et al., Bacterial quorum-sensing network architectures. Annu Rev Genet. 2009;43:197-222. doi: 10.1146/annurev-genet-102108-134304.
Patcher et al., The Wohl-Aue Reaction. I. Structure of Benzo [a] phenazine Oxides and Syntheses of 1,6-Dimethoxyphenazine and 1,6-Dichlorophenazine. J. Am. Chem. Soc., 1951;73(10):4958-4961. DOI: 10.1021/ja01154a144.
Payne et al., Drugs for bad bugs: confronting the challenges of antibacterial discovery. Nat Rev Drug Discov. Jan. 2007;6(1):29-40.
Perez-Lago et al., Persistent Infection by a *Mycobacterium tuberculosis* Strain That Was Theorized to Have Advantageous Properties, as It Was Responsible for a Massive Outbreak. J. Clin. Microbiol. Nov. 2015;53(11):3423-3429.
Prachayasittikul et al., 8-Hydroxyquinolines: a review of their metal chelating properties and medicinal applications. Drug Des Devel Ther. 2013 Oct 4;7:1157-78. doi: 10.2147/Dddt. S49763. eCollection 2013.

Price-Whelan et al., Rethinking 'secondary' metabolism: physiological roles for phenazine antibiotics. Nat Chem Biol. Feb. 2006;2(2):71-8.
Priyaja et al., Pyocyanin induced in vitro oxidative damage and its toxicity level in human, fish and insect cell lines for its selective biological applications. Cytotechnology. Jan. 2016;68(1):143-55. doi: 10.1007/s10616-014-9765-5.
Projan et al., Why is big Pharma getting out of antibacterial drug discovery? Curr Opin Microbiol. Oct. 2003;6(5):427-30.
Quah et al., N-acetylcysteine inhibits growth and eradicates biofilm of Enterococcus faecalis. J Endod. Jan. 2012;38(1):81-5. doi: 10.1016/j.joen.2011.10.004. Epub Nov. 21, 2011.
Rewcastle et al., Potential antitumor agents. 51. Synthesis and antitumor activity of substituted phenazine-1-carboxamides. J. Med. Chem., 1987;30(5):843-851. DOI: 10.1021/jm00388a017.
Shi et al., Pyrazinamide inhibits trans-translation in *Mycobacterium tuberculosis*. Science. Sep. 16, 2011;333(6049):1630-2. doi: 10.1126/science.1208813. Epub Aug. 11, 2011.
Stringer et al., Improved Small-Molecule Macroarray Platform for the Rapid Synthesis and Discovery of Antibacterial Chalcones. ACS Comb. Sci., 2011;13(2):175-180. DOI: 10.1021/co100053p.
Uckay et al., Foreign body infections due to *Staphylococcus epidermidis*. Ann Med. 2009;41(2):109-19. doi: 10.1080/07853890802337045.
Vivian et al., The Practical Synthesis of 1-Phenazinol. Nature 1956;178:753. doi:10.1038/178753a0.
Wang et al., Endogenous Phenazine Antibiotics Promote Anaerobic Survival of Pseudomonas aeruginosa via Extracellular Electron Transfer. J. Bacteriol. Jan. 2010;192(1):365-369.
Wolcott et al., The role of biofilms: are we hitting the right target? Plast Reconstr Surg. Jan. 2011;127 Suppl 1:28S-35S. doi: 10.1097/PRS.0b013e3181fca244.
Wood et al., Bacterial Persister Cell Formation and Dormancy. Appl. Environ. Microbiol. Dec. 2013;79(23):7116-7121.
Wood et al., Combatting bacterial persister cells. Biotechnol. Bioeng., 113: 476-483. doi:10.1002/bit.25721.
Worthington et al., Small molecule control of bacterial biofilms. Org. Biomol. Chem., 2012;10:7457-7474. DOI: 10.1039/C2OB25835H.
Wu et al,, Synthetic furanones inhibit quorum-sensing and enhance bacterial clearance in Pseudomonas aeruginosa lung infection in mice. J Antimicrob Chemother. Jun. 2004;53(6):1054-61. Epub Apr. 29, 2004.
Young et al., Confronting the scientific obstacles to global control of tuberculosis. J Clin Invest. Apr. 1, 2008;118(4):1255-1265. doi: 10.1172/JCI34614.
Zhang et al., Synthesis and Biological Evaluation of Novel 2-Methoxypyridylamino-Substituted Riminophenazine Derivatives as Antituberculosis Agents. Molecules 2014; 19(4):4380-4394; doi:10.3390/molecules19044380.
Zoysa et al., Antimicrobial Peptides with Potential for Biofilm Eradication: Synthesis and Structure Activity Relationship Studies of Battacin Peptides. J. Med. Chem., 2015;58(2):625-639. DOI: 10.1021/jm501084q.

\* cited by examiner

Figure 2

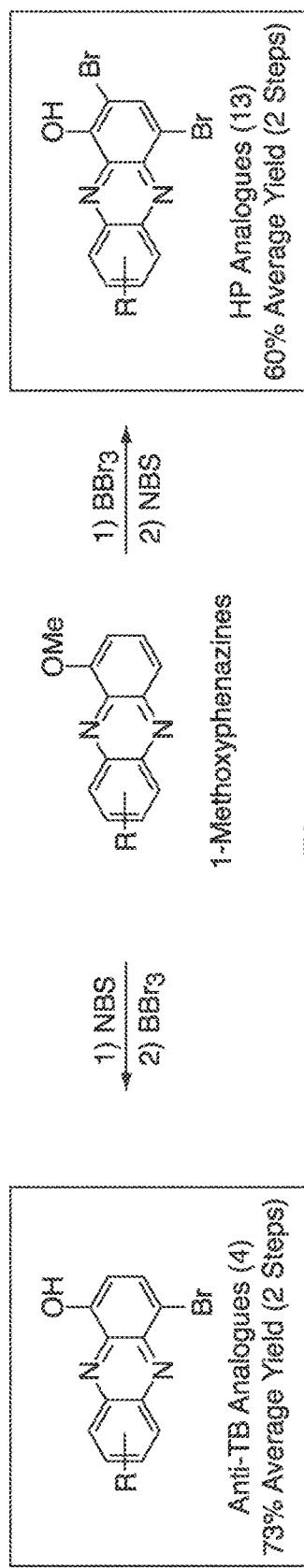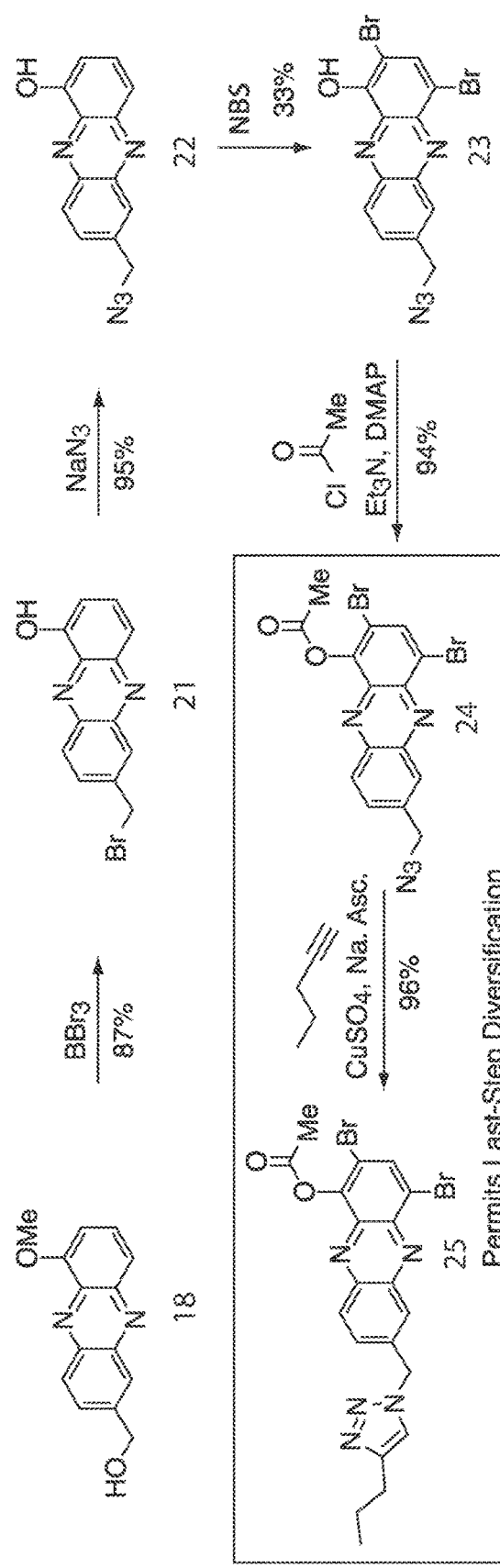
Figure 3
Figure 4

Live/Dead Staining of MRSA Biofilms

Chelation of HP 26 with $Fe^{2+}$

| Aniline | Wohl-Aue % Yield | BBr₃ % Yield | NBS % Yield | HP |
|---------|------------------|--------------|-------------|-----|
| 2-OMe aniline | 3% | 100% | 100%/60%[a] | 1-15 |
| 4-PhO aniline | 12.5% | 98% | 48% | 1-16 |
| 2-Me aniline | 6.6% | 99% | 81% | 1-17 |
| 2-Et aniline | 4.5% | 99% | 38% | 1-18 |
| 2,3-diMe aniline | 6.3% | 100% | 30% | 1-19 |
| 4-Me aniline | 2.3% | 97% | 77% | 1-20 |
| 2-Cl aniline | 3.2% | 99% | 42% | 1-21 |
| 4-Cl aniline | 11.9% | 100% | 31% | 1-22 |
| 2-Br aniline | 2.2% | 100% | 40% | 1-23 |

Figure 12

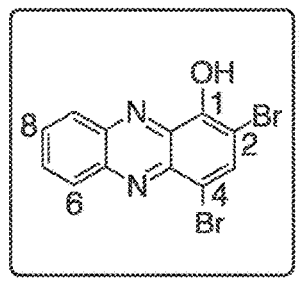

Potent Antibacterial and Biofilm Eradicator

Inhibits RNA and Protein Biosynthesis, but not DNA in Macromolecular Synthesis Inhibition Experiments Zinc(II) Enhances Antibacterial Activity

*Wohl-Aue Reaction Enables Rapid and Modular Synthesis of HPs*

6-Substituted HP Analogues

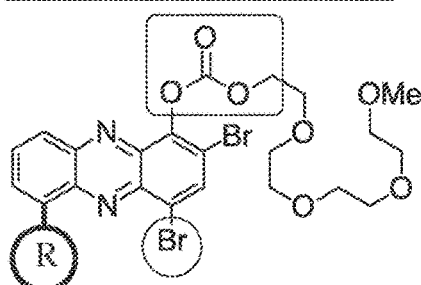

MRSA-1707
MIC / MBEC (μM)
R = -Me   0.003 / 9.38 improved water solibility;
does not bind metal(II) cations

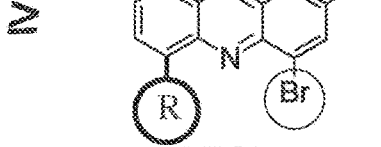

MRSA-1707
MIC / MBEC (μM)
R = -H    1.17 / 75
  -Me    0.30 / 6.25
  -Et    0.10 / 4.69
  -Cl    0.08 / 75
  -Br    0.05 / 9.38

8-Substituted HP Analogues

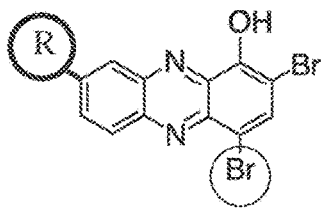

MRSA-1707
MIC / MBEC (μM)
R = -H     1.17 / 75
  -Me     2.35 / --
  -OPh    9.38 / --
  -Cl     0.15 / 37.5
  -Br     0.20 / 12.5 (previous)

Figure 21

Ullmann Condensation
A) 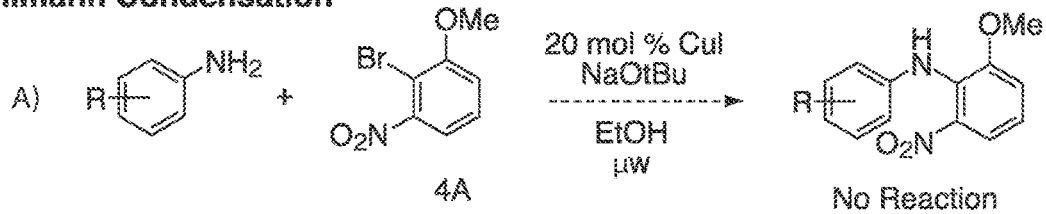
Buchwald-Hartwig Cross Coupling (BH)
B) 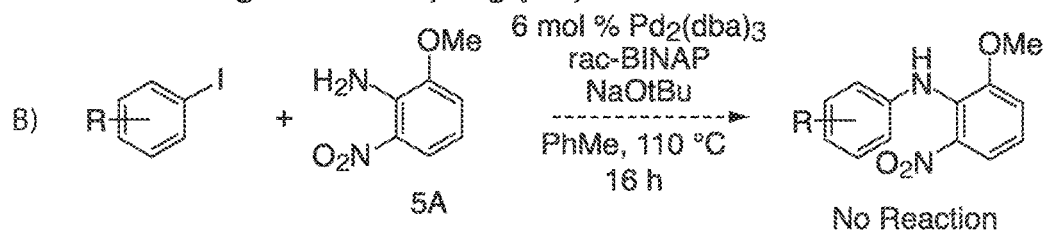
C) 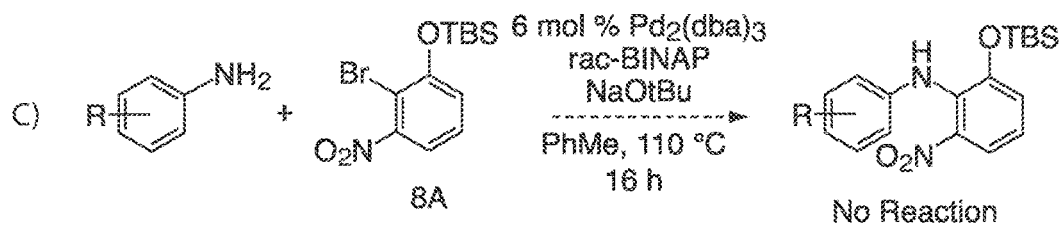
D) 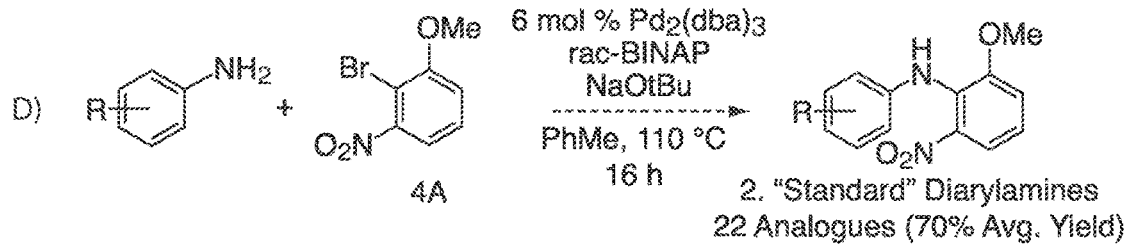
E) 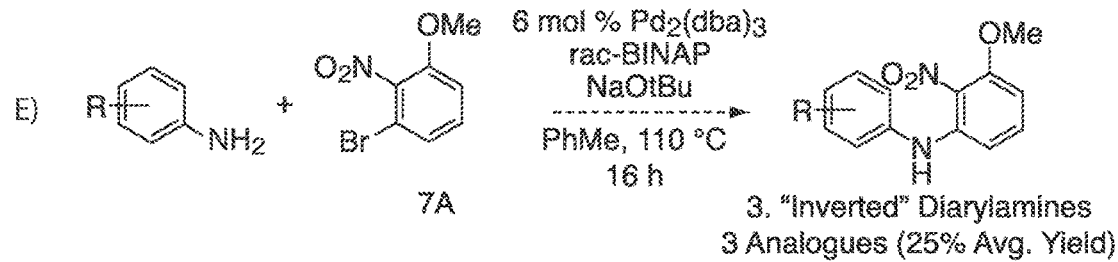
Figure 25

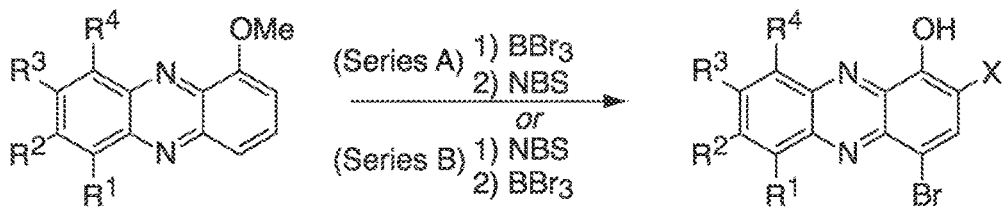

| 1-OMe Phenazine | R¹ | R² | R³ | R⁴ | X | BBr₃ Yield | NBS Yield | Series | HP |
|---|---|---|---|---|---|---|---|---|---|
| 32A | H | Me | H | H | Br | 91% | 52% | A | 52A |
| 33A | H | Et | H | H | Br | 93% | 74% | A | 53A |
| 34A | H | Pr | H | H | Br | 88% | 76% | A | 54A |
| 35A | H | t-Bu | H | H | Br | 80% | 61% | A | 55A |
| 36A | Me | H | Me | H | Br | 89% | 73% | A | 56A |
| 37A | H | H | Me | Me | Br | 83% | 66% | A | 57A |
| 38A | H | H | H | Et | Br | 90% | 76% | A | 58A |
| 39A | Me | Me | Me | H | Br | 89% | 84% | A | 59A |
| 41A | H | OEt | H | H | Br | 88% | 88% | A | 60A |
| 42A | H | Cl | H | H | Br | 92% | 95% | A | 61A |
| 44A | H | COOEt | H | H | Br | 85% | 35% | A | 62A |
| 46A | H | OPh | H | H | Br | 88% | 55% | A | 63A |
| 47A | H | NEt₂ | H | H | Br | 94% | 53% | A | 64A |
| 48A | H | CH₂Br | H | H | Br | 87% | 73% | A | 65A |
| 32A | H | Me | H | H | H | 96% | 88% | B | 66A |
| 33A | H | Et | H | H | H | 92% | 83% | B | 67A |
| 36A | Me | H | Me | H | H | 82% | 55% | B | 68A |
| 42A | H | Cl | H | H | H | 90% | 96% | B | 69A |
| Average Demethylation Yield: 89% | | | | | Average Bromination Yield: 71% | | | | |

Figure 27A

PHENAZINE DERIVATIVES AS ANTIMICROBIAL AGENTS

RELATED APPLICATIONS

This application is a national stage filing under 35 U.S.C. § 371 of International Application No. PCT/US2018/018538, filed Feb. 17, 2018, which claims priority under 35 U.S.C. § 119(e) to U.S. Provisional Applications, U.S. Ser. No. 62/460,282, filed Feb. 17, 2017, and U.S. Ser. No. 62/477,509, filed Mar. 28, 2017, the entire contents of each of which are incorporated herein by reference.

BACKGROUND OF THE INVENTION

The emergence of multidrug resistant microbial infections (e.g., bacterial infections) has led to a serious global crisis. Almost every class of antibiotic that has been introduced into the clinic has been met with the development of drug resistant bacteria (A. E. Clatworthy, E. Pierson, and D. T. Hung, *Nat. Chem. Biol.*, 2007, 3, 541-548; K. Lewis, *Nat. Rev. Drug Discov.*, 2013, 12, 371-387). Despite the growing need for new antimicrobial agents, many pharmaceutical companies have abandoned their antimicrobial discovery programs as the anticipated success with target-based, high-throughput screening (HTS) campaigns has yet to be realized (K. Lewis, *Nat. Rev. Drug Discov.*, 2013, 12, 371-387; S. J. Projan, *Curr. Opin. Microbiol.*, 2003, 6, 427-430; E. D. Brown and G. D. Wright, *Chem. Rev.*, 2005, 105, 759-774; D. J. Payne, M. N. Gwynn, D. J. Holmes, and D. L. Pompliano, *Nat. Rev. Drug Discov.*, 2007, 6, 29-40). The health care emergency that has resulted from drug resistant microbial infections has been gaining momentum over the past four decades as only two new classes of antibiotics have been introduced into the clinic (K. Lewis, *Nat. Rev. Drug Discov.*, 2013, 12, 371-387; E. D. Brown and G. D. Wright, *Chem. Rev.*, 2005, 105, 759-774).

A wide range of microorganisms produce potent antibiotics as agents of microbial warfare and competition. As a result, the large majority of the antibiotic arsenal is based on such natural products discovered in the antibiotic golden era between the 1940s and 1960s (e.g., penicillin, streptomycin, erythromycin, tetracycline, vancomycin) or their synthetic derivatives (Lewis, *Nat. Rev. Drug Discov.*, 2013, 12, 371-387). In fact, very few clinically useful treatment options for microbial infections have been developed from purely synthetic origins (e.g., sulfonamides, quinolones, oxazolidinones).

In addition to infections resulting from planktonic bacteria, biofilms also play a key role in pathogenesis. The NIH has stated that bacterial biofilms are associated with up to 80% of all bacterial infections. Biofilms are notorious for their resistance to conventional antibiotic treatments. Currently, there is a desperate need for clinically useful anti-biofilm agents as there are no FDA-approved drugs that effectively target biofilm machinery. Innovative antimicrobial strategies are needed to meet the biomedical challenges of microbial infections, especially those resulting from multidrug resistant microbial infections and pathogenic bacterial biofilms.

SUMMARY OF THE INVENTION

The present invention provides novel halogenated phenazine derivatives (HPs, HP analogues), such as compounds of Formula (I) (e.g., Formulae (II)-(XIX)), and salts, hydrates, solvates, polymorphs, co-crystals, tautomers, stereoisomers, isotopically labeled derivatives, prodrugs, thereof:

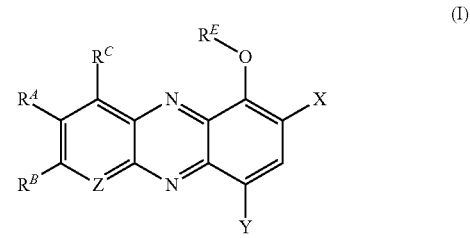

(I)

wherein X, Y, $R^A$, $R^B$, Z, $R^C$, $R^D$, and $R^E$ are as described herein, and use as antimicrobial agents (e.g., antibacterial activity, such as antibacterial activity against strains of *Staphylococcus aureus* (e.g., methicillin-resistant strains of *Staphylococcus aureus*), strains of *Staphylococcus epidermidis* (e.g., a methicillin-resistant strain of *Staphylococcus epidermidis* (MRSE)), and strains of *Enterococcus faecium* (e.g., vancomycin-resistant strains of *Enterococcus faecium*)). In one aspect, the compound of Formula (I) is of Formula (II):

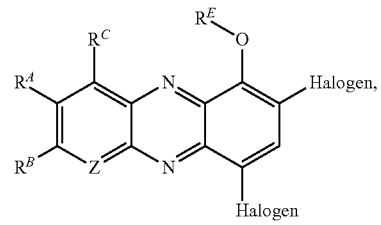

or a pharmaceutically acceptable salt, solvate, hydrate, polymorph, co-crystal, tautomer, stereoisomer, isotopically labeled derivative, or prodrug thereof.

In another aspect, the compound of Formula (I) is of the formula:

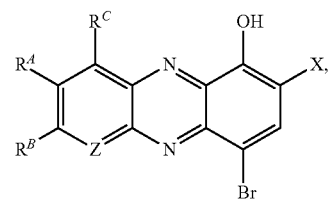

or a pharmaceutically acceptable salt, solvate, hydrate, polymorph, co-crystal, tautomer, stereoisomer, isotopically labeled derivative, or prodrug thereof.

In another aspect, the compound of Formula (I) is of the formula:

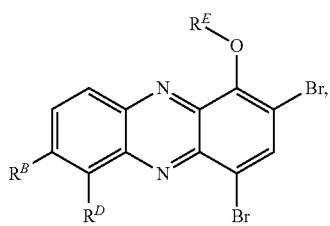

or a pharmaceutically acceptable salt, solvate, hydrate, polymorph, co-crystal, tautomer, stereoisomer, isotopically labeled derivative, or prodrug thereof.

In another aspect, the compound of Formula (I) is of the formula:

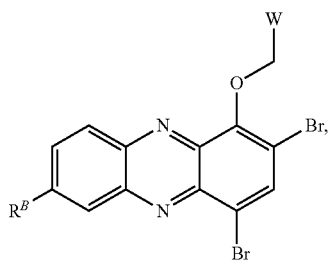

or a pharmaceutically acceptable salt, solvate, hydrate, polymorph, co-crystal, tautomer, stereoisomer, isotopically labeled derivative, or prodrug thereof; wherein: W is —OR$^A$ or —R$^A$.

In another aspect, the compound of Formula (I) is of the formula:

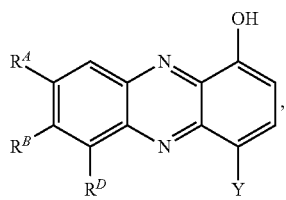

or a pharmaceutically acceptable salt, solvate, hydrate, polymorph, co-crystal, tautomer, stereoisomer, isotopically labeled derivative, or prodrug thereof.

Exemplary compounds of the invention include, but are not limited to:

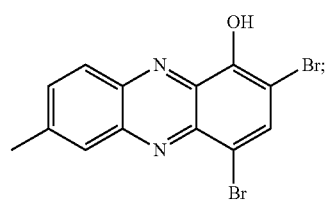

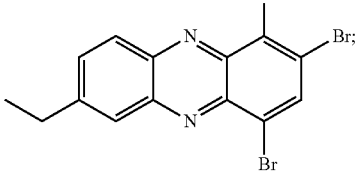

-continued

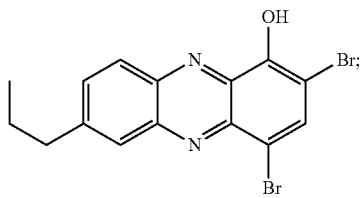

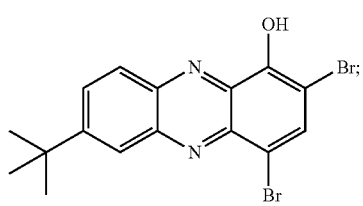

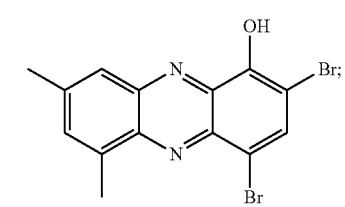

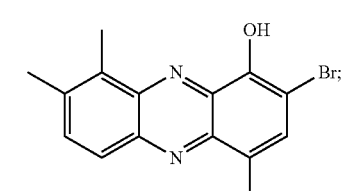

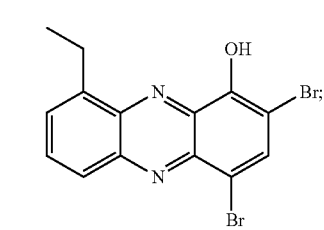

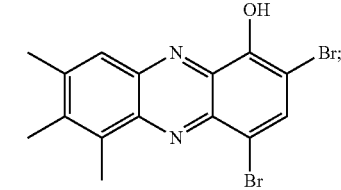

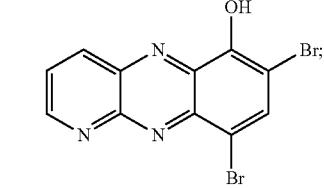

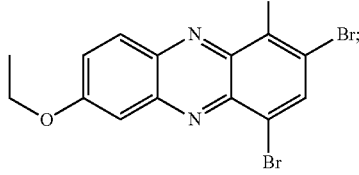

-continued
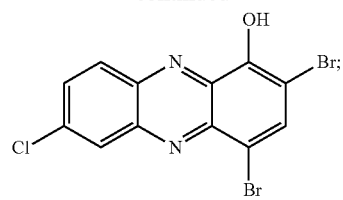
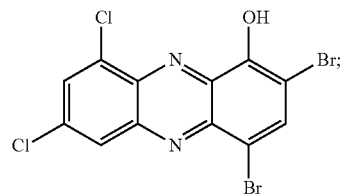
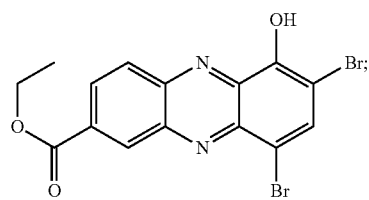
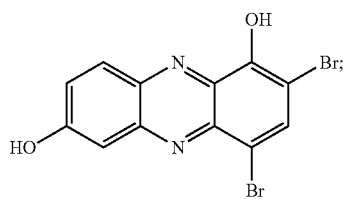
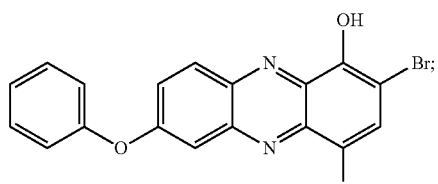
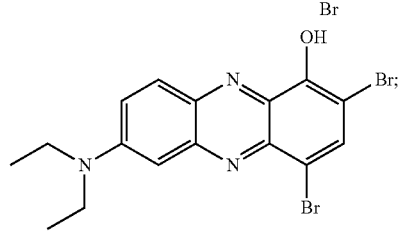
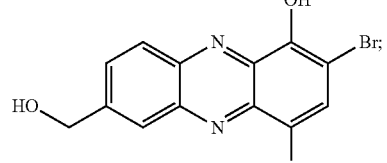
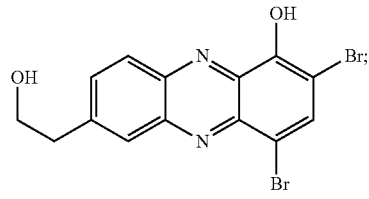
-continued
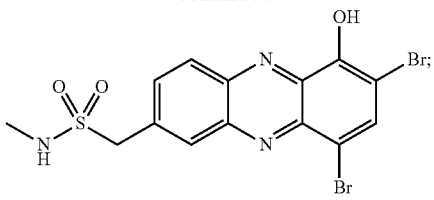
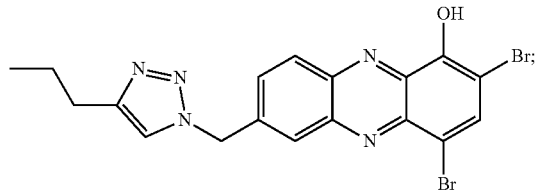
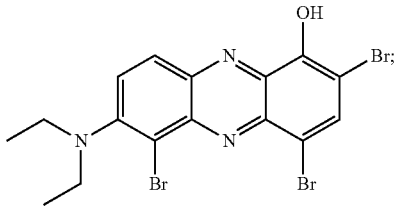
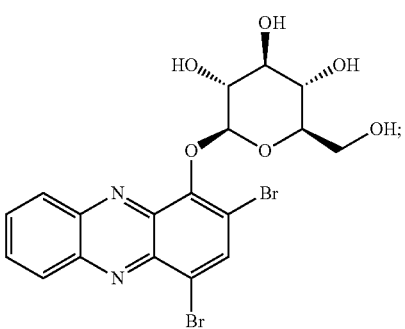
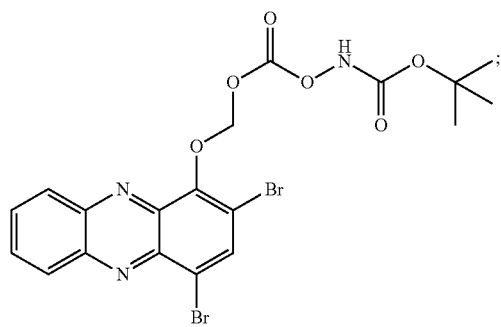
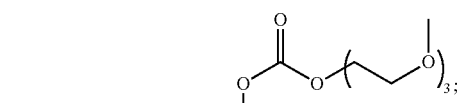
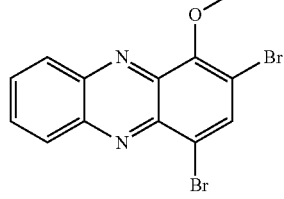

-continued

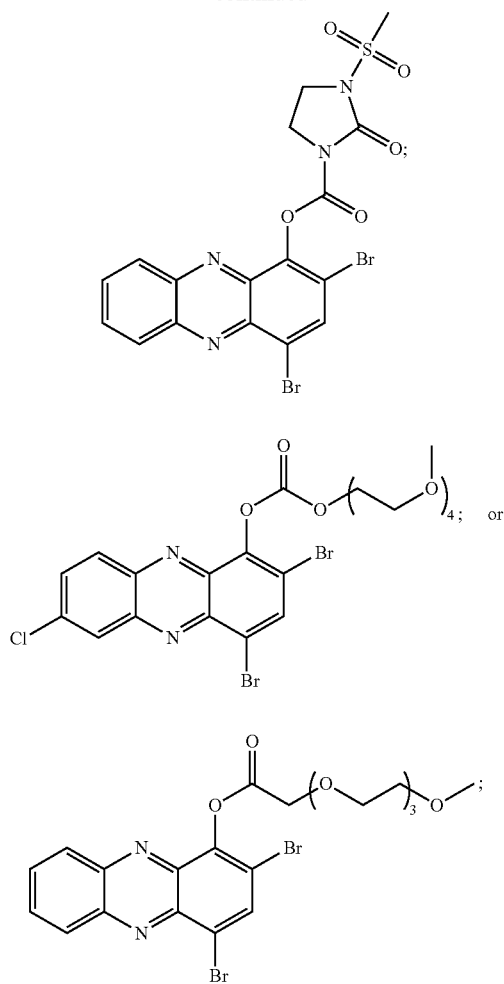

and pharmaceutically acceptable salts, solvates, hydrates, polymorphs, co-crystals, tautomers, stereoisomers, isotopically labeled derivatives, and prodrugs thereof.

Additional exemplary compounds of the invention include, but are not limited to:

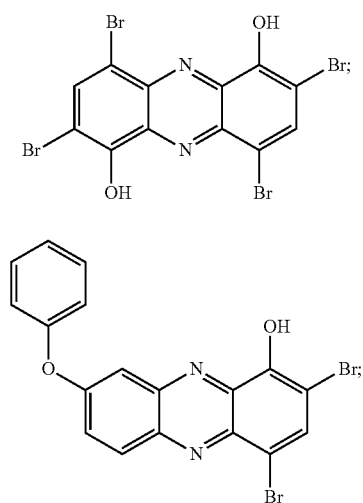

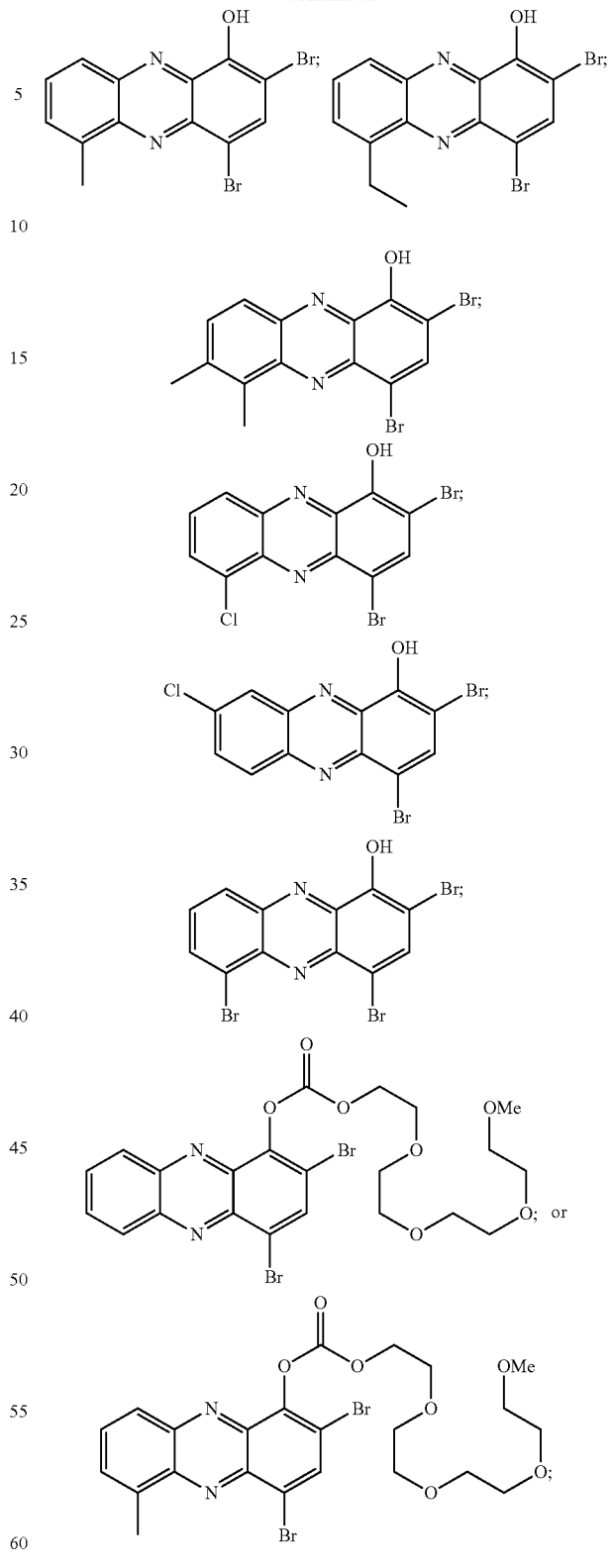

and pharmaceutically acceptable salts, solvates, hydrates, polymorphs, co-crystals, tautomers, stereoisomers, isotopically labeled derivatives, and prodrugs thereof.

Additional exemplary compounds of the invention include, but are not limited to:

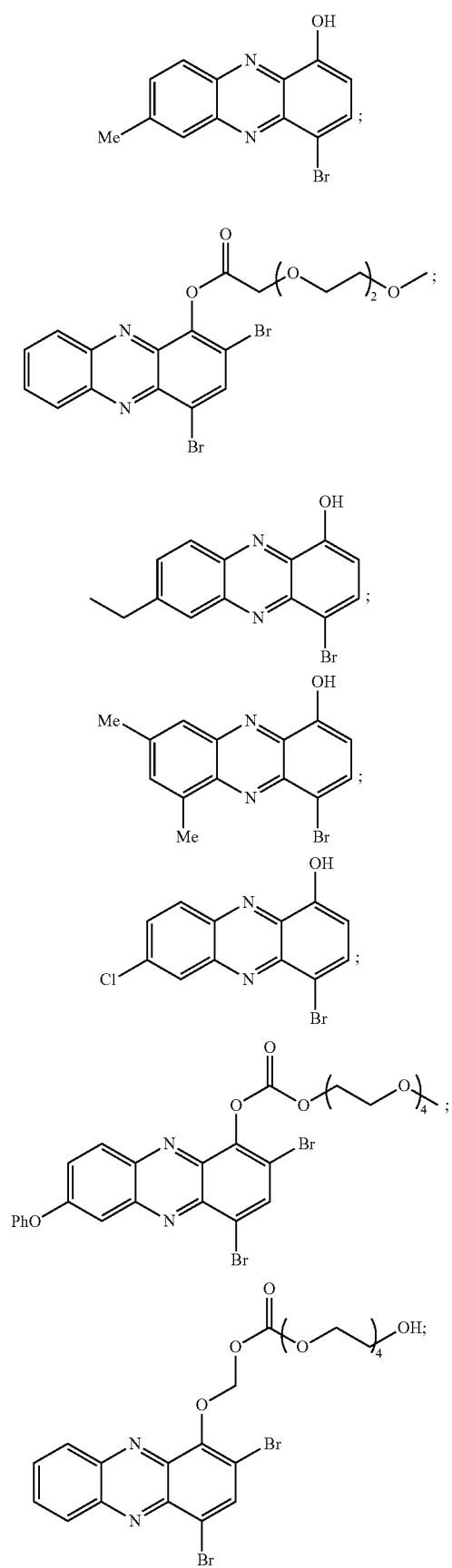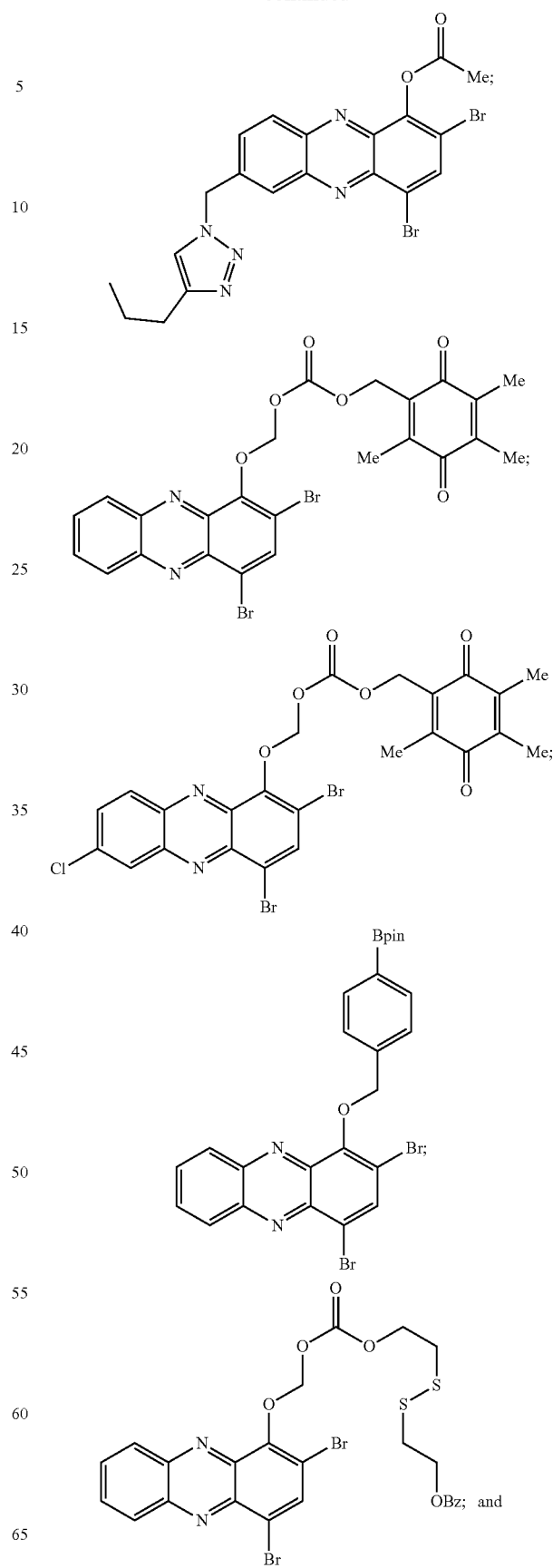

-continued

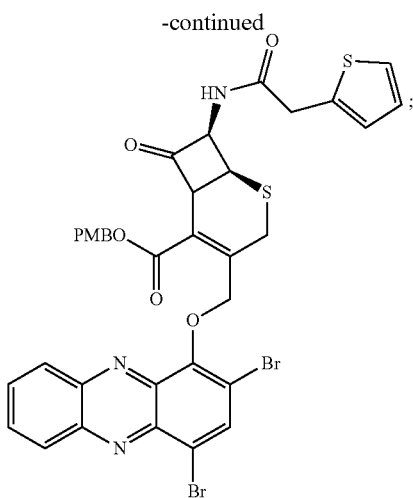

and pharmaceutically acceptable salts, solvates, hydrates, polymorphs, co-crystals, tautomers, stereoisomers, isotopically labeled derivatives, and prodrugs thereof.

The compounds of the invention may exhibit antimicrobial activity (e.g., antibacterial activity, such as antibacterial activity against strains of *Staphylococcus aureus* (e.g., methicillin-resistant strains of *Staphylococcus aureus*), strains of *Staphylococcus epidermidis* (e.g., a methicillin-resistant strain of *Staphylococcus epidermidis* (MRSE)), and strains of *Enterococcus faecium* (e.g., vancomycin-resistant strains of *Enterococcus faecium*)). Without wishing to be bound by any particular theory, it is thought that the compounds of the invention may act by a microbial warfare strategy (e.g., a reactive oxygen species (ROS)-based competition strategy) similar to the one employed by *Pseudomonas aeruginosa* (*P. aeruginosa*). The inventive compounds may generate ROS in, near, or around a microorganism (e.g., bacterium, mycobacterium, archaeon, protist, fungus, or parasite), which may be toxic to the microorganism. Moreover, the inventive compounds may be able to reduce, inhibit, and/or remove biofilms (e.g., *Staphylococcus aureus* biofilms (e.g., MRSA biofilms) and/or *Staphylococcus epidermidis* biofilms (e.g., MRSE biofilms)). The inventive compounds preferably have minimal or no adverse side effects. In certain embodiments, the inventive compounds have low cytotoxicity with respect to mammalian cells and/or demonstrate low hemolysis activity.

In certain embodiments, the compounds of the invention may exhibit low cytotoxicity against HeLa cells. In certain embodiments, the compounds of the invention may exhibit prodrug serum stability in human serum stability assays.

In another aspect, the present invention provides compositions including a compound of the invention and optionally an excipient. In certain embodiments, the composition includes an effective amount of the compound for disinfecting a surface. In certain embodiments, the composition is a pharmaceutical composition including a compound of the invention and optionally a pharmaceutically acceptable excipient. In certain embodiments, a pharmaceutical composition of the invention includes an effective amount of a compound of the invention for administration to a subject. In certain embodiments, the pharmaceutical composition is useful in a method of the invention (e.g., a method of treating a microbial infection, preventing a microbial infection, inhibiting the growth of a microorganism, inhibiting the reproduction of a microorganism, killing a microorganism, inhibiting the formation and/or growth of a biofilm, reducing or removing a biofilm, or disinfecting a surface). In certain embodiments, the microorganism is a microorganism described herein. In certain embodiments, the microorganism is a bacterium. In certain embodiments, the bacterium is a Gram-positive bacterium (e.g., a *Staphylococcus* species or *Enterococcus* species). In certain embodiments, the bacterium is a Gram-negative bacterium (e.g., an *Acinetobacter* species). In certain embodiments, the microorganism is a mycobacterium (e.g., a strain of *Mycobacterium tuberculosis*).

Another aspect of the present invention relates to methods of treating and/or preventing a microbial infection in a subject in need thereof, the method including administering to the subject a therapeutically or prophylactically effective amount of a compound or pharmaceutical composition of the invention. In certain embodiments, the microbial infection is treated and/or prevented by the inventive methods. The microbial infections that may be treated and/or prevented by the inventive methods include, but are not limited to, microbial respiratory tract infections, microbial gastrointestinal tract infections, microbial urogenital tract infections, microbial bloodstream infections, microbial ear infections, microbial skin infections, microbial oral infections, microbial dental infections, microbial wound or surgical site infections, microbial infections associated with cystic fibrosis, and microbial infections associated with implanted devices. In certain embodiments, the microbial infection described herein is a bacterial infection. In certain embodiments, the bacterium causing the bacterial infections is a Gram-positive bacterium (e.g., a *Staphylococcus* species or *Enterococcus* species). In certain embodiments, the bacterium causing the bacterial infections is a Gram-negative bacterium (e.g., an *Acinetobacter* species). In certain embodiments, the microbial infection described herein is a mycobacterial infection (e.g., an infection caused by *Mycobacterium tuberculosis*). In certain embodiments, the subject is a human. In certain embodiments, the subject is a human with cystic fibrosis. In certain embodiments, the subject is a non-human animal.

In another aspect, the present invention provides methods of inhibiting the growth of a microorganism (e.g., a bacterium, mycobacterium, archaeon, protist, fungus, or parasite) in vitro or in vivo.

In yet another aspect, the present invention provides methods of inhibiting the reproduction of a microorganism (e.g., a bacterium, mycobacterium, archaeon, protist, fungus, or parasite) in vitro or in vivo.

In yet another aspect, the present invention provides methods of killing a microorganism (e.g., a bacterium, mycobacterium, archaeon, protist, fungus, or parasite) in intro or in vivo.

In certain embodiments, an inventive method includes contacting a microorganism (e.g., bacterium, mycobacterium, archaeon, protist, fungus, or parasite) with a compound or pharmaceutical composition of the invention in an amount effective at inhibiting the growth and/or reproduction of or killing the microorganism.

Another aspect of the invention relates to methods of inhibiting the formation and/or growth of, reducing, or removing a biofilm, the method including contacting the biofilm with an effective amount of a compound or pharmaceutical composition of the invention. In certain embodiments, the biofilm includes a microorganism (e.g., a bacterium, mycobacterium, archaeon, protist, fungus, or parasite).

In certain embodiments, the biofilm includes bacteria. The biofilm may include one or more species of bacteria and/or other microorganisms.

Another aspect of the present invention relates to methods of disinfecting a surface, the methods including contacting the surface with an effective amount of a compound or composition of the invention. In certain embodiments, the surface is a biological surface (e.g., skin). In certain embodiments, the surface is a non-biological surface.

Another aspect of the present invention relates to kits comprising a container with a compound or composition (e.g., pharmaceutical composition) of the invention. The kits of the invention may include a single dose or multiple doses of the compound or pharmaceutical composition thereof. The provided kits may be useful in a method of the invention (e.g., a method of treating a microbial infection, preventing a microbial infection, inhibiting the growth of a microorganism (e.g., bacterium, mycobacterium, archaeon, protist, fungus, or parasite), inhibiting the reproduction of a microorganism, killing a microorganism, inhibiting the formation and/or growth of a biofilm, reducing or removing a biofilm, or disinfecting a surface). A kit of the invention may further include instructions for using the kit (e.g., instructions for using the compound or composition (e.g., pharmaceutical composition) included in the kit).

In another aspect, the present invention provides uses of the compounds and pharmaceutical compositions of the invention for manufacturing a medicament for treating and/or preventing a microbial infection.

In another aspect, the present invention provides the compounds and pharmaceutical compositions of the invention for use in methods of preventing and/or treating a microbial infection.

In another aspect, the present invention provides the compounds and pharmaceutical compositions of the invention for treating and/or preventing a microbial infection.

The present application refers to various issued patent, published patent applications, journal articles, and other publications, all of which are incorporated herein by reference. The details of one or more embodiments of the invention are set forth herein. Other features, objects, and advantages of the invention will be apparent from the Detailed Description, Examples, and Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and subrange within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" refers to alkyl, alkenyl, alkynyl, and carbocyclic groups. Likewise, the term "heteroaliphatic" as used herein, refers to heteroalkyl, heteroalkenyl, heteroalkynyl, and heterocyclic groups.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is substituted $C_{1-10}$ alkyl (such as substituted $C_{1-6}$ alkyl, e.g., —$CH_2F$, —$CHF_2$, —$CF_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

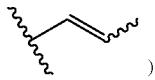
)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

The term "carbocyclyl" or "carbocyclic" refers to a radical of a nonaromatic cyclic hydrocarbon group having from 3 to 14 ring carbon atoms ("$C_{3-14}$ carbocyclyl") and zero heteroatoms in the nonaromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$).

Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

"Heterocyclyl" or "heterocyclic" refers to a radical of a 3- to 10-membered non aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered nonaromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing three heteroatoms include, without limitation, triazinyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 p electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix -ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group) if not otherwise provided explicitly. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)

OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)S R$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, $C_{6-10}$ aryl, 3-10 membered heterocyclyl, 5-10 membered heteroaryl; or two geminal R$^{gg}$ substituents can be joined to form =O or =S; wherein X$^-$ is a counterion.

In certain embodiments, the carbon atom substituents are independently halogen, substituted or unsubstituted $C_{1-6}$ alkyl, or —OR$^{aa}$.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F⁻, Cl⁻, Br⁻, I⁻), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —$ON(R^{bb})_2$, —$OC(=O)SR^{aa}$, —$OC(=O)R^{aa}$, —$OCO_2R^{aa}$, —$OC(=O)N(R^{bb})_2$, —$OC(=NR^{bb})R^{aa}$, —$OC(=NR^{bb})OR^{aa}$, —$OC(=NR^{bb})N(R^{bb})_2$, —$OS(=O)R^{aa}$, —$OSO_2R^{aa}$, —$OSi(R^{aa})_3$, —$OP(R^{cc})_2$, —$OP(R^{cc})_3^+X^-$, —$OP(OR^{cc})_2$, —$OP(OR^{cc})_3^+X^-$, —$OP(=O)(R^{aa})_2$, —$OP(=O)(OR^{cc})_2$, and —$OP(=O)(N(R^{bb}))_2$, wherein $X^-$, $R^{aa}$, $R^{bb}$, and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a mono-substituted amino or a disubstituted amino group.

"Acyl" refers to a moiety selected from the group consisting of —$C(=O)R^{aa}$, —CHO, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$C(=O)NR^{bb}SO_2R^{aa}$, —$C(=S)N(R^{bb})_2$, —$C(=O)SR^{aa}$, or —$C(=S)SR^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{bb})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)(OR^{cc})_2$, —$P(=O)(R^{aa})_2$, —$P(=O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is a nitrogen protecting group (also referred to as an amino protecting group). Nitrogen protecting groups include, but are not limited to, —OH, —$OR^{aa}$, —$N(R^{cc})_2$, —$C(=O)R^{aa}$, —$C(=O)N(R^{cc})_2$, —$CO_2R^{aa}$, —$SO_2R^{aa}$, —$C(=NR^{cc})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., $C(=O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —$C(=O)OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o- nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $-S(=O)_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethylbenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-dephenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, a sugar, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(R^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxymethyl (MOM), tert-butoxycarbonyl, methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyl-dithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate, alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, gluconate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I) (e.g., Formulae (II)-(XIX)) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound and wherein x is a number greater than 0. A given compound may form more than one type of hydrate, including, e.g., monohydrates (x is 1), lower hydrates (x is a number greater than 0 and smaller than 1, e.g., hemihydrates (R·0.5H$_2$O)), and polyhydrates (x is a number greater than 1, e.g., dihydrates (R·2H$_2$O) and hexahydrates (R·6H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Polymorph" refers to a particular polymorphic variant of a given compound. Polymorphism is the ability of a solid substance of a given chemical composition to exist in more than one form or crystalline structure. Polymorphism can exist as a result of differences in crystal packing (packing polymorphism), conformational differences (conformational polymorphism), or changes due to co-crystallization with other chemical entities (pseudopolymorphism). Polymorphism is an important aspect of pharmaceutical development, in which case drugs typically receive regulatory approval for only a single form. Distinct polymorphic forms frequently vary considerably in terms of their physical properties. Altered dissolution rates, thermal stability, and hygroscopicity are frequently observed.

The term "prodrugs" refers to compounds that have cleavable groups and become by solvolysis or under physiological conditions the compounds of Formula (I) (e.g., Formulae (II)-(XIX)), which are pharmaceutically active in vivo. Such examples include, but are not limited to, ester derivatives and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs, pp.* 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$ to $C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formula (I) (e.g., Formulae (II)-(XIX)) may be preferred.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or nonhuman animal. In certain embodiments, the nonhuman animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the nonhuman animal is a fish, reptile, or amphibian. The nonhuman animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The terms "administer," "administering," or "administration," refers to implanting, absorbing, ingesting, injecting, inhaling, or otherwise introducing an inventive compound, or a pharmaceutical composition thereof.

The terms "treatment," "treat," and "treating" refer to reversing, alleviating, delaying the onset of, or inhibiting the progress of a microbial infection (e.g., a bacterial infection or mycobacterial infection). In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of exposure to microorganisms, in light of a history of symptoms, and/or in light of genetic or other susceptibility factors). Treatment may also be continued after symptoms have resolved, for example, to delay and/or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses. In certain embodiments, an effective amount is an amount effective for inhibiting the growth of a microorganism, for inhibiting the reproduction of a microorganism, or for killing a microorganism. In certain embodiments, an effective amount is an amount effective for inhibiting the formation of a biofilm, for inhibiting the growth of a biofilm, for reducing a biofilm, or for clearing a biofilm. In certain embodiments, an effective amount is an amount effective for disinfecting a surface (e.g., killing at least 80%, at least 90%, at least 99%, at least 99.9%, or at least 99.99% of the microorganisms on the surface). In certain embodiments, an effective amount is an amount effective for killing a persister cell.

A "therapeutically effective amount" of a compound of Formula (I) (e.g., Formulae (II)-(XIX)) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent. In certain embodiments, a therapeutically effective amount is effective for treating a microbial infection (e.g., a bacterial infection or mycobacterial infection) in a subject, for inhibiting the growth and/or reproduction of a microorganism (e.g., a bacterium), for killing a microorganism (e.g., a bacterium), for inhibiting the formation and/or growth of a biofilm, for reducing or clearing a biofilm, and/or for disinfecting a surface.

A "prophylactically effective amount" of a compound of Formula (I) (e.g., Formulae (II)-(XIX)) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is effective for preventing a microbial infection (e.g., a bacterial infection or mycobacterial infection) in a subject, for inhibiting the growth and/or reproduction of a microorganism (e.g., a bacterium), for killing a microorganism (e.g., a bacterium), for inhibiting the formation and/or growth of a biofilm, for reducing or clearing a biofilm, and/or for disinfecting a surface.

The term "inhibition", "inhibiting", "inhibit," "inhibitory," or "inhibitor" refers to the ability of a compound to reduce, slow, halt, or prevent activity of a particular biological process (e.g., the growth or reproduction) of a microorganism (e.g., a bacterium, mycobacterium, archaeon, protist, fungus, or parasite) relative to vehicle.

The term "minimum inhibitory concentration" or "MIC" refers to the lowest concentration of a compound that will inhibit the visible growth of a microorganism (e.g., a bacterium, mycobacterium, archaeon, protist, fungus, or parasite) after overnight (e.g., about 16 to about 20 hours, or about 16 to about 18 hours) incubation of the microorganism with the compound at about 37° C.

The term "half maximal inhibitory concentration" or "$IC_{50}$" of a compound refers to the concentration of the compound that inhibits the growth of half of an inoculum of a microorganism (e.g., a bacterium, mycobacterium, archaeon, protist, fungus, or parasite).

The term "microorganism" refers to a microscopic organism, which may be a single-cell or multicellular organism. In certain embodiments, the microorganism is a bacterium, mycobacterium, archaeon, protist (e.g., protozoon, alga), fungus (e.g., yeast, mold), or parasite. In certain embodiments, the microorganism is a bacterium. In certain embodiments, the length or diameter of a microorganism is at most about 10 cm, at most about 1 cm, at most about 1 mm, at most about 100 µm, at most about 10 µm, at most about 1 µm, at most about 100 nm, or at most about 10 nm. In certain embodiments, the length or diameter of a microorganism is at most about 10 µm.

The term "biofilm" refers to a group of microorganisms (e.g., bacteria) in which cells of the microorganisms stick to each other on a surface. These adherent cells are frequently embedded within a self-produced matrix of extracellular polymeric substance (EPS). The EPS is a polymeric conglomeration generally composed of extracellular DNA, proteins, and polysaccharides. Biofilms may form on living or non-living surfaces and can be prevalent in natural, industrial, and hospital settings. The cells growing in a biofilm are physiologically distinct from planktonic cells of the same microorganism, which are single-cells that may float or swim in a liquid medium. Biofilms have been found to be involved in a wide variety of microbial infections. Biofilms are formed by numerous Gram-negative and Gram-positive bacterial species. Non-limiting examples include *Bacillus* spp, *Staphylococcus* spp, *Pseudomonas* spp, and *Acinetobacter* spp.

The term "microbial warfare" refers to a first microorganism producing a substance (e.g., an antibiotic) that is toxic to a second microorganism but is not toxic or less toxic, compared to the second microorganism, to the first microorganism. When a second microorganism in close proximity to the first microorganism contacts the substance, the growth and/or reproduction of the second microorganism may be inhibited, or the second microorganism may be killed. As a result, the first microorganism may gain a competitive advantage over the second microorganism in close proximity to the first microorganism in terms of survival, growth, and/or reproduction.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

The term "planktonic" refers to any of the group of passively floating, drifting, or somewhat motile organisms occurring in a liquid medium (e.g., an aqueous solution). This group includes, but is not limited to, microscopic bacteria, algae, or protozoa.

BRIEF DESCRIPTION OF THE DRAWINGS

The accompanying drawings, which constitute a part of this specification, illustrate several embodiments of the invention and together with the description, serve to explain the principles of the invention.

Figure 2:
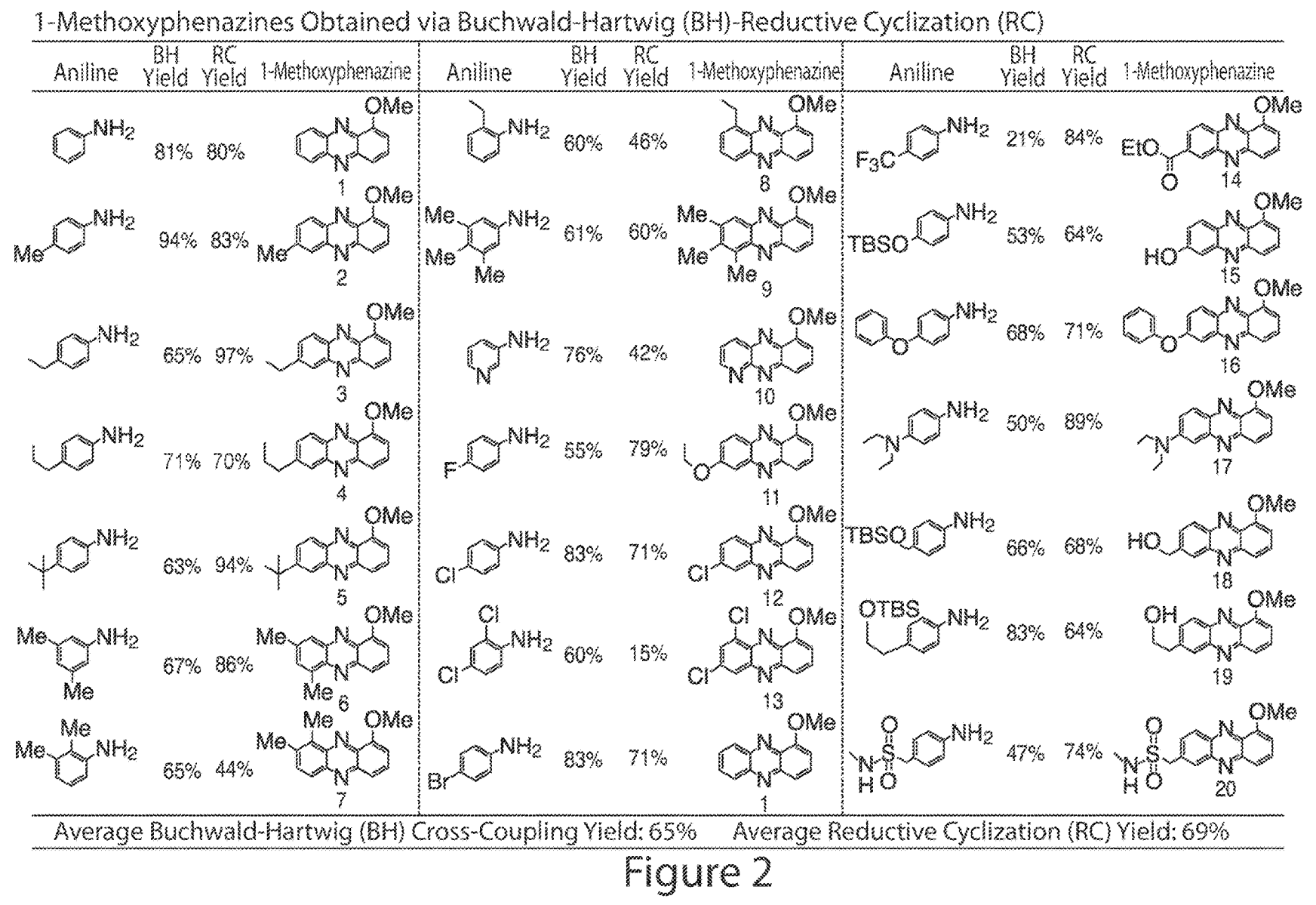

FIG. 2 shows the 1-methoxyphenazines obtained via Buchwald-Hartwig (BH)-Reductive Cyclization (RC).

FIG. 3 shows the demethylation and bromination reactions used to prepare the compounds of Formula (I).

FIG. 4 shows the preparation of Compound 25.

FIG. 12 shows the compounds of Formula (I) (e.g., Formulae (II)-(XIX)) obtained via Wohl-Aue cyclization route.

FIG. 21 shows the structure-activity relationship (SAR) against MRSA-1707 for various 6- and 8-substituted HPs.

FIG. 24A: Phenazine syntheses previously utilized in the present experiments with the associated shortcomings. FIG. 24B: Synthetic strategy and theoretical substrate scope of cross-coupling/reductive cyclization using varied orientations of coupling starting materials.

FIG. 25. Investigation into coupling conditions for diarylamine intermediate synthesis.

FIGS. 27A and 27B. FIG. 27A: Synthesis of the halogenated phenazine library with corresponding demethylation and bromination yields. Note: [a] Series A analogues were synthesized to target MRSA, MRSE, and VRE while Series B analogues were synthesized to target MtB. [b] $R^1$=Br following bromination reaction. [c] Primary bromide obtained following demethylation of 48A. FIG. 27B: SAR of anti-MtB (H37Ra) analogues relative to the corresponding dibrominated counterparts (MRSA=MRSA BAA-1707).

FIG. 30A: Calgary Biofilm Device (CBD) assay for MBC/MBEC determination of select HPs against MRSA BAA-1707. FIG. 30B: Live/dead fluorescence imaging of eradicated MRSE biofilms following treatment with HP 61A. FIG. 30C: UV-Vis evaluation of QuAOCOM 86A stability in LB media. FIG. 30D: QuAOCOM MRSA BAA-1707 agar diffusion assay: a) DMSO, b) HP 61A, c). HP QuAOCOM 87A. Zones of inhibition are 424.7±27.3 mm and 285.9±15.0 mm for 61A and 87A, respectively.

DETAILED DESCRIPTION OF CERTAIN EMBODIMENTS OF THE INVENTION

Figure 1:
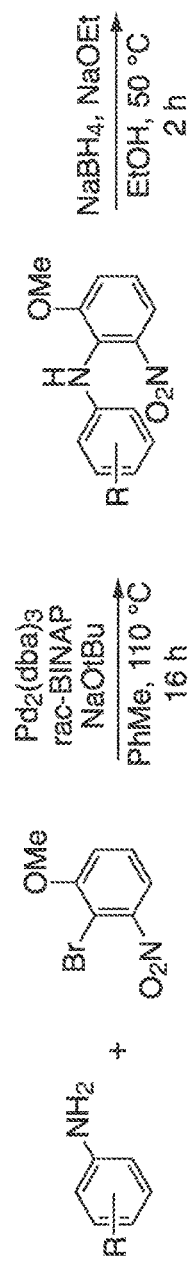
FIG. 1 shows the synthetic process used to assemble the phenazine compounds of the invention.
Figure 5:
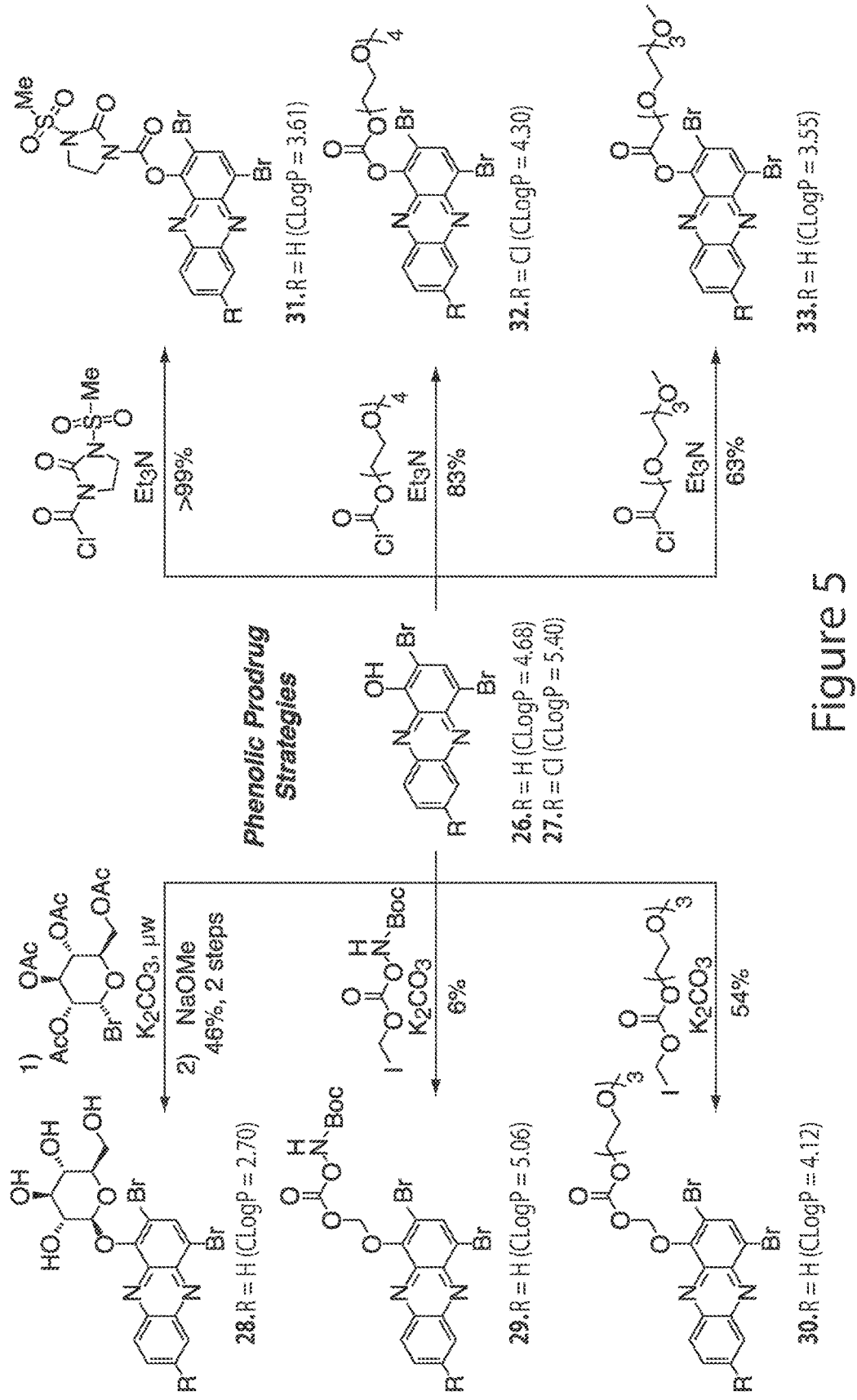
FIG. 5 shows the synthetic approaches to preparing various prodrugs of the compounds of Formula (I).

Other antimicrobial phenazine derivatives have been reported in international PCT application publication, WO 2015/100331, published Jul. 2, 2015, which is incorporated herein by reference. The present invention provides, in one aspect, novel phenazine derivatives, such as compounds Formula (I) (e.g., Formulae (II)-(XIX)), and salts (e.g., pharmaceutically acceptable salts), solvates, hydrates, polymorphs, co-crystals, tautomers, stereoisomers, isotopically labeled derivatives, and prodrugs thereof. The compounds of the invention are expected to be antimicrobial agents and, without wishing to be bound by any particular theory, may act by a microbial warfare strategy (e.g., a reactive oxygen species (ROS)-based competition strategy). The present invention also provides compositions including pharmaceutical compositions, kits, uses, and methods that involve the compounds of the invention and may be useful in preventing and/or treating a microbial infection in a subject, inhibiting the growth and/or reproduction of a microorganism (e.g., bacterium, mycobacterium, archaeon, protist, fungus, or parasite), killing a microorganism, inhibiting the formation and/or growth of a biofilm, reducing or removing a biofilm, or disinfecting a surface. In certain embodiments, the microorganism is a bacterium. In certain embodiments, the bacterium is a Gram-positive bacterium (e.g., a species of *Staphylococcus* or *Enterococcus*). In certain embodiments, the bacterium is a Gram-negative bacterium (e.g., an *Acinetobacter* species).

Many past successes in antibiotic discovery have been grounded on microbial warfare agents/strategies from microorganisms. Therefore, future antimicrobial treatments may also depend on the discovery and implementation of innovative microbial-inspired antimicrobial strategies. One such strategy is the use of redox-active phenazine antibiotics by *Pseudomonas* during competition with other bacteria and fungi through the formation of reactive oxygen species (ROS) (A. Price-Whelan, L. E. P. Dietrich, and D. K. Newman, *Nat. Chem. Biol.*, 2006, 2, 71-78; Z. A. Machan, T. L. Pitt, W. White, D. Watson, G. W. Taylor, P. J. Cole, and R. Wilson, *J. Med. Microbiol.*, 1991, 34, 213-217). One example of this competition is in young cystic fibrosis (CF) patients (Z. A. Machan, T. L. Pitt, W. White, D. Watson, G. W. Taylor, P. J. Cole, and R. Wilson, *J. Med. Microbiol.*, 1991, 34, 213-217). Many times, individuals with CF first develop *Staphylococcus aureus* lung infections when they are young. As the CF patient ages, *Pseudomonas aeruginosa* co-infects the lung and successfully competes against *S. aureus* for this niche using redox-active phenazine antibiotics.

Certain phenazine derivatives, such as compounds 301-305 (shown below) are known antimicrobial agents. Pyocyanine (compound 301) is one of the toxins produced by the Gram negative bacterium *Pseudomonas aeruginosa*. It is thought that *Pseudomonas aeruginosa* employs a microbial warfare strategy by producing these toxins in competing with other microorganisms (e.g., other bacteria). Pyocyanine is able to oxidize and reduce other molecules (Hassan et al., *J. Bacteriology* 1980, 141, 156-163) and can kill microbes competing against *Pseudomonas aeruginosa* as well as mammalian cells of the lungs that *Pseudomonas aeruginosa* has infected during cystic fibrosis. Due to its redox-active properties, pyocyanine can generate reactive oxygen species (ROS), which may be toxic to bacteria. It has been reported that the reduction potential and redox-cycling capabilities of phenazine are electronically influenced by functional group substitutions on the phenazinyl ring system (Price-Whelan et al., *Nat. Chem. Biol.*, 2006, 2, 71-78; Wang et al., *J. Bacteriol.*, 2010, 192, 365-369). Therefore, the redox-active properties of a phenazine derivative may be altered by structurally modifying the phenazine derivative. However, there is no teaching or suggestion in the art on how a known phenazine may be structurally modified to improve its properties, such as antimicrobial activity.

301

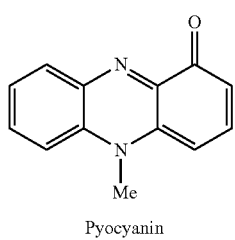

Pyocyanin

302

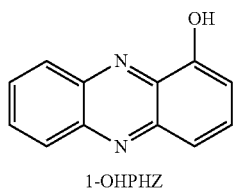

1-OHPHZ

303

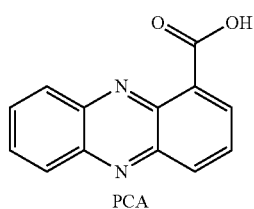

PCA

304

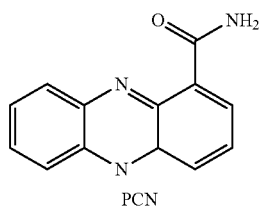

PCN

-continued

305

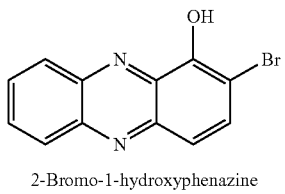

2-Bromo-1-hydroxyphenazine

In certain embodiments, the compounds of the invention are improved phenazine derivatives and showed unexpected and superior properties compared to known phenazine derivatives, such as enhanced inhibitory activity against bacteria, e.g., *Staphylococcus aureus* (*S. aureus*), *Staphylococcus epidermidis* (*S. epidermidis*), and/or *Enterococcus faecium*. *Staphylococcus aureus* is a human pathogen that is notorious for life-threatening drug-resistant infections in hospitals and the community (H. F. Chambers and F. R. DeLeo, *Nat. Rev. Microbiol.*, 2009, 7, 629-641). In the United States alone, there are more annual deaths from methicillin-resistant *Staphylococcus aureus* (MRSA) related microbial infections than AIDS (IDSA Policy Paper d CID 2011:52 (Suppl 5) d S397). *Staphylococcus epidermidis* is also a pathogen of great importance as it is particularly prevalent in persistent microbial infections associated with catheters (I. Uckay, D. Pittet, P. Vaudaux, H. Sax, D. Lew, and F. Waldvogel, *Ann. Med.*, 2009, 41, 109-119).

Without wishing to be bound by any particular theory, it is thought that the compounds of the invention may act by a microbial warfare strategy (e.g., an ROS-based competition strategy) similar to the one employed by *Pseudomonas aeruginosa*. The inventive compounds may be capable of undergoing reduction and oxidation (redox) reactions and forming ROS in, near, or around a microorganism (e.g., bacterium, mycobacterium, archaeon, protist, fungus, or parasite). An inventive compound may accept a single electron, yielding a relatively stable anion radical, and may readily undergo a redox cycle. A compound of the invention may be reduced by the nicotinamide adenine dinucleotide (NADH$^+$) in a microorganism and may divert electron flow within the microorganism from the normal cytochrome pathway to an ROS-producing pathway. As a result, the production of ROS, such as $O_2^-$ and $H_2O_2$, which are toxic to the microorganism, may be increased.

Furthermore, compounds disclosed herein may be effective agents for the inhibition of biofilm growth and/or clearance of existing biofilms. Bacterial biofilms are surface-attached bacterial communities that are encased within a secreted matrix of biomolecules (e.g., extracellular DNA, proteins, polysaccharides) known as the extracellular polymeric substance (EPS). Bacterial cells within a biofilm take on a completely different physiology than their free-swimming planktonic counterparts and are notorious for being highly resistant to conventional antibiotic treatments and host immune responses (Donlan, R. M. and Costerton, J. W. *Clin. Microbiol. Rev.* 2002, 15, 167-193). The National Institutes of Health has reported that biofilms are present in up to 80% of all bacterial infections. Unfortunately, biofilms are notorious for their resistance to conventional antibiotic treatments, and therefore our current arsenal of antibiotics does not include agents that effectively target biofilm machinery or clear established biofilms in a clinical setting. Such antibiofilm agents would lead to significant breakthroughs in how bacterial infections are treated and would result in the effective treatment of many life-threatening bacterial infections.

Bacterial biofilm formation is governed by a signaling process known as quorum sensing, which is used by bacteria to monitor population density and control bacterial virulence (Camilli, A. and Bassler, B. L. *Science* 2006, 311, 1113-1116; Ng, W. L. and Bassler, B. L. *Annu. Rev. Genet.* 2009, 43, 197-222). Quorum sensing is used by free-swimming, individual planktonic bacteria to coordinate the simultaneous attachment and colonization of a surface followed by biofilm formation and maturation. The coordinated surface attachment of bacteria overwhelms immune responses mounted by host organisms, enabling the successful colonization of surfaces (e.g., tissue surfaces) by bacteria. Bacterial biofilms are known to be greater than 1000-fold more resistant to conventional antibiotics when compared to their planktonic counterparts. Therapeutic strategies targeting quorum sensing and/or biofilm formation and dispersion phenotypes have become a promising antibacterial strategy as small molecules capable of inhibiting bacterial biofilm formation via non-growth inhibitory mechanisms or clearing pre-formed bacterial biofilms are of clinical importance. Without wishing to be bound by any particular theory, compounds described herein may function by disrupting quorum sensing, leading to inhibitors of biofilm formation and clearing of pre-formed biofilms.

The inventive compounds preferably have minimal to no adverse side effects. In certain embodiments, the compounds exhibit low cytotoxicity against mammalian (e.g., human) cells. In certain embodiments, the compounds show low hemolysis activity.

Compounds

One aspect of the invention relates to compounds that are believed to be antimicrobial agents. In certain embodiments, the compounds of the invention are compound of Formula (I):

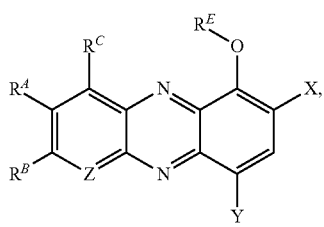

(I)

and salts (e.g., pharmaceutically acceptable salts), solvates, hydrates, polymorphs, co-crystals, tautomers, stereoisomers, isotopically labeled derivatives, and prodrugs thereof, wherein:

X is hydrogen or halogen;

Y is halogen;

Z is N or $CR^D$;

$R^A$ is hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^1$, $-N(R^1)_2$, $-SR^1$, $-CN$, $-SCN$, $-C(=NR^1)R^1$, $-C(=NR^1)OR^1$, $-C(=NR^1)N(R^1)_2$, $-C(=O)R^1$, $-C(=O)OR^1$, $-C(=O)N(R^1)_2$, $-NO_2$, $-NR^1C(=O)R^1$, $-NR^1C(=O)OR^1$, $-NR^1C(=O)N(R^1)_2$, $-OC(=O)R^1$, $-OC(=O)$ $OR^1$, or $-OC(=O)N(R^1)_2$, wherein each instance of $R^1$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^1$ are joined to form a substituted or unsubstituted heterocyclic or substituted or unsubstituted heteroaryl ring;

$R^B$ is hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^2$, $-N(R^2)_2$, $-SR^2$, $-CN$, $-SCN$, $-C(=NR^2)R^2$, $-C(=NR^2)OR^2$, $-C(=NR^2)N(R^2)_2$, $-C(=O)R^2$, $-C(=O)OR^2$, $-C(=O)N(R^2)_2$, $-NO_2$, $-NR^2C(=O)R^2$, $-NR^2C(=O)OR^2$, $-NR^2C(=O)N(R^2)_2$, $-OC(=O)R^2$, $-OC(=O)OR^2$, or $-OC(=O)N(R^2)_2$, wherein each instance of $R^2$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^2$ are joined to form a substituted or unsubstituted heterocyclic or substituted or unsubstituted heteroaryl ring;

$R^C$ is hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^3$, $-N(R^3)_2$, $-SR^3$, $-CN$, $-SCN$, $-C(=NR^3)R^3$, $-C(=NR^3)OR^3$, $-C(=NR^3)N(R^3)_2$, $-C(=O)R^3$, $-C(=O)OR^3$, $-C(=O)N(R^3)_2$, $-NO_2$, $-NR^3C(=O)R^3$, $-NR^3C(=O)OR^3$, $-NR^3C(=O)N(R^3)_2$, $-OC(=O)R^3$, $-OC(=O)OR^3$, or $-OC(=O)N(R^3)_2$, wherein each instance of $R^3$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^3$ are joined to form a substituted or unsubstituted heterocyclic or substituted or unsubstituted heteroaryl ring;

$R^D$ is hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^4$, $-N(R^4)_2$, $-SR^4$, $-CN$, $-SCN$, $-C(=NR^4)R^4$, $-C(=NR^4)OR^4$, $-C(=NR^4)N(R^4)_2$, $-C(=O)R^4$, $-C(=O)OR^4$, —C(=O)N(R⁴)₂, —NO₂, —NR⁴C(=O)R⁴, —NR⁴C(=O)OR⁴, —NR⁴C(=O)N(R⁴)₂, —OC(=O)R⁴, —OC(=O)OR⁴, or —OC(=O)N(R⁴)₂, wherein each instance of R⁴ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R⁴ are joined to form a substituted or unsubstituted heterocyclic or substituted or unsubstituted heteroaryl ring; and R$^E$ is hydrogen, an oxygen protecting group, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=NR⁵)R⁵, —C(=NR⁵)OR⁵, —C(=NR⁵)N(R⁵)₂, —C(=O)R⁵, —C(=O)OR⁵, or —C(=O)N(R⁵)₂, wherein each instance of R⁵ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R⁵ are joined to form a substituted or unsubstituted heterocyclic or substituted or unsubstituted heteroaryl ring provided that when R$^C$ and R$^E$ are both hydrogen, Z is CR$^D$, and R$^D$ is hydrogen, then R$^A$ and R$^B$ are not the same.

In another aspect, the compound of Formula (I) is of the formula:

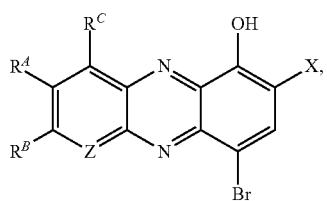

or a pharmaceutically acceptable salt, solvate, hydrate, polymorph, co-crystal, tautomer, stereoisomer, isotopically labeled derivative, or prodrug thereof.

In another aspect, the compound of Formula (I) is of the formula:

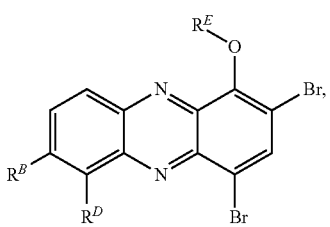

or a pharmaceutically acceptable salt, solvate, hydrate, polymorph, co-crystal, tautomer, stereoisomer, isotopically labeled derivative, or prodrug thereof.

In another aspect, the compound of Formula (I) is of the formula:

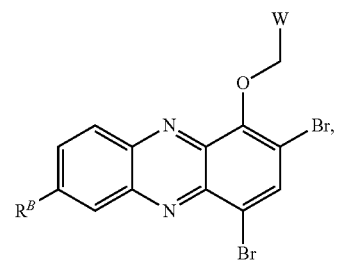

or a pharmaceutically acceptable salt, solvate, hydrate, polymorph, co-crystal, tautomer, stereoisomer, isotopically labeled derivative, or prodrug thereof; wherein: W is —OR$^A$ or —R$^A$.

In another aspect, the compound of Formula (I) is of the formula:

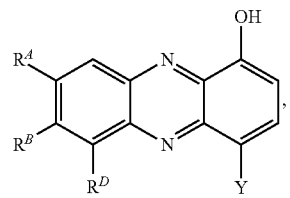

or a pharmaceutically acceptable salt, solvate, hydrate, polymorph, co-crystal, tautomer, stereoisomer, isotopically labeled derivative, or prodrug thereof.

Formula (I) includes substituent X on the phenazinyl ring. In certain embodiments, X is hydrogen. In certain embodiments, X is halogen. In certain embodiments, X is F. In certain embodiments, X is Cl. In certain embodiments, X is Br. In certain embodiments, X is I. In certain embodiments, X is substituted or unsubstituted alkyl (e.g., substituted or unsubstituted $C_{1-6}$ alkyl). In certain embodiments, X is Me. In certain embodiments, X is substituted methyl (e.g., —CH₂F, —CHF₂, —CF₃, or Bn). In certain embodiments, X is Et, substituted ethyl (e.g., fluorinated ethyl (e.g., perfluoroethyl)), Pr, substituted propyl (e.g., fluorinated propyl (e.g., perfluoropropyl)), Bu, substituted butyl (e.g., fluorinated butyl (e.g., perfluorobutyl)), unsubstituted pentyl, substituted pentyl (e.g., fluorinated pentyl (e.g., perfluoropentyl)), unsubstituted hexyl, or substituted hexyl (e.g., fluorinated hexyl (e.g., perfluorohexyl)). In certain embodiments, X is substituted or unsubstituted alkenyl (e.g., substituted or unsubstituted $C_{2-6}$ alkenyl). In certain embodiments, X is substituted or unsubstituted vinyl. In certain embodiments, X is unsubstituted allyl. In certain embodiments, X is substituted allyl. In certain embodiments, X is substituted or unsubstituted alkynyl (e.g., substituted or unsubstituted $C_{2-6}$ alkynyl).

Formula (I) also includes substituent Y on the phenazinyl ring. In certain embodiments, Y is halogen. In certain embodiments, Y is F. In certain embodiments, Y is Cl. In certain embodiments, Y is Br. In certain embodiments, Y is I. In certain embodiments, Y is substituted or unsubstituted alkyl (e.g., substituted or unsubstituted $C_{1-6}$ alkyl). In certain embodiments, Y is Me. In certain embodiments, Y is substituted methyl (e.g., —CH$_2$F, —CHF$_2$, —CF$_3$, or Bn). In certain embodiments, Y is Et, substituted ethyl (e.g., fluorinated ethyl (e.g., perfluoroethyl)), Pr, substituted propyl (e.g., fluorinated propyl (e.g., perfluoropropyl)), Bu, substituted butyl (e.g., fluorinated butyl (e.g., perfluorobutyl)), unsubstituted pentyl, substituted pentyl (e.g., fluorinated pentyl (e.g., perfluoropentyl)), unsubstituted hexyl, or substituted hexyl (e.g., fluorinated hexyl (e.g., perfluorohexyl)). In certain embodiments, Y is n-Bu. In certain embodiments, Y is substituted or unsubstituted alkenyl (e.g., substituted or unsubstituted C$_{2-6}$ alkenyl). In certain embodiments, Y is substituted or unsubstituted vinyl. In certain embodiments, Y is unsubstituted allyl. In certain embodiments, Y is substituted allyl. In certain embodiments, Y is substituted or unsubstituted alkynyl (e.g., substituted or unsubstituted C$_{2-6}$ alkynyl).

In certain embodiments, X is hydrogen; and Y is F. In certain embodiments, X is hydrogen; and Y is Cl. In certain embodiments, X is hydrogen; and Y is Br. In certain embodiments, X is hydrogen; and Y is I. In certain embodiments, X is Cl; and Y is F. In certain embodiments, both X and Y are Cl. In certain embodiments, X is Cl; and Y is Br. In certain embodiments, X is Cl; and Y is I. In certain embodiments, X is Br; and Y is F. In certain embodiments, X is Br; and Y is Cl. In certain embodiments, both X and Y are Br. In certain embodiments, X is Br; and Y is I. In certain embodiments, X is I; and Y is F. In certain embodiments, X is I; and Y is Cl. In certain embodiments, X is I; and Y is Br. In certain embodiments, both X and Y are I. In certain embodiments, X is halogen; and Y is substituted or unsubstituted alkyl (e.g., substituted or unsubstituted C$_{1-6}$ alkyl). In certain embodiments, X is halogen; and Y is substituted or unsubstituted alkenyl (e.g., substituted or unsubstituted C$_{2-6}$ alkenyl). In certain embodiments, X is substituted or unsubstituted alkyl (e.g., substituted or unsubstituted C$_{1-6}$ alkyl); and Y is halogen. In certain embodiments, X is substituted or unsubstituted alkenyl (e.g., substituted or unsubstituted C$_{2-6}$ alkenyl); and Y is halogen. In certain embodiments, X is halogen; and X and Y are the same. In certain embodiments, X is halogen; and X and Y are not the same. In certain embodiments, at least one of X and Y is halogen. In certain embodiments, each X and Y is halogen.

Formula (I) also includes substituent $R^A$ on the phenazinyl ring. In certain embodiments, $R^A$ is hydrogen. In certain embodiments, $R^A$ is not hydrogen. In certain embodiments, $R^A$ is halogen. In certain embodiments, $R^A$ is F. In certain embodiments, $R^A$ is Cl. In certain embodiments, $R^A$ is Br. In certain embodiments, $R^A$ is I. In certain embodiments, $R^A$ is substituted or unsubstituted alkyl. In certain embodiments, $R^A$ is substituted or unsubstituted C$_{1-6}$ alkyl. In certain embodiments, $R^A$ is Me. In certain embodiments, $R^A$ is substituted methyl (e.g., —CH$_2$F, —CHF$_2$, —CF$_3$, or Bn). In certain embodiments, $R^A$ is Et, substituted ethyl (e.g., fluorinated ethyl (e.g., perfluoroethyl)), Pr, substituted propyl (e.g., fluorinated propyl (e.g., perfluoropropyl)), Bu, or substituted butyl (e.g., fluorinated butyl (e.g., perfluorobutyl)). In certain embodiments, $R^A$ is substituted or unsubstituted alkenyl (e.g., substituted or unsubstituted C$_{2-6}$ alkenyl). In certain embodiments, $R^A$ is substituted or unsubstituted alkynyl (e.g., substituted or unsubstituted C$_{2-6}$ alkynyl). In certain embodiments, $R^A$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^A$ is substituted or unsubstituted cyclopropyl, substituted or unsubstituted cyclobutyl, substituted or unsubstituted cyclopentyl, or substituted or unsubstituted cyclohexyl. In certain embodiments, $R^A$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^A$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, $R^A$ is substituted or unsubstituted aryl (e.g., substituted or unsubstituted, 6- to 10-membered aryl). In certain embodiments, $R^A$ is unsubstituted phenyl. In certain embodiments, $R^A$ is substituted phenyl. In certain embodiments, $R^A$ is substituted or unsubstituted naphthyl. In certain embodiments, $R^A$ is substituted or unsubstituted heteroaryl. In certain embodiments, $R^A$ is substituted or unsubstituted, 5- to 6-membered, monocyclic heteroaryl, wherein one, two, three, or four atoms in the heteroaryl ring system are independently nitrogen, oxygen, or sulfur. In certain embodiments, $R^A$ is substituted or unsubstituted, 9- to 10-membered, bicyclic heteroaryl, wherein one, two, three, or four atoms in the heteroaryl ring system are independently nitrogen, oxygen, or sulfur. In certain embodiments, $R^A$ is —OR$^1$ (e.g., —OH, —O(substituted or unsubstituted C$_{1-6}$ alkyl) (e.g., —OMe, —OCF$_3$, —OEt, —OPr, —OBu, or —OBn), or —O(substituted or unsubstituted phenyl) (e.g., —OPh)). In certain embodiments, $R^A$ is —OMe. In certain embodiments, $R^A$ is —SR$^1$ (e.g., —SH, —S(substituted or unsubstituted C$_{1-6}$ alkyl) (e.g., —SMe, —SEt, —SPr, —SBu, or —SBn), or —S(substituted or unsubstituted phenyl) (e.g., —SPh)). In certain embodiments, $R^A$ is —N(R$^1$)$_2$ (e.g., —NH$_2$, —NH(substituted or unsubstituted C$_{1-6}$ alkyl) (e.g., —NHMe), or —N(substituted or unsubstituted C$_{1-6}$ alkyl)-(substituted or unsubstituted C$_{1-6}$ alkyl) (e.g., —NMe$_2$)). In certain embodiments, $R^A$ is —CN or —SCN. In certain embodiments, $R^A$ is —NO$_2$. In certain embodiments, $R^A$ is —C(=NR$^1$)R$^1$, —C(=NR$^1$)OR$^1$, or —C(=NR$^1$)N(R$^1$)$_2$. In certain embodiments, $R^A$ is —C(=O)R$^1$ (e.g., —C(=O)(substituted or unsubstituted alkyl) (e.g., —C(=O)Me) or —C(=O)(substituted or unsubstituted phenyl)). In certain embodiments, $R^A$ is —C(=O)OR$^1$ (e.g., —C(=O)OH, —C(=O)O(substituted or unsubstituted alkyl) (e.g., —C(=O)OMe), or —C(=O)O(substituted or unsubstituted phenyl)). In certain embodiments, $R^A$ is —C(=O)N(R$^1$)$_2$ (e.g., —C(=O)NH$_2$, —C(=O)NH(substituted or unsubstituted alkyl) (e.g., —C(=O)NHMe), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, $R^A$ is —NR$^1$C(=O)R$^1$ (e.g., —NHC(=O)(substituted or unsubstituted C$_{1-6}$ alkyl) (e.g., —NHC(=O)Me) or —NHC(=O)(substituted or unsubstituted phenyl)). In certain embodiments, $R^A$ is —NR$^1$C(=O)OR$^1$. In certain embodiments, $R^A$ is —NR$^1$C(=O)N(R$^1$)$_2$ (e.g., —NHC(=O)NH$_2$, —NHC(=O)NH(substituted or unsubstituted C$_{1-6}$ alkyl) (e.g., —NHC(=O)NHMe)). In certain embodiments, $R^A$ is —OC(=O)R$^1$ (e.g., —OC(=O)(substituted or unsubstituted alkyl) or —OC(=O)(substituted or unsubstituted phenyl)), —OC(=O)OR$^1$ (e.g., —OC(=O)O(substituted or unsubstituted alkyl) or —OC(=O)O(substituted or unsubstituted phenyl)), or —OC(=O)N(R$^1$)$_2$ (e.g., —OC(=O)NH$_2$, —OC(=O)NH(substituted or unsubstituted alkyl), —OC (=O)NH(substituted or unsubstituted phenyl), —OC(=O) N(substituted or unsubstituted alkyl)-(substituted or unsubstituted alkyl), or —OC(=O)N(substituted or unsubstituted phenyl)-(substituted or unsubstituted alkyl)).

In certain embodiments, $R^A$ is selected from the group consisting of

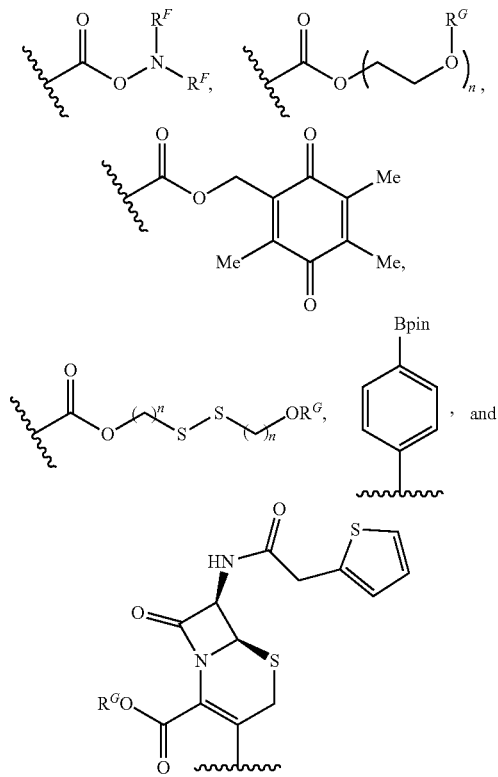

when $R^E$ is —CH$_2$W. In certain embodiments, a compound of Formula (I) may include two $R^A$ substituents. In certain embodiments, the two $R^A$ substituents are the same. In certain embodiments, the two $R^A$ substituents are different.

Formula (I) may include one or more instances of substituent $R^1$. When Formula (I) includes two or more instances of $R^1$, any two instances of $R^1$ may be the same or different from each other. In certain embodiments, at least one instance of $R^1$ is H. In certain embodiments, each instance of $R^1$ is H. In certain embodiments, at least one instance of $R^1$ is substituted or unsubstituted alkyl (e.g., substituted or unsubstituted $C_{1-6}$ alkyl (e.g., Me)). In certain embodiments, at least one instance of $R^1$ is substituted or unsubstituted acyl, substituted or unsubstituted alkenyl (e.g., substituted or unsubstituted $C_{2-6}$ alkenyl), substituted or unsubstituted alkynyl (e.g., substituted or unsubstituted $C_{2-6}$ alkynyl), substituted or unsubstituted carbocyclyl (e.g., substituted or unsubstituted, 3- to 7-membered, monocyclic carbocyclyl comprising zero, one, or two double bonds in the carbocyclic ring system), substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur), substituted or unsubstituted aryl (e.g., substituted or unsubstituted phenyl), substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur), a nitrogen protecting group (e.g., Bn, Boc, Cbz, Fmoc, trifluoroacetyl, triphenylmethyl, acetyl, or Ts) when attached to a nitrogen atom, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridinesulfenyl, or triphenylmethyl) when attached to a sulfur atom. In certain embodiments, two instances of $R^1$ are joined to form a substituted or unsubstituted heterocyclic or substituted or unsubstituted heteroaryl ring.

Formula (I) also includes substituent $R^B$ on the phenazinyl ring. In certain embodiments, $R^B$ is hydrogen. In certain embodiments, $R^B$ is not hydrogen. In certain embodiments, $R^B$ is halogen. In certain embodiments, $R^B$ is F. In certain embodiments, $R^B$ is Cl. In certain embodiments, $R^B$ is Br. In certain embodiments, $R^B$ is I. In certain embodiments, $R^B$ is substituted or unsubstituted alkyl. In certain embodiments, $R^B$ is substituted or unsubstituted $C_{1-6}$ alkyl. In certain embodiments, $R^B$ is Me. In certain embodiments, $R^B$ is substituted methyl (e.g., —CH$_2$F, —CHF$_2$, —CF$_3$, or Bn). In certain embodiments, $R^B$ is Et, substituted ethyl (e.g., fluorinated ethyl (e.g., perfluoroethyl)), Pr, substituted propyl (e.g., fluorinated propyl (e.g., perfluoropropyl)), Bu, or substituted butyl (e.g., fluorinated butyl (e.g., perfluorobutyl)). In certain embodiments, $R^B$ is substituted or unsubstituted alkenyl (e.g., substituted or unsubstituted $C_{2-6}$ alkenyl). In certain embodiments, $R^B$ is substituted or unsubstituted alkynyl (e.g., substituted or unsubstituted $C_{2-6}$ alkynyl). In certain embodiments, $R^B$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^B$ is substituted or unsubstituted cyclopropyl, substituted or unsubstituted cyclobutyl, substituted or unsubstituted cyclopentyl, or substituted or unsubstituted cyclohexyl. In certain embodiments, $R^B$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^B$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, $R^B$ is substituted or unsubstituted aryl (e.g., substituted or unsubstituted, 6- to 10-membered aryl). In certain embodiments, $R^B$ is unsubstituted phenyl. In certain embodiments, $R^B$ is substituted phenyl. In certain embodiments, $R^B$ is substituted or unsubstituted naphthyl. In certain embodiments, $R^B$ is substituted or unsubstituted heteroaryl. In certain embodiments, $R^B$ is substituted or unsubstituted, 5- to 6-membered, monocyclic heteroaryl, wherein one, two, three, or four atoms in the heteroaryl ring system are independently nitrogen, oxygen, or sulfur. In certain embodiments, $R^B$ is substituted or unsubstituted, 9- to 10-membered, bicyclic heteroaryl, wherein one, two, three, or four atoms in the heteroaryl ring system are independently nitrogen, oxygen, or sulfur. In certain embodiments, $R^B$ is OR$^2$ (e.g., —OH, —O(substituted or unsubstituted $C_{1-6}$ alkyl) (e.g., —OMe, —OCF$_3$, —OEt, —OPr, —OBu, or —OBn), or —O(substituted or unsubstituted phenyl) (e.g., —OPh)). In certain embodiments, $R^B$ is —OMe. In certain embodiments, $R^B$ is —$SR^2$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^B$ is —$N(R^2)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^B$ is —CN or —SCN. In certain embodiments, $R^B$ is —$NO_2$. In certain embodiments, $R^B$ is —$C(=NR^2)R^2$, —$C(=NR^2)OR^2$, or —$C(=NR^2)N(R^2)_2$. In certain embodiments, $R^B$ is —$C(=O)R^2$ (e.g., —C(=O)(substituted or unsubstituted alkyl) (e.g., —C(=O)Me) or —C(=O)(substituted or unsubstituted phenyl)). In certain embodiments, $R^B$ is —$C(=O)OR^2$ (e.g., —C(=O)OH, —C(=O)O(substituted or unsubstituted alkyl) (e.g., —C(=O)OMe), or —C(=O)O(substituted or unsubstituted phenyl)). In certain embodiments, $R^B$ is —$C(=O)N(R^2)_2$ (e.g., —$C(=O)NH_2$, —C(=O)NH(substituted or unsubstituted alkyl) (e.g., —C(=O)NHMe), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, $R^B$ is —$NR^2C(=O)R^2$ (e.g., —NHC(=O)(substituted or unsubstituted $C_{1-6}$ alkyl) (e.g., —NHC(=O)Me) or —NHC(=O)(substituted or unsubstituted phenyl)). In certain embodiments, $R^B$ is —$NR^2C(=O)OR^2$. In certain embodiments, $R^B$ is —$NR^2C(=O)N(R^2)_2$ (e.g., —$NHC(=O)NH_2$, —NHC(=O)NH(substituted or unsubstituted $C_{1-6}$ alkyl) (e.g., —NHC(=O)NHMe)). In certain embodiments, $R^B$ is —$OC(=O)R^2$ (e.g., —OC(=O)(substituted or unsubstituted alkyl) or —OC(=O)(substituted or unsubstituted phenyl)), —$OC(=O)OR^2$ (e.g., —OC(=O)O(substituted or unsubstituted alkyl) or —OC(=O)O(substituted or unsubstituted phenyl)), or —$OC(=O)N(R^2)_2$ (e.g., —$OC(=O)NH_2$, —OC(=O)NH(substituted or unsubstituted alkyl), —OC(=O)NH(substituted or unsubstituted phenyl), —OC(=O)N(substituted or unsubstituted alkyl)-(substituted or unsubstituted alkyl), or —OC(=O)N(substituted or unsubstituted phenyl)-(substituted or unsubstituted alkyl)).

Formula (I) may include one or more instances of substituent $R^2$. When Formula (I) includes two or more instances of $R^2$, any two instances of $R^2$ may be the same or different from each other. In certain embodiments, at least one instance of $R^2$ is H. In certain embodiments, each instance of $R^2$ is H. In certain embodiments, at least one instance of $R^2$ is substituted or unsubstituted alkyl (e.g., substituted or unsubstituted $C_{1-6}$ alkyl (e.g., Me)). In certain embodiments, at least one instance of $R^2$ is substituted or unsubstituted acyl, substituted or unsubstituted alkenyl (e.g., substituted or unsubstituted $C_{2-6}$ alkenyl), substituted or unsubstituted alkynyl (e.g., substituted or unsubstituted $C_{2-6}$ alkynyl), substituted or unsubstituted carbocyclyl (e.g., substituted or unsubstituted, 3- to 7-membered, monocyclic carbocyclyl comprising zero, one, or two double bonds in the carbocyclic ring system), substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur), substituted or unsubstituted aryl (e.g., substituted or unsubstituted phenyl), substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur), a nitrogen protecting group (e.g., Bn, Boc, Cbz, Fmoc, trifluoroacetyl, triphenylmethyl, acetyl, or Ts) when attached to a nitrogen atom, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom. In certain embodiments, two instances of $R^2$ are joined to form a substituted or unsubstituted heterocyclic or substituted or unsubstituted heteroaryl ring.

Formula (I) also includes substituent $R^C$ on the phenazinyl ring. In certain embodiments, $R^C$ is hydrogen. In certain embodiments, $R^C$ is not hydrogen. In certain embodiments, $R^C$ is halogen. In certain embodiments, $R^C$ is F. In certain embodiments, $R^C$ is Cl. In certain embodiments, $R^C$ is Br. In certain embodiments, $R^C$ is I. In certain embodiments, $R^C$ is substituted or unsubstituted alkyl. In certain embodiments, $R^C$ is substituted or unsubstituted $C_{1-6}$ alkyl. In certain embodiments, $R^C$ is Me. In certain embodiments, $R^C$ is substituted methyl (e.g., —$CH_2F$, —$CHF_2$, —$CF_3$, or Bn). In certain embodiments, $R^C$ is Et, substituted ethyl (e.g., fluorinated ethyl (e.g., perfluoroethyl)), Pr, substituted propyl (e.g., fluorinated propyl (e.g., perfluoropropyl)), Bu, or substituted butyl (e.g., fluorinated butyl (e.g., perfluorobutyl)). In certain embodiments, $R^C$ is substituted or unsubstituted alkenyl (e.g., substituted or unsubstituted $C_{2-6}$ alkenyl). In certain embodiments, $R^C$ is substituted or unsubstituted alkynyl (e.g., substituted or unsubstituted $C_{2-6}$ alkynyl). In certain embodiments, $R^C$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^C$ is substituted or unsubstituted cyclopropyl, substituted or unsubstituted cyclobutyl, substituted or unsubstituted cyclopentyl, or substituted or unsubstituted cyclohexyl. In certain embodiments, $R^C$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^C$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, $R^C$ is substituted or unsubstituted aryl (e.g., substituted or unsubstituted, 6- to 10-membered aryl). In certain embodiments, $R^C$ is unsubstituted phenyl. In certain embodiments, $R^C$ is substituted phenyl. In certain embodiments, $R^C$ is substituted or unsubstituted naphthyl. In certain embodiments, $R^C$ is substituted or unsubstituted heteroaryl. In certain embodiments, $R^C$ is substituted or unsubstituted, 5- to 6-membered, monocyclic heteroaryl, wherein one, two, three, or four atoms in the heteroaryl ring system are independently nitrogen, oxygen, or sulfur. In certain embodiments, $R^C$ is substituted or unsubstituted, 9- to 10-membered, bicyclic heteroaryl, wherein one, two, three, or four atoms in the heteroaryl ring system are independently nitrogen, oxygen, or sulfur. In certain embodiments, $R^C$ is —$OR^3$ (e.g., —OH, —O(substituted or unsubstituted $C_{1-6}$ alkyl) (e.g., —OMe, —$OCF_3$, —OEt, —OPr, —OBu, or —OBn), or —O(substituted or unsubstituted phenyl) (e.g., —OPh)). In certain embodiments, $R^C$ is —OMe. In certain embodiments, $R^C$ is —$SR^3$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^C$ is —$N(R^3)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^C$ is —CN or —SCN. In certain embodiments, $R^C$ is —$NO_2$. In certain embodiments, $R^C$ is —$C(=NR^3)R^3$, —$C(=NR^3)OR^3$, or —$C(=NR^3)N(R^3)_2$. In certain embodiments, $R^C$ is —$C(=O)R^3$ (e.g., —C(=O)(substituted or unsubstituted alkyl) (e.g., —C(=O)Me) or —C(=O)(substituted or unsubstituted phenyl)). In certain embodiments, $R^C$ is —$C(=O)OR^3$ (e.g., —C(=O)OH, —C(=O)O(substituted or unsubstituted alkyl) (e.g., —C(=O)OMe), or —C(=O)O(substituted or unsubstituted phenyl)). In certain embodiments, $R^C$ is —$C(=O)N(R^3)_2$ (e.g., —$C(=O)NH_2$, —C(=O)NH(substituted or unsubstituted alkyl) (e.g., —C(=O)NHMe), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, $R^C$ is —$NR^3C(=O)R^3$ (e.g., —NHC(=O)(substituted or unsubstituted $C_{1-6}$ alkyl) (e.g., —NHC(=O)Me) or —NHC(=O)(substituted or unsubstituted phenyl)). In certain embodiments, $R^C$ is —$NR^3C(=O)OR^3$. In certain embodiments, $R^C$ is —$NR^3C(=O)N(R^3)_2$ (e.g., —$NHC(=O)NH_2$, —NHC(=O)NH(substituted or unsubstituted $C_{1-6}$ alkyl) (e.g., —NHC(=O)NHMe)). In certain embodiments, $R^C$ is —$OC(=O)R^3$ (e.g., —OC(=O)(substituted or unsubstituted alkyl) or —OC(=O)(substituted or unsubstituted phenyl)), —$OC(=O)OR^3$ (e.g., —OC(=O)O(substituted or unsubstituted alkyl) or —OC(=O)O(substituted or unsubstituted phenyl)), or —$OC(=O)N(R^3)_2$ (e.g., —$OC(=O)NH_2$, —OC(=O)NH(substituted or unsubstituted alkyl), —OC(=O)NH(substituted or unsubstituted phenyl), —OC(=O)N(substituted or unsubstituted alkyl)-(substituted or unsubstituted alkyl), or —OC(=O)N(substituted or unsubstituted phenyl)-(substituted or unsubstituted alkyl)).

Formula (I) may include one or more instances of substituent $R^3$. When Formula (I) includes two or more instances of $R^3$, any two instances of $R^3$ may be the same or different from each other. In certain embodiments, at least one instance of $R^3$ is H. In certain embodiments, each instance of $R^3$ is H. In certain embodiments, at least one instance of $R^3$ is substituted or unsubstituted alkyl (e.g., substituted or unsubstituted $C_{1-6}$ alkyl (e.g., Me)). In certain embodiments, at least one instance of $R^3$ is substituted or unsubstituted acyl, substituted or unsubstituted alkenyl (e.g., substituted or unsubstituted $C_{2-6}$ alkenyl), substituted or unsubstituted alkynyl (e.g., substituted or unsubstituted $C_{2-6}$ alkynyl), substituted or unsubstituted carbocyclyl (e.g., substituted or unsubstituted, 3- to 7-membered, monocyclic carbocyclyl comprising zero, one, or two double bonds in the carbocyclic ring system), substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur), substituted or unsubstituted aryl (e.g., substituted or unsubstituted phenyl), substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur), a nitrogen protecting group (e.g., Bn, Boc, Cbz, Fmoc, trifluoroacetyl, triphenylmethyl, acetyl, or Ts) when attached to a nitrogen atom, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridinesulfenyl, or triphenylmethyl) when attached to a sulfur atom. In certain embodiments, two instances of $R^3$ are joined to form a substituted or unsubstituted heterocyclic or substituted or unsubstituted heteroaryl ring.

Formula (I) also includes substituent $R^D$ on the phenazinyl ring. In certain embodiments, $R^D$ is hydrogen. In certain embodiments, $R^D$ is not hydrogen. In certain embodiments, $R^D$ is halogen. In certain embodiments, $R^D$ is F. In certain embodiments, $R^D$ is Cl. In certain embodiments, $R^D$ is Br. In certain embodiments, $R^D$ is I. In certain embodiments, $R^D$ is substituted or unsubstituted alkyl. In certain embodiments, $R^D$ is substituted or unsubstituted $C_{1-6}$ alkyl. In certain embodiments, $R^D$ is Me. In certain embodiments, $R^D$ is substituted methyl (e.g., —$CH_2F$, —$CHF_2$, —$CF_3$, or Bn). In certain embodiments, $R^D$ is Et, substituted ethyl (e.g., fluorinated ethyl (e.g., perfluoroethyl)), Pr, substituted propyl (e.g., fluorinated propyl (e.g., perfluoropropyl)), Bu, or substituted butyl (e.g., fluorinated butyl (e.g., perfluorobutyl)). In certain embodiments, $R^D$ is substituted or unsubstituted alkenyl (e.g., substituted or unsubstituted $C_{2-6}$ alkenyl). In certain embodiments, $R^D$ is substituted or unsubstituted alkynyl (e.g., substituted or unsubstituted $C_{2-6}$ alkynyl). In certain embodiments, $R^D$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^D$ is substituted or unsubstituted cyclopropyl, substituted or unsubstituted cyclobutyl, substituted or unsubstituted cyclopentyl, or substituted or unsubstituted cyclohexyl. In certain embodiments, $R^D$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^D$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, $R^D$ is substituted or unsubstituted aryl (e.g., substituted or unsubstituted, 6- to 10-membered aryl). In certain embodiments, $R^D$ is unsubstituted phenyl. In certain embodiments, $R^D$ is substituted phenyl. In certain embodiments, $R^D$ is substituted or unsubstituted naphthyl. In certain embodiments, $R^D$ is substituted or unsubstituted heteroaryl. In certain embodiments, $R^D$ is substituted or unsubstituted, 5- to 6-membered, monocyclic heteroaryl, wherein one, two, three, or four atoms in the heteroaryl ring system are independently nitrogen, oxygen, or sulfur. In certain embodiments, $R^D$ is substituted or unsubstituted, 9- to 10-membered, bicyclic heteroaryl, wherein one, two, three, or four atoms in the heteroaryl ring system are independently nitrogen, oxygen, or sulfur. In certain embodiments, $R^D$ is —$OR^4$ (e.g., —OH, —O(substituted or unsubstituted $C_{1-6}$ alkyl) (e.g., —OMe, —$OCF_3$, —OEt, —OPr, —OBu, or —OBn), or —O(substituted or unsubstituted phenyl) (e.g., —OPh)). In certain embodiments, $R^D$ is —OMe. In certain embodiments, $R^D$ is —$SR^4$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^D$ is —$N(R^4)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^D$ is —CN or —SCN. In certain embodiments, $R^D$ is —$NO_2$. In certain embodiments, $R^D$ is —C(=$NR^4$)$R^4$, —C(=$NR^4$)$OR^4$, or —C(=$NR^4$)$N(R^4)_2$. In certain embodiments, $R^D$ is —C(=O)$R^4$ (e.g., —C(=O)(substituted or unsubstituted alkyl) (e.g., —C(=O)Me) or —C(=O)(substituted or unsubstituted phenyl)). In certain embodiments, $R^D$ is —C(=O)$OR^4$ (e.g., —C(=O)OH, —C(=O)O(substituted or unsubstituted alkyl) (e.g., —C(=O)OMe), or —C(=O)O(substituted or unsubstituted phenyl)). In certain embodiments, $R^D$ is —C(=O)$N(R^4)_2$ (e.g., —C(=O)$NH_2$, —C(=O)NH(substituted or unsubstituted alkyl) (e.g., —C(=O)NHMe), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, $R^D$ is —$NR^4$C(=O)$R^4$ (e.g., —NHC(=O)(substituted or unsubstituted $C_{1-6}$ alkyl) (e.g., —NHC(=O)Me) or —NHC(=O)(substituted or unsubstituted phenyl)). In certain embodiments, $R^D$ is —$NR^4$C(=O)$OR^4$. In certain embodiments, $R^D$ is —$NR^4$C(=O)$N(R^4)_2$ (e.g., —NHC(=O)$NH_2$, —NHC(=O)NH(substituted or unsubstituted $C_{1-6}$ alkyl) (e.g., —NHC(=O)NHMe)). In certain embodiments, $R^D$ is —OC(=O)$R^4$ (e.g., —OC(=O)(substituted or unsubstituted alkyl) or —OC(=O)(substituted or unsubstituted phenyl)), —OC(=O)$OR^4$ (e.g., —OC(=O)O(substituted or unsubstituted alkyl) or —OC(=O)O(substituted or unsubstituted phenyl)), or —OC(=O)$N(R^4)_2$ (e.g., —OC(=O)$NH_2$, —OC(=O)NH(substituted or unsubstituted alkyl), —OC(=O)NH(substituted or unsubstituted phenyl), —OC(=O)N(substituted or unsubstituted alkyl)-(substituted or unsubstituted alkyl), or —OC(=O)N(substituted or unsubstituted phenyl)-(substituted or unsubstituted alkyl)).

Formula (I) may include one or more instances of substituent $R^4$. When Formula (I) includes two or more instances of $R^4$, any two instances of $R^4$ may be the same or different from each other. In certain embodiments, at least one instance of $R^4$ is H. In certain embodiments, each instance of $R^4$ is H. In certain embodiments, at least one instance of $R^4$ is substituted or unsubstituted alkyl (e.g., substituted or unsubstituted $C_{1-6}$ alkyl (e.g., Me)). In certain embodiments, at least one instance of $R^4$ is substituted or unsubstituted acyl, substituted or unsubstituted alkenyl (e.g., substituted or unsubstituted $C_{2-6}$ alkenyl), substituted or unsubstituted alkynyl (e.g., substituted or unsubstituted $C_{2-6}$ alkynyl), substituted or unsubstituted carbocyclyl (e.g., substituted or unsubstituted, 3- to 7-membered, monocyclic carbocyclyl comprising zero, one, or two double bonds in the carbocyclic ring system), substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur), substituted or unsubstituted aryl (e.g., substituted or unsubstituted phenyl), substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur), a nitrogen protecting group (e.g., Bn, Boc, Cbz, Fmoc, trifluoroacetyl, triphenylmethyl, acetyl, or Ts) when attached to a nitrogen atom, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridinesulfenyl, or triphenylmethyl) when attached to a sulfur atom. In certain embodiments, two instances of $R^4$ are joined to form a substituted or unsubstituted heterocyclic or substituted or unsubstituted heteroaryl ring.

Formula (I) also includes substituent $R^E$ on the phenazinyl ring. In certain embodiments, $R^E$ is hydrogen. In certain embodiments, $R^E$ is not hydrogen. In certain embodiments, $R^E$ is substituted or unsubstituted alkyl. In certain embodiments, $R^E$ is substituted or unsubstituted $C_{1-6}$ alkyl. In certain embodiments, $R^E$ is Me. In certain embodiments, $R^E$ is substituted methyl (e.g., —$CH_2F$, —$CHF_2$, —$CF_3$, or Bn). In certain embodiments, $R^E$ is Et, substituted ethyl (e.g., fluorinated ethyl (e.g., perfluoroethyl)), Pr, substituted propyl (e.g., fluorinated propyl (e.g., perfluoropropyl)), Bu, or substituted butyl (e.g., fluorinated butyl (e.g., perfluorobutyl)). In certain embodiments, $R^E$ is substituted or unsubstituted alkenyl (e.g., substituted or unsubstituted $C_{2-6}$ alkenyl). In certain embodiments, $R^E$ is substituted or unsubstituted alkynyl (e.g., substituted or unsubstituted $C_{2-6}$ alkynyl). In certain embodiments, $R^E$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^E$ is substituted or unsubstituted cyclopropyl, substituted or unsubstituted cyclobutyl, substituted or unsubstituted cyclopentyl, or substituted or unsubstituted cyclohexyl. In certain embodiments, $R^E$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^E$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, $R^E$ is substituted or unsubstituted aryl (e.g., substituted or unsubstituted, 6- to 10-membered aryl). In certain embodiments, $R^E$ is unsubstituted phenyl. In certain embodiments, $R^E$ is substituted phenyl. In certain embodiments, $R^E$ is substituted or unsubstituted naphthyl. In certain embodiments, $R^E$ is substituted or unsubstituted heteroaryl. In certain embodiments, $R^E$ is substituted or unsubstituted, 5- to 6-membered, monocyclic heteroaryl, wherein one, two, three, or four atoms in the heteroaryl ring system are independently nitrogen, oxygen, or sulfur. In certain embodiments, $R^E$ is substituted or unsubstituted, 9- to 10-membered, bicyclic heteroaryl, wherein one, two, three, or four atoms in the heteroaryl ring system are independently nitrogen, oxygen, or sulfur. In certain embodiments, $R^E$ is —C(=$NR^5$)$R^5$, —C(=$NR^5$)$OR^5$, or —C(=$NR^5$)$N(R^5)_2$. In certain embodiments, $R^E$ is —C(=O)$R^5$ (e.g., —C(=O)(substituted or unsubstituted alkyl) (e.g., —C(=O)Me) or —C(=O)(substituted or unsubstituted phenyl)). In certain embodiments, $R^E$ is —C(=O)$OR^5$ (e.g., —C(=O)OH, —C(=O)O(substituted or unsubstituted alkyl) (e.g., —C(=O)OMe), or —C(=O)O(substituted or unsubstituted phenyl)). In certain embodiments, $R^E$ is —C(=O)N($R^5$)$_2$ (e.g., —C(=O)NH$_2$, —C(=O)NH(substituted or unsubstituted alkyl) (e.g., —C(=O)NHMe), —C(=O)NH(substituted or unsubstituted phenyl), —C(=O)N(substituted or unsubstituted alkyl)-(substituted or unsubstituted alkyl), or —C(=O)N (substituted or unsubstituted phenyl)-(substituted or unsubstituted alkyl)). In certain embodiments, $R^E$ is an oxygen protecting group. In certain embodiments, $R^E$ is a sugar (e.g., glucosyl, fructosyl, galactosyl, deoxyribosyl, ribosyl, and the like). In certain embodiments, $R^E$ is unsubstituted acyl (e.g., acetyl, etc.). In certain embodiments, $R^E$ is substituted acyl (e.g., trifluoroacetyl, etc.). In certain embodiments, $R^E$ is

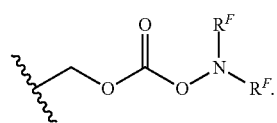

In certain embodiments, $R^E$ is

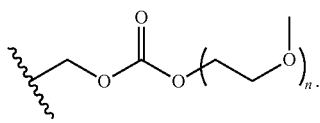

In certain embodiments, $R^E$ is

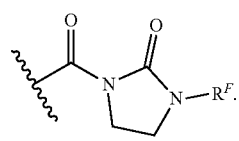

In certain embodiments, $R^E$ is

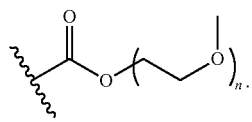

In certain embodiments, $R^E$ is

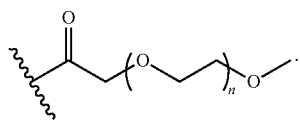

Formula (I) also includes substituent $R^E$ on the phenazinyl ring. In certain embodiments, $R^E$ is —C(=O)$R^5$, wherein $R^5$ is

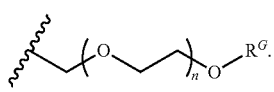

In certain embodiments, $R^E$ is —CH$_2$C(=O)O$R^5$. In certain embodiments, $R^E$ is —CH$_2$C(=O)O$R^5$, wherein $R^5$ is a substituted or unsubstituted carbocyclyl. In certain embodiments, $R^E$ is selected from a group consisting of substituted or unsubstituted aryl,

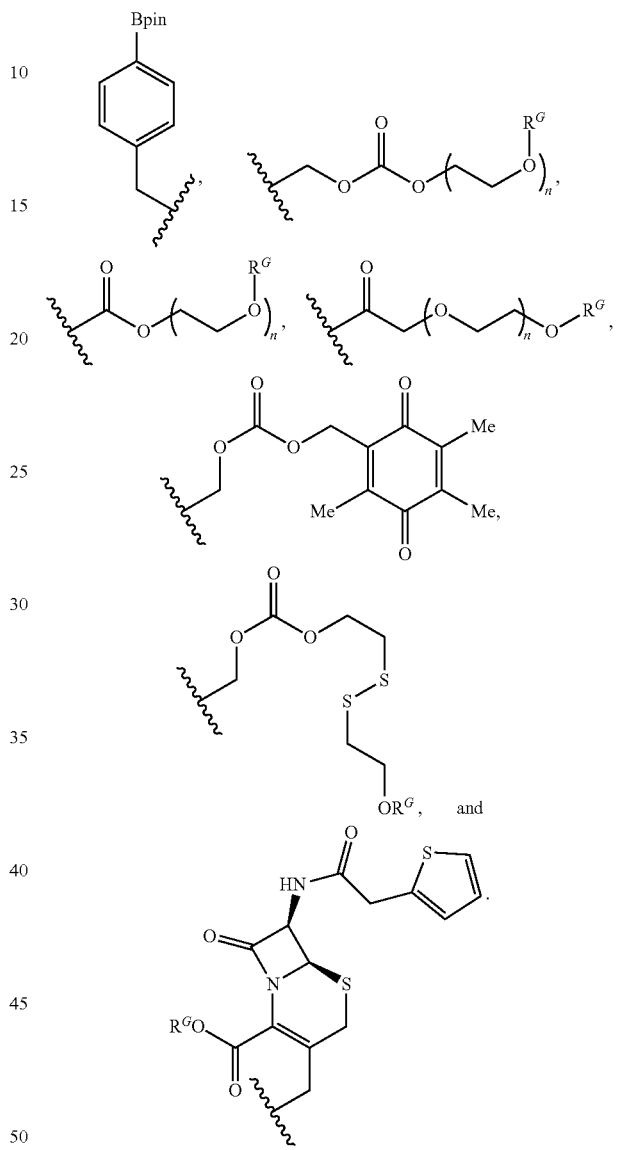

Formula (I) also includes substituent $R^E$ on the phenazinyl ring. In certain embodiments, $R^E$ is —CH$_2$W, wherein W is —O$R^A$ or —$R^A$. In certain embodiments, $R^A$ is a substituted or unsubstituted acyl. In certain embodiments, $R^A$ is a substituted or unsubstituted aryl. In certain embodiments, $R^A$ is a substituted or unsubstituted alkyl. In certain embodiments, $R^A$ is

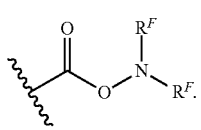

In certain embodiments, $R^A$ is

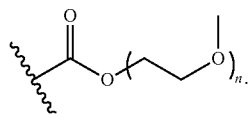

In certain embodiments, $R^A$ is

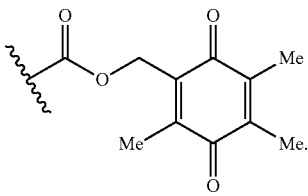 [SMILES: *C(=O)OCC1=C(C)C(=O)C(C)=C(C)C1=O]

In certain embodiments, $R^A$ is

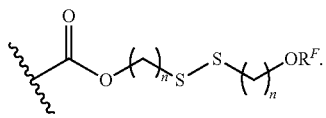

In certain embodiments, $R^A$ is

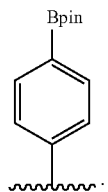

In certain embodiments, $R^D$ is

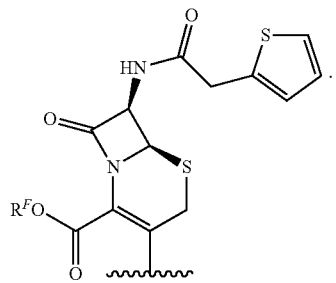

In certain embodiments, each n is independently 1-10. In certain embodiments, each n is independently 1-9. In certain embodiments, each n is independently 1-8. In certain embodiments, each n is independently 1-7. In certain embodiments, each n is independently 1-6. In certain embodiments, each n is independently 1-5. In certain embodiments, each n is independently 1-4. In certain embodiments, each n is independently 1-3. In certain embodiments, each n is independently 1-2. In certain embodiments, each n is independently 1. The ranges described herein for n are inclusive ranges of integers. For example, when each n is independently 1-10, each n is independently 1, 2, 3, 4, 5, 6, 7, 8, 9, or 10.

Formula (I) may include one or more instances of substituent $R^5$. When Formula (I) includes two or more instances of $R^5$, any two instances of $R^5$ may be the same or different from each other. In certain embodiments, at least one instance of $R^5$ is H. In certain embodiments, each instance of $R^5$ is H. In certain embodiments, at least one instance of $R^5$ is substituted or unsubstituted alkyl (e.g., substituted or unsubstituted $C_{1-6}$ alkyl (e.g., Me)). In certain embodiments, at least one instance of $R^5$ is substituted or unsubstituted acyl, substituted or unsubstituted alkenyl (e.g., substituted or unsubstituted $C_{2-6}$ alkenyl), substituted or unsubstituted alkynyl (e.g., substituted or unsubstituted $C_{2-6}$ alkynyl), substituted or unsubstituted carbocyclyl (e.g., substituted or unsubstituted, 3- to 7-membered, monocyclic carbocyclyl comprising zero, one, or two double bonds in the carbocyclic ring system), substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur), substituted or unsubstituted aryl (e.g., substituted or unsubstituted phenyl), substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur), a nitrogen protecting group (e.g., Bn, Boc, Cbz, Fmoc, trifluoroacetyl, triphenylmethyl, acetyl, or Ts) when attached to a nitrogen atom, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridinesulfenyl, or triphenylmethyl) when attached to a sulfur atom. In certain embodiments, two instances of $R^5$ are joined to form a substituted or unsubstituted heterocyclic or substituted or unsubstituted heteroaryl ring.

Formula (I) may include one or more instances of substituent $R^F$. In certain embodiments, $R^F$ is a hydrogen. In certain embodiments $R^F$ is a nitrogen protecting group.

Formula (I) may include one or more instances of substituent $R^G$. In certain embodiments, $R^G$ is a hydrogen. In certain embodiments, $R^G$ is an oxygen protecting group.

In certain embodiments, both $R^A$ and $R^B$ are H. In certain embodiments, each of $R^A$ and $R^B$ is independently hydrogen or halogen. In certain embodiments, each of $R^A$ and $R^B$ is independently hydrogen, halogen, or substituted or unsubstituted $C_{1-6}$ alkyl (e.g., Me). In certain embodiments, each of $R^A$ and $R^B$ is independently hydrogen, halogen, substituted or unsubstituted $C_{1-6}$ alkyl (e.g., Me), or —O(substituted or unsubstituted $C_{1-6}$ alkyl) (e.g., —OMe). In certain embodiments, $R^A$ is H; and $R^B$ is halogen (e.g., F, Cl, Br, or I). In certain embodiments, $R^A$ is H; and $R^B$ is substituted or unsubstituted $C_{1-6}$ alkyl (e.g., Me). In certain embodiments, $R^A$ is halogen (e.g., F, Cl, Br, and I); and $R^B$ is H. In certain embodiments, $R^A$ is substituted or unsubstituted $C_{1-6}$ alkyl; and $R^B$ is H. In certain embodiments, both $R^A$ and $R^B$ are halogen. In certain embodiments, both $R^A$ and $R^B$ are halogen; and $R^A$ and $R^B$ are the same. In certain embodiments, both $R^A$ and $R^B$ are halogen; and $R^A$ and $R^B$ are not the same. In certain embodiments, each of $R^A$ and $R^B$ is independently Cl, Br, or I. In certain embodiments, both $R^A$ and $R^B$ are Cl. In certain embodiments, $R^A$ is Cl; and $R^B$ is Br. In certain embodiments, $R^A$ is Cl; and $R^B$ is I. In certain embodiments, $R^A$ is Br; and $R^B$ is Cl. In certain embodiments, both $R^A$ and $R^B$ are Br. In certain embodiments, $R^A$ is Br; and $R^B$ is I. In certain embodiments, $R^A$ is I; and $R^B$ is Cl. In certain embodiments, $R^A$ is I; and $R^B$ is Br. In certain embodiments, both $R^A$ and $R^B$ are I. In certain embodiments, both $R^A$ and $R^B$ are substituted or unsubstituted $C_{1-6}$ alkyl (e.g., Me). In certain embodiments, $R^A$ is substituted or unsubstituted $C_{1-6}$ alkyl (e.g., Me); and $R^B$ is halogen (e.g., Cl, Br, or I). In certain embodiments, $R^A$ is halogen (e.g., Cl, Br, or I); and $R^B$ is substituted or unsubstituted $C_{1-6}$ alkyl (e.g., Me). In certain embodiments, $R^A$ is —O(substituted or unsubstituted $C_{1-6}$ alkyl) (e.g., —OMe); and $R^B$ is hydrogen, halogen, substituted or unsubstituted $C_{1-6}$ alkyl (e.g., Me), or —O(substituted or unsubstituted $C_{1-6}$ alkyl) (e.g., —OMe). In certain embodiments, $R^A$ is hydrogen, halogen, substituted or unsubstituted $C_{1-6}$ alkyl (e.g., Me), or —O(substituted or unsubstituted $C_{1-6}$ alkyl) (e.g., —OMe); and $R^B$ is —O(substituted or unsubstituted $C_{1-6}$ alkyl) (e.g., —OMe).

In certain embodiments, both $R^A$ and $R^C$ are H. In certain embodiments, each of $R^A$ and $R^C$ is independently hydrogen or halogen. In certain embodiments, each of $R^A$ and $R^C$ is independently hydrogen, halogen, or substituted or unsubstituted $C_{1-6}$ alkyl (e.g., Me). In certain embodiments, each of $R^A$ and $R^C$ is independently hydrogen, halogen, substituted or unsubstituted $C_{1-6}$ alkyl (e.g., Me), or —O(substituted or unsubstituted $C_{1-6}$ alkyl) (e.g., —OMe). In certain embodiments, $R^A$ is H; and $R^C$ is halogen (e.g., F, Cl, Br, or I). In certain embodiments, $R^A$ is H; and $R^C$ is substituted or unsubstituted $C_{1-6}$ alkyl (e.g., Me). In certain embodiments, $R^A$ is halogen (e.g., F, Cl, Br, and I); and $R^C$ is H. In certain embodiments, $R^A$ is substituted or unsubstituted $C_{1-6}$ alkyl; and $R^C$ is H. In certain embodiments, both $R^A$ and $R^C$ are halogen. In certain embodiments, both $R^A$ and $R^C$ are halogen; and $R^A$ and $R^C$ are the same. In certain embodiments, both $R^A$ and $R^C$ are halogen; and $R^A$ and $R^C$ are not the same. In certain embodiments, each of $R^A$ and $R^C$ is independently Cl, Br, or I. In certain embodiments, both $R^A$ and $R^C$ are Cl. In certain embodiments, $R^A$ is Cl; and $R^C$ is Br. In certain embodiments, $R^A$ is Cl; and $R^C$ is I. In certain embodiments, $R^A$ is Br; and $R^C$ is Cl. In certain embodiments, both $R^A$ and $R^C$ are Br. In certain embodiments, $R^A$ is Br; and $R^C$ is I. In certain embodiments, $R^A$ is I; and $R^C$ is Cl. In certain embodiments, $R^A$ is I; and $R^C$ is Br. In certain embodiments, both $R^A$ and $R^C$ are I. In certain embodiments, both $R^A$ and $R^C$ are substituted or unsubstituted $C_{1-6}$ alkyl (e.g., Me). In certain embodiments, $R^A$ is substituted or unsubstituted $C_{1-6}$ alkyl (e.g., Me); and $R^C$ is halogen (e.g., Cl, Br, or I). In certain embodiments, $R^A$ is halogen (e.g., Cl, Br, or I); and $R^C$ is substituted or unsubstituted $C_{1-6}$ alkyl (e.g., Me). In certain embodiments, $R^A$ is —O(substituted or unsubstituted $C_{1-6}$ alkyl) (e.g., —OMe); and $R^C$ is hydrogen, halogen, substituted or unsubstituted $C_{1-6}$ alkyl (e.g., Me), or —O(substituted or unsubstituted $C_{1-6}$ alkyl) (e.g., —OMe). In certain embodiments, $R^A$ is hydrogen, halogen, substituted or unsubstituted $C_{1-6}$ alkyl (e.g., Me), or —O(substituted or unsubstituted $C_{1-6}$ alkyl) (e.g., —OMe); and $R^C$ is —O(substituted or unsubstituted $C_{1-6}$ alkyl) (e.g., —OMe).

In certain embodiments, both $R^A$ and $R^D$ are H. In certain embodiments, each of $R^A$ and $R^D$ is independently hydrogen or halogen. In certain embodiments, each of $R^A$ and $R^D$ is independently hydrogen, halogen, or substituted or unsubstituted $C_{1-6}$ alkyl (e.g., Me). In certain embodiments, each of $R^A$ and $R^D$ is independently hydrogen, halogen, substituted or unsubstituted $C_{1-6}$ alkyl (e.g., Me), or —O(substituted or unsubstituted $C_{1-6}$ alkyl) (e.g., —OMe). In certain embodiments, $R^A$ is H; and $R^D$ is halogen (e.g., F, Cl, Br, or I). In certain embodiments, $R^A$ is H; and $R^D$ is substituted or unsubstituted $C_{1-6}$ alkyl (e.g., Me). In certain embodiments, $R^A$ is halogen (e.g., F, Cl, Br, and I); and $R^D$ is H. In certain embodiments, $R^A$ is substituted or unsubstituted $C_{1-6}$ alkyl; and $R^D$ is H. In certain embodiments, both $R^A$ and $R^D$ are halogen. In certain embodiments, both $R^A$ and $R^D$ are halogen; and $R^A$ and $R^D$ are the same. In certain embodiments, both $R^A$ and $R^D$ are halogen; and $R^A$ and $R^D$ are not the same. In certain embodiments, each of $R^A$ and $R^D$ is independently Cl, Br, or I. In certain embodiments, both $R^A$ and $R^D$ are Cl. In certain embodiments, $R^A$ is Cl; and $R^D$ is Br. In certain embodiments, $R^A$ is Cl; and $R^D$ is I. In certain embodiments, $R^A$ is Br; and $R^D$ is Cl. In certain embodiments, both $R^A$ and $R^D$ are Br. In certain embodiments, $R^A$ is Br; and $R^D$ is I. In certain embodiments, $R^A$ is I; and $R^D$ is Cl. In certain embodiments, $R^A$ is I; and $R^D$ is Br. In certain embodiments, both $R^A$ and $R^D$ are I. In certain embodiments, both $R^A$ and $R^D$ are substituted or unsubstituted $C_{1-6}$ alkyl (e.g., Me). In certain embodiments, $R^A$ is substituted or unsubstituted $C_{1-6}$ alkyl (e.g., Me); and $R^D$ is halogen (e.g., Cl, Br, or I). In certain embodiments, $R^A$ is halogen (e.g., Cl, Br, or I); and $R^D$ is substituted or unsubstituted $C_{1-6}$ alkyl (e.g., Me). In certain embodiments, $R^A$ is —O(substituted or unsubstituted $C_{1-6}$ alkyl) (e.g., —OMe); and $R^D$ is hydrogen, halogen, substituted or unsubstituted $C_{1-6}$ alkyl (e.g., Me), or —O(substituted or unsubstituted $C_{1-6}$ alkyl) (e.g., —OMe). In certain embodiments, $R^A$ is hydrogen, halogen, substituted or unsubstituted $C_{1-6}$ alkyl (e.g., Me), or —O(substituted or unsubstituted $C_{1-6}$ alkyl) (e.g., —OMe); and $R^D$ is —O(substituted or unsubstituted $C_{1-6}$ alkyl) (e.g., —OMe).

In certain embodiments, both $R^B$ and $R^C$ are H. In certain embodiments, each of $R^B$ and $R^C$ is independently hydrogen or halogen. In certain embodiments, each of $R^B$ and $R^C$ is independently hydrogen, halogen, or substituted or unsubstituted $C_{1-6}$ alkyl (e.g., Me). In certain embodiments, each of $R^B$ and $R^C$ is independently hydrogen, halogen, substituted or unsubstituted $C_{1-6}$ alkyl (e.g., Me), or —O(substituted or unsubstituted $C_{1-6}$ alkyl) (e.g., —OMe). In certain embodiments, $R^B$ is H; and $R^C$ is halogen (e.g., F, Cl, Br, or I). In certain embodiments, $R^B$ is H; and $R^C$ is substituted or unsubstituted $C_{1-6}$ alkyl (e.g., Me). In certain embodiments, $R^B$ is halogen (e.g., F, Cl, Br, and I); and $R^C$ is H. In certain embodiments, $R^B$ is substituted or unsubstituted $C_{1-6}$ alkyl; and $R^C$ is H. In certain embodiments, both $R^B$ and $R^C$ are halogen. In certain embodiments, both $R^B$ and $R^C$ are halogen; and $R^B$ and $R^C$ are the same. In certain embodiments, both $R^B$ and $R^C$ are halogen; and $R^B$ and $R^C$ are not the same. In certain embodiments, each of $R^B$ and $R^C$ is independently Cl, Br, or I. In certain embodiments, both $R^B$ and $R^C$ are Cl. In certain embodiments, $R^B$ is Cl; and $R^C$ is Br. In certain embodiments, $R^B$ is Cl; and $R^C$ is I. In certain embodiments, $R^B$ is Br; and $R^C$ is Cl. In certain embodiments, both $R^B$ and $R^C$ are Br. In certain embodiments, $R^B$ is Br; and $R^C$ is I. In certain embodiments, $R^B$ is I; and $R^C$ is Cl. In certain embodiments, $R^B$ is I; and $R^C$ is Br. In certain embodiments, both $R^B$ and $R^C$ are I. In certain embodiments, both $R^B$ and $R^C$ are substituted or unsubstituted $C_{1-6}$ alkyl (e.g., Me). In certain embodiments, $R^B$ is substituted or unsubstituted $C_{1-6}$ alkyl (e.g., Me); and $R^C$ is halogen (e.g., Cl, Br, or I). In certain embodiments, $R^B$ is halogen (e.g., Cl, Br, or I); and $R^C$ is substituted or unsubstituted $C_{1-6}$ alkyl (e.g., Me). In certain embodiments, $R^B$ is —O(substituted or unsubstituted $C_{1-6}$ alkyl) (e.g., —OMe); and $R^C$ is hydrogen, halogen, substituted or unsubstituted $C_{1-6}$ alkyl (e.g., Me), or —O(substituted or unsubstituted $C_{1-6}$ alkyl) (e.g., —OMe). In certain embodiments, $R^B$ is hydrogen, halogen, substituted or unsubstituted $C_{1-6}$ alkyl (e.g., Me), or —O(substituted or unsubstituted $C_{1-6}$ alkyl) (e.g., —OMe); and $R^C$ is —O(substituted or unsubstituted $C_{1-6}$ alkyl) (e.g., —OMe).

In certain embodiments, both $R^B$ and $R^D$ are H. In certain embodiments, each of $R^B$ and $R^D$ is independently hydrogen or halogen. In certain embodiments, each of $R^B$ and $R^D$ is independently hydrogen, halogen, or substituted or unsubstituted $C_{1-6}$ alkyl (e.g., Me). In certain embodiments, each of $R^B$ and $R^D$ is independently hydrogen, halogen, substituted or unsubstituted $C_{1-6}$ alkyl (e.g., Me), or —O(substituted or unsubstituted $C_{1-6}$ alkyl) (e.g., —OMe). In certain embodiments, $R^B$ is H; and $R^D$ is halogen (e.g., F, Cl, Br, or I). In certain embodiments, $R^B$ is H; and $R^D$ is substituted or unsubstituted $C_{1-6}$ alkyl (e.g., Me). In certain embodiments, $R^B$ is halogen (e.g., F, Cl, Br, and I); and $R^D$ is H. In certain embodiments, $R^B$ is substituted or unsubstituted $C_{1-6}$ alkyl; and $R^D$ is H. In certain embodiments, both $R^B$ and $R^D$ are halogen. In certain embodiments, both $R^B$ and $R^D$ are halogen; and $R^B$ and $R^D$ are the same. In certain embodiments, both $R^B$ and $R^D$ are halogen; and $R^B$ and $R^D$ are not the same. In certain embodiments, each of $R^B$ and $R^D$ is independently Cl, Br, or I. In certain embodiments, both $R^B$ and $R^D$ are Cl. In certain embodiments, $R^B$ is Cl; and $R^D$ is Br. In certain embodiments, $R^B$ is Cl; and $R^D$ is I. In certain embodiments, $R^B$ is Br; and $R^D$ is Cl. In certain embodiments, both $R^B$ and $R^D$ are Br. In certain embodiments, $R^B$ is Br; and $R^D$ is I. In certain embodiments, $R^B$ is I; and $R^D$ is Cl. In certain embodiments, $R^B$ is I; and $R^D$ is Br. In certain embodiments, both $R^B$ and $R^D$ are I. In certain embodiments, both $R^B$ and $R^D$ are substituted or unsubstituted $C_{1-6}$ alkyl (e.g., Me). In certain embodiments, $R^B$ is substituted or unsubstituted $C_{1-6}$ alkyl (e.g., Me); and $R^D$ is halogen (e.g., Cl, Br, or I). In certain embodiments, $R^B$ is halogen (e.g., Cl, Br, or I); and $R^D$ is substituted or unsubstituted $C_{1-6}$ alkyl (e.g., Me). In certain embodiments, $R^B$ is —O(substituted or unsubstituted $C_{1-6}$ alkyl) (e.g., —OMe); and $R^D$ is hydrogen, halogen, substituted or unsubstituted $C_{1-6}$ alkyl (e.g., Me), or —O(substituted or unsubstituted $C_{1-6}$ alkyl) (e.g., —OMe). In certain embodiments, $R^B$ is hydrogen, halogen, substituted or unsubstituted $C_{1-6}$ alkyl (e.g., Me), or —O(substituted or unsubstituted $C_{1-6}$ alkyl) (e.g., —OMe); and $R^D$ is —O(substituted or unsubstituted $C_{1-6}$ alkyl) (e.g., —OMe).

In certain embodiments, both $R^C$ and $R^D$ are H. In certain embodiments, each of $R^C$ and $R^D$ is independently hydrogen or halogen. In certain embodiments, each of $R^C$ and $R^D$ is independently hydrogen, halogen, or substituted or unsubstituted $C_{1-6}$ alkyl (e.g., Me). In certain embodiments, each of $R^C$ and $R^D$ is independently hydrogen, halogen, substituted or unsubstituted $C_{1-6}$ alkyl (e.g., Me), or —O(substituted or unsubstituted $C_{1-6}$ alkyl) (e.g., —OMe). In certain embodiments, $R^C$ is H; and $R^D$ is halogen (e.g., F, Cl, Br, or I). In certain embodiments, $R^C$ is H; and $R^D$ is substituted or unsubstituted $C_{1-6}$ alkyl (e.g., Me). In certain embodiments, $R^C$ is halogen (e.g., F, Cl, Br, and I); and $R^D$ is H. In certain embodiments, $R^C$ is substituted or unsubstituted $C_{1-6}$ alkyl; and $R^D$ is H. In certain embodiments, both $R^C$ and $R^D$ are halogen. In certain embodiments, both $R^C$ and $R^D$ are halogen; and $R^C$ and $R^D$ are the same. In certain embodiments, both $R^C$ and $R^D$ are halogen; and $R^C$ and $R^D$ are not the same. In certain embodiments, each of $R^C$ and $R^D$ is independently Cl, Br, or I. In certain embodiments, both $R^C$ and $R^D$ are Cl. In certain embodiments, $R^C$ is Cl; and $R^D$ is Br. In certain embodiments, $R^C$ is Cl; and $R^D$ is I. In certain embodiments, $R^C$ is Br; and $R^D$ is Cl. In certain embodiments, both $R^C$ and $R^D$ are Br. In certain embodiments, $R^C$ is Br; and $R^D$ is I. In certain embodiments, $R^C$ is I; and $R^D$ is Br. In certain embodiments, both $R^C$ and $R^D$ are I. In certain embodiments, both $R^C$ and $R^D$ are substituted or unsubstituted $C_{1-6}$ alkyl (e.g., Me). In certain embodiments, $R^C$ is substituted or unsubstituted $C_{1-6}$ alkyl (e.g., Me); and $R^D$ is halogen (e.g., Cl, Br, or I). In certain embodiments, $R^C$ is halogen (e.g., Cl, Br, or I); and $R^D$ is substituted or unsubstituted $C_{1-6}$ alkyl (e.g., Me). In certain embodiments, $R^C$ is —O(substituted or unsubstituted $C_{1-6}$ alkyl) (e.g., —OMe); and $R^D$ is hydrogen, halogen, substituted or unsubstituted $C_{1-6}$ alkyl (e.g., Me), or —O(substituted or unsubstituted $C_{1-6}$ alkyl) (e.g., —OMe). In certain embodiments, $R^C$ is hydrogen, halogen, substituted or unsubstituted $C_{1-6}$ alkyl (e.g., Me), or —O(substituted or unsubstituted $C_{1-6}$ alkyl) (e.g., —OMe); and $R^D$ is —O(substituted or unsubstituted $C_{1-6}$ alkyl) (e.g., —OMe).

In certain embodiments, $R^B$ is halogen, substituted or unsubstituted $C_{1-6}$ alkyl (e.g., Me), or —O(substituted or unsubstituted $C_{1-6}$ alkyl) (e.g., —OMe), and each of $R^A$, $R^C$, and $R^D$ is H. In certain embodiments, $R^B$ is halogen or substituted or unsubstituted $C_{1-6}$ alkyl (e.g., Me). In certain embodiments, $R^B$ is halogen (e.g., F, Cl, Br, or I). In certain embodiments, $R^B$ is substituted or unsubstituted $C_{1-6}$ alkyl (e.g., Me). In certain embodiments, $R^B$ is Cl. In certain embodiments, $R^B$ is Br. In certain embodiments, $R^B$ is I. In certain embodiments, $R^B$ is unsubstituted $C_{1-6}$ alkyl (e.g., Me). In certain embodiments, $R^B$ is substituted $C_{1-6}$ alkyl.

In certain embodiments, $R^C$ is halogen, substituted or unsubstituted $C_{1-6}$ alkyl (e.g., Me), or —O(substituted or unsubstituted $C_{1-6}$ alkyl) (e.g., —OMe), and each of $R^A$, $R^B$, and $R^D$ is H. In certain embodiments, $R^C$ is halogen or substituted or unsubstituted $C_{1-6}$ alkyl (e.g., Me). In certain embodiments, $R^C$ is halogen (e.g., F, Cl, Br, or I). In certain embodiments, $R^C$ is substituted or unsubstituted $C_{1-6}$ alkyl (e.g., Me). In certain embodiments, $R^C$ is Cl. In certain embodiments, $R^C$ is Br. In certain embodiments, $R^C$ is I. In certain embodiments, $R^C$ is unsubstituted $C_{1-6}$ alkyl (e.g., Me). In certain embodiments, $R^C$ is substituted $C_{1-6}$ alkyl.

In certain embodiments, $R^A$ is halogen, substituted or unsubstituted $C_{1-6}$ alkyl (e.g., Me), or —O(substituted or unsubstituted $C_{1-6}$ alkyl) (e.g., —OMe), and each of $R^B$, $R^C$, and $R^D$ is H. In certain embodiments, $R^A$ is halogen or substituted or unsubstituted $C_{1-6}$ alkyl (e.g., Me). In certain embodiments, $R^A$ is halogen (e.g., F, Cl, Br, or I). In certain embodiments, $R^A$ is substituted or unsubstituted $C_{1-6}$ alkyl (e.g., Me). In certain embodiments, $R^A$ is Cl. In certain embodiments, $R^A$ is Br. In certain embodiments, $R^A$ is I. In certain embodiments, $R^A$ is unsubstituted $C_{1-6}$ alkyl (e.g., Me). In certain embodiments, $R^A$ is substituted $C_{1-6}$ alkyl.

In certain embodiments, $R^D$ is halogen, substituted or unsubstituted $C_{1-6}$ alkyl (e.g., Me), or —O(substituted or unsubstituted $C_{1-6}$ alkyl) (e.g., —OMe), and each of $R^A$, $R^B$, and $R^C$ is H. In certain embodiments, $R^D$ is halogen or substituted or unsubstituted $C_{1-6}$ alkyl (e.g., Me). In certain embodiments, $R^D$ is halogen (e.g., F, Cl, Br, or I). In certain embodiments, $R^D$ is substituted or unsubstituted $C_{1-6}$ alkyl (e.g., Me). In certain embodiments, $R^D$ is Cl. In certain embodiments, $R^D$ is Br. In certain embodiments, $R^D$ is I. In certain embodiments, $R^D$ is unsubstituted $C_{1-6}$ alkyl (e.g., Me). In certain embodiments, $R^D$ is substituted $C_{1-6}$ alkyl.

In certain embodiments, $R^A$ and $R^D$ are each independently halogen, substituted or unsubstituted $C_{1-6}$ alkyl (e.g., Me), or —O(substituted or unsubstituted $C_{1-6}$ alkyl) (e.g., —OMe), and each of $R^B$ and $R^C$ is hydrogen. In certain embodiments, both $R^A$ and $R^D$ are halogen. In certain embodiments, both $R^A$ and $R^D$ are halogen; and $R^A$ and $R^D$ are not the same. In certain embodiments, each of $R^A$ and $R^D$ is independently Cl, Br, or I. In certain embodiments, both $R^A$ and $R^D$ are Cl. In certain embodiments, $R^A$ is Cl; and $R^D$ is Br. In certain embodiments, $R^A$ is Cl; and $R^D$ is I. In certain embodiments, $R^A$ is Br; and $R^D$ is Cl. In certain embodiments, both $R^A$ and $R^D$ are Br. In certain embodiments, $R^A$ is Br; and $R^D$ is I. In certain embodiments, $R^A$ is I; and $R^D$ is Cl. In certain embodiments, $R^A$ is I; and $R^D$ is Br. In certain embodiments, both $R^A$ and $R^D$ are I. In certain embodiments, both $R^A$ and $R^D$ are substituted or unsubstituted $C_{1-6}$ alkyl (e.g., Me). In certain embodiments, $R^A$ is substituted or unsubstituted $C_{1-6}$ alkyl (e.g., Me); and $R^D$ is halogen (e.g., Cl, Br, or I). In certain embodiments, $R^A$ is halogen (e.g., Cl, Br, or I); and $R^D$ is substituted or unsubstituted $C_{1-6}$ alkyl (e.g., Me). In certain embodiments, $R^A$ is —O(substituted or unsubstituted $C_{1-6}$ alkyl) (e.g., —OMe); and $R^D$ is hydrogen, halogen, substituted or unsubstituted $C_{1-6}$ alkyl (e.g., Me), or —O(substituted or unsubstituted $C_{1-6}$ alkyl) (e.g., —OMe). In certain embodiments, $R^A$ is hydrogen, halogen, substituted or unsubstituted $C_{1-6}$ alkyl (e.g., Me), or —O(substituted or unsubstituted $C_{1-6}$ alkyl) (e.g., —OMe); and $R^D$ is —O(substituted or unsubstituted $C_{1-6}$ alkyl) (e.g., —OMe).

In certain embodiments, both $R^A$ and $R^C$ are each independently halogen, substituted or unsubstituted $C_{1-6}$ alkyl (e.g., Me), or —O(substituted or unsubstituted $C_{1-6}$ alkyl) (e.g., —OMe), and each of $R^B$ and $R^D$ is hydrogen. In certain embodiments, $R^A$ is substituted or unsubstituted $C_{1-6}$ alkyl; and $R^C$ is H. In certain embodiments, both $R^A$ and $R^C$ are halogen. In certain embodiments, both $R^A$ and $R^C$ are halogen; and $R^A$ and $R^C$ are the same. In certain embodiments, both $R^A$ and $R^C$ are halogen; and $R^A$ and $R^C$ are not the same. In certain embodiments, each of $R^A$ and $R^C$ is independently Cl, Br, or I. In certain embodiments, both $R^A$ and $R^C$ are Cl. In certain embodiments, $R^A$ is Cl; and $R^C$ is Br. In certain embodiments, $R^A$ is Cl; and $R^C$ is I. In certain embodiments, $R^A$ is Br; and $R^C$ is Cl. In certain embodiments, both $R^A$ and $R^C$ are Br. In certain embodiments, $R^A$ is Br; and $R^C$ is I. In certain embodiments, $R^A$ is I; and $R^C$ is Cl. In certain embodiments, $R^A$ is I; and $R^C$ is Br. In certain embodiments, both $R^A$ and $R^C$ are I. In certain embodiments, both $R^A$ and $R^C$ are substituted or unsubstituted $C_{1-6}$ alkyl (e.g., Me). In certain embodiments, $R^A$ is substituted or unsubstituted $C_{1-6}$ alkyl (e.g., Me); and $R^C$ is halogen (e.g., Cl, Br, or I). In certain embodiments, $R^A$ is halogen (e.g., Cl, Br, or I); and $R^C$ is substituted or unsubstituted $C_{1-6}$ alkyl (e.g., Me). In certain embodiments, $R^A$ is —O(substituted or unsubstituted $C_{1-6}$ alkyl) (e.g., —OMe); and $R^C$ is hydrogen, halogen, substituted or unsubstituted $C_{1-6}$ alkyl (e.g., Me), or —O(substituted or unsubstituted $C_{1-6}$ alkyl) (e.g., —OMe). In certain embodiments, $R^A$ is hydrogen, halogen, substituted or unsubstituted $C_{1-6}$ alkyl (e.g., Me), or —O(substituted or unsubstituted $C_{1-6}$ alkyl) (e.g., —OMe); and $R^C$ is —O(substituted or unsubstituted $C_{1-6}$ alkyl) (e.g., —OMe).

In certain embodiments, both $R^B$ and $R^C$ are each independently halogen, substituted or unsubstituted $C_{1-6}$ alkyl (e.g., Me), or —O(substituted or unsubstituted $C_{1-6}$ alkyl) (e.g., —OMe), and each of $R^A$ and $R^D$ is hydrogen. In certain embodiments, both $R^B$ and $R^C$ are halogen. In certain embodiments, both $R^B$ and $R^C$ are halogen; and $R^B$ and $R^C$ are the same. In certain embodiments, both $R^B$ and $R^C$ are halogen; and $R^B$ and $R^C$ are not the same. In certain embodiments, each of $R^B$ and $R^C$ is independently Cl, Br, or I. In certain embodiments, both $R^B$ and $R^C$ are Cl. In certain embodiments, $R^B$ is Cl; and $R^C$ is Br. In certain embodiments, $R^B$ is Cl; and $R^C$ is I. In certain embodiments, $R^B$ is Br; and $R^C$ is Cl. In certain embodiments, both $R^B$ and $R^C$ are Br. In certain embodiments, $R^B$ is Br; and $R^C$ is I. In certain embodiments, $R^B$ is I; and $R^C$ is Cl. In certain embodiments, $R^B$ is I; and $R^C$ is Br. In certain embodiments, both $R^B$ and $R^C$ are I. In certain embodiments, both $R^B$ and $R^C$ are substituted or unsubstituted $C_{1-6}$ alkyl (e.g., Me). In certain embodiments, $R^B$ is substituted or unsubstituted $C_{1-6}$ alkyl (e.g., Me); and $R^C$ is halogen (e.g., Cl, Br, or I). In certain embodiments, $R^B$ is halogen (e.g., Cl, Br, or I); and $R^C$ is substituted or unsubstituted $C_{1-6}$ alkyl (e.g., Me). In certain embodiments, $R^B$ is —O(substituted or unsubstituted $C_{1-6}$ alkyl) (e.g., —OMe); and $R^C$ is hydrogen, halogen, substituted or unsubstituted $C_{1-6}$ alkyl (e.g., Me), or —O(substituted or unsubstituted $C_{1-6}$ alkyl) (e.g., —OMe). In certain embodiments, $R^B$ is hydrogen, halogen, substituted or unsubstituted $C_{1-6}$ alkyl (e.g., Me), or —O(substituted or unsubstituted $C_{1-6}$ alkyl) (e.g., —OMe); and $R^C$ is —O(substituted or unsubstituted $C_{1-6}$ alkyl) (e.g., —OMe).

In certain embodiments, both $R^B$ and $R^D$ are each independently halogen, substituted or unsubstituted $C_{1-6}$ alkyl (e.g., Me), or —O(substituted or unsubstituted $C_{1-6}$ alkyl) (e.g., —OMe), and each of $R^A$ and $R^C$ is hydrogen. In certain embodiments, both $R^B$ and $R^D$ are halogen. In certain embodiments, both $R^B$ and $R^D$ are halogen; and $R^B$ and $R^D$ are the same. In certain embodiments, both $R^B$ and $R^D$ are halogen; and $R^B$ and $R^D$ are not the same. In certain embodiments, each of $R^B$ and $R^D$ is independently Cl, Br, or I. In certain embodiments, both $R^B$ and $R^D$ are Cl. In certain embodiments, $R^B$ is Cl; and $R^D$ is Br. In certain embodiments, $R^B$ is Cl; and $R^D$ is I. In certain embodiments, $R^B$ is Br; and $R^D$ is Cl. In certain embodiments, both $R^B$ and $R^D$ are Br. In certain embodiments, $R^B$ is Br; and $R^D$ is I. In certain embodiments, $R^B$ is I; and $R^D$ is Cl. In certain embodiments, $R^B$ is I; and $R^D$ is Br. In certain embodiments, both $R^B$ and $R^D$ are I. In certain embodiments, both $R^B$ and $R^D$ are substituted or unsubstituted $C_{1-6}$ alkyl (e.g., Me). In certain embodiments, $R^B$ is substituted or unsubstituted $C_{1-6}$ alkyl (e.g., Me); and $R^D$ is halogen (e.g., Cl, Br, or I). In certain embodiments, $R^B$ is halogen (e.g., Cl, Br, or I); and $R^D$ is substituted or unsubstituted $C_{1-6}$ alkyl (e.g., Me). In certain embodiments, $R^B$ is —O(substituted or unsubstituted $C_{1-6}$ alkyl) (e.g., —OMe); and $R^D$ is hydrogen, halogen, substituted or unsubstituted $C_{1-6}$ alkyl (e.g., Me), or —O(substituted or unsubstituted $C_{1-6}$ alkyl) (e.g., —OMe). In certain embodiments, $R^B$ is hydrogen, halogen, substituted or unsubstituted $C_{1-6}$ alkyl (e.g., Me), or —O(substituted or unsubstituted $C_{1-6}$ alkyl) (e.g., —OMe); and $R^D$ is —O(substituted or unsubstituted $C_{1-6}$ alkyl) (e.g., —OMe).

In certain embodiments, $R^A$, $R^B$ and $R^D$ are each independently halogen, substituted or unsubstituted $C_{1-6}$ alkyl (e.g., Me), or —O(substituted or unsubstituted $C_{1-6}$ alkyl) (e.g., —OMe), and $R^C$ is hydrogen.

In certain embodiments, $R^B$, $R^C$ and $R^D$ are each independently halogen, substituted or unsubstituted $C_{1-6}$ alkyl (e.g., Me), or —O(substituted or unsubstituted $C_{1-6}$ alkyl) (e.g., —OMe), and $R^A$ is hydrogen.

In certain embodiments, both X and Y are independently halogen. In certain embodiments, each of X and Y is independently bromo or iodo. In certain embodiments, both X and Y are bromo. In certain embodiments, both X and Y are iodo. In certain embodiments, X is bromo; and Y is iodo. In other embodiments, X is bromo; and Y is iodo.

In certain embodiments, each $R^A$ is independently hydrogen, substituted or unsubstituted acyl, substituted or unsubstituted alkyl, halogen, —OR$^1$, —N(R$^1$)$_2$, —C(=O)R$^1$, —C(=O)N(R$^1$)$_2$, or —C(=O)OR$^1$;

each $R^B$ is independently hydrogen, substituted or unsubstituted acyl, substituted or unsubstituted alkyl, halogen, —OR$^2$, —N(R$^2$)$_2$, —C(=O)R$^2$, —C(=O)N(R$^2$)$_2$, or —C(=O)OR$^2$;

each $R^C$ is independently hydrogen, substituted or unsubstituted acyl, substituted or unsubstituted alkyl, halogen, —OR³, —N(R³)₂, —C(=O)R³, —C(=O)N(R³)₂, or —C(=O)OR³; and each $R^D$ is independently hydrogen, substituted or unsubstituted acyl, substituted or unsubstituted alkyl, halogen, —OR⁴, —N(R⁴)₂, —C(=O)R⁴, —C(=O)N(R⁴)₂, or —C(=O)OR⁴.

In certain embodiments, each of $R^A$, $R^B$, $R^C$, and $R^D$ is independently hydrogen, fluoro, chloro, bromo, alkyl, haloalkyl, hydroxyl, alkoxycarbonyl, aryloxy, dialkylamino, hydroxyalkyl, (alkyltriazolyl)alkyl, or ((alkylamino)sulfonyl)alkyl.

In certain embodiments, each of $R^A$, $R^B$, $R^C$, and $R^D$ is independently hydrogen, fluoro, chloro, bromo, methyl, ethyl, trifluoromethyl, hydroxyl, ethoxycarbonyl, phenoxy, diethylamino, hydroxymethyl, hydroxyethyl, 1-(4-propyl-1,2,3-triazolyl)methyl, or ((methylamino)sulfonyl)methyl.

In certain embodiments, $R^E$ is an oxygen protecting group.

In certain embodiments, Z is —CR^D.

In certain embodiments, $R^E$ is a sugar, substituted or unsubstituted acyl, substituted or unsubstituted alkyl,

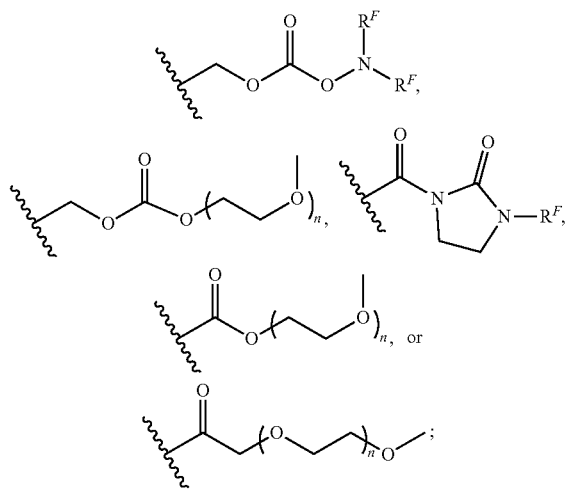

wherein each n is independently 1-10; and
each $R^F$ is independently hydrogen or a nitrogen protecting group.

In certain embodiments, the compound of Formula (I) is of Formula (II):

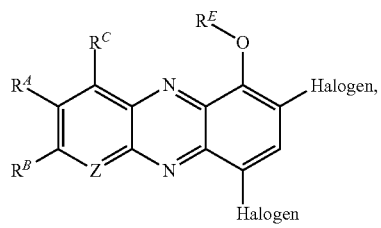

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (III):

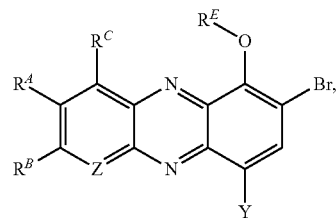

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (IV):

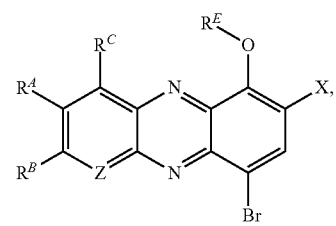

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (V):

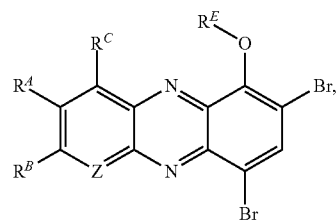

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (VI):

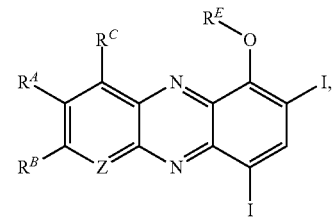

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (VII):

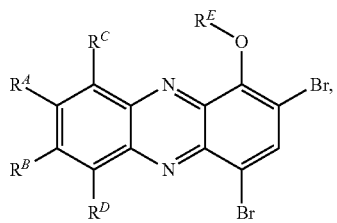

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (VIII):

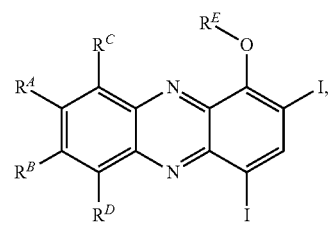

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (IX):

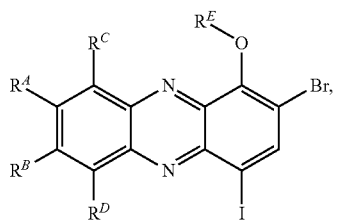

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (X):

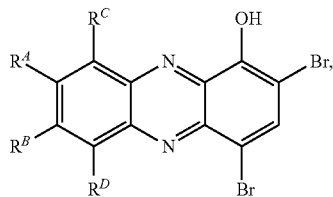

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (XI):

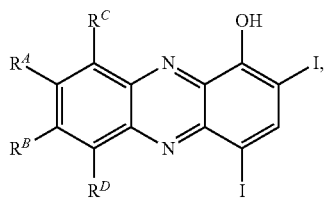

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (XII):

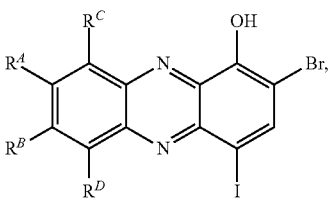

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (XIII):

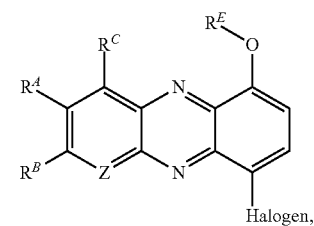

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (XIV):

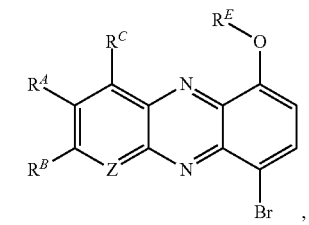

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (XV):

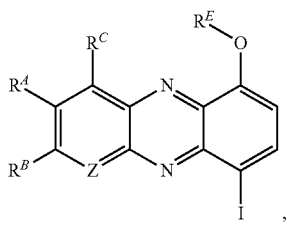

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (XVI):

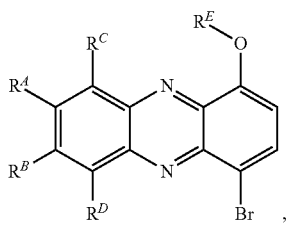

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (XVII):

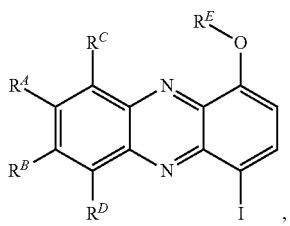

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of Formula (XVIII):

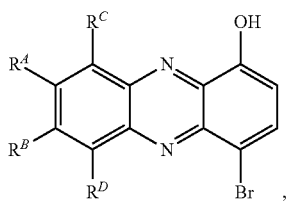

or a pharmaceutically acceptable salt, solvate, hydrate, polymorph, co-crystal, tautomer, stereoisomer, isotopically labeled derivative, or prodrug thereof.

In certain embodiments, the compound of Formula (X) is of Formula (XIX):

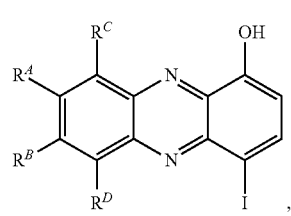

or a pharmaceutically acceptable salt, solvate, hydrate, polymorph, co-crystal, tautomer, stereoisomer, isotopically labeled derivative, or prodrug thereof.

Exemplary compounds of Formula (I) (e.g. 2., Formulae (II)-(XIX)) include:

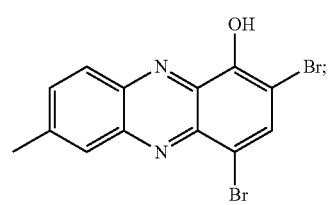

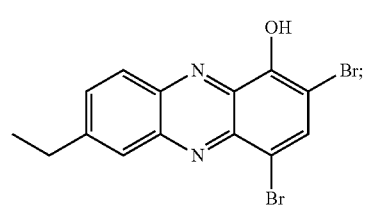

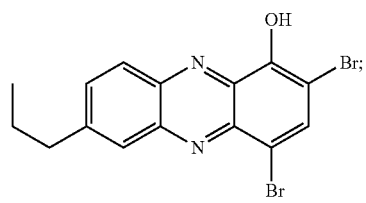

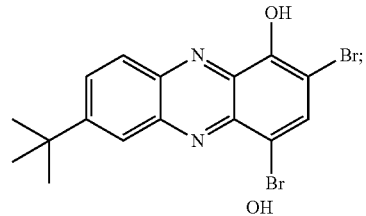

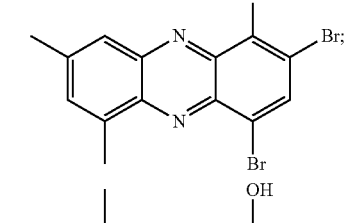

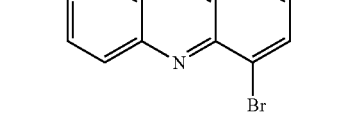

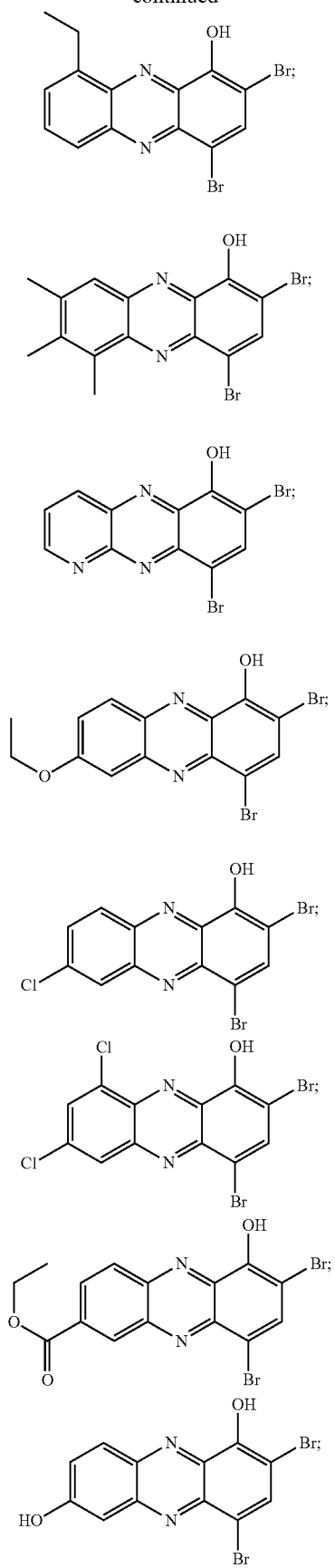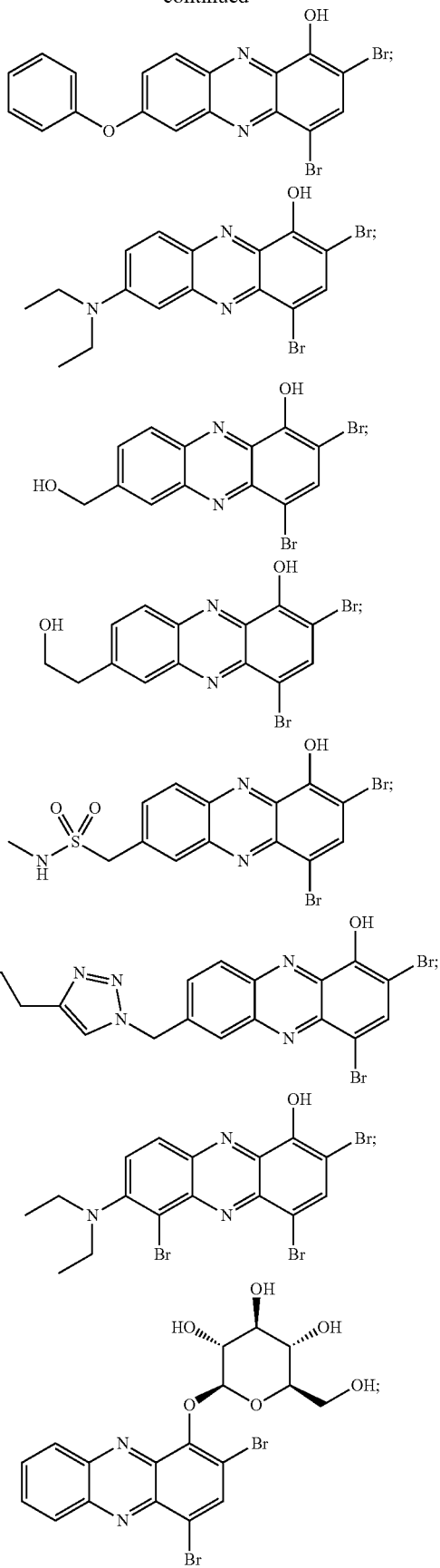

-continued
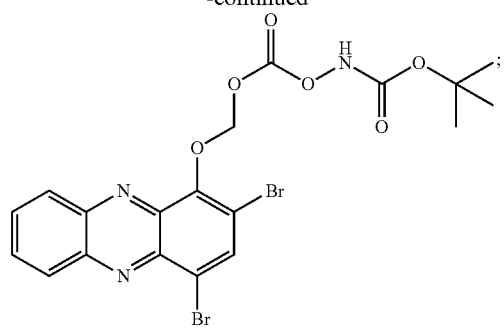
and pharmaceutically acceptable salts, solvates, hydrates, polymorphs, co-crystals, tautomers, stereoisomers, isotopically labeled derivatives, and prodrugs thereof.
Additional exemplary compounds of Formula (I) (e.g., Formulae (II)-(XIX)) include:
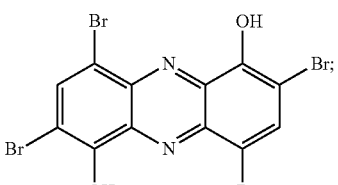
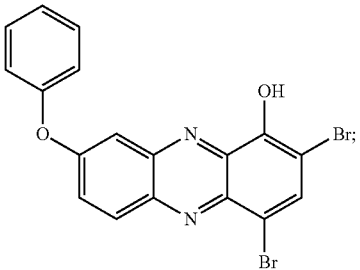
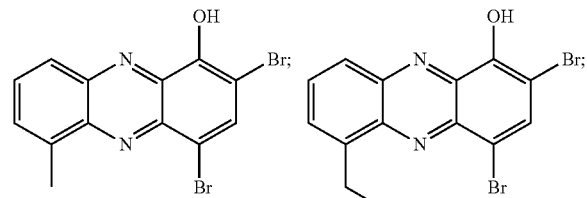
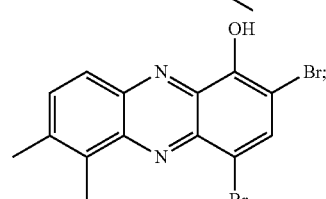
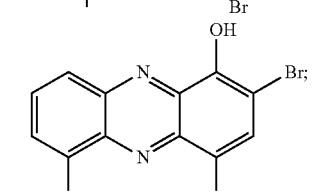
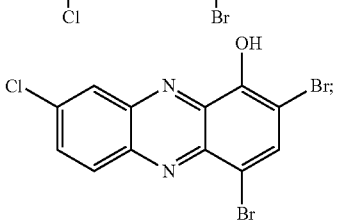
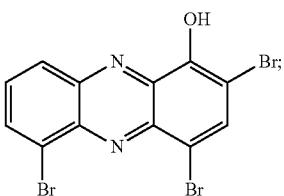
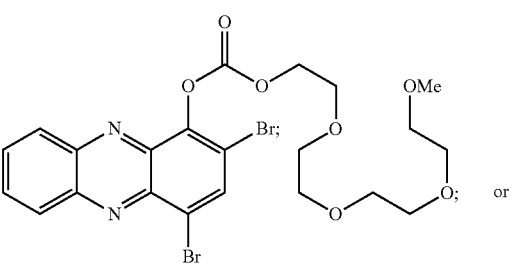

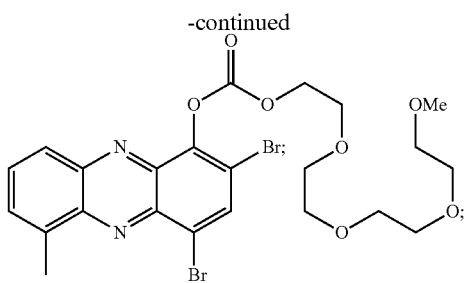

and pharmaceutically acceptable salts, solvates, hydrates, polymorphs, co-crystals, tautomers, stereoisomers, isotopically labeled derivatives, and prodrugs thereof.

Additional exemplary compounds of Formula (I) include:

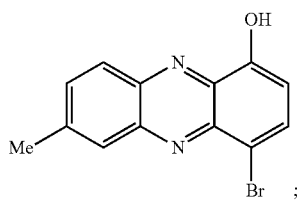

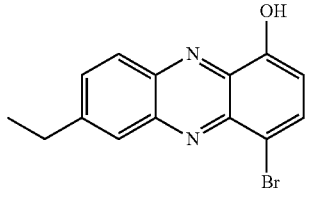

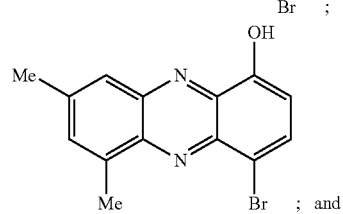

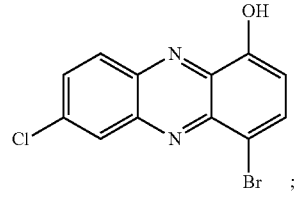

and pharmaceutically acceptable salts, solvates, hydrates, polymorphs, co-crystals, tautomers, stereoisomers, isotopically labeled derivatives, and prodrugs thereof.

Additional exemplary compounds of Formula (I) include:

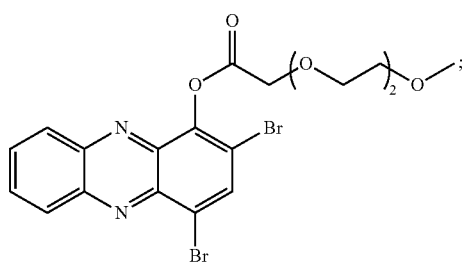

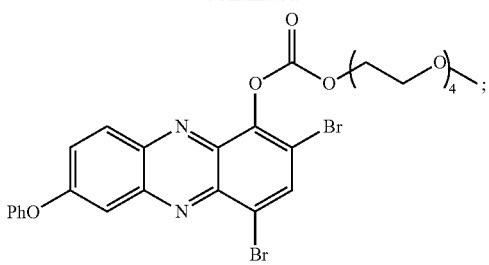

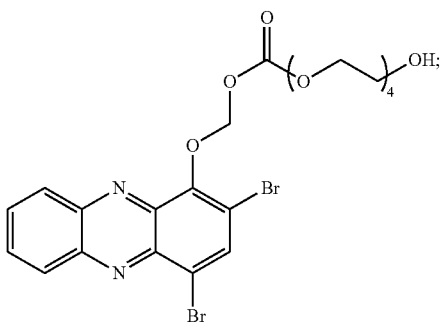

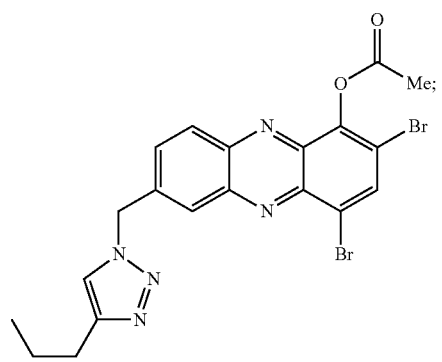

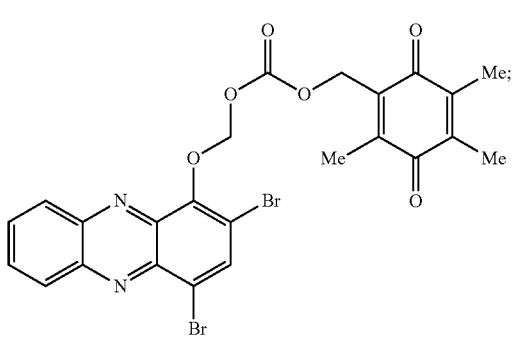

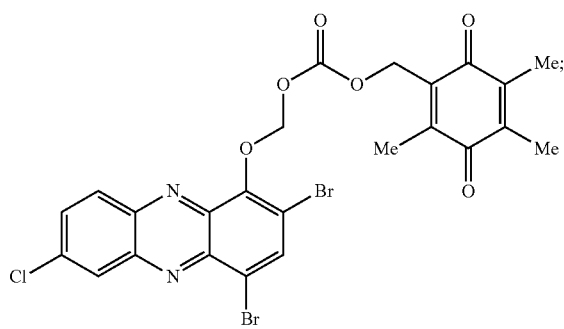

-continued

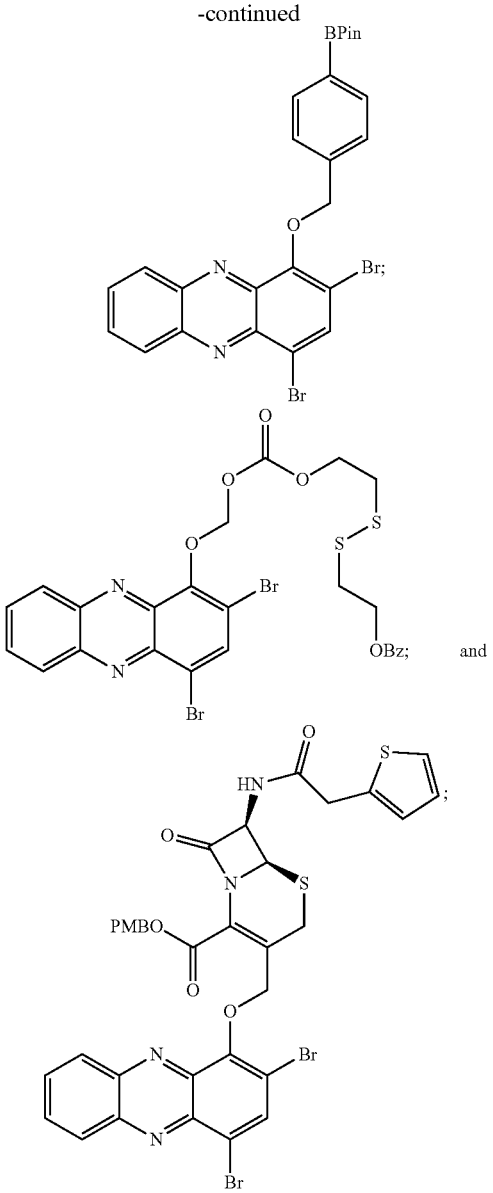

and pharmaceutically acceptable salts, solvates, hydrates, polymorphs, co-crystals, tautomers, stereoisomers, isotopically labeled derivatives, and prodrugs thereof.

In certain embodiments, the compounds of the invention are the compounds described herein, and salts (e.g., pharmaceutically acceptable salts), solvates, hydrates, polymorphs, co-crystals, tautomers, stereoisomers, isotopically labeled derivatives, and prodrugs thereof. In certain embodiments, the compounds of the invention are the compounds described herein, and pharmaceutically acceptable salts thereof. In certain embodiments, the compounds of the invention are the compounds described herein, and pharmaceutically acceptable salts thereof. In certain embodiments, the compounds of the invention are the compounds of Formula (I), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (II), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (I), and salts (e.g., pharmaceutically acceptable salts) thereof. In certain embodiments, the compounds of the invention are the compounds of Formula (III), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (III), and salts (e.g., pharmaceutically acceptable salts) thereof. In certain embodiments, the compounds of the invention are the compounds of Formula (IV), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (IV), and salts (e.g., pharmaceutically acceptable salts) thereof. In certain embodiments, the compounds of the invention are the compounds of Formula (V), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (V), and salts (e.g., pharmaceutically acceptable salts) thereof. In certain embodiments, the compounds of the invention are the compounds of Formula (VI), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (VI), and salts (e.g., pharmaceutically acceptable salts) thereof. In certain embodiments, the compounds of the invention are the compounds of Formula (VII), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (VII), and salts (e.g., pharmaceutically acceptable salts) thereof. In certain embodiments, the compounds of the invention are the compounds of Formula (VIII), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (VIII), and salts (e.g., pharmaceutically acceptable salts) thereof. In certain embodiments, the compounds of the invention are the compounds of Formula (IX), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (IX), and salts (e.g., pharmaceutically acceptable salts) thereof. In certain embodiments, the compounds of the invention are the compounds of Formula (X), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (X), and salts (e.g., pharmaceutically acceptable salts) thereof. In certain embodiments, the compounds of the invention are the compounds of Formula (XI), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (XI), and salts (e.g., pharmaceutically acceptable salts) thereof. In certain embodiments, the compounds of the invention are the compounds of Formula (XII), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (XII), and salts (e.g., pharmaceutically acceptable salts) thereof. In certain embodiments, the compounds of the invention are the compounds of Formula (XIII), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (XIII), and salts (e.g., pharmaceutically acceptable salts) thereof. In certain embodiments, the compounds of the invention are the compounds of Formula (XIV), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (XIV), and salts (e.g., pharmaceutically acceptable salts) thereof. In certain embodiments, the compounds of the invention are the compounds of Formula (XV), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (XV), and salts (e.g., pharmaceutically acceptable salts) thereof. In certain embodiments, the compounds of the invention are the compounds of Formula (XVI), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (XVI), and salts (e.g., pharmaceutically acceptable salts) thereof. In certain embodiments, the compounds of the invention are the compounds of Formula (XVII), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (XVII), and salts (e.g., pharmaceutically acceptable salts) thereof.

In certain embodiments, the compounds of the invention are the compounds of Formula (XVIII), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (XVIII), and salts (e.g., pharmaceutically acceptable salts) thereof. In certain embodiments, the compounds of the invention are the compounds of Formula (XIX), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (XIX), and salts (e.g., pharmaceutically acceptable salts) thereof.

In certain embodiments, the compounds of the invention are substantially pure. In certain embodiments, a compound of the invention is at least about 90%, at least about 95%, at least about 97%, at least about 98%, at least about 99%, or at least about 99.5% free of impurities.

The compounds of the invention have been found to be antimicrobial agents (e.g., antibacterial agents). Without wishing to be bound by a particular theory, the compounds of the invention may be redox-active and may generate reactive oxygen species (ROS). The inventive compounds may thus act as microbial warfare agents and inhibit the growth and/or reproduction of or kill a microorganism (e.g., bacterium, mycobacterium, archaeon, protist, fungus, or parasite) by oxidizing and/or reducing molecules (e.g., catalase, cytokine, nicotinamide adenine dinucleotide phosphate (NADPH), and nicotinamide adenine dinucleotide phosphate ($NADP^+$)) in, near, or around the microorganism. The activity of a compound of the invention against a microorganism may be measured by the minimum inhibitory concentration (MIC) of the compound in inhibiting the viability, growth, or replication of the microorganism. In certain embodiments, the MIC of a compound of the invention is an MIC in inhibiting the viability the microorganism. In certain embodiments, the MIC value of an inventive compound in inhibiting a microorganism is at most about 1 nM, at most about 3 nM, at most about 10 nM, at most about 30 nM, at most about 100 nM, at most about 300 nM, at most about 1 μM, at most about 3 μM, at most about 10 μM, at most about 30 μM, or at most about 100 μM. In certain embodiments, the MIC value of an inventive compound in inhibiting a microorganism is at least about 1 nM, at least about 3 nM, at least about 10 nM, at least about 30 nM, at least about 100 nM, at least about 300 nM, at least about 1 μM, at least about 3 μM, at least about 10 μM, or at least about 30 μM. In certain embodiments, MIC values are measured according to the guidelines of the Clinical and Laboratory Standards Institute (CLSI) (which is incorporated herein by reference) (e.g., a broth microdilution method). In certain embodiments, MIC values are measured by a method described herein.

The activity of a compound of the invention against a microorganism may also be measured by the half maximal inhibitory concentration ($IC_{50}$) of the compound in inhibiting the viability, growth, or replication of the microorganism. In certain embodiments, the $IC_{50}$ of a compound of the invention is an MIC in inhibiting the viability the microorganism. In certain embodiments, the $IC_{50}$ value of an inventive compound in inhibiting a microorganism is at most about 1 nM, at most about 3 nM, at most about 10 nM, at most about 30 nM, at most about 100 nM, at most about 300 nM, at most about 1 μM, at most about 3 μM, at most about 10 μM, at most about 30 μM, or at most about 100 μM. In certain embodiments, the $IC_{50}$ value of an inventive compound in inhibiting a microorganism is at least about 1 nM, at least about 3 nM, at least about 10 nM, at least about 30 nM, at least about 100 nM, at least about 300 nM, at least about 1 μM, at least about 3 μM, at least about 10 μM, or at least about 30 μM. In certain embodiments, $IC_{50}$ values are measured according to the guidelines of the CLSI (e.g., a microdilution method). In certain embodiments, $IC_{50}$ values are measured by a method described herein.

The compounds of the invention may selectively inhibit the growth and/or reproduction of or kill a microorganism. In certain embodiments, a compound of the invention is more active in inhibiting the growth and/or reproduction of or killing a first microorganism (e.g., a microorganism described herein) than in inhibiting the growth and/or reproduction of or killing a host cell. In certain embodiments, a compound of the invention is more active in inhibiting the growth and/or reproduction of or killing a first microorganism than in inhibiting the growth and/or reproduction of or killing a second microorganism. The selectivity of an inventive compound in inhibiting the growth and/or reproduction of or killing a first microorganism over a host cell or a second microorganism may be determined by the quotient of the MIC value of the inventive compound in inhibiting the growth and/or reproduction of or killing the host cell or second microorganism over the MIC value of the inventive compound in inhibiting the growth and/or reproduction of or killing the first microorganism. The selectivity of an inventive compound in inhibiting the growth and/or reproduction of or killing a first microorganism over a host cell or a second microorganism may also be determined by the quotient of the $IC_{50}$ value of the inventive compound in inhibiting the growth and/or reproduction of or killing the host cell or second microorganism over the $IC_{50}$ value of the inventive compound in inhibiting the growth and/or reproduction of or killing the first microorganism. In certain embodiments, the selectivity of an inventive compound in inhibiting the growth and/or reproduction of or killing a first microorganism over a host cell or a second microorganism is at least about 3-fold, at least about 10-fold, at least about 30-fold, at least about 100-fold, at least about 1,000-fold, at least about 10,000-fold, or at least about 100,000-fold.

The compounds of the invention may be inactive against MRSA, MRSE, VRE, MtB, or any other microorganism described herein. The term "inactive" refers to a compound with a measure MIC value greater than 100 μM. In certain embodiments, a compound of Formula (I), wherein $R^C$ is not hydrogen, is not active against MRSA. In certain embodiments, a compound of Formula (I), wherein $R^C$ is not hydrogen, is not active against MRSE. In certain embodiments, a compound of Formula (I), wherein $R^C$ is not hydrogen, is not active against VRE. In certain embodiments, a compound of Formula (I), wherein $R^C$ is not hydrogen, is not active against MtB. In certain embodiments, a compound of Formula (I), wherein $R^C$ is substituted or unsubstituted alkyl, is not active against MRSA. In certain embodiments, a compound of Formula (I), wherein $R^C$ is substituted or unsubstituted alkyl, is not active against MRSE. In certain embodiments, a compound of Formula (I), wherein $R^C$ is substituted or unsubstituted alkyl, is not active against VRE. In certain embodiments, a compound of Formula (I), wherein $R^C$ is substituted or unsubstituted alkyl, is not active against MtB.

The compounds of the invention may be active against MRSA, MRSE, VRE, MtB, or any other microorganism described herein. The term "active" refers to a compound with a measured MIC value less than 100 μM. In certain embodiments, a compound of Formula (I), wherein $R^B$ is not hydrogen, is active against MRSA. In certain embodiments, a compound of Formula (I), wherein $R^B$ is not hydrogen, is active against MRSE. In certain embodiments, a compound of Formula (I), wherein $R^B$ is not hydrogen, is active against VRE. In certain embodiments, a compound of Formula (I), wherein $R^B$ is not hydrogen, is active against MRSE. In certain embodiments, a compound of Formula (I), wherein $R^B$ is not hydrogen, is active against MtB. In certain embodiments, $R^B$ is halogen, substituted or unsubstituted alkyl, $-OR^2$, or $-N(R^2)_2$, wherein $R^2$ is substituted or unsubstituted alkyl or substituted or unsubstituted aryl, is active against MRSA. In certain embodiments, $R^B$ is halogen, substituted or unsubstituted alkyl, $-OR^2$, or $-N(R^2)_2$, wherein $R^2$ is substituted or unsubstituted alkyl or substituted or unsubstituted aryl, is active against MRSE. In certain embodiments, $R^B$ is halogen, substituted or unsubstituted alkyl, $-OR^2$, or $-N(R^2)_2$, wherein $R^2$ is substituted or unsubstituted alkyl or substituted or unsubstituted aryl, is active against VRE. In certain embodiments, $R^B$ is halogen, substituted or unsubstituted alkyl, $-OR^2$, or $-N(R^2)_2$, wherein $R^2$ is substituted or unsubstituted alkyl or substituted or unsubstituted aryl, is active against MtB.

The compounds of the invention may show low cytotoxicity toward mammalian cells (e.g., cytotoxicity $IC_{50}$ against HeLa cells being greater than 100 μM). The compounds of the invention may show low hemolysis activity (e.g., not more than 1%, not more than 2%, not more than 4%, or not more than 6% hemolysis of red blood cells (RBCs) when treated with the compound at 200 μM).

The compounds of the invention may be a prodrug halogenated phenazine. The compounds of the invention may be a non-prodrug halogenated phenazine. The serum stability half-life of prodrug halogenated phenazine compounds can be compared utilizing a prodrug serum stability assay. In certain embodiments, the prodrug serum stability half-life of a compound of the invention is not more than 1 minute. In certain embodiments, the prodrug serum stability half-life of a compound of the invention is between 1 minute and 10 minutes. In certain embodiments, the prodrug serum stability half-life of a compound of the invention is between 10 minutes and 20 minutes. In certain embodiments, the prodrug serum stability half-life of a compound of the invention is between 10 minutes and 20 minutes. In certain embodiments, the prodrug serum stability half-life of a compound of the invention is between 20 minutes and 100 minutes. In certain embodiments, the prodrug serum stability half-life of a compound of the invention is between 100 minutes and 200 minutes. In certain embodiments, the prodrug serum stability half-life of a compound of the invention is between 200 minutes and 300 minutes. In certain embodiments, the prodrug serum stability half-life of a compound of the invention is greater than 250 minutes. All of the ranges listed are inclusive.

Compositions, Kits, and Administration

The present invention also provides compositions (e.g., pharmaceutical compositions) comprising a compound of the invention (e.g., a compound of Formula (I) (e.g., Formulae (II)-(XIX))), or pharmaceutically acceptable salts thereof), and optionally an excipient (e.g., pharmaceutically acceptable excipient).

In certain embodiments, a composition of the invention is useful for disinfecting a surface. In certain embodiments, the compound of the invention is provided in an effective amount in the composition. In certain embodiments, the amount of the compound included in the composition is effective for killing at least 80%, at least 90%, at least 95%, at least 99%, at least 99.9%, or at least 99.99% of the microorganisms on the surface. In certain embodiments, the amount of the compound included in the composition is effective for killing at most 90%, at most 95%, at most 99%, at most 99.9%, at most 99.99%, or at most 99.999% of the microorganisms on the surface. A composition of the invention may include one or more excipients (e.g., water, detergent, bleach, surfactant) (e.g., pharmaceutically acceptable excipients).

In certain embodiments, a composition of the invention is a pharmaceutical composition comprising a compound of the invention and optionally a pharmaceutically acceptable excipient. In certain embodiments, the compound of the invention is provided in an effective amount in the pharmaceutical composition. In certain embodiments, the effective amount of the compound is a therapeutically effective amount. In certain embodiments, the effective amount of the compound is a prophylactically effective amount. The pharmaceutical compositions of the invention may be useful in the inventive methods. In certain embodiments, the pharmaceutical compositions are useful in treating a microbial infection (e.g., a bacterial infection or mycobacterial infection). In certain embodiments, the pharmaceutical compositions are useful in preventing a microbial infection (e.g., a bacterial infection or mycobacterial infection). In certain embodiments, the pharmaceutical compositions are useful in inhibiting the growth of a microorganism (e.g., a microorganism described herein). In certain embodiments, the pharmaceutical compositions are useful in inhibiting the reproduction of a microorganism. In certain embodiments, the pharmaceutical compositions are useful in killing a microorganism. In certain embodiments, the pharmaceutical compositions are useful in inhibiting the formation and/or growth of a biofilm. In certain embodiments, the pharmaceutical compositions are useful in reducing or removing a biofilm. In certain embodiments, the pharmaceutical compositions are useful in disinfecting a surface. In certain embodiments, the pharmaceutical compositions are useful in cleaning a surface.

Pharmaceutical compositions described herein can be prepared by any method known in the art of pharmacology. In general, such preparatory methods include the steps of bringing the compound of the invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabolactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behenate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadow foam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a microbial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Jet injection devices which deliver liquid vaccines to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable. Alternatively or additionally, conventional syringes can be used in the classical manteaux method of intradermal administration.

Formulations suitable for topical administration include, but are not limited to, liquid and/or semi liquid preparations such as liniments, lotions, oil-in-water and/or water-in-oil emulsions such as creams, ointments, and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets, and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

It will be also appreciated that a compound or composition, as described herein, can be administered in combination with one or more additional pharmaceutical agents. In certain embodiments, the additional pharmaceutical agent is different from a compound of the invention, or a pharmaceutically acceptable salt, solvate, hydrate, polymorph, co-crystal, tautomer, stereoisomer, isotopically labeled derivative, or prodrug thereof. The compounds or compositions can be administered in combination with additional pharmaceutical agents to improve their potency, efficacy, and/or bioavailability, reduce and/or modify their metabolism, inhibit their excretion, and/or modify their distribution within the body. It will also be appreciated that the therapy employed may achieve a desired effect for the same disorder, and/or it may achieve different effects. In certain embodiments, the combination of a compound of the invention and an additional pharmaceutical agent shows a synergistic effect.

The compound or composition can be administered concurrently with, prior to, or subsequent to, one or more additional pharmaceutical agents, which are different from the compound or composition and may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents in combination be utilized at levels that do not exceed the levels at which they are utilized individually. In some embodiments, the levels utilized in combination will be lower than those utilized individually.

Exemplary additional pharmaceutical agents include, but are not limited to, antibiotics (e.g., antibacterial agents, antiviral agents, anti-fungal agents), anti-inflammatory agents, anti-pyretic agents, and pain-relieving agents. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a chelator of a metal ion or metal atom. In certain embodiments, the additional pharmaceutical agent is a chelator of a divalent metal ion (e.g., Mg(II), Ca(II), Sr(II), Mn(II), Fe(II), Co(II), Ni(II), Cu(II), or Zn(II)). In certain embodiments, the additional pharmaceutical agent is a chelator of Cu(II), Mg(II), or Fe(II). In certain embodiments, the additional pharmaceutical agent is disodium 4,5-dihydroxy-1,3-benzenedisulfonate (TIRON). In certain embodiments, the additional pharmaceutical agent is 2,2'-dipyridyl, desferrioxamine (DFO, DESFERAL), deferasirox (EXJADE), deferiprone (L1, FERRIPROX), FERALEX-G, CaNa$_3$DTPA, dexrazoxane, a phosphorothioate-oligonucleotide, desferrithiocin, or desazadesferrithiocin, or a derivative thereof. In certain embodiments, the additional pharmaceutical agent is an antibiotic. In certain embodiments, the additional pharmaceutical agent is an antibiotic effective against a microorganism described herein. In certain embodiments, the additional pharmaceutical agent is an antibiotic effective against a bacterium. In certain embodiments, the additional pharmaceutical agent is an antibiotic effective against a Gram-positive bacterium (e.g., a *Staphylococcus* species or *Enterococcus* species). In certain embodiments, the additional pharmaceutical agent is an antibiotic effective against a Gram-negative bacterium (e.g., an *Acinetobacter* species). In certain embodiments, the additional pharmaceutical agent is an antibiotic effective against a multidrug-resistant bacterium. In certain embodiments, the additional pharmaceutical agent is a β-lactam antibiotic. In certain embodiments, the additional pharmaceutical agent is a penicillin (e.g., a penam, such as an aminopenicillin (e.g., amoxicillin, an ampicillin (e.g., pivampicillin, hetacillin, bacampicillin, metampicillin, talampicillin), epicillin), a carboxypenicillin (e.g., a carbenicillin (e.g., carindacillin), ticarcillin, temocillin), a ureidopenicillin (e.g., azlocillin, piperacillin, mezlocillin), a mecillinam (e.g., pivmecillinam), sulbenicillin, benzylpenicillin, clometocillin, benzathine benzylpenicillin, procaine benzylpenicillin, azidocillin, penamecillin, phenoxymethylpenicillin, propicillin, benzathine phenoxymethylpenicillin, pheneticillin, a cloxacillin (e.g., dicloxacillin, flucloxacilline), oxacillin, methicillin, nafcillin), a penem (e.g., faropenem), a carbapenem (e.g., biapenem, ertapenem, an antipseudomonal (e.g., doripenem, imipenem, meropenem), panipenem), a cephalosporin (e.g., a cephem, such as cefazolin, cefacetrile, cefadroxil, cefalexin, cefaloglycin, cefalonium, cefaloridine, cefalotin, cefapirin, cefatrizine, cefazedone, cefazaflur, cefradine, cefroxadine, ceftezole, cefaclor, cefamandole, cefminox, cefonicid, ceforanide, cefotiam, cefprozil, cefbuperazone, cefuroxime, cefuzonam, a cephamycin (e.g, cefoxitin, cefotetan, cefmetazole), a carbacephem (e.g., loracarbef), cefixime, ceftriaxone, an antipseudomonal (e.g., ceftazidime, cefoperazone), cefcapene, cefdaloxime, cefdinir, cefditoren, cefetamet, cefmenoxime, cefodizime, cefotaxime, cefpimizole, cefpiramide, cefpodoxime, cefsulodin, cefteram, ceftibuten, ceftiolene, ceftizoxime, an oxacephem (e.g., flomoxef, latamoxef), cefepime, cefozopran, cefpirome, cefquinome, ceftobiprole, ceftaroline fosamil, ceftiofur, cefquinome, cefovecin), a monobactam (e.g., aztreonam, tigemonam, carumonam, nocardicin A), an aminoglycoside (e.g., amikacin, gentamicin, kanamycin, neomycin, netilmicin, tobramycin, paromomycin, spectinomycin), an ansamycin (e.g., geldanamycin, herbimycin, rifaximin), a glycopeptide (e.g., teicoplanin, vancomycin, telavancin), a lincosamide (e.g., clindamycin, lincomycin), a lipopeptide (e.g., daptomycin), a macrolide (e.g., azithromycin, clarithromycin, dirithromycin, erythromycin, roxithromycin, troleandomycin, telithromycin, spiramycin), a nitrofuran (e.g., furazolidone, nitrofurantoin), an oxazolidonone (e.g., linezolid, posizolid, radezolid, torezolid), a polypeptide (e.g., bacitracin, colistin, polymyxin B), a quinolone (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin), a sulfonamide (e.g., mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim, sulfonamidochrysoidine), a tetracycline (e.g., demeclocycline, doxycycline, minocycline, oxytetracycline, tetracycline), clofazimine, dapsone, capreomycin, cycloserine, ethambutol, ethionamide, isoniazid, pyrazinamide, rifampin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, or trimethoprim. In certain embodiments, the additional pharmaceutical agent is an antiviral agent. In certain embodiments, the additional pharmaceutical agent is (−)-Oseltamivir, β-D-ribofuranose, 1-acetate 2,3,5-tribenzoate, 1-Docosanol, 2-Amino-6-chloropurine, 5-Iodo-2'-deoxyuridine, 6-Chloropurine, Abacavir sulfate, Abacavir-epivir mixt., Acyclovir, Acyclovir sodium, Adefovir dipivoxil, Amantadine (e.g., Amantadine hydrochloride), Amantadine hydrochloride, anti-HIV agent (e.g., Abacavir, Amprenavir, Atazanavir, Azidothymidine, Bryostatin (e.g., Bryostatin 1, Bryostatin 10, Bryostatin 11, Bryostatin 12, Bryostatin 13, Bryostatin 14, Bryostatin 15, Bryostatin 16, Bryostatin 17, Bryostatin 18, Bryostatin 19, Bryostatin 2, Bryostatin 20, Bryostatin 3, Bryostatin 4, Bryostatin 5, Bryostatin 6, Bryostatin 7, Bryostatin 8, Bryostatin 9), Dideoxycytidine, Dideoxyinosine, Efavirenz, Indinavir, Lamivudine, Lopinavir, Nevirapine, Ritonavir, Saquinavir, Stavudine, Tenofovir), Azauridine, ombivir, Deoxynojirimycin, Docosanol, Fomivirsen sodium, Foscarnet, Ganciclovir, Integrase inhibitors (e.g., 5CITEP, Chloropeptin I, Complestatin, Dolutegravir, Elvitegravir, L 708906, L 731988, MK 2048, Raltegravir, Raltegravir potassium), MK 5172, MK 8742, Palivizumab, Pegylated interferon alfa-2b, Phosphonoacetic acid, Ribavirin, Simeprevir, Sofosbuvir, Tubercidin, Vidarabine, or virus entry inhibitor (e.g., Enfuvirtide, Maraviroc). In certain embodiments, the additional pharmaceutical agent is a fungicide. In certain embodiments, the additional pharmaceutical agent is (−)-Fumagillin, (−)-Metalaxyl, 1,2,5-Fluorocytosine, Acrisorcin, Anilazine, Antifouling agent, Azoxystrobin, Benomyl, Bordeaux mixture, Captan, Carbendazim, Caspofungin acetate, Chlorothalonil, Clotrimazole, Dichlofluanid, Dinocap, Dodine, Fenhexamid, Fenpropimorph, Ferbam, Fluconazole, Fosetyl Al, Griseofulvin, Guanidine (e.g., Agmatine, Amiloride hydrochloride, Biguanide (e.g., Imidodicarbonimidic diamide, N,N-dimethyl-, hydrochloride (1:1) (e.g., Metformin hydrochloride), Metformin), Cimetidine, Guanethidine, Guanfacine, Guanidine, Guanidinium, Methylguanidine, Sulfaguanidine), Iprobenfos, Iprodione, Isoprothiolane, Itraconazole, Ketoconazole, Mancozeb, Metalaxyl, Metiram, Miconazole, Natamycin, Nystatin, Oxycarboxine, Pentachloronitrobenzene, Prochloraz, Procymidone, Propiconazole, Pyrazophos, Reduced viscotoxin A3, Salicylanilide, Tebuconazole, Terbinafine, Thiabendazole, Thiophanate, Thiophanate methyl, Triadimefon, Vinclozolin, or Voriconazole. In certain embodiments, the additional pharmaceutical agent is a protozoacide. In certain embodiments, the additional pharmaceutical agent is Amebicide, Antimalarial (e.g., Artemisinin, Chloroquine (e.g., Chloroquine phosphate), Mefloquine, Sulfadoxine), Coccidiostat, Leishmanicide, Trichomonacide, or Trypanosomicide (e.g., Eflornithine). In certain embodiments, the additional pharmaceutical agent is a parasiticide. In certain embodiments, the additional pharmaceutical agent is antihelmintic (e.g., Abamectin, Dimethylformocarbothialdine, Niclosamide, Schistosomicide), protozoacide (e.g., Amebicide, antimalarial (e.g., Artemisinin, chloroquine (e.g., chloroquine phosphate), Mefloquine, Sulfadoxine), coccidiostat, leishmanicide, trichomonacide, or trypanosomicide (e.g., Eflornithine)).

In certain embodiments, the pharmaceutical composition is substantially free (e.g., at least 70% free, at least 80% free, at least 90% free, at least 95% free, at least 99% free, or at least 99.9% free) of a metal ion or metal atom. In certain embodiments, the pharmaceutical composition is substantially free of a divalent metal ion (e.g., Mg(II), Ca(II), Sr(II), Mn(II), Fe(II), Co(II), Ni(II), Cu(II), or Zn(II)). In certain embodiments, the pharmaceutical composition is substantially free of Cu(II), Mg(II), or Fe(II).

Also encompassed by the invention are kits (e.g., pharmaceutical packs). The kits provided may comprise a compound or composition (e.g., pharmaceutical composition) of the invention and a container (e.g., a vial, ampule, bottle, syringe, dispenser package, tube, inhaler, and/or other suitable container). In some embodiments, a kit of the invention further includes a second container comprising an excipient (e.g., pharmaceutically acceptable excipient) for dilution or suspension of an inventive compound or composition. In some embodiments, the compound or composition of the invention provided in a first container and a second container are combined to form one unit dosage form.

In one aspect, the present invention provides kits including a first container comprising a compound or composition of the invention. In certain embodiments, a kit of the invention includes a first container comprising a compound of Formula (I) (e.g., Formulae (II)-(XIX)), or a pharmaceutically acceptable salt thereof, or a composition thereof.

In certain embodiments, the kits are useful in treating a microbial infection in a subject in need thereof. In certain embodiments, the kits are useful in preventing a microbial infection in a subject in need thereof. In certain embodiments, the microbial infection is a bacterial infection. In certain embodiments, the bacterial infection is an infection caused by a Gram-positive bacterium. In certain embodiments, the bacterial infection is an infection caused by a Gram-negative bacterium. In certain embodiments, the microbial infection is a mycobacterial infection. In certain embodiments, the kits are useful in inhibiting the growth of a microorganism. In certain embodiments, the kits are useful in inhibiting the reproduction of a microorganism. In certain embodiments, the kits are useful in killing a microorganism. In certain embodiments, the kits are useful in inhibiting the formation and/or growth of a biofilm. In certain embodiments, the kits are useful in reducing or removing a biofilm. In certain embodiments, the kits are useful in disinfecting a surface. In certain embodiments, the kits are useful for screening a library of compounds to identify a compound that is useful in the methods of the invention. In certain embodiments, the kit further includes instructions for using the compound or pharmaceutical composition included in the kit (e.g., for administering a subject in need of treatment of a microbial infection a compound or pharmaceutical composition of the invention, for contacting a microorganism with a compound or pharmaceutical composition of the invention, or for contacting a biofilm with a compound or pharmaceutical composition of the invention). The kits may also include information as required by a regulatory agency such as the U.S. Food and Drug Administration (FDA). In certain embodiments, the information included in the kits is prescribing information. In certain embodiments, the kits and instructions provide for treating a microbial infection in a subject in need thereof. In certain embodiments, the kits and instructions provide for preventing a microbial infection in a subject in need thereof. In certain embodiments, the kits and instructions provide for inhibiting the growth of a microorganism. In certain embodiments, the kits and instructions provide for inhibiting the reproduction of a microorganism. In certain embodiments, the kits and instructions provide for killing a microorganism. In certain embodiments, the kits and instructions provide for inhibiting the formation and/or growth of a biofilm. In certain embodiments, the kits and instructions provide for reducing or removing a biofilm. In certain embodiments, the kits and instructions provide for disinfecting a surface. In certain embodiments, the kits and instructions provide for screening a library of compounds to identify a compound that is useful in the methods of the invention. The kit of the invention may include one or more additional agents described herein (e.g., additional pharmaceutical agents) as a separate composition.

Methods of Treatment and Uses

Current antibiotics operate primarily through growth-dependent mechanisms and effectively target rapidly-dividing bacteria; however, non-replicative bacteria (e.g., dormant persister cells, bacterial biofilms) display high levels of antibiotic tolerance contributing to persistent and recurring bacterial infection. [1-3] In recent years, the knowledge of bacterial biofilms (surface-attached bacterial communities with altered physiologies, gene expression profiles and growth-rates)[4,5] and persister cells[6] has grown considerably, yet the ability to target persistent bacterial phenotypes remains an unmet challenge. In order to target and eradicate non-replicating bacteria, innovative strategies to identify antibacterial agents that operate through growth-independent mechanisms may be employed.

Although there has been much interest in identifying non-growth altering biofilm inhibitors and dispersal agents over the past two decades,[7] few classes of biofilm-eradicating agents are known. Biofilm-eradicating agents typically operate through the disruption of bacterial membranes (e.g., antimicrobial peptides,[8,9] quaternary ammonium cations/QACs[10]). Although these compounds are indeed valuable, new biofilm-eradicating agents with complementary modes of action are of great importance and have multiple therapeutic applications to address persistent bacterial infections.

Considering the marine environment as an extensive source of microbial diversity and new antibacterial agents,[11] it stands to reason that such sources are fertile grounds for the discovery of biofilm-eradicating agents. Despite marine sources being largely unexplored, several classes of chemically diverse quorum sensing (the bacterial signaling process that controls biofilm formation and maintenance) modulators [12-15] and biofilm inhibitors/dispersal agents have been identified from marine organisms.[7b,16]

The present invention also provides methods for treating a microbial infection (e.g., bacterial infection or mycobacterial infection) in a subject in need thereof. In certain embodiments, the microbial infection is treated by the inventive methods. In certain embodiments, the present invention further provides methods for preventing a microbial infection (e.g., bacterial infection or mycobacterial infection) in a subject in need thereof. In certain embodiments, the microbial infection is prevented by the inventive methods.

In certain embodiments, the subject described herein is an animal. In certain embodiments, the subject is a non-human animal. In certain embodiments, the subject is a mammal. In certain embodiments, the subject is a human. In certain embodiments, the subject is a human with cystic fibrosis. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent, dog, or non-human primate. In certain embodiments, the subject is a non-human transgenic animal, such as a transgenic mouse or transgenic pig.

In certain embodiments, the methods of the invention include administering to a subject in need thereof an effective amount of a compound or pharmaceutical composition of the invention. In certain embodiments, the methods of the invention include administering to a subject in need thereof an effective amount of a compound of Formula (I) (e.g., Formulae (II)-(XIX)), or a pharmaceutically acceptable salt thereof, or a pharmaceutical composition thereof. In certain embodiments, the methods of the invention include administering to a subject in need thereof a therapeutically effective amount of a compound of the invention, or a pharmaceutical composition thereof. In certain embodiments, the methods of the invention include administering to a subject in need thereof a prophylactically effective amount of a compound of the invention, or a pharmaceutical composition thereof.

In certain embodiments, the microbial infection that is treated and/or prevented by the inventive methods or using the inventive compounds or pharmaceutical compositions thereof is caused by a multidrug-resistant microorganism and/or a microorganism resistant to methicillin, penicillin, ciprofloxacin, rifampin, vancomycin, daptomycin, linezolid, any other antibiotic described herein, or a combination thereof. In certain embodiments, the microbial infection is a microbial respiratory tract infection. In certain embodiments, the microbial infection is microbial pneumonia. In certain embodiments, the microbial infection is microbial sinusitis. In certain embodiments, the microbial infection is tuberculosis (TB). In certain embodiments, the microbial infection is microbial Crohn's disease, paratuberculosis, Buruli ulcer, leprosy, or aquarium granuloma. In certain embodiments, the microbial infection is a microbial gastrointestinal tract infection. In certain embodiments, the microbial infection is microbial diarrhea. In certain embodiments, the microbial infection is a microbial urogenital tract infection. In certain embodiments, the microbial infection is a microbial bloodstream infection. In certain embodiments, the microbial infection is microbial hemolytic uremic syndrome. In certain embodiments, the microbial infection is microbial endocarditis. In certain embodiments, the microbial infection is a microbial ear infection. In certain embodiments, the microbial infection is a microbial skin infection (e.g., microbial acne vulgaris). In certain embodiments, the microbial infection is a microbial oral infection. In certain embodiments, the microbial infection is a microbial dental infection. In certain embodiments, the microbial infection is gingivitis. In certain embodiments, the microbial infection is dental plaque caused by a microorganism. In certain embodiments, the microbial infection is microbial meningitis. In certain embodiments, the microbial infection is a microbial wound or surgical site infection. In certain embodiments, the microbial infection is a microbial burn wound infection. In certain embodiments, the microbial infection is a microbial infection associated with cystic fibrosis. In certain embodiments, the microbial infection is a microbial infection associated with an implanted device. In certain embodiments, the microbial infection is a microbial infection associated with a dental implant. In certain embodiments, the microbial infection is a microbial infection associated with a catheter. In certain embodiments, the microbial infection is a microbial infection associated with a heart valve. In certain embodiments, the microbial infection is a microbial infection associated with an intrauterine device. In certain embodiments, the microbial infection is a microbial infection associated with a joint prosthesis. In certain embodiments, the microbial infection is a bacterial infection. In certain embodiments, the bacterial infection is caused by a Gram-positive bacterium (e.g., a Gram-positive bacterium described herein). In certain embodiments, the bacterial infection is caused by a Gram-negative bacterium (e.g., a Gram-negative bacterium described herein). In certain embodiments, the bacterial infection is caused by a multidrug-resistant bacterium. In certain embodiments, the bacterial infection is caused by a strain of *Staphylococcus aureus*. In certain embodiments, the bacterial infection is a methicillin-resistant *Staphylococcus aureus* (MRSA)-related infection. In certain embodiments, the bacterial infection is caused by a strain of *Staphylococcus epidermidis* (e.g., MRSE). In certain embodiments, the bacterial infection is an MRSE-related infection. In certain embodiments, the bacterial infection is caused by a strain of *Enterococcus faecium*. In certain embodiments, the bacterial infection is caused by *Acinetobacter baumannii* (*A. baumannii*). In certain embodiments, the microbial infection is a mycobacterial infection. In certain embodiments, the microbial infection is caused by a mycobacterium (e.g., a strain of *Mycobacterium tuberculosis*). In certain embodiments, the microbial infection is caused by an archaeon. In certain embodiments, the microbial infection is caused by a protist. In certain embodiments, the microbial infection is caused by a protozoon. In certain embodiments, the microbial infection is caused by an alga. In certain embodiments, the microbial infection is caused by a fungus. In certain embodiments, the microbial infection is caused by yeast. In certain embodiments, the microbial infection is caused by a mold. In certain embodiments, the microbial infection is caused by a parasite. In certain embodiments, the microbial infection is a microbial infection associated with a biofilm.

Another aspect of the present invention relates to methods of inhibiting the growth of a microorganism using a compound of the invention, or a pharmaceutical composition thereof. In certain embodiments, an inventive method selectively inhibits the growth of a first microorganism (e.g., a microorganism described herein), compared to the inhibition of the growth of a host cell or a second microorganism. In certain embodiments, the growth of a microorganism is inhibited by the inventive methods. In certain embodiments, the growth of a first microorganism is selectively inhibited by the inventive methods, compared to the inhibition of the growth of a host cell or a second microorganism.

Another aspect of the present invention relates to methods of inhibiting the reproduction of a microorganism using a compound of the invention, or a pharmaceutical composition thereof. In certain embodiments, an inventive method selectively inhibits the reproduction of a first microorganism (e.g., a microorganism described herein), compared to the inhibition of the reproduction of a host cell or a second microorganism. In certain embodiments, the reproduction of a microorganism is inhibited by the inventive methods. In certain embodiments, the reproduction of a first microorganism is selectively inhibited by the inventive methods, compared to the inhibition of the reproduction of a host cell or a second microorganism.

Another aspect of the present invention relates to methods of inhibiting the viability of a microorganism using a compound of the invention, or a pharmaceutical composition thereof. In certain embodiments, an inventive method selectively inhibits the viability of a first microorganism (e.g., a microorganism described herein), compared to the inhibition of the viability of a host cell or a second microorganism. In certain embodiments, the viability of a microorganism is inhibited by the inventive methods. In certain embodiments, the viability of a first microorganism is selectively inhibited by the inventive methods, compared to the inhibition of the viability of a host cell or a second microorganism.

Another aspect of the present invention relates to methods of killing a microorganism using a compound of the invention, or a pharmaceutical composition thereof. In certain embodiments, an inventive method selectively kills a first microorganism (e.g., a microorganism described herein), compared to the killing of a host cell or a second microorganism. In certain embodiments, a microorganism is killed by the inventive methods. In certain embodiments, a first microorganism is selectively killed by the inventive methods, compared to the killing of a host cell or a second microorganism.

In certain embodiments, the methods of the invention include contacting a microorganism with an effective amount of a compound or pharmaceutical composition of the invention. In certain embodiments, the methods of the invention include contacting a microorganism with an effective amount of a compound of Formula (I) (e.g., Formulae (II)-(XIX)), or a pharmaceutically acceptable salt thereof, or a pharmaceutical composition thereof. In certain embodiments, the methods of the invention include contacting a microorganism with a therapeutically effective amount of a compound of the invention, or a pharmaceutical composition thereof. In certain embodiments, the methods of the invention include contacting a microorganism with a prophylactically effective amount of a compound of the invention, or a pharmaceutical composition thereof.

In a growth process of a microorganism (e.g., a bacterium), the microorganism may secrete viscous substances to form a biofilm. A biofilm is typically formed on a living or non-living, solid or liquid surface. In certain embodiments, a biofilm is formed on the surface of a biological sample (e.g., a tooth, oral soft tissue, middle ear, gastrointestinal tract, urogenital tract, respiratory tract, or eye). In certain embodiments, a biofilm is formed on the surface of an implanted device (e.g., a dental implant, catheter, heart valve, intrauterine device, or joint prosthesis). In certain embodiments, the biofilm is in vitro. In certain embodiments, the biofilm is in vivo. In certain embodiments, the biofilm described herein comprises a microorganism. In certain embodiments, the biofilm comprises a microorganism (e.g., bacterium). In certain embodiments, the biofilm comprises a strain of *Staphylococcus aureus* (e.g., a methicillin-resistant strain of *Staphylococcus aureus*). In certain embodiments, the biofilm comprises a strain of *Staphylococcus epidermidis* (e.g., a strain of MRSE). Free-floating microorganisms may accumulate on a surface, and the resulting biofilm may grow. In a biofilm, the concentration of microorganisms may be high and/or the resistance of the microorganisms in the biofilm to antimicrobial agents may be high. Antimicrobials may be inactivated or fail to penetrate into the biofilm. Therefore, microbial infections associated with a biofilm (e.g., microbial infections caused by a biofilm) are typically more difficult to treat than microbial infections not associated with a biofilm.

Another aspect of the present invention relates to methods of inhibiting the formation of a biofilm using a compound of the invention, or a pharmaceutical composition thereof. In certain embodiments, the formation of a biofilm is inhibited by the inventive methods.

Another aspect of the present invention relates to methods of inhibiting the growth of a biofilm using a compound of the invention, or a pharmaceutical composition thereof. In certain embodiments, the growth of a biofilm is inhibited by the inventive methods.

Another aspect of the present invention relates to methods of reducing a biofilm using a compound of the invention, or a pharmaceutical composition thereof. In certain embodiments, a biofilm is reduced by the inventive methods, e.g., reduced by at least 10%, at least 20%, at least 30%, at least 50%, at least 70%, at least 90%, at least 99%, at least 99.9%, or at least 99.99%, in terms of the volume of the biofilm. In certain embodiments, a biofilm is reduced by the inventive methods by not more than 10%, not more than 20%, not more than 30%, not more than 50%, not more than 70%, not more than 90%, not more than 99%, not more than 99.9%, or not more than 99.99%, in terms of the volume of the biofilm. In certain embodiments, a biofilm is reduced by the inventive methods by at least 10%, at least 20%, at least 30%, at least 50%, at least 70%, at least 90%, at least 99%, at least 99.9%, or at least 99.99%, in terms of the number of microorganisms (e.g., bacteria) in the biofilm. In certain embodiments, a biofilm is reduced by the inventive methods by not more than 10%, not more than 20%, not more than 30%, not more than 50%, not more than 70%, not more than 90%, not more than 99%, not more than 99.9%, or not more than 99.99%, in terms of the number of microorganisms (e.g., bacteria) in the biofilm.

Another aspect of the present invention relates to methods of removing a biofilm (e.g., eradicating a biofilm (e.g., reducing the volume of the biofilm by at least 99% and/or killing essentially all (e.g., at least 99%) of the microorganisms (e.g., bacteria) in the biofilm)) using a compound of the invention, or a pharmaceutical composition thereof. In certain embodiments, a biofilm is removed by the inventive methods. In certain embodiments, a biofilm reduced or removed by a method of the invention does not regrow one day, two days, four days, one week, two weeks, three weeks, or one month subsequent to the biofilm being subject to the method.

In certain embodiments, the methods of the invention include contacting a biofilm with an effective amount of a compound or pharmaceutical composition of the invention. In certain embodiments, the methods of the invention include contacting a biofilm with an effective amount of a compound of Formula (I) (e.g., Formulae (II)-(XIX)), or a pharmaceutically acceptable salt thereof, or a pharmaceutical composition thereof. In certain embodiments, the methods of the invention include contacting a biofilm with a therapeutically effective amount of a compound of the invention, or a pharmaceutical composition thereof. In certain embodiments, the methods of the invention include contacting a biofilm with a prophylactically effective amount of a compound of the invention, or a pharmaceutical composition thereof.

Another aspect of the present invention relates to methods of disinfecting a surface, the methods including contacting the surface with an effective amount of a compound or composition (e.g., pharmaceutical composition) of the invention. In certain embodiments, the number of viable microorganisms on the surface is reduced after the surface is contacted with the compound or composition. In certain embodiments, the surface is a biological surface, such as skin (e.g., skin of: the hands, feet, arms, legs, face, neck, torso, or cavity (e.g., oral cavity)) of a subject. In certain embodiments, the surface is a non-biological surface (e.g., a surface in a household, industrial, or medical setting, such as a surface of: a kitchen, bathroom, table top, floor, wall, window, utensil, cutlery, crockery, or medical device). A non-biological surface may be a surface of a solid material, such as plastic, wood, bamboo, metal, ceramic, glass, concrete, stone, paper, fabric, or a combination thereof. A non-biological surface may be painted or non-painted, or coated or non-coated. In certain embodiments, the amount of the compound or composition is effective for killing at least 80%, at least 90%, at least 95%, at least 99%, at least 99.9%, or at least 99.99% of the microorganisms on the surface.

In certain embodiments, the microorganism described herein is a bacterium. In certain embodiments, the microorganism is multidrug-resistant. In certain embodiments, the microorganism is resistant to methicillin, penicillin, ciprofloxacin, rifampin, vancomycin, daptomycin, linezolid, or a combination thereof. In certain embodiments, the microorganism is associated with a biofilm (e.g., present in and/or on a biofilm, able to form a biofilm, and/or able to increase the size of a biofilm). In certain embodiments, the bacterium is a Gram-positive bacterium. In certain embodiments, the bacterium is a multidrug-resistant bacterium. In certain embodiments, the bacterium is a *Staphylococcus* species. In certain embodiments, the bacterium is a *Staphylococcus aureus* (*S. aureus*) strain (e.g., ATCC 25923). In certain embodiments, the bacterium is methicillin-resistant *Staphylococcus aureus* (MRSA). In certain embodiments, the bacterium is the methicillin-resistant *Staphylococcus aureus* clinical isolate (MRSA-2, a clinical isolate from a patient treated at Shands Hospital; obtained from the Emerging Pathogens Institute at the University of Florida), such as the methicillin-resistant *Staphylococcus aureus* clinical isolate reported in Abouelhassan et al., *Bioorg. Med. Chem. Lett.*, 2014, 24, 5076. In certain embodiments, the bacterium is a *Staphylococcus epidermidis* (*S. epidermidis*) strain (e.g., ATCC 12228 or ATCC 35984). In certain embodiments, the bacterium is an MRSE strain. In certain embodiments, the bacterium is a *Staphylococcus auricularis, Staphylococcus carnosus, Staphylococcus condimenti, Staphylococcus massiliensis, Staphylococcus piscifermentans, Staphylococcus simulans, Staphylococcus capitis, Staphylococcus caprae, Staphylococcus saccharolyticus, Staphylococcus devriesei, Staphylococcus haemolyticus, Staphylococcus hominis, Staphylococcus chromogenes, Staphylococcus felis, Staphylococcus delphini, Staphylococcus hyicus, Staphylococcus intermedius, Staphylococcus lutrae, Staphylococcus microti, Staphylococcus muscae, Staphylococcus pseudintermedius, Staphylococcus rostri, Staphylococcus schleiferi, Staphylococcus lugdunensis, Staphylococcus*

*arlettae, Staphylococcus cohnii, Staphylococcus equorum, Staphylococcus gallinarum, Staphylococcus kloosii, Staphylococcus leei, Staphylococcus nepalensis, Staphylococcus saprophyticus, Staphylococcus succinus, Staphylococcus xylosus, Staphylococcus fleurettii, Staphylococcus lentus, Staphylococcus sciuri, Staphylococcus stepanovicii, Staphylococcus vitulinus, Staphylococcus simulans, Staphylococcus pasteuri,* or *Staphylococcus warneri* strain. In certain embodiments, the bacterium is a *Streptococcus* species. In certain embodiments, the bacterium is a *Streptococcus agalactiae, Streptococcus anginosus, Streptococcus bovis, Streptococcus canis, Streptococcus constellatus, Streptococcus dysgalactiae, Streptococcus equinus, Streptococcus iniae, Streptococcus intermedius, Streptococcus mitis, Streptococcus mutans, Streptococcus oxalis, Streptococcus parasanguinis, Streptococcus peroris, Streptococcus pneumoniae, Streptococcus pseudopneumoniae, Streptococcus pyogenes, Streptococcus ratti, Streptococcus salivarius, Streptococcus tigurinus, Streptococcus thermophilus, Streptococcus sanguinis, Streptococcus sobrinus, Streptococcus suis, Streptococcus uberis, Streptococcus vestibularis, Streptococcus viridans,* or *Streptococcus zooepidemicus* strain. In certain embodiments, the bacterium is an *Enterococcus* species. In certain embodiments, the bacterium is an *Enterococcus avium, Enterococcus durans, Enterococcus faecalis, Enterococcus faecium, Enterococcus gallinarum, Enterococcus hirae,* or *Enterococcus solitarius* strain. In certain embodiments, the bacterium is an *Enterococcus faecium* strain (e.g., a vancomycin-resistant strain of *Enterococcus faecium* (VRE); ATCC 700221). In certain embodiments, the bacterium is a *Listeria* species. In certain embodiments, the bacterium is a *Listeria fleischmannii, Listeria grayi, Listeria innocua, Listeria ivanovii, Listeria marthii, Listeria monocytogenes, Listeria rocourtiae, Listeria seeligeri, Listeria weihenstephanensis,* or *Listeria welshimeri* strain. In certain embodiments, the bacterium is a *Clostridium* species. In certain embodiments, the bacterium is a *Clostridium acetobutylicum, Clostridium argentinense, Clostridium aerotolerans, Clostridium baratii, Clostridium beijerinckii, Clostridium bifermentans, Clostridium botulinum, Clostridium butyricum, Clostridium cadaveris, Clostridium cellulolyticum, Clostridium chauvoei, Clostridium clostridioforme, Clostridium colicanis, Clostridium difficile, Clostridium estertheticum, Clostridium fallax, Clostridium feseri, Clostridium formicaceticum, Clostridium histolyticum, Clostridium innocuum, Clostridium kluyveri, Clostridium ljungdahlii, Clostridium lavalense, Clostridium leptum, Clostridium novyi, Clostridium oedematiens, Clostridium paraputrificum, Clostridium perfringens* (Alias: *Clostridium welchii*), *Clostridium phytofermentans, Clostridium piliforme, Clostridium ragsdalei, Clostridium ramosum, Clostridium scatologenes, Clostridium septicum, Clostridium sordellii, Clostridium sporo genes, Clostridium sticklandii, Clostridium tertium, Clostridium tetani, Clostridium thermocellum, Clostridium thermosaccharolyticum,* or *Clostridium tyrobutyricum* strain. In certain embodiments, the bacterium is a Gram-negative bacterium. In certain embodiments, the bacterium is a bacterium described herein, provided that the bacterium is not a Gram-negative bacterium. In certain embodiments, the Gram-negative bacterium is an *Escherichia* species. In certain embodiments, the Gram-negative bacterium is an *Escherichia coli* (*E. coli*) strain (e.g., ATCC 33475, K-12, CFT073, ATCC 43895). In certain embodiments, the Gram-negative bacterium is an *Escherichia albertii* strain, *Escherichia blattae* strain, *Escherichia fergusonii* strain, *Escherichia hermannii* strain, or *Escherichia vulneris* strain. In certain embodiments, the Gram-negative bacterium is a *Pseudomonas* species. In certain embodiments, the Gram-negative bacterium is a *Pseudomonas aeruginosa* strain. In certain embodiments, the Gram-negative bacterium is a *Pseudomonas alcaligenes* strain, *Pseudomonas anguilliseptica* strain, *Pseudomonas argentinensis* strain, *Pseudomonas borbori* strain, *Pseudomonas citronellolis* strain, *Pseudomonas flavescens* strain, *Pseudomonas mendocina* strain, *Pseudomonas nitroreducens* strain, *Pseudomonas oleovorans* strain, *Pseudomonas pseudoalcaligenes* strain, *Pseudomonas resinovorans* strain, *Pseudomonas straminea* strain, *Pseudomonas chlororaphis* strain, *Pseudomonas fluorescens* strain, *Pseudomonas pertucinogena* strain, *Pseudomonas putida* strain, *Pseudomonas stutzeri* strain, or *Pseudomonas syringae* strain. In certain embodiments, the Gram-negative bacterium is a *Klebsiella* species. In certain embodiments, the Gram-negative bacterium is a *Klebsiella granulomatis* strain, *Klebsiella oxytoca* strain, *Klebsiella pneumoniae* strain, *Klebsiella terrigena* strain, or *Klebsiella planticola* strain. In certain embodiments, the Gram-negative bacterium is a strain of *Klebsiella pneumoniae* (*K. pneumoniae*). In certain embodiments, the Gram-negative bacterium is a *Salmonella* species. In certain embodiments, the Gram-negative bacterium is a *Salmonella bongori* strain or *Salmonella enterica* strain, e.g., *Salmonella typhi*. In certain embodiments, the Gram-negative bacterium is an *Acinetobacter* species. In certain embodiments, the Gram-negative bacterium is an *Acinetobacter baumannii* strain. In certain embodiments, the Gram-negative bacterium is an *Acinetobacter baylyi* strain, *Acinetobacter bouvetii* strain, *Acinetobacter calcoaceticus* strain, *Acinetobacter gerneri* strain, *Acinetobacter grimontii* strain, *Acinetobacter haemolyticus* strain, *Acinetobacter johnsonii* strain, *Acinetobacter junii* strain, *Acinetobacter lwoffii* strain, *Acinetobacter parvus* strain, *Acinetobacter pittii* strain, *Acinetobacter radioresistens* strain, *Acinetobacter schindleri* strain, *Acinetobacter tandoii* strain, *Acinetobacter tjernbergiae* strain, *Acinetobacter towneri* strain, *Acinetobacter ursingii* strain, or *Acinetobacter gyllenbergii* strain. In certain embodiments, the microorganism is a mycobacterium. In certain embodiments, the microorganism is a strain of *Mycobacterium tuberculosis*. In certain embodiments, the microorganism is a strain of: *Mycobacterium bovis, Mycobacterium bovis* BCG, *Mycobacterium africanum, Mycobacterium canetti, Mycobacterium caprae, Mycobacterium microti, Mycobacterium pinnipedii, Mycobacterium avium, Mycobacterium avium paratuberculosis, Mycobacterium avium silvaticum, Mycobacterium avium hominissuis, Mycobacterium colombiense, Mycobacterium indicus pranii, Mycobacterium gastri, Mycobacterium kansasii, Mycobacterium hiberniae, Mycobacterium nonchromogenicum, Mycobacterium terrae, Mycobacterium triviale, Mycobacterium ulcerans, Mycobacterium pseudoshottsii, Mycobacterium shottsii, Mycobacterium triplex, Mycobacterium genavense, Mycobacterium florentinum, Mycobacterium lentiflavum, Mycobacterium palustre, Mycobacterium kubicae, Mycobacterium parascrofulaceum, Mycobacterium heidelbergense, Mycobacterium interjectum, Mycobacterium simiae, Mycobacterium bohemicum, Mycobacterium botniense, Mycobacterium branderi, Mycobacterium celatum, Mycobacterium chimaera, Mycobacterium conspicuum, Mycobacterium cookii, Mycobacterium doricum, Mycobacterium farcinogenes, Mycobacterium haemophilum, Mycobacterium heckeshornense, Mycobacterium intracellulare, Mycobacterium lacus, Mycobacterium leprae, Mycobacterium lepraemurium, Mycobacterium lepromatosis, Mycobacte-* rium malmoense, Mycobacterium marinum, Mycobacterium monacense, Mycobacterium montefiorense, Mycobacterium murale, Mycobacterium nebraskense, Mycobacterium saskatchewanense, Mycobacterium scrofulaceum, Mycobacterium shimoidei, Mycobacterium szulgai, Mycobacterium tusciae, Mycobacterium xenopi, Mycobacterium yongonense, Mycobacterium intermedium, Mycobacterium abscessus, Mycobacterium chelonae, Mycobacterium bolletii, Mycobacterium fortuitum, Mycobacterium fortuitum subsp. acetamidolyticum, Mycobacterium boenickei, Mycobacterium peregrinum, Mycobacterium porcinum, Mycobacterium senegalense, Mycobacterium septicum, Mycobacterium neworleansense, Mycobacterium houstonense, Mycobacterium mucogenicum, Mycobacterium mageritense, Mycobacterium brisbanense, Mycobacterium cosmeticum, Mycobacterium parafortuitum, Mycobacterium austroafricanum, Mycobacterium diernhoferi, Mycobacterium hodleri, Mycobacterium neoaurum, Mycobacterium frederiksbergense, Mycobacterium aurum, Mycobacterium vaccae, Mycobacterium chitae, Mycobacterium fallax, Mycobacterium confluentis, Mycobacterium flavescens, Mycobacterium madagascariense, Mycobacterium phlei, Mycobacterium smegmatis Mycobacterium goodii, Mycobacterium wolinskyi, Mycobacterium the rmoresistibile, Mycobacterium gadium, Mycobacterium komossense, Mycobacterium obuense, Mycobacterium sphagni, Mycobacterium agri, Mycobacterium aichiense, Mycobacterium alvei, Mycobacterium arupense, Mycobacterium brumae, Mycobacterium canariasense, Mycobacterium chubuense, Mycobacterium conceptionense, Mycobacterium duvalii, Mycobacterium elephantis, Mycobacterium gilvum, Mycobacterium hassiacum, Mycobacterium holsaticum, Mycobacterium immunogenum, Mycobacterium massiliense, Mycobacterium moriokaense, Mycobacterium psychrotolerans, Mycobacterium pyrenivorans, Mycobacterium vanbaalenii, Mycobacterium pulveris, Mycobacterium arosiense, Mycobacterium aubagnense, Mycobacterium caprae, Mycobacterium chlorophenolicum, Mycobacterium fluoroanthenivorans, Mycobacterium kumamotonense, Mycobacterium novocastrense, Mycobacterium parmense, Mycobacterium phocaicum, Mycobacterium poriferae, Mycobacterium rhodesiae, Mycobacterium seoulense, or Mycobacterium tokaiense.

In certain embodiments, the microorganism described herein is an archaeon. In certain embodiments, the microorganism is a protist. In certain embodiments, the microorganism is a protozoon. In certain embodiments, the microorganism is an alga. In certain embodiments, the microorganism is a fungus. In certain embodiments, the microorganism is yeast. In certain embodiments, the microorganism is a mold. In certain embodiments, the microorganism is a parasite.

In certain embodiments, the microorganism described herein is in vitro. In certain embodiments, the microorganism is in vivo.

In certain embodiments, a method of the invention is an in vitro method. In certain embodiments, a method of the invention is an in vivo method.

In another aspect, the present invention provides uses of the compounds, compositions, and pharmaceutical compositions of the invention for manufacturing a medicament for treating a microbial infection (e.g., bacterial infection or mycobacterial infection).

In another aspect, the present invention provides uses of the compounds, compositions, and pharmaceutical compositions of the invention for manufacturing a medicament for preventing a microbial infection (e.g., bacterial infection or mycobacterial infection).

In another aspect, the present invention provides the compounds, compositions, and pharmaceutical compositions of the invention for use in treating a microbial infection (e.g., bacterial infection or mycobacterial infection).

In another aspect, the present invention provides the compounds, compositions, and pharmaceutical compositions of the invention for use in preventing a microbial infection (e.g., bacterial infection or mycobacterial infection).

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope. A compound described herein may be referred to by using two or more different compound numbers. A compound described herein may be tested two or more times under the same or different conditions for determining a property and, therefore, may show different values of the property.

Example 1

Synthesis of the Compounds

The compounds provided herein can be prepared from readily available starting materials using the following general methods and procedures. It will be appreciated that where typical or preferred process conditions (e.g., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, N.Y., 1991, and references cited therein.

The compounds of the invention can be prepared using previously reported synthetic protocols (e.g., E. Breitmaier, *J. Org. Chem.*, 1976, 41, 2104-2108; D. L. Vivan, *Nature*, 1956, 178, 753; M. Conda-Sheridan et al., *J. Med. Chem.*, 2010, 53, 8688-8699; G. W. Rewcastle et al., *J. Med. Chem.*, 1987, 30, 843-851; international PCT application publication, WO 2015/100331, published Jul. 2, 2015; each of which is incorporated herein by reference).

General Experimental Information

All synthetic reactions were carried out under an inert atmosphere of argon unless otherwise specified.

All reagents for chemical synthesis were purchased from commercial sources and used without further purification. Reagents were purchased at ≥95% purity and commercially available controls were used in the biological investigations without further purification. All microwave reactions were carried out in sealed tubes in an Anton Paar Monowave 300 Microwave Synthesis Reactor. A constant power was applied to ensure reproducibility. Temperature control was automated via IR sensor and all indicated temperatures correspond to the maximal temperature reached during each experiment. Analytical thin layer chromatography (TLC) was performed using 250 µm Silica Gel 60 F254 pre-coated plates (EMD Chemicals Inc.). Flash column chromatography was performed using 230-400 Mesh 60 Å Silica Gel from Sorbent Technologies. All melting points were obtained, uncorrected, using a Mel-Temp capillary melting point apparatus from Laboratory Services, Inc.

NMR experiments were recorded using broadband probes on a Varian Mercury-Plus-400 spectrometer via VNMR-J software (400 MHz for $^1$H and 100 MHz for $^{13}$C). All spectra are presented using MestReNova 11.0 (Mnova) software and are displayed without the use of the signal suppression function. Spectra were obtained in the following solvents (reference peaks also included for $^1$H and $^{13}$C NMRs): CDCl$_3$ ($^1$H NMR: 7.26 ppm; $^{13}$C NMR: 77.23 ppm) and d$_6$-DMSO ($^1$H NMR: 2.50 ppm; $^{13}$C NMR: 39.52 ppm). All NMR experiments were performed at room temperature. Chemical shift values (δ) are reported in parts per million (ppm) for all $^1$H NMR and $^{13}$C NMR spectra. $^1$H NMR multiplicities are reported as: br=broad, s=singlet, d=doublet, t=triplet, q=quartet, m=multiplet. High-Resolution Mass Spectrometry (HRMS) were obtained for all new compounds from the Chemistry Department at the University of Florida.

All compounds evaluated in biological assays were determined to be ≥95% pure via LC-MS using a Shimadzu Prominence HPLC system, AB Sciex 3200 QTRAP spectrometer and a Kinetex C18 column (50 mm×2.1 mm×2.6 µm) with a 35-minute linear gradient from 10-65% acetonitrile in 0.5% formic acid at a flow rate of 0.25 mL/min. Bacterial strains used during these investigations include: methicillin-resistant *Staphylococcus aureus* (Clinical Isolate from Shands Hospital in Gainesville, Fla.: MRSA-2; ATCC strains: BAA-1707, BAA-44) methicillin-resistant *Staphylococcus epidermidis* (MRSE strain ATCC 35984), and vancomycin-resistant *Enterococcus faecium* (VRE strain ATCC 700221). All compounds were stored as DMSO stocks at room temperature in the absence of light for several months at a time without observing any loss in biological activity. To ensure compound integrity of the DMSO stock solutions, DMSO stocks of the test compounds were not subjected to freeze-thaw cycles.

Buchwald-Hartwig (BH)-Reductive Cyclization (RC) Route

Select compounds of the invention were prepared according to the methods shown in FIGS. 1-5. Various anilines were reacted with bromo-nitroanisoles under Buchwald-Hartwig cross coupling conditions followed by reductive cyclization to afford Compounds 1-20. BBr$_3$ mediated demethylation followed by bromination with N-bromosuccinimide (NBS) afforded Compounds 26, 27, 34-38, and 40-42. Attachment of water-solubilizing prodrugs to Compounds 26 and 27 afforded Compounds 28-33.

Exemplary calculated properties of select compounds of the invention are shown in Table 1.

TABLE 1

Exemplary calculated properties of select compounds of the invention

| Compound # | cLogP |
|---|---|
| 28 | 2.70 |
| 29 | 5.06 |

TABLE 1-continued

Exemplary calculated properties of select compounds of the invention

| Compound # | cLogP |
|---|---|
| 30 | 4.12 |
| 31 | 3.61 |
| 32 | 4.30 |
| 33 | 3.55 |

Wohl-Aue Route

Figure 11:
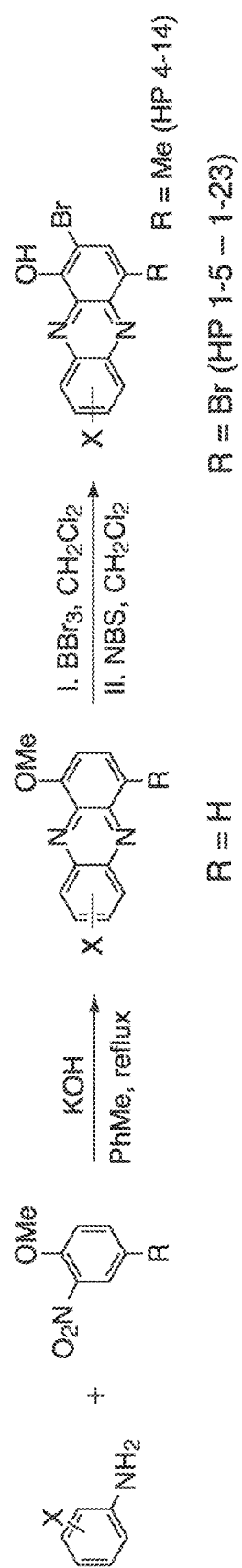
FIG. 11 shows a synthetic route using the Wohl-Aue reaction to assemble the phenazine core of the compounds of Formula (I) (e.g., Formulae (II)-(XIX)).

The Wohl-Aue reaction[33,34] involves the base-promoted condensation between a nitroarene and an aniline to yield a phenazine (FIG. 11). With the potential to diversify the HP scaffold at the 6-,7-,8- and 9-positions with an array of substituted aniline building blocks, 2-nitroanisole was utilized in Wohl-Aue condensation reactions with a panel of 9 diverse anilines to produce the corresponding HPs in three steps, enabling rapid and extensive biological evaluations (FIG. 12). After the Wohl-Aue reaction, 1-methoxyphenazines were subjected to boron tribromide demethylation to afford 1-hydroxyphenazines (33-100% yield, 88% average yield). Final bromination with N-bromosuccinimide (NBS) produced 2,4-dibromo-HP analogues 1-15 to 1-23 (30-81% yield, 50% average yield, 9 examples).

General Wohl-Aue Procedure

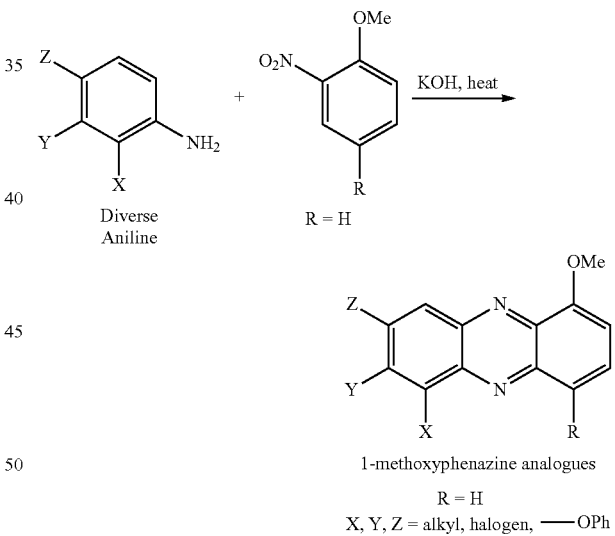

Diverse Aniline

R = H 1-methoxyphenazine analogues

R = H
X, Y, Z = alkyl, halogen, ——OPh

To a round-bottom flask is added the aniline (1 eq.), the nitroanisole (1.1 eq.), and potassium hydroxide (5.0 eq.) in toluene. The reaction is then allowed to reflux for about 10 hours. After the reaction is complete, the resulting mixture is then transferred to a separatory funnel with brine and extracted with dichloromethane. The organic layers are combined, filtered and concentrated in vacuo. The resulting crude solid is purified via column chromatography using hexanes:ethyl acetate to afford the corresponding 1-methoxyphenazine compounds.

This general Wohl-Aue procedure was used to prepare the following 1-methoxyphenazine compounds.

Example 1-37

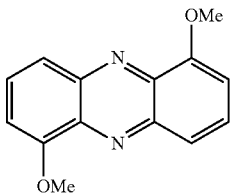

1-37

Yield: 3% yield; 650 mg of 1-37 was isolated as a yellow solid.

$^1$H NMR (400 MHz, CDCl$_3$): δ 7.98 (dd, J=8.9, 1.1 Hz, 2H), 7.73 (dd, J=8.9, 7.6 Hz, 2H), 7.08 (dd, J=7.6, 1.1 Hz, 2H), 4.16 (s, 6H).

$^{13}$C NMR (100 MHz, CDCl$_3$): δ 155.1, 143.2, 137.1, 130.3, 122.2, 107.0, 56.7.

Note: NMR spectra matches those previously reported.

Example 1-38

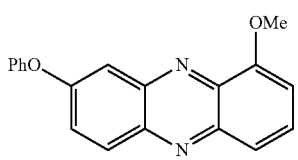

1-38

Yield: 13% yield; 566 mg of 1-38 was isolated as a yellow solid.

$^1$H NMR (400 MHz, CDCl$_3$): δ 8.19 (d, J=9.4 Hz, 1H), 7.79 (dd, J=8.9, 1.1 Hz, 1H), 7.73 (dd, J=9.4, 2.7 Hz, 1H), 7.67 (dd, J=8.8, 7.6 Hz, 1H), 7.51 (d, J=2.7 Hz, 1H), 7.49-7.42 (m, 2H), 7.28 (m, 1H), 7.24-7.17 (m, 2H), 7.04 (d, J=7.6 Hz, 1H), 4.12 (s, 3H). Note: TMS was used as a reference (0.00 ppm) due to the CHCl$_3$ signal being buried in a concentrated NMR sample.

$^{13}$C NMR (100 MHz, CDCl$_3$): δ 160.5, 154.9, 154.9, 143.4, 143.2, 141.0, 136.9, 131.0, 130.5, 129.5, 126.3, 125.6, 121.6, 121.4, 110.9, 106.9, 56.5.

HRMS (ESI): calc. for C$_{19}$H$_{15}$N$_2$O$_2$ [M+H]$^+$: 303.1128, found: 303.1132.

MP: 187-189° C.

Example 1-39

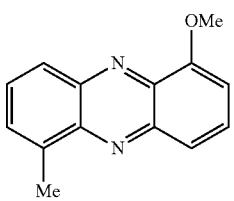

1-39

Yield: 7% yield; 444 mg of 1-39 was isolated as a yellow solid.

$^1$H NMR (400 MHz, d$_6$-DMSO): δ 8.10 (dd, J=8.2, 1.9 Hz, 1H), 7.88-7.75 (m, 4H), 7.27 (d, J=7.4 Hz, 1H), 4.07 (s, 3H), 2.83 (s, 3H).

$^{13}$C NMR (100 MHz, d$_6$-DMSO): δ 154.9, 142.7, 142.2, 141.8, 136.9, 136.0, 131.0, 130.4, 130.3, 127.6, 120.9, 107.2, 56.0, 17.3.

HRMS (ESI): calc. for C$_{14}$H$_{13}$N$_2$O [M+H]$^+$: 225.1022, found: 225.1021.

MP: 189-191° C.

Example 1-40

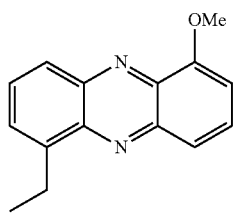

1-40

Yield: 5% yield; 212 mg of 1-40 was isolated as an orange solid.

$^1$H NMR (400 MHz, CDCl$_3$): δ 8.23 (m, 1H), 7.86 (dd, J=8.7, 1.1 Hz, 1H), 7.79-7.68 (m, 2H), 7.66 (dq, J=6.8, 1.1 Hz, 1H), 7.06 (dd, J=7.5, 1.1 Hz, 1H), 4.18 (s, 3H), 3.43 (q, J=7.5 Hz, 2H), 1.45 (t, J=7.5 Hz, 3H).

$^{13}$C NMR (100 MHz, CDCl$_3$): δ 155.2, 143.7, 143.5, 142.8, 142.6, 136.6, 130.4, 130.0, 128.3, 128.2, 122.2, 106.4, 56.6, 24.3, 14.9.

HRMS (ESI): calc. for C$_{15}$H$_{15}$N$_2$O [M+H]$^+$: 239.1179, found: 239.1177.

MP: 132-134° C.

Example 1-41

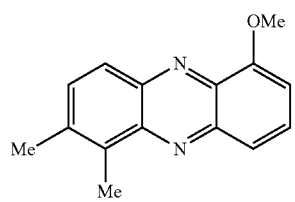

1-41

Yield: 6% yield; 300 mg of 1-41 was isolated as a red solid.

$^1$H NMR (400 MHz, CDCl$_3$): δ 8.14 (m, 1H), 7.85 (dd, J=8.9, 1.1 Hz, 1H), 7.70 (dd, J=8.9, 7.6 Hz, 1H), 7.64 (d, J=8.9 Hz, 1H), 7.03 (d, J=7.6 Hz, 1H), 4.17 (s, 3H), 2.86 (s, 3H), 2.57 (s, 3H).

$^{13}$C NMR (100 MHz, CDCl$_3$): δ 155.1, 143.6, 143.2, 141.3, 138.1, 135.8, 134.2, 134.0, 129.8, 127.1, 122.0, 106.0, 56.5, 20.9, 13.3.

HRMS (ESI): calc. for C$_{15}$H$_{15}$N$_2$O [M+H]$^+$: 239.1179, found: 239.1172.

MP: 156-158° C.

Example 1-42

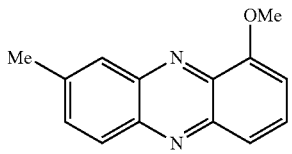

Yield: 2% yield; 158 mg of 1-42 was isolated as a yellow solid.

$^1$H NMR (400 MHz, CDCl$_3$): δ 8.14 (dq, J=1.8, 1.1 Hz, 1H), 8.09 (d, J=8.9 Hz, 1H), 7.79 (dd, J=8.9, 1.1 Hz, 1H), 7.72-7.64 (m, 2H), 7.03 (dd, J=7.6, 1.1 Hz, 1H), 4.15 (s, 3H), 2.62 (d, J=1.1 Hz, 3H).

$^{13}$C NMR (100 MHz, CDCl$_3$): δ 155.2, 143.9, 142.5, 142.5, 141.0, 136.9, 134.0, 130.1, 128.9, 128.5, 121.6, 106.5, 56.6, 22.4.

HRMS (ESI): calc. for C$_{14}$H$_{13}$N$_2$O [M+H]$^+$: 225.1022, found: 225.1027.

MP: 181-183° C.

Example 1-43

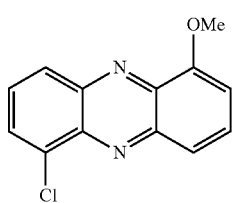

Yield: 3% yield; 155 mg of 1-43 was isolated as a yellow solid.

$^1$H NMR (400 MHz, CDCl$_3$): δ 8.33 (dd, J=8.8, 1.4 Hz, 1H), 7.97 (m, 1H), 7.95 (d, J=1.3 Hz, 1H), 7.80 (dd, J=8.9, 7.7 Hz, 1H), 7.73 (dd, J=8.8, 7.3 Hz, 1H), 7.11 (dd, J=7.7, 1.1 Hz, 1H), 4.18 (s, 3H).

$^{13}$C NMR (100 MHz, CDCl$_3$): δ 155.1, 144.3, 142.8, 140.4, 137.3, 133.0, 131.4, 130.4, 129.6, 129.6, 122.0, 107.4, 56.8.

HRMS (ESI): calc. for C$_{13}$H$_{10}$ClN$_2$O [M+H]$^+$: 245.0476, found: 245.0451.

MP: 221-223° C.

Example 1-44

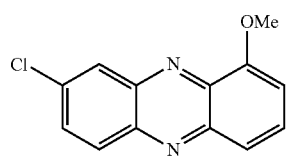

Yield: 12% yield; 292 mg of 1-44 was isolated as a yellow solid.

$^1$H NMR (400 MHz, CDCl$_3$): δ 8.41 (d, J=2.3 Hz, 1H), 8.17 (d, J=9.2 Hz, 1H), 7.87-7.71 (m, 3H), 7.10 (dd, J=7.3, 1.4 Hz, 1H), 4.18 (s, 3H).

$^{13}$C NMR (100 MHz, CDCl$_3$): 155.2, 144.3, 142.2, 142.1, 137.3, 136.4, 132.3, 131.0, 130.8, 128.7, 121.6, 107.2, 56.7.

HRMS (ESI): calc. for C$_{13}$H$_{10}$ClN$_2$O [M+H]$^+$: 245.0476, found: 245.0473.

MP: 206-208° C.

Example 1-45

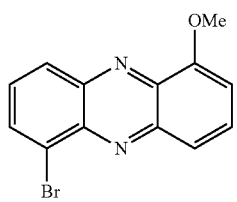

Yield: 1% yield; 106 mg of 1-45 was isolated as an orange solid.

$^1$H NMR (400 MHz, CDCl$_3$): δ 8.38 (dd, J=8.7, 1.2 Hz, 1H), 8.20 (dd, J=7.3, 1.2 Hz, 1H), 7.98 (dd, J=8.9, 1.1 Hz, 1H), 7.81 (dd, J=8.9, 7.6 Hz, 1H), 7.68 (dd, J=8.8, 7.3 Hz, 1H), 7.12 (dd, J=7.6, 1.1 Hz, 1H), 4.19 (s, 3H).

$^{13}$C NMR (100 MHz, CDCl$_3$): δ 155.1, 144.6, 142.8, 141.1, 137.4, 134.2, 131.4, 130.4, 130.3, 124.2, 122.1, 107.4, 56.8.

HRMS (ESI): calc. for C$_{13}$H$_9$BrN$_2$ONa [M+Na]$^+$ 310.9805, found: 310.9805. MP: 224-226° C.

General Procedure for Demethylation of 1-Methoxyphenazines

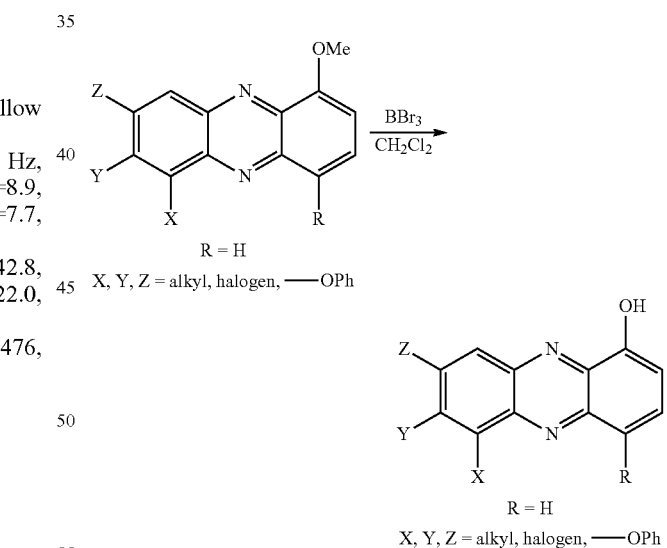

To a round bottom flask, 1-39 (376 mg, 1.68 mmol) was dissolved in anhydrous dichloromethane (50 mL) and cooled to −78° C. before dropwise addition of a 1M boron tribromide solution in dichloromethane (10.0 mL, 10.0 mmol). The reaction was allowed to stir at −78° C. for 1 hour, and then allowed to reach ambient temperature overnight. The reaction was then heated to reflux for 8 hours until complete (monitored by TLC). Upon completion of the reaction, brine (50 mL) was added to quench the reaction. The contents of the resulting biphasic mixture were then transferred to a separatory funnel and dichloromethane was used to extract the product. The resulting organic layers were dried with sodium sulfate, filtered through cotton, and removed in vacuo. The resulting solid was purified via column chromatography using dichloromethane to elute compound 1-60 as a yellow solid (100%, 350 mg). Note: Some 1-hydroxyphenazines were purified with the addition of 1% acetic acid to 99% dichloromethane via column chromatography.

This general demethylation procedure was used to prepare the following 1-hydroxyphenazine compounds.

Example 1-60

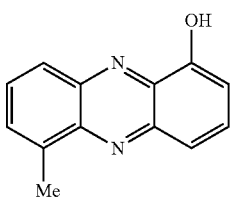

Yield: 99% yield; 350 mg of 1-60 was isolated as a yellow solid.

$^1$H NMR (400 MHz, CDCl$_3$): δ 8.21 (s, 1H), 8.04 (d, J=8.5 Hz, 1H), 7.81 (dd, J=8.9, 1.1 Hz, 1H), 7.78-7.63 (m, 3H), 7.22 (dd, J=7.3, 1.2 Hz, 1H), 2.92 (s, 3H).

$^{13}$C NMR (100 MHz, CDCl$_3$): δ 151.7, 144.0, 143.2, 141.5, 138.2, 134.3, 131.4, 130.5, 130.0, 127.2, 120.5, 108.8, 18.0.

HRMS (ESI): calc. for C$_{13}$H$_{11}$N$_2$O [M+H]$^+$: 211.0866, found: 211.0873.

MP: 178-180° C.

Example 1-61

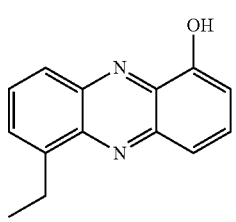

Yield: 99% yield; 84 mg of 1-61 was isolated as a yellow solid.

$^1$H NMR (400 MHz, CDCl$_3$): δ 8.21 (s, 1H), 8.03 (d, J=8.7 Hz, 1H), 7.80 (dd, J=9.0, 1.2 Hz, 1H), 7.77-7.70 (m, 2H), 7.65 (d, J=6.8 Hz, 1H), 7.21 (dd, J=7.3, 1.2 Hz, 1H), 3.43 (q, J=7.5 Hz, 2H), 1.45 (t, J=7.5 Hz, 3H).

$^{13}$C NMR (100 MHz, CDCl$_3$): δ 151.7, 144.0, 143.4, 143.2, 141.5, 134.3, 131.3, 130.7, 128.2, 127.1, 120.6, 108.8, 24.5, 15.0.

HRMS (ESI): calc. for C$_{14}$H$_{13}$N$_2$O [M+H]$^+$: 225.1022, found: 225.1024.

MP: 118-120° C.

Example 1-62

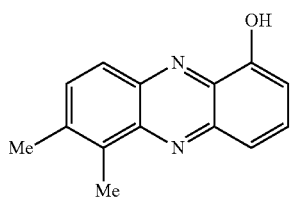

Yield: 100% yield; 139 mg of 1-62 was isolated as a yellow solid.

$^1$H NMR (400 MHz, d$_6$-DMSO): δ 10.49 (s, 1H), 8.03 (d, J=8.9 Hz, 1H), 7.79-7.71 (m, 2H), 7.69 (dd, J=8.7, 1.4 Hz, 1H), 7.15 (dt, J=7.3, 1.4 Hz, 1H), 2.78 (s, 3H), 2.56 (s, 3H).

$^1$H NMR (400 MHz, CDCl$_3$): δ 8.17 (s, 1H), 7.93 (d, J=8.9 Hz, 1H), 7.78 (dd, J=8.8, 1.0 Hz, 1H), 7.71 (dd, J=8.9, 7.3 Hz, 1H), 7.61 (d, J=8.8 Hz, 1H), 7.18 (dd, J=7.3, 1.0 Hz, 1H), 2.85 (s, 3H), 2.57 (s, 3H).

$^{13}$C NMR (100 MHz, d$_6$-DMSO): δ 153.4, 142.9, 142.2, 140.2, 138.0, 134.7, 134.1, 133.3, 131.4, 126.2, 119.3, 110.0, 20.3, 13.0.

$^{13}$C NMR (100 MHz, CDCl$_3$): δ 151.7, 143.9, 143.2, 140.3, 138.1, 134.5, 133.7, 131.1, 126.0, 120.5, 108.4, 21.0, 13.5. Note: One $^{13}$C signal missing, likely due to overlap.

HRMS (ESI): calc. for C$_{14}$H$_{13}$N$_2$O [M+H]$^+$: 225.1022, found: 225.1029.

MP: 144-146° C.

Example 1-63

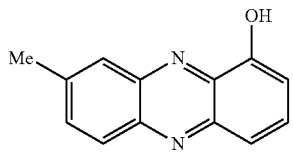

Yield: 97% yield; 75 mg of 1-63 was isolated as a yellow solid.

$^1$H NMR (400 MHz, CDCl$_3$): δ 8.21 (s, 1H), 8.13 (d, J=8.9 Hz, 1H), 7.94 (m, 1H), 7.77-7.69 (m, 2H), 7.67 (dd, J=8.9, 2.0 Hz, 1H), 7.21 (dd, J=6.9, 1.6 Hz, 1H), 2.64 (d, J=1.1 Hz, 3H).

$^{13}$C NMR (100 MHz, CDCl$_3$): δ 151.8, 143.3, 143.0, 141.3, 141.3, 134.6, 133.8, 131.2, 129.1, 127.3, 120.0, 109.0, 22.3.

HRMS (ESI): calc. for C$_{13}$H$_{11}$N$_2$O [M+H]$^+$: 211.0866, found: 211.0873.

MP: 147-149° C.

Example 1-64

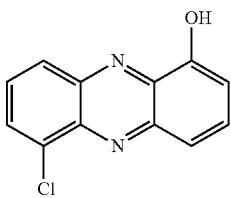

Yield: >99% yield; 92 mg of 1-64 was isolated as a yellow solid.

$^1$H NMR (400 MHz, CDCl$_3$): δ 8.15 (dd, J=8.8, 1.3 Hz, 1H), 8.10 (s, 1H), 7.97 (dd, J=7.3, 1.3 Hz, 1H), 7.91 (dd, J=8.9, 1.1 Hz, 1H), 7.81 (dd, J=8.9, 7.4 Hz, 1H), 7.74 (dd, J=8.8, 7.3 Hz, 1H), 7.27 (dd, J=7.4, 1.1 Hz, 1H).

$^{13}$C NMR (100 MHz, CDCl$_3$): δ 151.6, 143.8, 141.8, 140.9, 135.0, 133.5, 132.7, 130.4, 129.9, 128.5, 120.6, 109.9.

HRMS (ESI): calc. for C$_{12}$H$_8$ClN$_2$O [M+H]$^+$: 231.0320, found: 231.0331.

MP: 185-187° C.

Example 1-65

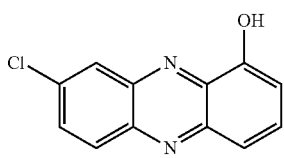

Yield: 100% yield; 85 mg of 1-65 was isolated as an orange solid.

$^1$H NMR (400 MHz, CDCl$_3$): δ 8.23 (d, J=2.3 Hz, 1H), 8.21 (d, J=9.3, Hz, 1H), 8.10 (s, 1H), 7.81-7.75 (m, 3H), 7.27 (dd, J=6.2, 2.6 Hz, 1H).

$^{13}$C NMR (100 MHz, CDCl$_3$): δ 151.8, 144.0, 142.8, 141.2, 136.8, 135.1, 132.4, 132.3, 131.2, 127.7, 120.2, 109.9.

HRMS (ESI): calc. for C$_{12}$H$_8$ClN$_2$O [M+H]$^+$: 231.0320, found: 231.0330.

MP: 190-192° C.

Example 1-66

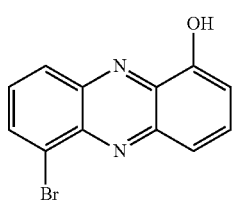

Yield: 100% yield; 72 mg of 1-66 was isolated as a yellow solid.

$^1$H NMR (400 MHz, CDCl$_3$): δ 8.22 (m, 1H), 8.20 (s, 1H), 8.09 (s, 1H), 7.93 (dd, J=8.9, 1.1 Hz, 1H), 7.82 (dd, J=8.9, 7.4 Hz, 1H), 7.69 (m, 1H), 7.28 (dd, J=7.4, 1.1 Hz, 1H).

$^{13}$C NMR (100 MHz, CDCl$_3$): δ 151.5, 144.0, 141.6, 141.5, 135.0, 134.0, 132.6, 130.4, 129.2, 124.6, 120.5, 109.9.

HRMS (ESI): calc. for C$_{12}$H$_8$BrN$_2$O [M+H]$^+$: 274.9815, found: 274.9824.

MP: 171-173° C.

General Procedure for Dibromination of 1-Hydroxyphenazines

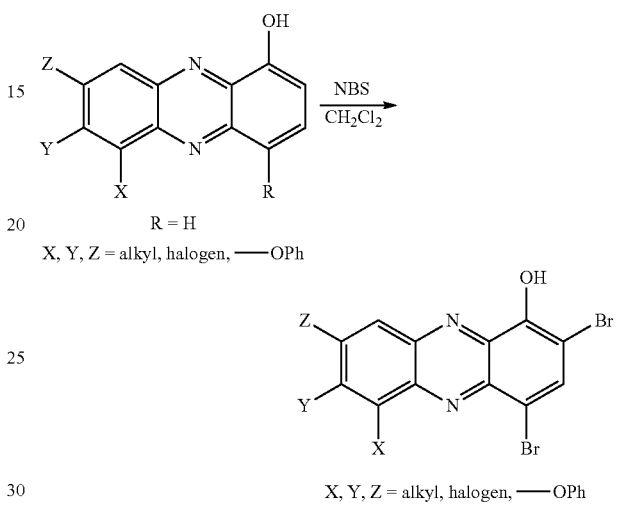

R = H
X, Y, Z = alkyl, halogen, —OPh

X, Y, Z = alkyl, halogen, —OPh 1-60 (156 mg, 0.742 mmol) and N-bromosuccinimide (277 mg, 1.56 mmol) were dissolved in dichloromethane (60.0 mL) and allowed to stir at room temperature for 4 hours. The reaction contents were washed with brine (60.0 mL) and extracted with dichloromethane. The extracts were dried with sodium sulfate, filtered, and concentrated in vacuo. The resulting solid was purified via column chromatography using 99:1 dichloromethane:acetic acid to elute 1-17 as a yellow solid.

This general dibromination procedure was used to prepare the following 1-hydroxydibromophenazine compounds.

Example 1-16

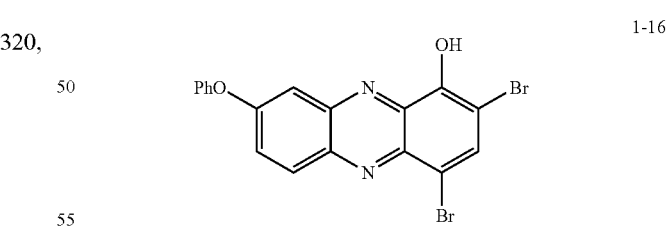

Yield: 48% yield; 78 mg of 1-16 was isolated as a yellow solid.

$^1$H NMR (400 MHz, d$_6$-DMSO): δ 11.26 (s, 1H), 8.40-8.29 (m, 2H), 7.96 (dd, J=9.5, 2.8 Hz, 1H), 7.60 (dd, J=8.0, 7.7 Hz, 2H), 7.43-7.34 (m, 3H), 7.26 (d, J=2.8 Hz, 1H).

$^{13}$C NMR (100 MHz, d$_6$-DMSO): δ 161.0, 154.0, 150.4, 142.4, 140.2, 138.3, 135.7, 135.3, 131.5, 130.7, 126.9, 126.0, 121.3, 111.5, 108.6, 104.6.

HRMS (ESI): calc. for C$_{18}$H$_{11}$Br$_2$N$_2$O$_2$ [M+H]$^+$: 446.9162, found: 446.9161.

MP: Decom. 203° C.

Example 1-17

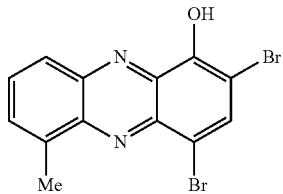

Yield: 81% yield; 220 mg of 1-17 was isolated as a yellow solid.

$^1$H NMR (400 MHz, d$_6$-DMSO): δ 11.51 (s, 1H), 8.40 (s, 1H), 8.18 (m, 1H), 7.93 (dd, J=8.0, 6.8 Hz, 1H), 7.89 (m, 1H), 2.88 (s, 3H).

$^{13}$C NMR (100 MHz, d$_6$-DMSO): δ 150.8, 142.1, 141.5, 138.5, 137.4, 136.5, 135.1, 132.0, 131.1, 126.7, 111.9, 104.4, 16.9.

HRMS (DART): calc. for C$_{13}$H$_9$Br$_2$N$_2$O [M+H]$^+$: 366.9076, found: 366.9087.

MP: 214-216° C.

Example 1-18

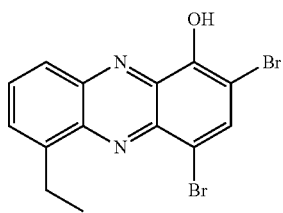

Yield: 38% yield; 51 mg of 1-18 was isolated as a yellow solid.

$^1$H NMR (400 MHz, d$_6$-DMSO): δ 11.52 (br. s, 1H), 8.41 (s, 1H), 8.20 (dd, J=8.7, 1.5 Hz, 1H), 7.97 (dd, J=8.7, 6.9 Hz, 1H), 7.89 (m, 1H), 3.39 (q, J=7.5 Hz, 2H), 1.43 (t, J=7.5 Hz, 3H).

$^{13}$C NMR (100 MHz, d$_6$-DMSO): δ 150.8, 143.1, 141.5, 141.5, 138.5, 136.4, 135.1, 132.2, 129.6, 126.7, 111.9, 104.4, 23.8, 14.7.

HRMS (ESI): calc. for C$_{14}$H$_{11}$Br$_2$N$_2$O [M+H]$^+$: 382.9213, found: 382.9220.

MP: 145-147° C.

Example 1-19

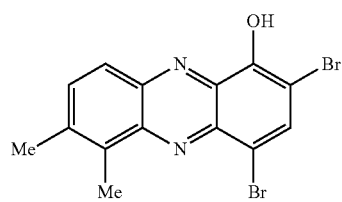

Yield: 30% yield; 71 mg of 1-19 was isolated as a yellow solid.

$^1$H NMR (400 MHz, d$_6$-DMSO): δ 11.43 (s, 1H), 8.35 (s, 1H), 8.06 (d, J=8.9 Hz, 1H), 7.83 (d, J=8.9 Hz, 1H), 2.80 (s, 3H), 2.55 (s, 3H).

$^{13}$C NMR (100 MHz, d$_6$-DMSO): δ 150.7, 141.8, 140.2, 139.4, 138.4, 136.2, 135.7, 134.3, 133.8, 125.5, 111.9, 103.8, 20.3, 12.8.

HRMS (ESI): calc. for C$_{14}$H$_{10}$Br$_2$N$_2$ONa [M+Na]$^+$: 404.9032, found: 404.9026.

MP: 212-214° C.

Example 1-20

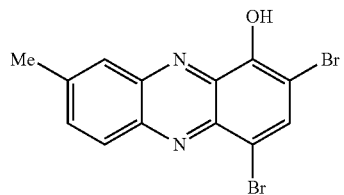

Yield: 77% yield; 77 mg of 1-20 was isolated as a yellow solid.

$^1$H NMR (400 MHz, d$_6$-DMSO): 11.46 (s, 1H), 8.38 (s, 1H), 8.22 (dt, J=8.9, 0.5 Hz, 1H), 8.09 (ddd, J=1.9, 1.2, 0.7 Hz, 1H), 7.91 (ddd, J=8.9, 1.9, 0.5 Hz, 1H), 2.67 (d, J=1.1 Hz, 3H).

$^{13}$C NMR (100 MHz, d$_6$-DMSO): δ 150.8, 142.9, 141.7, 141.5, 139.0, 136.2, 135.4, 135.1, 128.9, 126.8, 111.5, 104.3, 21.8.

HRMS (ESI): calc. for C$_{13}$H$_9$Br$_2$N$_2$O [M+H]$^+$: 368.9056, found: 368.9055.

MP: 213-215° C.

Example 1-21

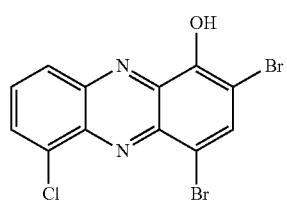

Yield: 42% yield; 55 mg of 1-21 was isolated as a yellow solid.

$^1$H NMR (400 MHz, d$_6$-DMSO): δ 11.69 (s, 1H), 8.50 (s, 1H), 8.33 (dd, J=8.8, 1.2 Hz, 1H), 8.26 (dd, J=7.4, 1.2 Hz, 1H), 8.00 (dd, J=8.8, 7.4 Hz, 1H).

$^{13}$C NMR (100 MHz, d$_6$-DMSO): δ 150.9, 142.0, 139.4, 139.3, 137.6, 135.9, 132.1, 131.7, 131.5, 128.4, 111.7, 105.4.

HRMS (DART): calc. for C$_{12}$H$_6$Br$_2$ClN$_2$O [M+H]$^+$: 386.8530, found: 386.8521.

MP: 230-232° C.

Example 1-22

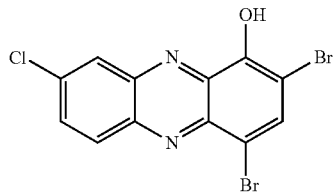

Yield: 31% yield; 37 mg of 1-22 was isolated as a yellow solid.

$^1$H NMR (400 MHz, $d_6$-DMSO): δ 11.62 (s, 1H), 8.45 (s, 1H), 8.42-8.30 (m, 2H), 8.05 (dd, J=9.2, 2.4 Hz, 1H).

$^{13}$C NMR (100 MHz, $d_6$-DMSO): δ 150.9, 141.4, 141.2, 139.6, 137.3, 136.7, 135.9, 132.9, 131.4, 127.1, 111.5, 105.3.

HRMS (DART): calc. for $C_{12}H_6Br_2ClN_2O$ [M+H]$^+$: 386.8530, found: 386.8524.

MP: 245-247° C.

Example 1-23

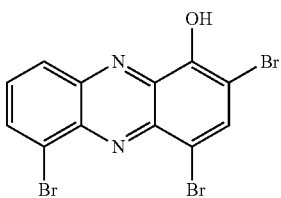

Yield: 40% yield; 41 mg of 23 was isolated as a yellow solid.

$^1$H NMR (400 MHz, $d_6$-DMSO): δ 11.69 (s, 1H), 8.50 (s, 1H), 8.45 (dd, J=7.3, 1.2 Hz, 1H), 8.36 (dd, J=8.8, 1.2 Hz, 1H), 7.94 (dd, J=8.8, 7.3 Hz, 1H).

$^{13}$C NMR (100 MHz, $d_6$-DMSO): δ 150.8, 141.9, 140.0, 139.6, 137.6, 135.9, 135.1, 132.3, 129.0, 123.6, 111.6, 105.4. HRMS (DART): calc. for $C_{12}H_6Br_3N_2O$ [M+H]$^+$: 432.8005, found: 432.8004.

Synthesis of Example 1-15

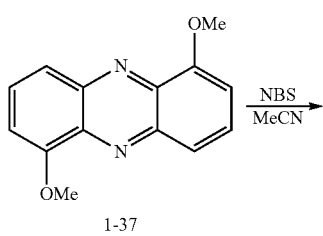

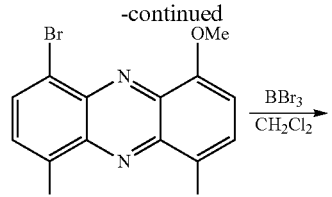

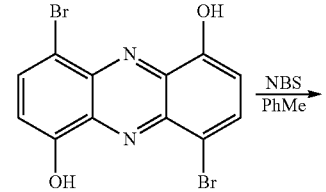

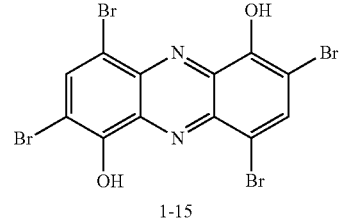

To an 8 mL sealed microwave vial was added 1-37 (121 mg, 0.50 mmol) in acetonitrile (4 mL). The resulting mixture was then heated at 80° C. in the microwave reactor for 12 minutes. The solvent was removed in vacuo and the resulting solid was purified via column chromatography using dichloromethane to elute, affording 1-57, isolated as a yellow solid (99%, 198 mg).

$^1$H NMR (400 MHz, CDCl$_3$): δ 8.12 (d, J=8.3 Hz, 2H), 7.02 (d, J=8.3 Hz, 2H), 4.17 (s, 6H). $^{13}$C NMR (100 MHz, CDCl$_3$): δ 154.4, 139.2, 136.5, 133.1, 113.3, 107.3, 56.1. HRMS (ESI): calc. for $C_{14}H_{11}Br_2N_2O_2$ [M+H]$^+$: 398.9162, found: 398.9153. MP: >260° C.

To a round bottom flask was added 1-57 (160 mg, 0.40 mmol) dissolved in anhydrous dichloromethane (20 mL). The mixture was brought to −78° C. in a dry ice bath before dropwise addition of 1M boron tribromide solution in dichloromethane (4.02 mL, 4.02 mmol). The reaction was left to stir at −78° C. for 1 hour, and then allowed to reach ambient temperature for reaction overnight. The reaction was heated to reflux for 8 hours until complete (monitored by TLC). Brine (20 mL) was then added to the mixture to quench the reaction. The mixture was then transferred to a separatory funnel, and then extracted with dichloromethane. Organic extracts were dried with sodium sulfate, filtered through cotton, and removed in vacuo. The resulting crude product was purified via column chromatography using dichloromethane to elute 1-58 as a red solid (100%, 149 mg).

$^1$H NMR (400 MHz, $d_6$-DMSO): δ 10.78 (br. s, 2H), 8.16 (d, J=8.2 Hz, 2H), 7.21 (d, J=8.2 Hz, 2H). $^{13}$C NMR (100 MHz, $d_6$-DMSO): δ 153.6, 139.2, 136.3, 134.7, 111.8, 110.7. HRMS (DART): calc. for $C_{12}H_7N_2O_2Br_2$ [M+H]$^+$: 368.8869, found: 368.8860. MP: >260° C. 1-58 (30.0 mg, 0.08 mmol) and N-bromosuccinimide (43.7 mg, 0.18 mmol) were suspended in 1 mL toluene and allowed to stir at room temperature for 1 hour. The reaction contents were filtered. The filtrate was washed with dichloromethane (6 mL), resulting product 1-15 as a dark red solid (60%, 26 mg). $^1$H NMR (400 MHz, $d_6$-DMSO): δ 11.07 (s, 2H), 8.51 (s, 2H). $^{13}$C NMR (100 MHz, $d_6$-DMSO): δ 150.6, 138.5, 137.8, 135.8, 111.6, 106.6. HRMS (DART): calc. for $C_{12}H_5Br_4N_2O_2$ [M+H]$^+$: 524.7079, found: 524.7058. MP: >260° C.

General Procedure for the Synthesis of HP-Carbonates

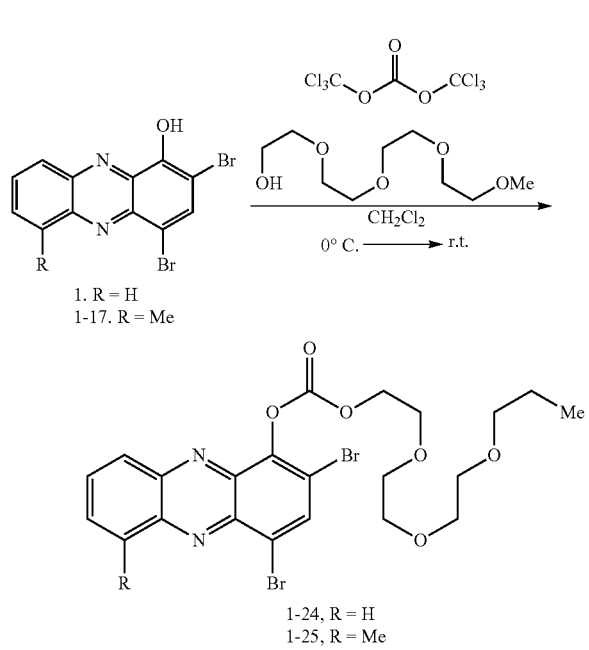

1. R = H
1-17. R = Me 1-24, R = H
1-25, R = Me

Tetraethyleneglycol monomethyl ether (69 μL 0.33 mmol) was placed in an oven-dried round-bottomed flask and dissolved in anhydrous dichloromethane (1 mL). The solution was then cooled to 0° C. Pyridine (37 μL, 0.47 mmol) and triethylamine (11 μL 0.73 mmol) were then added via syringe, followed by triphosgene (48.2 mg, 0.16 mmol) dissolved in dichloromethane (1 mL). The resulting mixture was stirred from 0° C. to room temperature and continued to stir at room temperature for 5 hours. Then the reaction was cooled to 0° C. before the addition of a solution of 1-17 (86 mg, 0.23 mmol) and triethylamine (49 μL 0.35 mmol) in anhydrous dichloromethane was added dropwise. The reaction solution was stirred for 5 min at 0° C. and then allowed to reach ambient temperature and stirred at room temperature overnight. After the reaction was complete, the reaction mixture was poured into a separatory funnel containing 1M ammonium chloride (20 mL), and the biphasic mixture was shaken vigorously. Upon separation of layers, the aqueous layer was re-extracted with dichloromethane (2×30 mL). Organic extracts were collected, dried over sodium sulfate, filtered, and concentrated under vacuum. The resulting crude material was purified using flash column chromatography with 3:1 hexanes:ethyl acetate to 100% ethyl acetate as eluent to yield 1-25 as a yellow oil (135 mg, 96%).

This general carbonate-formation procedure was used to prepare the following dibromophenazine compounds.

Example 1-24

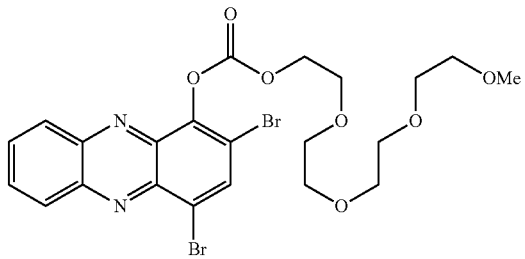

1-24

Yield: 80% yield; 92 mg of 1-24 was isolated as a yellow oil. $^1$H NMR (400 MHz, CDCl$_3$): δ 8.35 (m, 1H), 8.34 (s, 1H), 8.28 (m, 1H), 7.96-7.88 (m, 2H), 4.53 (m, 2H), 3.88 (m, 2H), 3.73 (m, 2H), 3.71-3.62 (m, 8H), 3.54 (m, 2H), 3.37 (s, 3H). $^{13}$C NMR (100 MHz, CDCl$_3$): δ 152.3, 144.6, 143.7, 143.5, 140.2, 137.6, 135.8, 132.5, 132.1, 130.2, 130.0, 122.6, 116.8, 72.1, 71.0, 70.9, 70.8, 70.8, 70.7, 69.0, 68.9, 59.2. HRMS (ESI): calc. for $C_{22}H_{25}Br_2N_2O_7$ [M+H]$^+$: 589.0004, found: 588.9998.

Example 1-25

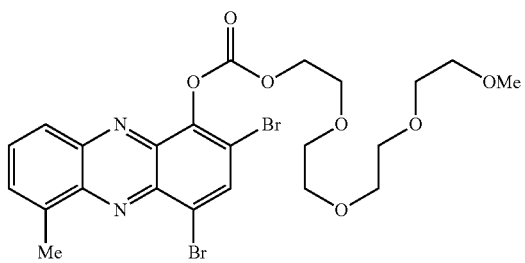

1-25

Yield: 96% yield; 135 mg of 1-25 was isolated as a yellow oil. $^1$H NMR (400 MHz, CDCl$_3$): δ 8.33 (s, 1H), 8.11 (ddd, J=8.7, 1.5, 0.8 Hz, 1H), 7.80 (dd, J=8.7, 6.8 Hz, 1H), 7.74 (m, 1H), 4.53 (m, 2H), 3.88 (m, 2H), 3.73 (m, 2H), 3.71-3.61 (m, 8H), 3.55 (m, 2H), 3.37 (s, 3H), 2.97 (s, 3H). $^{13}$C NMR (100 MHz, CDCl$_3$): δ 152.3, 144.3, 143.6, 143.2, 139.2, 138.7, 137.1, 135.2, 132.4, 131.1, 127.6, 123.2, 116.5, 72.1, 71.0, 70.8, 70.8, 70.8, 70.7, 68.9, 68.9 (determined by HSQC), 59.2, 17.5. HRMS (ESI): calc. for $C_{23}H_{27}Br_2N_2O_7$ [M+H]$^+$: 603.0161, found: 603.0164.

General Procedure for Mono-Bromination of the 4-Position of 1-methoxyphenazines (93A-96A)

1-Methoxyphenazines (0.49 mmol) was dissolved in dichloromethane (15 mL) before N-bromosuccinimide (140.9 mg, 0.79 mmol) was added and the reaction was brought to reflux. The mixture was left to stir overnight until complete (monitored by TLC with dichloromethane). At this time, the reaction was concentrated and adsorbed onto silica gel (via dissolving the crude reaction contents and silica gel in dichloromethane, then concentrating via rotavap) and purified via column chromatography using dichloromethane to elute pure 4-bromo-1-methoxyphenazines as yellow solids.

4-Bromo-1-methoxy-7-methylphenazine (93A). Yield: 88%; 172.5 mg was isolated as a yellow solid. $^1$H NMR (400 MHz, CDCl$_3$): δ 8.27 (dt, J=8.9, 0.5 Hz, 1H), 8.12 (ddd, J=1.9, 1.2, 0.7 Hz, 1H), 8.03 (d, J=8.2 Hz, 1H), 7.69 (dd, J=8.9, 1.9 Hz, 1H), 6.91 (d, J=8.3 Hz, 1H), 4.14 (s, 3H), 2.63 (d, J=1.1 Hz, 3H). $^{13}$C NMR (100 MHz, CDCl$_3$): δ 155.3, 143.9, 142.5, 141.3, 141.2, 136.7, 134.3, 133.1, 129.4, 128.1, 114.3, 106.6, 56.8, 22.4. HRMS (ESI): calc. for C$_{14}$H$_{12}$BrN$_2$O [M+H]$^+$: 303.0128, found: 303.0140. MP: 148-150° C.

9-Bromo-6-methoxy-1,3-dimethylphenazine (94A). Yield: 55%; 71.6 mg was isolated as a yellow solid. $^1$H NMR (400 MHz, CDCl$_3$): δ 8.00 (d, J=8.2 Hz, 1H), 7.98 (m, 1H), 7.55 (m, 1H), 6.92 (d, J=8.2 Hz, 1H), 4.15 (s, 3H), 2.93 (t, J=0.8 Hz, 3H), 2.59 (d, J=1.1 Hz, 3H). $^{13}$C NMR (100 MHz, CDCl$_3$): δ 155.1, 142.9, 142.2, 142.0, 139.8, 137.7, 136.9, 133.7, 132.1, 125.9, 115.2, 106.9, 56.7, 22.6, 17.4. HRMS (ESI): calc. for C$_{15}$H$_{14}$BrN$_2$O [M+H]$^+$: 317.0284, found: 317.0300. MP: 170-172° C.

4-Bromo-7-ethyl-1-methoxyphenazine (95A). Yield: 83%; 154.7 mg was isolated as a yellow solid. $^1$H NMR (400 MHz, CDCl$_3$): δ 8.21 (dd, J=8.9, 0.6 Hz, 1H), 8.04 (m, 1H), 7.92 (d, J=8.3 Hz, 1H), 7.64 (dd, J=9.0, 1.9 Hz, 1H), 6.79 (d, J=8.3 Hz, 1H), 4.05 (s, 3H), 2.86 (qd, J=7.6, 1.1 Hz, 2H), 1.32 (t, J=7.6 Hz, 3H). $^{13}$C NMR (100 MHz, CDCl$_3$): δ 155.1, 148.2, 143.8, 141.3, 140.9, 136.5, 133.2, 132.9, 129.3, 126.3, 114.0, 106.4, 56.6, 29.3, 14.5. HRMS (ESI): calc. for C$_{15}$H$_{14}$BrN$_2$O [M+H]$^+$: 317.0284, found: 317.0295. MP: 137-139° C.

4-Bromo-7-chloro-1-methoxyphenazine (96A). Yield: 96%; 151.7 mg was isolated as a yellow solid. $^1$H NMR (400 MHz, CDCl$_3$): δ 8.37 (dd, J=2.3, 0.6 Hz, 1H), 8.33 (dd, J=9.3, 0.6 Hz, 1H), 8.08 (d, J=8.3 Hz, 1H), 7.78 (dd, J=9.3, 2.3 Hz, 1H), 6.95 (d, J=8.3 Hz, 1H), 4.16 (s, 3H). $^{13}$C NMR (100 MHz, CDCl$_3$): δ 155.3, 143.6, 141.5, 140.9, 137.8, 137.2, 134.1, 132.7, 131.2, 128.4, 114.3, 107.3, 56.9. HRMS (ESI): calc. for C$_{13}$H$_8$BrClN$_2$ONa [M+Na]$^+$: 346.9379, found: 346.9392. MP: 189-191° C.

General Boron Tribromide Demethylation Procedure.

To a round bottom flask was added the desired 1-methoxyphenazine (1.07 mmol) dissolved in anhydrous dichloromethane (18 mL). The mixture was brought to −78° C. in a dry ice bath before dropwise addition of 1M boron tribromide solution in dichloromethane (6.4 mL, 6.41 mmol). The reaction was left to stir at −78° C. for 1 hour, and then allowed to reach ambient temperature for reaction overnight. The reaction was heated to reflux for 8 hours until complete (monitored by TLC). The solution was transferred to a separatory funnel containing an aqueous solution of saturated sodium bicarbonate, and then extracted with dichloromethane. Organic solvents were dried with sodium sulfate, filtered through cotton, and removed in vacuo. The resulting solid was purified via column chromatography using dichloromethane to elute pure 1-hydroxyphenazines as yellow solids. Note: Analogous procedures were used for all demethylation reactions using BBr$_3$.

4-Bromo-7-methylphenazin-1-ol (66A). Yield: 96%; 122.6 mg was isolated as a yellow solid. $^1$H NMR (400 MHz, CDCl$_3$): δ 8.19 (s, 1H), 8.17 (ddd, J=1.9, 1.2, 0.7 Hz, 1H), 8.12 (dt, J=8.9, 0.5 Hz, 1H), 8.05 (d, J=8.1 Hz, 1H), 7.72 (dd, J=8.9, 1.9 Hz, 1H), 7.10 (d, J=8.1 Hz, 1H), 2.67 (d, J=1.2 Hz, 3H). $^{13}$C NMR (100 MHz, CDCl$_3$): δ 151.9, 144.7, 142.5, 141.0, 140.3, 134.6, 134.4, 128.5, 128.5, 112.2, 109.2, 22.5. HRMS (ESI): calc. for C$_{13}$H$_{10}$BrN$_2$O [M+H]$^+$: 288.9971, found: 288.9978. MP: 179-181° C. Note: One $^{13}$C NMR signal missing in the aromatic region, likely due to overlap.

4-Bromo-7-ethylphenazin-1-ol (67A). Yield: 92%; 136.1 mg was isolated as a yellow solid. $^1$H NMR (400 MHz, CDCl$_3$): δ 8.17 (br. s, 1H), 8.11 (m, 1H), 8.04 (dd, J=8.9, 0.6 Hz, 1H), 8.01 (d, J=8.1 Hz, 1H), 7.68 (m, 1H), 7.06 (d, J=8.1 Hz, 1H), 2.93 (qd, J=7.5, 1.1 Hz, 2H), 1.40 (t, J=7.5 Hz, 3H). $^{13}$C NMR (100 MHz, CDCl$_3$): δ 151.8, 148.3, 144.7, 140.8, 140.3, 134.5, 134.3, 133.7, 128.4, 126.8, 112.1, 109.1, 29.5, 14.6. HRMS (ESI): calc. for C$_{14}$H$_{12}$BrN$_2$O [M+H]$^+$: 303.0128, found: 303.0126. MP: 96-98° C.

4-Bromo-6,8-dimethylphenazin-1-ol (68A). Yield: 82%; 56.3 mg was isolated as a yellow solid. $^1$H NMR (400 MHz, CDCl$_3$): δ 8.15 (br. s, 1H), 7.99 (d, J=8.1 Hz, 1H), 7.75 (m, 1H), 7.53 (dd, J=2.0, 1.1 Hz, 1H), 7.08 (d, J=8.1 Hz, 1H), 2.91 (s, 3H), 2.60 (d, J=1.1 Hz, 3H). $^{13}$C NMR (100 MHz, CDCl$_3$): δ 151.6, 142.9, 142.4, 141.8, 139.5, 138.1, 134.6, 133.6, 133.3, 124.8, 113.0, 109.3, 22.6, 17.6. HRMS (ESI): calc. for C$_{14}$H$_{12}$BrN$_2$O [M+H]$^+$: 303.0128, found: 303.0130. MP: 180-182° C.

4-Bromo-7-chlorophenazin-1-ol (69A). Yield: 90%; 120.2 mg was isolated as a yellow solid. $^1$H NMR (400 MHz, DMSO-d$_6$): δ 10.98 (br. s, 1H), 8.33 (d, J=2.3 Hz, 1H), 8.30 (d, J=9.3 Hz, 1H), 8.16 (d, J=8.2 Hz, 1H), 7.95 (dd, J=9.3, 2.3 Hz, 1H), 7.13 (d, J=8.2 Hz, 1H). $^{13}$C NMR (100 MHz, DMSO-d$_6$): δ 153.9, 142.7, 140.6, 139.9, 136.5, 136.4, 135.6, 132.1, 131.2, 127.5, 111.4, 110.3. HRMS (ESI): calc. for C$_{12}$H$_5$BrClN$_2$O [M−H]$^-$: 308.9257, found: 308.9258. MP: 199-201° C.

7-(Bromomethyl)phenazin-1-ol (70A). Yield: 87%; 93.9 mg was isolated as a yellow solid. $^1$H NMR (400 MHz, CDCl$_3$): δ 8.24-8.18 (m, 2H), 8.14 (s, 1H), 7.85 (dd, J=9.0, 2.1 Hz, 1H), 7.79-7.75 (m, 2H), 7.24 (m, 1H), 4.73 (s, 2H). $^{13}$C NMR (100 MHz, CDCl$_3$): δ 152.0, 144.4, 144.0, 141.0, 140.6, 135.1, 132.3, 131.7, 130.2, 129.2, 120.2, 109.5, 32.8. HRMS (DART): calc. for C$_{13}$H$_{10}$BrN$_2$O [M+H]$^+$: 288.9971, found: 288.9985. MP: 160-162° C. Note: Product obtained from BBr$_3$ demethylation of HP 48A. NMR spectra acquired at 40° C.

7-(2-Bromoethyl)phenazin-1-ol (71A). Yield: 53%; 70.3 mg was isolated as a yellow solid. $^1$H NMR (400 MHz, CDCl$_3$): δ 8.21 (br. s, 1H), 8.15 (dd, J=8.9, 0.6 Hz, 1H), 8.07 (dt, J=1.9, 0.8 Hz, 1H), 7.78-7.74 (m, 2H), 7.68 (dd, J=8.9, 2.0 Hz, 1H), 7.22 (dd, J=4.6, 3.9 Hz, 1H), 3.75 (t, J=7.3 Hz, 2H), 3.46 (t, J=7.3 Hz, 2H). $^{13}$C NMR (100 MHz, CDCl$_3$): δ 151.9, 144.2, 144.1, 142.0, 140.5, 134.7, 132.1, 132.1, 129.5, 128.6, 120.1, 109.0, 39.4, 31.8. HRMS (ESI): calc. for C$_{14}$H$_{12}$BrN$_2$O [M+H]$^+$: 303.0128, found: 303.0128. MP: 155-157° C. Note: Product obtained from BBr$_3$ demethylation of HP 50A.

7-Methylphenazin-1-ol (97A). Yield: 97%; 224.4 mg was isolated as a yellow solid. $^1$H NMR (400 MHz, CDCl$_3$): δ 8.30 (br. s, 1H), 7.96 (d, J=8.9 Hz, 1H), 7.91 (ddd, J=1.9, 1.1, 0.7 Hz, 1H), 7.74-7.64 (m, 2H), 7.55 (dd, J=8.9, 1.9 Hz, 1H), 7.16 (dd, J=5.8, 2.7 Hz, 1H), 2.58 (d, J=1.1 Hz, 3H). $^{13}$C NMR (100 MHz, CDCl$_3$): δ 151.9, 144.2, 143.8, 141.6, 140.0, 134.2, 133.5, 131.7, 128.6, 127.8, 119.9, 108.6, 22.4. HRMS (ESI): calc. for C$_{13}$H$_{11}$N$_2$O [M+H]$^+$: 211.0866, found: 211.0872. MP: 151-153° C. Note: Compound has been previously reported (CAS: 1393525-06-8), but no characterization data were found for comparison.

7-Ethylphenazin-1-ol (98A). Yield: 93%; 245.8 mg was isolated as a yellow solid. $^1$H NMR (400 MHz, CDCl$_3$): δ 8.31 (s, 1H), 8.00 (d, J=9.0 Hz, 1H), 7.95 (m, 1H), 7.73-7.67 (m, 2H), 7.60 (dd, J=9.0, 2.0 Hz, 1H), 7.17 (dd, J=6.2, 2.3 Hz, 1H), 2.89 (qd, J=7.5, 1.0 Hz, 2H), 1.37 (t, J=7.5 Hz, 3H). $^{13}$C NMR (100 MHz, CDCl$_3$): δ 151.9, 147.5, 144.4, 143.8, 140.3, 134.3, 132.7, 131.7, 128.8, 126.3, 119.9, 108.7, 29.4, 14.6. HRMS (ESI): calc. for C$_{14}$H$_{13}$N$_2$O [M+H]$^+$:

225.1022, found: 225.1023. MP: 99-101° C. Note: Compound has been previously reported (CAS: 21233-58-9), but no characterization data were found for comparison.

7-Propylphenazin-1-ol (99A). Yield: 88%; 227.8 mg was isolated as a yellow solid. $^1$H NMR (400 MHz, CDCl$_3$): δ 8.30 (br. s, 1H), 8.03 (dd, J=8.9, 0.6 Hz, 1H), 7.96 (dd, J=1.9, 0.9 Hz, 1H), 7.76-7.64 (m, 2H), 7.61 (dd, J=8.9, 1.9 Hz, 1H), 7.17 (dd, J=6.4, 2.1 Hz, 1H), 2.84 (td, J=7.5, 0.9 Hz, 2H), 1.85-1.73 (m, 2H), 1.00 (t, J=7.3 Hz, 3H). $^{13}$C NMR (100 MHz, CDCl$_3$): δ 151.9, 146.1, 144.4, 143.9, 140.3, 134.3, 132.9, 131.7, 128.8, 127.2, 119.9, 108.7, 38.5, 23.7, 14.0. HRMS (ESI): calc. for C$_{15}$H$_{15}$N$_2$O [M+H]$^+$: 239.1179, found: 239.1184. MP: 100-102° C.

7-(tert-Butyl)phenazin-1-ol (100A). Yield: 80%; 286.1 mg was isolated as a yellow oily residue. $^1$H NMR (400 MHz, CDCl$_3$): δ 8.42 (s, 1H), 8.09 (dd, J=2.1, 0.6 Hz, 1H), 7.97 (dd, J=9.2, 0.6 Hz, 1H), 7.81 (dd, J=9.2, 2.2 Hz, 1H), 7.69 (dd, J=8.9, 1.5 Hz, 1H), 7.65 (dd, J=8.9, 7.1 Hz, 1H), 7.14 (dd, J=7.0, 1.5 Hz, 1H), 1.41 (s, 9H). $^{13}$C NMR (100 MHz, CDCl$_3$): δ 154.2, 151.9, 144.2, 143.8, 140.0, 134.4, 131.5, 130.3, 128.5, 124.0, 119.8, 108.8, 35.6, 30.8. HRMS (ESI): calc. for C$_{16}$H$_{17}$N$_2$O [M+H]$^+$: 253.1335, found: 253.1341.

6,8-Dimethylphenazin-1-ol (101A). Yield: 89%; 187.2 mg was isolated as a yellow solid. $^1$H NMR (400 MHz, CDCl$_3$): δ 8.20 (br. s, 1H), 7.77 (dd, J=8.9, 1.1 Hz, 1H), 7.75 (ddq, J=1.9, 1.3, 0.8 Hz, 1H), 7.68 (dd, J=8.9, 7.3 Hz, 1H), 7.47 (m, 1H), 7.19 (dd, J=7.4, 1.1 Hz, 1H), 2.86 (t, J=0.8 Hz, 3H), 2.57 (d, J=1.1 Hz, 3H). $^{13}$C NMR (100 MHz, CDCl$_3$): δ 151.6, 142.9, 142.7, 141.7, 141.2, 137.5, 134.3, 133.0, 130.7, 125.3, 120.5, 108.7, 22.4, 17.9. HRMS (ESI): calc. for C$_{14}$H$_{13}$N$_2$O [M+H]$^+$: 225.1022, found: 225.1025. MP: 154-156° C.

8,9-Dimethylphenazin-1-ol (102A). Yield: 83%; 89.1 mg was isolated as a yellow solid. $^1$H NMR (400 MHz, CDCl$_3$): δ 8.15 (s, 1H), 7.87 (d, J=8.9 Hz, 1H), 7.70-7.62 (m, 2H), 7.51 (d, J=8.9 Hz, 1H), 7.14 (dd, J=5.8, 2.7 Hz, 1H), 2.66 (s, 3H), 2.45 (s, 3H). $^{13}$C NMR (100 MHz, CDCl$_3$): δ 151.8, 143.1, 142.7, 140.4, 138.0, 134.7, 133.4, 131.0, 126.5, 119.7, 108.5, 20.7, 13.2. HRMS (ESI): calc. for C$_{14}$H$_{13}$N$_2$O [M+H]$^+$: 225.1022, found: 225.1021. MP: 164-166° C. Note: One $^{13}$C NMR signal missing in the aromatic region, likely due to signal overlap.

9-Ethylphenazin-1-ol (103A). Yield: 90%; 88.1 mg was isolated as a yellow solid. $^1$H NMR (400 MHz, CDCl$_3$): δ 8.20 (s, 1H), 8.01 (ddd, J=8.8, 1.2, 0.7 Hz, 1H), 7.72-7.64 (m, 3H), 7.54 (dq, J=6.8, 1.2 Hz, 1H), 7.16 (dd, J=5.8, 2.8 Hz, 1H), 3.29 (q, J=7.5 Hz, 2H), 1.38 (t, J=7.5 Hz, 3H). $^{13}$C NMR (100 MHz, CDCl$_3$): δ 151.8, 144.5, 143.4, 142.8, 139.9, 133.5, 131.6, 130.9, 128.1, 127.6, 119.8, 108.7, 24.2, 14.7. HRMS (ESI): calc. for C$_{14}$H$_{13}$N$_2$O [M+H]$^+$: 225.1022, found: 225.1019. MP: 102-104° C.

6,7,8-Trimethylphenazin-1-ol (104A). Yield: 89%; 175.2 mg was isolated as a yellow solid. $^1$H NMR (400 MHz, CDCl$_3$): δ 8.17 (br. s, 1H), 7.79 (m, 1H), 7.76 (dd, J=8.9, 1.2 Hz, 1H), 7.67 (dd, J=8.9, 7.4 Hz, 1H), 7.17 (dd, J=7.4, 1.2 Hz, 1H), 2.88 (s, 3H), 2.55 (d, J=1.2 Hz, 3H), 2.47 (s, 3H). $^{13}$C NMR (100 MHz, CDCl$_3$): δ 151.6, 143.2, 142.8, 142.0, 140.4, 138.7, 134.1, 133.8, 130.5, 125.4, 120.5, 108.3, 22.1, 17.1, 13.8. HRMS (ESI): calc. for C$_{15}$H$_{15}$N$_2$O [M+H]$^+$: 239.1179, found: 239.1185. MP: 167-169° C.

7-Ethoxyphenazin-1-ol (105A). Yield: 88%; 89.2 mg was isolated as a yellow solid. $^1$H NMR (400 MHz, CDCl$_3$): δ 8.18 (br. s, 1H), 8.00 (dd, J=9.4, 0.5 Hz, 1H), 7.70 (dd, J=8.9, 7.1 Hz, 1H), 7.66 (dd, J=8.8, 1.5 Hz, 1H), 7.45 (dd, J=9.4, 2.7 Hz, 1H), 7.35 (dd, J=2.7, 0.5 Hz, 1H), 7.14 (dd, J=7.0, 1.5 Hz, 1H), 4.22 (q, J=7.0 Hz, 2H), 1.53 (t, J=7.0 Hz, 3H). $^{13}$C NMR (100 MHz, CDCl$_3$): δ 160.9, 152.1, 145.9, 143.8, 138.4, 133.0, 131.9, 130.2, 126.8, 119.3, 108.1, 105.2, 64.5, 14.7. HRMS (ESI): calc. for C$_{14}$H$_{13}$N$_2$O$_2$ [M+H]$^+$: 241.0972, found: 241.0973. MP: 137-139° C.

7-Chlorophenazin-1-ol (106A). Yield: 92%; 226.1 mg was isolated as a yellow solid. $^1$H NMR (400 MHz, DMSO-d$_6$): δ 10.71 (s, 1H), 8.30 (m, 1H), 8.28 (dd, J=5.0, 0.5 Hz, 1H), 7.92 (dd, J=9.3, 2.3 Hz, 1H), 7.82 (dd, J=8.8, 7.5 Hz, 1H), 7.66 (dd, J=8.8, 1.2 Hz, 1H), 7.21 (dd, J=7.5, 1.2 Hz, 1H). $^{13}$C NMR (100 MHz, DMSO-d$_6$): δ 153.7, 144.0, 142.8, 139.7, 135.8, 135.6, 132.8, 131.4, 131.3, 127.4, 118.9, 110.9. MP: 180-182° C., lit. 203-204° C.$^{50}$ Note: Compound has been previously reported (CAS: 105908-75-6), but no spectra were found for comparison.

Ethyl 6-hydroxyphenazine-2-carboxylate (107A). Yield: 85%; 49.5 mg was isolated as a yellow solid. $^1$H NMR (400 MHz, CDCl$_3$): δ 8.99 (dd, J=1.9, 0.7 Hz, 1H), 8.38 (dd, J=9.1, 1.9 Hz, 1H), 8.23 (dd, J=9.1, 0.7 Hz, 1H), 8.17 (s, 1H), 7.82-7.75 (m, 2H), 7.27 (m, 1H), 4.50 (q, J=7.1 Hz, 2H), 1.49 (t, J=7.1 Hz, 3H). $^{13}$C NMR (100 MHz, CDCl$_3$): δ 165.8, 151.8, 144.6, 143.4, 142.5, 135.6, 132.9, 132.6, 132.4, 129.6, 129.5, 120.4, 110.2, 62.0, 14.5. HRMS (ESI): calc. for C$_{15}$H$_{13}$N$_2$O$_3$ [M+H]$^+$: 269.0921, found: 269.0930. MP: 161-163° C.

7-Phenoxyphenazin-1-ol (108A). Yield: 88%; 333.6 mg was isolated as a yellow solid. $^1$H NMR (400 MHz, CDCl$_3$): δ 8.18 (dd, J=9.5, 0.5 Hz, 1H), 8.14 (br. s, 1H), 7.76-7.68 (m, 2H), 7.64 (dd, J=8.9, 1.2 Hz, 1H), 7.52-7.41 (m, 2H), 7.38 (dd, J=2.7, 0.5 Hz, 1H), 7.28 (m, 1H), 7.25-7.20 (m, 2H), 7.18 (dd, J=7.4, 1.2 Hz, 1H). $^{13}$C NMR (100 MHz, CDCl$_3$): δ 160.7, 154.9, 152.1, 145.4, 144.0, 138.7, 133.6, 132.3, 130.9, 130.5, 126.0, 125.6, 121.2, 119.5, 110.5, 108.5. HRMS (ESI): calc. for C$_{18}$H$_{13}$N$_2$O$_2$ [M+H]$^+$: 289.0972, found: 289.0979. MP: 148-150° C.

7-(Diethylamino)phenazin-1-ol (109A). Yield: 94%; 79.4 mg was isolated as a red oily residue. $^1$H NMR (400 MHz, CDCl$_3$): δ 8.15 (br. s, 1H), 7.95 (d, J=9.6 Hz, 1H), 7.62 (dd, J=8.8, 7.2 Hz, 1H), 7.56 (dd, J=8.8, 1.4 Hz, 1H), 7.48 (dd, J=9.6, 2.8 Hz, 1H), 7.04 (d, J=2.8 Hz, 1H), 7.02 (dd, J=7.2, 1.3 Hz, 1H), 3.55 (q, J=7.1 Hz, 4H), 1.29 (t, J=7.1 Hz, 6H). $^{13}$C NMR (100 MHz, CDCl$_3$): δ 152.2, 149.1, 146.7, 144.4, 137.2, 131.8, 131.5, 130.1, 122.7, 118.8, 106.6, 101.6, 45.2, 13.0. HRMS (DART): calc. for C$_{16}$H$_{18}$N$_3$O [M+H]$^+$: 268.1444, found: 268.1444.

General Di-Bromination Procedure

Desired 1-hydroxyphenazines (0.24 mmol) and N-bromosuccinimide, (86.2 mg, 0.48 mmol) were dissolved in dichloromethane (15 mL) and allowed to stir at room temperature for 2 hours. The reaction was diluted with dichloromethane and quenched with brine (3×20 mL). The organic layer was dried with sodium sulfate, filtered and concentrated. The reaction contents were then concentrated, adsorbed onto silica gel and purified via column chromatography using dichloromethane to elute pure 2,4-dibromo-hydroxyphenazine analogues as yellow solids.

2,4-Dibromo-7-methylphenazin-1-ol (52A). Yield: 52%; 51.2 mg was isolated as a yellow solid. $^1$H NMR (400 MHz, CDCl$_3$): δ 8.50 (br. s, 1H), 8.21 (s, 1H), 8.17-8.15 (m, 1H), 8.14 (d, J=9.0 Hz, 1H), 7.75 (dd, J=8.9, 1.9 Hz, 1H), 2.67 (d, J=1.1 Hz, 3H). $^{13}$C NMR (100 MHz, CDCl$_3$): δ 149.3, 144.4, 142.9, 140.4, 140.1, 137.1, 135.3, 133.9, 128.5, 128.4, 113.0, 102.6, 22.5. HRMS (ESI): calc. for C$_{13}$H$_9$Br$_2$N$_2$O [M+H]$^+$: 368.9056, found: 368.9071. MP: 200-202° C.

2,4-Dibromo-7-ethylphenazin-1-ol (53A). Yield: 74%; 117.9 mg was isolated as a yellow solid. $^1$H NMR (400 MHz, CDCl$_3$): δ 8.48 (br. s, 1H), 8.19 (s, 1H), 8.15-8.10 (m, 2H), 7.76 (dd, J=8.9, 2.0 Hz, 1H), 2.96 (qd, J=7.5, 1.1 Hz, 2H), 1.42 (t, J=7.5 Hz, 3H). $^{13}$C NMR (100 MHz, CDCl$_3$): δ 149.0, 148.6, 144.3, 140.4, 139.8, 136.8, 134.3, 133.6, 128.2, 126.7, 112.7, 102.4, 29.3, 14.4. HRMS (ESI): calc. for C$_{14}$H$_{11}$Br$_2$N$_2$O [M+H]$^+$: 382.9213, found: 382.9302. MP: 160-162° C.

2,4-Dibromo-7-propylphenazin-1-ol (54A). Yield: 76%; 89.6 mg was isolated as a yellow solid. $^1$H NMR (400 MHz, CDCl$_3$): δ 8.50 (br. s, 1H), 8.20 (s, 1H), 8.17-8.10 (m, 2H), 7.76 (dd, J=9.0, 1.9 Hz, 1H), 2.90 (td, J=7.4, 0.9 Hz, 2H), 1.93-1.70 (m, 2H), 1.03 (t, J=7.4 Hz, 3H). $^{13}$C NMR (100 MHz, CDCl$_3$): δ 149.3, 147.4, 144.5, 140.6, 140.0, 137.0, 134.7, 133.9, 128.4, 127.9, 113.0, 102.6, 38.6, 23.8, 14.0. HRMS (ESI): calc. for C$_{15}$H$_{13}$Br$_2$N$_2$O [M+H]$^+$: 396.9369, found: 396.9389. MP: 139-141° C.

2,4-Dibromo-7-(tert-butyl)phenazin-1-ol (55A). Yield: 61%; 139.1 mg was isolated as a yellow solid. $^1$H NMR (400 MHz, CDCl$_3$): δ 8.50 (br. s, 1H), 8.26 (dd, J=2.1, 0.6 Hz, 1H), 8.17 (s, 1H), 8.14 (dd, J=9.2, 0.6 Hz, 1H), 8.01 (dd, J=9.2, 2.1 Hz, 1H), 1.49 (s, 9H). $^{13}$C NMR (100 MHz, CDCl$_3$): δ 155.5, 149.3, 144.4, 140.4, 140.0, 136.9, 134.0, 132.2, 128.2, 124.8, 112.9, 102.6, 36.0, 30.9. HRMS (ESI): calc. for C$_{16}$H$_{15}$Br$_2$N$_2$O [M+H]$^+$: 410.9526, found: 410.9529. MP: 176-178° C.

2,4-Dibromo-6,8-dimethylphenazin-1-ol (56A). Yield: 73%; 87.4 mg was isolated as a yellow solid. $^1$H NMR (400 MHz, DMSO-d$_6$): δ 11.33 (br. s, 1H), 8.32 (s, 1H), 7.85 (dt, J=2.0, 1.1 Hz, 1H), 7.68 (m, 1H), 2.80 (s, 3H), 2.59 (d, J=1.1 Hz, 3H). $^{13}$C NMR (100 MHz, DMSO-d$_6$): δ 150.6, 142.5, 141.6, 141.0, 137.9, 136.7, 135.7, 134.9, 133.8, 124.5, 111.9, 104.2, 21.9, 16.8. HRMS (ESI): calc. for C$_{14}$H$_{11}$Br$_2$N$_2$O [M+H]$^+$: 382.9213, found: 382.9208. MP: 216-218° C.

2,4-Dibromo-8,9-dimethylphenazin-1-ol (57A). Yield: 66%; 70.7 mg was isolated as a yellow solid. $^1$H NMR (400 MHz, DMSO-d$_6$): δ 11.10 (s, 1H), 8.37 (s, 1H), 8.04 (d, J=8.9 Hz, 1H), 7.89 (d, J=8.9 Hz, 1H), 2.90 (s, 3H), 2.58 (s, 3H). $^{13}$C NMR (100 MHz, DMSO-d$_6$): δ 150.7, 141.9, 140.7, 139.5, 138.4, 136.0, 135.9, 134.3, 125.9, 111.5, 103.8, 20.3, 13.3. HRMS (ESI): calc. for C$_{14}$H$_9$Br$_2$N$_2$O [M+H]$^-$: 380.9067, found: 380.9067. MP: 232-234° C. Note: One $^{13}$C NMR signal missing in the aromatic region, likely due to signal overlap.

2,4-Dibromo-9-ethylphenazin-1-ol (58A). Yield: 76%; 113.5 mg was isolated as a yellow solid. $^1$H NMR (400 MHz, CDCl$_3$): δ 8.50 (s, 1H), 8.22-8.19 (m, 1H), 8.21 (s, 1H), 7.85 (dd, J=8.8, 6.9 Hz, 1H), 7.73 (dq, J=6.9, 1.1 Hz, 1H), 3.38 (q, J=7.5 Hz, 2H), 1.45 (t, J=7.5 Hz, 3H). $^{13}$C NMR (100 MHz, CDCl$_3$): δ 149.2, 144.7, 142.7, 140.4, 139.7, 137.1, 133.2, 131.9, 129.9, 128.2, 113.0, 102.9, 24.4, 14.7. HRMS (ESI): calc. for C$_{14}$H$_9$Br$_2$N$_2$O [M–H]$^-$: 380.9067, found: 380.9078. MP: 161-163° C.

2,4-Dibromo-6,7,8-trimethylphenazin-1-ol (59A). Yield: 84%; 83.8 mg was isolated as a yellow solid. $^1$H NMR (400 MHz, CDCl$_3$): δ 8.14 (s, 1H), 7.82 (m, 1H), 2.93 (s, 3H), 2.59 (d, J=1.1 Hz, 3H), 2.50 (s, 3H). $^{13}$C NMR (100 MHz, CDCl$_3$): δ 149.0, 144.1, 142.8, 140.6, 140.1, 138.5, 135.8, 134.9, 133.4, 124.9, 113.8, 102.2, 22.3, 17.3, 13.8. HRMS (ESI): calc. for C$_{15}$H$_{13}$Br$_2$N$_2$O [M+H]$^+$: 396.9369, found: 396.9389. MP: 226-228° C.

2,4-Dibromo-7-ethoxyphenazin-1-ol (60A). Yield: 88%; 48.0 mg was isolated as a yellow solid. $^1$H NMR (400 MHz, CDCl$_3$): δ 8.45 (br. s, 1H), 8.20 (s, 1H), 8.09 (dd, J=9.4, 0.5 Hz, 1H), 7.57 (dd, J=9.4, 2.7 Hz, 1H), 7.52 (dd, J=2.7, 0.5 Hz, 1H), 4.28 (q, J=7.1 Hz, 2H), 1.56 (t, J=7.1 Hz, 3H). $^{13}$C NMR (100 MHz, CDCl$_3$): δ 161.8, 149.5, 146.3, 140.0, 138.8, 137.1, 132.6, 129.9, 128.6, 112.3, 105.8, 101.8, 64.9, 14.8. HRMS (ESI): calc. for C$_{14}$H$_{11}$Br$_2$N$_2$O$_2$ [M+H]$^+$: 396.9182, found: 396.9168. MP: 205-207° C.

2,4-Dibromo-7-chlorophenazin-1-ol (61A). Yield: 90%; 184.0 mg was isolated as a yellow solid. $^1$H NMR (400 MHz, DMSO-d$_6$): δ 11.62 (s, 1H), 8.43 (s, 1H), 8.36 (d, J=2.3 Hz, 1H), 8.32 (d, J=9.3 Hz, 1H), 8.01 (dd, J=9.3, 2.3 Hz, 1H). $^{13}$C NMR (100 MHz, DMSO-d$_6$): δ 151.0, 142.7, 139.9, 139.8, 137.6, 136.8, 135.5, 132.9, 130.8, 127.7, 111.3, 104.9. HRMS (ESI): calc. for C$_{12}$H$_4$Br$_2$ClN$_2$O [M+H]$^-$: 386.8363, found: 386.8356. MP: 234-236° C.

Ethyl 7,9-dibromo-6-hydroxyphenazine-2-carboxylate (62A). Yield: 35%; 23.2 mg was isolated as a yellow solid. $^1$H NMR (400 MHz, DMSO-d$_6$): δ 11.71 (s, 1H), 8.83 (d, J=1.7 Hz, 1H), 8.50 (s, 1H), 8.46 (d, J=9.1 Hz, 1H), 8.41 (dd, J=9.1, 1.8 Hz, 1H), 4.46 (q, J=7.1 Hz, 2H), 1.43 (t, J=7.1 Hz, 3H). $^{13}$C NMR (100 MHz, DMSO-d$_6$): δ 164.8, 151.0, 142.6, 141.8, 140.2, 137.6, 136.5, 132.4, 131.7, 130.0, 129.8, 111.7, 105.8, 61.7, 14.1. HRMS (ESI): calc. for C$_{15}$H$_{11}$Br$_2$N$_2$O$_3$ [M+H]$^+$: 426.9111, found: 426.9128. MP: 240-242° C.

2,4-Dibromo-7-phenoxyphenazin-1-ol (63A). Yield: 55%; 37.1 mg was isolated as a yellow solid. $^1$H NMR (400 MHz, DMSO-d$_6$): δ 11.54 (s, 1H), 8.41-8.34 (m, 2H), 7.93 (dd, J=9.4, 2.7 Hz, 1H), 7.59 (t, J=7.7 Hz, 2H), 7.44-7.32 (m, 3H), 7.20 (d, J=2.7 Hz, 1H). $^{13}$C NMR (100 MHz, DMSO-d$_6$): δ 160.7, 154.1, 151.1, 143.9, 139.6, 138.7, 137.0, 134.3, 131.1, 130.7, 126.9, 125.8, 120.9, 110.9, 109.5, 103.7. HRMS (ESI): calc. for C$_{18}$H$_{11}$Br$_2$N$_2$O$_2$ [M+H]$^+$: 446.9162, found: 446.9169. MP: 240° C. (decomp).

2,4,6-Tribromo-7-(diethylamino)phenazin-1-ol (64A). Yield: 53%; 51.1 mg was isolated as a red oily residue. $^1$H NMR (400 MHz, CDCl$_3$): δ 8.30 (br. s, 1H), 8.20 (s, 1H), 8.05 (d, J=9.5 Hz, 1H), 7.76 (d, J=9.5 Hz, 1H), 3.53 (q, J=7.1 Hz, 4H), 1.21 (t, J=7.1 Hz, 6H). $^{13}$C NMR (100 MHz, CDCl$_3$): δ 152.7, 149.0, 143.6, 140.2, 139.4, 137.3, 132.8, 129.5, 127.6, 114.4, 113.3, 102.5, 46.7, 13.5. HRMS (DART): calc. for C$_{16}$H$_{15}$I3r$_3$N$_3$O [M+H]$^+$: 503.8740, found: 503.8758.

2,4-Dibromo-7-(bromomethyl)phenazin-1-ol (65A). Yield: 73%; 78.6 mg was isolated as a yellow solid. $^1$H NMR (400 MHz, DMSO-d$_6$): δ 11.58 (br. s, 1H), 8.43 (s, 1H), 8.41 (d, J=1.9 Hz, 1H), 8.34 (d, J=9.0 Hz, 1H), 8.05 (dd, J=9.0, 1.9 Hz, 1H), 5.05 (s, 2H). $^{13}$C NMR (100 MHz, DMSO-d$_6$): δ 151.0, 142.4, 142.1, 140.9, 139.7, 137.0, 135.6, 133.4, 129.5, 128.7, 111.4, 104.7, 33.4. HRMS (ESI): calc. for C$_{13}$H$_6$Br$_3$N$_2$O [M+H]$^-$: 444.8016, found: 444.8013. MP: 214-216° C.

Synthesis of
7-(azidomethyl)-2,4-dibromophenazin-1-yl acetate
(73A)

HP 65A (33.6 mg, 0.08 mmol) was added to a round-bottom flask and dissolved in N,N-dimethylformamide (4 mL). Sodium azide (12.2 mg, 0.188 mmol) was added and the reaction was stirred at room temperature for 2 hours. Following completion by TLC, the reaction was diluted with ethyl acetate and quenched with brine (3×50 mL). The organic layer was dried with sodium sulfate, filtered and concentrated. The crude solid was then dissolved in dichloromethane (10 mL). Triethylamine (6 µL, 0.04 mmol), a catalytic amount of 4-dimethylaminopyridine, then acetyl chloride (3 µL, 0.03 mmol) were added at room temperature. The reaction was allowed to stir for one hour before being quenched with an aqueous solution of saturated sodium bicarbonate. The resulting mixture was then transferred to a separatory funnel and extracted with dichloromethane. The organic layer was then dried with anhydrous sodium sulfate, filtered, and concentrated in vacuo. The crude solid was purified via flash column chromatography using dichloromethane as the eluent to afford the product as a yellow oily residue (20.1 mg, 59% over two steps). $^1$H NMR (400 MHz, CDCl$_3$): δ 8.35 (s, 1H), 8.30 (m, 1H), 8.25 (d, J=9.0 Hz, 1H), 7.83 (dd, J=9.0, 1.9 Hz, 1H), 4.66 (s, 2H), 2.61 (s, 3H). $^{13}$C NMR (100 MHz, CDCl$_3$): δ 168.3, 145.2, 143.4, 143.1, 140.6, 139.9, 137.9, 136.1, 132.1, 130.7, 128.4, 122.3, 117.5, 54.7, 20.9. HRMS (ESI): calc. for C$_{15}$H$_{10}$Br$_2$N$_5$O$_2$ [M+H]$^+$: 451.9176, found: 451.9176.

Synthesis of 2,4-dibromo-7-((4-propyl-1H-1,2,3-triazol-1-yl)methyl)phenazin-1-yl acetate (74A)

Anhydrous copper sulfate (2.2 mg, 0.01 mmol) and sodium ascorbate (8.0 mg, 0.04 mmol) were dissolved in a solution of tert-butanol:H$_2$O (1:2, 300 μL) and was added to a round-bottom flask containing 73A (12.2 mg, 0.06 mmol). 1-Pentyne (16.0 μL, 0.16 mmol) was added, followed by dichloromethane (3.0 mL). The biphasic mixture was vigorously stirred at room temperature for 16 hours until starting material was fully consumed as determined by TLC analysis. The mixture was quenched with brine (2×50 mL) and the product was extracted with dichloromethane. The organics were collected, dried with sodium sulfate, filtered and concentrated to afford pure 74A (96%, 13.5 mg) as a yellow solid. $^1$H NMR (600 MHz, DMSO-d$_6$): δ 8.68 (s, 1H), 8.28 (d, J=9.0 Hz, 1H), 8.08-8.06 (m, 2H), 7.93 (dd, J=9.0, 1.9 Hz, 1H), 5.93 (s, 2H), 2.62 (t, J=7.5 Hz, 2H), 2.57 (s, 3H), 1.62 (sextet, J=7.4 Hz, 2H), 0.91 (t, J=7.4 Hz, 3H). $^{13}$C NMR (150 MHz, DMSO-d$_6$): δ 168.0, 147.3, 144.5, 142.5, 142.1, 141.2, 139.7, 137.1, 135.8, 132.6, 129.9, 127.3, 122.7, 121.6, 117.2, 52.2, 27.1, 22.2, 20.4, 13.6. HRMS (ESI): calc. for C$_{20}$H$_{18}$Br$_2$N$_5$O$_2$ [M+H]$^+$: 519.9803, found: 519.9793. MP: 203-205° C.

General Procedure for the Synthesis of HP Esters/Carbamates from Commercially Available Acid Chlorides or Carbamoyl Chlorides.

To a stirring solution HP 1A (62.0 mg, 0.18 mmol), triethylamine (48 μL, 0.35 mmol), and a catalytic amount of 4-dimethylaminopyridine in dichloromethane (20 mL) was added the acid chloride or carbamoyl chloride reagent (0.35 mmol) at room temperature. The reaction was allowed to stir for two hours before being quenched with an aqueous solution of saturated sodium bicarbonate. The resulting mixture was then transferred to a separatory funnel and ethyl acetate was added to extract the product. The organic layer was sequentially washed with water and brine before being collected. The organic layer was then dried with anhydrous sodium sulfate, filtered, and concentrated in vacuo. The respective ester or carbamate derivative was purified via flash column chromatography using hexanes:ethyl acetate (99:1 to 80:20) to elute, yielding pure products as yellow solids.

2,4-Dibromophenazin-1-yl 2-(2-(2-methoxyethoxy)ethoxy)acetate (75A). Yield: 63%; 53.3 mg was isolated as a yellow solid. $^1$H NMR (400 MHz, CDCl$_3$): δ 8.33, (m, 1H), 8.32 (s, 1H), 8.18 (m, 1H), 7.94-7.84 (m, 2H), 4.78 (s, 2H), 4.01-3.96 (m, 2H), 3.82-3.76 (m, 2H), 3.72-3.68 (m, 2H), 3.60-3.54 (m, 2H), 3.38 (s, 3H). $^{13}$C NMR (100 MHz, CDCl$_3$): δ 168.2, 144.6, 143.7, 143.4, 140.2, 137.4, 135.7, 132.4, 132.1, 130.1, 129.8, 122.5, 117.0, 72.1, 71.4, 70.8, 68.6, 59.2. HRMS (ESI): calc. for C$_{19}$H$_{19}$Br$_2$N$_2$O$_5$ [M+H]$^+$: 514.9636, found: 514.9630. MP: 184-186° C. Note: One $^{13}$C NMR signal missing in the aliphatic region, likely due to signal overlap.

2,4-Dibromophenazin-1-yl 3-(methylsulfonyl)-2-oxoimidazolidine-1-carboxylate (76A). Yield: >99%; 95.7 mg was isolated as a pale yellow solid. $^1$H NMR (600 MHz, CDCl$_3$): δ 8.38-8.35 (m, 1H), 8.36 (s, 1H), 8.27 (m, 1H), 7.97-7.90 (m, 2H), 4.37-4.28 (m, 2H), 4.11 (t, J=7.9 Hz, 2H), 3.45 (s, 3H). $^{13}$C NMR (150 MHz, CDCl$_3$): δ 149.9, 147.9, 143.9, 143.8, 143.6, 140.3, 137.5, 135.6, 132.6, 132.3, 130.3, 130.0, 123.3, 117.3, 41.6, 41.0, 40.3. HRMS (ESI): calc. for C$_{17}$H$_{13}$Br$_2$N$_4$O$_5$S [M+H]$^+$: 544.8948, found: 544.8949. MP: >250° C.

General Procedure for the Synthesis of HP-Carbonates (77A, 78A)

Tetraethyleneglycol monomethyl ether (101.4 μL, 0.48 mmol) was placed in an oven-dried round-bottomed flask and dissolved in anhydrous dichloromethane (2 mL) and cooled to 0° C. Pyridine (46.4 μL, 0.58 mmol) and triethylamine (16.8 μL 0.12 mmol) was then added via syringe, followed by triphosgene (71.2 mg, 0.24 mmol) dissolved in dichloromethane (2 mL). The resulting mixture was stirred from 0° C. to room temperature and continued to stir at room temperature for 5 hours. The reaction was then cooled to 0° C. before the addition of solution of 61A (118.2 mg, 0.30 mmol) and triethylamine (63 μL 0.45 mmol) in anhydrous dichloromethane was added to the reaction dropwise. The reaction was allowed to reach ambient temperature for reaction overnight. After the reaction was complete by TLC, the reaction mixture was poured into a separatory funnel containing brine (20 mL). The organic layer was drawn and the extracts were collected, dried over sodium sulfate, filtered, and concentrated under vacuum. The resulting crude material was purified using flash column chromatography with 3:1 hexanes:ethyl acetate to 100% ethyl acetate as eluent to yield products as yellow solids.

2,4-Dibromo-7-chlorophenazin-1-yl (2,5,8,11-tetraoxatridecan-13-yl) carbonate (77A). Yield: 99%; 183.1 mg was isolated as a yellow solid. $^1$H NMR (400 MHz, CDCl$_3$): δ 8.35 (d, J=2.3 Hz, 1H), 8.34 (s, 1H), 8.22 (d, J=9.3 Hz, 1H), 7.83 (dd, J=9.3, 2.3 Hz, 1H), 4.57-4.47 (m, 2H), 3.91-3.80 (m, 2H), 3.76-3.71 (m, 2H), 3.70-3.60 (m, 8H), 3.58-3.50 (m, 2H), 3.36 (s, 3H). $^{13}$C NMR (100 MHz, CDCl$_3$): δ 152.3, 144.5, 143.5, 141.9, 140.5, 138.4, 137.5, 136.5, 133.9, 131.2, 128.5, 122.5, 117.3, 72.1, 71.0, 70.8, 70.8, 70.8, 70.7, 69.0, 68.9, 59.2. HRMS (ESI): calc. for C$_{22}$H$_{23}$Br$_2$ClN$_2$O$_7$Na [M+Na]$^+$: 644.9433, found: 644.9433. MP: 66-68° C.

2,4-Dibromo-7-phenoxyphenazin-1-yl (2,5,8,11-tetraoxatridecan-13-yl) carbonate (78A). Yield: 71%; 47.9 mg was isolated as a yellow solid. $^1$H NMR (600 MHz, CDCl$_3$): δ 8.29 (s, 1H), 8.25 (d, J=9.4 Hz, 1H), 7.78 (dd, J=9.4, 2.7 Hz, 1H), 7.49 (t, J=8.0 Hz, 2H), 7.42 (d, J=2.7 Hz, 1H), 7.31 (t, J=7.5 Hz, 1H), 7.23-7.20 (m, 2H), 4.56-4.51 (m, 2H), 3.91-3.87 (m, 2H), 3.74 (dd, J=5.9, 3.5 Hz, 2H), 3.72-3.62 (m, 8H), 3.57-3.54 (m, 2H), 3.37 (s, 3H). $^{13}$C NMR (150 MHz, CDCl$_3$): δ 161.8, 154.5, 152.4, 145.1, 144.7, 141.0, 140.4, 136.4, 135.9, 131.6, 130.6, 128.1, 126.0, 121.9, 121.3, 115.5, 110.0, 72.1, 71.0, 70.9, 70.8, 70.8, 70.7, 69.0, 68.9, 59.2. HRMS (ESI): calc. for C$_{28}$H$_{29}$Br$_2$N$_2$O$_8$ [M+H]$^+$: 681.0267, found: 681.0275. MP: 49-51° C.

Synthesis of HP-glycoconjugate prodrug 79A ((2S,3R,4S,5S,6R)-2-((2,4-dibromophenazin-1-yl)oxy)-6-(hydroxymethyl)tetrahydro-2H-pyran-3,4,5-triol)

To a sealed microwave vial was added HP 2A (50.0 mg, 0.14 mmol), potassium carbonate (39.0 mg, 0.28 mmol) in methanol (5 mL). The resulting mixture was heated to 80° C. in the microwave reactor for a single 5 minute cycle.

After that time, acetobromo-α-D-glucose (145 mg, 0.35 mmol) was added to the reaction vial. The reaction was cooled to room temperature and the solvent was removed in vacuo. The crude residue was taken up in ethyl acetate, transferred to a separatory funnel and then washed with water and extracted with ethyl acetate three times. The organic layers were combined, dried with anhydrous sodium sulfate, filtered and concentrated in vacuo. The crude solid was dissolved in methanol (6 mL) and sodium ethoxide (40.8 mg, 0.60 mmol) was added. The reaction was allowed to stir for 16 hours, then was diluted with dichloromethane and transferred to a separatory funnel. The organic layer was drawn and the extracts were collected, dried over sodium sulfate, filtered, and concentrated under vacuum. The crude solid was rinsed with ice-cold water and methanol, then dried in vacuo to afford pure desired product as a pale yellow solid (17.7 mg, 24% over 2 steps). $^1$H NMR (600 MHz, DMSO-$d_6$): δ 8.56 (s, 1H), 8.38-8.26 (m, 2H), 8.14-8.02 (m, 2H), 6.03 (d, J=7.7 Hz, 1H), 5.57 (d, J=4.9 Hz, 1H), 5.11 (d, J=5.2 Hz, 1H), 4.98 (d, J=5.2 Hz, 1H), 4.20 (t, J=5.7 Hz, 1H), 3.59-3.40 (m, 2H), 3.38-3.25 (m, 2H, partially buried under water signal), 3.14 (m, 2H). $^{13}$C NMR (150 MHz, DMSO-$d_6$): δ 148.9, 142.3, 141.4, 139.8, 137.8, 136.4, 132.6, 132.5, 129.3, 129.3, 118.0, 115.8, 104.0, 77.8, 76.9, 74.8, 69.9, 60.8. HRMS (DART): calc. for $C_{18}H_{17}Br_2N_2O_6$ [M+H]$^+$: 516.9429, found: 516.9435. MP: 199-201° C.

Synthesis of tetraethylene glycol mono(tert-butyldiphenylsilyl)ether 110A

To a stirring solution of tetraethylene glycol (2.10 g, 10.8 mmol) and pyridine (95.4 μL, 0.188 mmol, 0.11 equivalents) in dichloromethane (10 mL) was added tert-butyl(chloro)diphenylsilane (280 μL, 1.08 mmol, 0.1 equivalents) at 0° C. The reaction was allowed to stir for one hour, slowly reaching ambient temperature, before being quenched with an aqueous solution of saturated sodium bicarbonate. The resulting mixture was then transferred to a separatory funnel and ethyl acetate was added to extract the product. The organic layer was sequentially washed with sodium bicarbonate and brine before being collected. The organic layer was then dried with anhydrous sodium sulfate, filtered, and concentrated in vacuo. The resulting crude oil was purified using flash column chromatography with 99:1 to 80:20 hexanes:ethyl acetate to separate mono-silylated ($R_f$=0.3 in 3:1 hexanes:ethyl acetate) and bis-silylated ($R_f$=0.8) products, affording 110A as a colorless oil (53%, 244.6 mg). Note: $^1$H NMR and $^{13}$C NMR tabulation match those previously reported.[51]

Procedure for the synthesis of 2-((2-hydroxyethyl)disulfaneyl)ethyl benzoate (111A)

To a stirring solution of 2,2'-disulfanediylbis(ethan-1-ol) (735 μL, 6.00 mmol) and triethylamine (835 μL, 6.00 mmol) in dichloromethane (15 mL) was added benzoyl chloride (349 μL, 3.00 mmol) at 0° C. The reaction was allowed to stir for two hours, slowly reaching ambient temperature, before being quenched with an aqueous solution of saturated sodium bicarbonate. The resulting mixture was then transferred to a separatory funnel and ethyl acetate was added to extract the product. The organic layer was sequentially washed with sodium bicarbonate and brine before being collected. The organic layer was then dried with anhydrous sodium sulfate, filtered, and concentrated in vacuo. The resulting crude oil was purified using flash column chromatography with 99:1 to 80:20 hexanes:ethyl acetate to separate mono-benzoyl ($R_f$=0.3 in 3:1 hexanes:ethyl acetate) and bis-benzoyl ($R_f$=0.7) products, affording 111A as a colorless oil (46%, 358.4 mg). $^1$H NMR (400 MHz, CDCl$_3$): δ 8.05-8.00 (m, 2H), 7.54 (m, 1H), 7.45-7.38 (m, 2H), 4.57 (t, J=6.7 Hz, 2H), 3.86 (t, J=5.9 Hz, 2H), 3.03 (t, J=6.7 Hz, 2H), 2.87 (t, J=5.9 Hz, 2H), 2.76 (br. s, 1H). $^{13}$C NMR (100 MHz, CDCl$_3$): δ 166.6, 133.3, 129.8, 129.7, 128.5, 63.0, 60.3, 41.6, 37.1. HRMS (ESI): calc. for $C_{11}H_{16}O_3S_2Na$ [M+Na]$^+$: 281.0277, found: 281.0286.

General Procedure for the Synthesis of Alkyloxy Chloromethyl Carbonates (113A-116A)

To a stirring solution of desired alcohol (3.00 mmol) and pyridine (290 μL, 3.60 mmol) in dichloromethane (10 mL) at 0° C. was added chloromethyl chloroformate (320 μL, 3.60 mmol). The reaction was allowed to stir for 22 hours, slowly reaching ambient temperature overnight. The reaction was then quenched with an aqueous solution of saturated sodium bicarbonate. The resulting mixture was then transferred to a separatory funnel and ethyl acetate was added to extract the product. The organic layer was sequentially washed with sodium bicarbonate and brine before being collected. The organic layer was then dried with anhydrous sodium sulfate, filtered, and concentrated in vacuo. Products were obtained as relatively pure oils and were taken on to subsequent reactions without further purification.

Chloromethyl (2-(2-(2-methoxyethoxy)ethoxy)ethyl) carbonate (113A). Yield: >99%; 919.0 mg was isolated as a pale yellow oil. $^1$H NMR (400 MHz, CDCl$_3$): δ 5.53 (s, 2H), 4.16-4.11 (m, 2H), 3.55-3.49 (m, 2H), 3.46-3.38 (m, 6H), 3.33-3.29 (m, 2H), 3.13 (s, 3H). $^{13}$C NMR (100 MHz, CDCl$_3$): δ 152.9, 72.0, 71.4, 70.2, 70.1, 70.0, 68.1, 67.6, 58.4. Note: Compound has been previously reported (CAS: 209551-63-3), but no spectra were found for comparison.

Chloromethyl (2,2-dimethyl-3,3-diphenyl-4,7,10,13-tetraoxa-3-silapentadecan-15-yl) carbonate (114A). Yield: 88%; 259.4 mg was isolated as a colorless oil. $^1$H NMR (400 MHz, CDCl$_3$): δ 7.70-7.65 (m, 4H), 7.43-7.33 (m, 6H), 5.70 (s, 2H), 4.36-4.31 (m, 2H), 3.80 (dd, J=5.9, 4.8 Hz, 2H), 3.74-3.70 (m, 2H), 3.66-3.57 (m, 10H), 1.04 (s, 9H). HRMS (ESI): calc. for $C_{26}H_{37}ClO_7SiNa$ [M+Na]$^+$: 547.1889, found: 547.1915.

2-((2-(((Chloromethoxy)carbonyl)oxy)ethyl)disulfaneyl)ethyl benzoate (115A). Yield: 46%; 358.4 mg was isolated as a colorless oil. $^1$H NMR (400 MHz, CDCl$_3$): δ 8.06-8.01 (m, 2H), 7.56 (ddt, J=7.9, 6.9, 1.4 Hz, 1H), 7.47-7.39 (m, 2H), 5.71 (s, 2H), 4.57 (t, J=6.5 Hz, 2H), 4.47 (t, J=6.6 Hz, 2H), 3.07 (t, J=6.5 Hz, 2H), 2.99 (t, J=6.6 Hz, 2H). $^{13}$C NMR (100 MHz, CDCl$_3$): δ 166.4, 153.3, 133.3, 129.9, 129.8, 128.5, 72.4, 66.7, 62.8, 37.4, 36.9. HRMS (ESI): calc. for $C_{13}H_{15}ClO_5S_2Na$ [M+Na]$^+$: 372.9942, found: 372.9952.

Chloromethyl ((2,4,5-trimethyl-3,6-dioxocyclohexa-1,4-dien-1-yl)methyl) carbonate (116A). Yield: 63%; 583.7 mg was isolated as a yellow oily residue. $^1$H NMR (500 MHz, CDCl$_3$): δ 5.69 (s, 2H), 5.15 (s, 2H), 2.12 (s, 3H), 2.01 (m, 6H). $^{13}$C NMR (125 MHz, CDCl$_3$): δ 187.3, 185.5, 153.3, 145.8, 141.5, 141.0, 135.4, 72.6, 61.6, 12.7, 12.7, 12.6. HRMS (ESI): calc. for $C_{12}H_{14}ClO_5$ [M+H]$^+$: 273.0527, found: 273.0527. Note: Compound is unstable and requires rapid advancement to subsequent reactions.

Synthesis of Alkyloxycarbonyloxymethyl ("AOCOM") Carbonate Prodrugs (80A, 81A, 85A, 86A, 87A)

To a stirring solution of the desired alkyloxy chloromethyl carbonate (0.08 mmol) in acetone (2 mL) was added sodium iodide (10.5 mg, 0.07 mmol). The reaction was allowed to stir for two hours at room temperature. Then, this mixture was added to a stirring solution of 2A (23.5 mg, 0.07 mmol) and potassium carbonate (11.0 mg, 0.08 mmol) in acetone (2 mL). After stirring for 14 additional hours, the reaction was quenched by addition of deionized water. The resulting mixture was then transferred to a separatory funnel and ethyl acetate was added to extract the product. The organic layer was sequentially washed with sodium bicarbonate and brine before being collected. The organic layer was then dried with anhydrous sodium sulfate, filtered, and concentrated in vacuo. The resulting crude material was purified using flash column chromatography with 3:1 hexanes:ethyl acetate to 100% ethyl acetate as eluent to yield AOCOM prodrugs as yellow solids.

((2,4-Dibromophenazin-1-yl)oxy)methyl (2-(2-(2-methoxyethoxy)ethoxy)ethyl) carbonate (80A). Yield: 54%; 43.4 mg was isolated as a yellow solid. $^1$H NMR (400 MHz, CDCl$_3$): δ 8.37 (m, 1H), 8.32 (s, 1H), 8.28 (m, 1H), 7.97-7.89 (m, 2H), 6.26 (s, 2H), 4.34-4.29 (m, 2H), 3.73-3.68 (m, 2H), 3.62 (d, J=5.5 Hz, 6H), 3.56-3.51 (m, 2H), 3.37 (s, 3H). $^{13}$C NMR (100 MHz, CDCl$_3$): δ 154.7, 149.7, 143.5, 143.0, 140.7, 138.4, 136.5, 132.3, 132.0, 130.2, 129.8, 120.5, 116.8, 92.4, 72.1, 70.9, 70.8, 70.8, 68.9, 67.8, 59.3. HRMS (ESI): calc. for C$_{21}$H$_{23}$Br$_2$N$_2$O$_7$ [M+H]$^+$: 574.9848, found: 574.9821. MP: 116-118° C.

((2,4-Dibromophenazin-1-yl)oxy)methyl (2,2-dimethyl-3,3-diphenyl-4,7,10,13-tetraoxa-3-silapentadecan-15-yl) carbonate (81A). Yield: 69%; 38.2 mg was isolated as a yellow oily residue. $^1$H NMR (400 MHz, CDCl$_3$): δ 8.36 (m, 1H), 8.30 (s, 1H), 8.27 (m, 1H), 7.96-7.88 (m, 2H), 7.68 (dt, J=6.5, 1.7 Hz, 4H), 7.44-7.33 (m, 6H), 6.25 (s, 2H), 4.33-4.28 (m, 2H), 3.80 (t, J=5.4 Hz, 2H), 3.71-3.66 (m, 2H), 3.66-3.56 (m, 10H), 1.04 (s, 9H). $^{13}$C NMR (100 MHz, CDCl$_3$): δ 154.7, 149.7, 143.5, 143.0, 140.7, 138.4, 136.4, 135.8, 133.9, 132.3, 132.0, 130.2, 129.8, 127.8, 120.5, 116.7, 92.3, 72.6, 70.9, 70.9, 70.9, 70.8, 68.9, 67.8, 63.6, 27.0, 19.4. HRMS (ESI): calc. for C$_{38}$H$_{43}$Br$_2$N$_2$O$_8$Si [M+H]$^+$: 843.1134, found: 843.1147. Note: One $^{13}$C NMR signal missing in the aromatic region, likely due to signal overlap.

2-((2-(((((2,4-Dibromophenazin-1-yl)oxy)methoxy)carbonyl)oxy)ethyl)disulfaneyl)ethyl benzoate (85A). Yield: 60%; 69.8 mg was isolated as a yellow solid. $^1$H NMR (400 MHz, CDCl$_3$): δ 8.35 (m, 1H), 8.30 (s, 1H), 8.27 (m, 1H), 8.03 (m, 2H), 7.93 (ddd, J=5.6, 4.7, 3.1 Hz, 2H), 7.54 (m, 1H), 7.42 (t, J=7.7 Hz, 2H), 6.26 (s, 2H), 4.56 (t, J=6.5 Hz, 2H), 4.43 (t, J=6.6 Hz, 2H), 3.05 (t, J=6.5 Hz, 2H), 2.95 (t, J=6.6 Hz, 2H). $^{13}$C NMR (100 MHz, CDCl$_3$): δ 166.5, 154.5, 149.6, 143.5, 142.9, 140.7, 138.3, 136.4, 133.3, 132.4, 132.0, 130.2, 130.0, 129.9, 129.7, 128.6, 120.5, 116.7, 92.4, 66.3, 62.9, 37.5, 37.1. HRMS (ESI): calc. for C$_{25}$H$_{20}$Br$_2$N$_2$O$_6$S$_2$Na [M+Na]$^+$: 690.9002, found: 690.8986. MP: 123-125° C.

((2,4-Dibromophenazin-1-yl)oxy)methyl((2,4,5-trimethyl-3,6-dioxocyclohexa-1,4-dien-1-yl)methyl) carbonate (86A). Yield: 13%; 9.1 mg was isolated as a yellow solid. $^1$H NMR (500 MHz, CDCl$_3$): δ 8.36 (m, 1H), 8.28 (s, 1H), 8.28 (m, 1H), 7.95-7.89 (m, 2H), 6.27 (s, 2H), 5.12 (s, 2H), 2.10 (s, 3H), 2.04 (m, 3H), 2.02 (m, 3H). $^{13}$C NMR (125 MHz, CDCl$_3$): δ 187.3, 185.5, 154.4, 149.6, 145.6, 143.5, 143.0, 141.3, 141.0, 140.7, 138.3, 136.4, 135.7, 132.4, 132.0, 130.2, 129.8, 120.5, 116.7, 92.5, 61.1, 12.8, 12.7, 12.6. HRMS (ESI): calc. for C$_{24}$H$_{19}$Br$_2$N$_2$O$_6$ [M+H]$^+$: 590.9586, found: 590.9577. MP: 181-183° C.

((2,4-dibromo-7-chlorophenazin-1-yl)oxy)methyl((2,4,5-trimethyl-3,6-dioxocyclohexa-1,4-dien-1-yl)methyl) carbonate (87A). Yield: 8%; 15.0 mg was isolated as a yellow solid. $^1$H NMR (500 MHz, CDCl$_3$): δ 8.38 (d, J=2.3 Hz, 1H), 8.30 (s, 1H), 8.23 (d, J=9.2 Hz, 1H), 7.85 (dd, J=9.2, 2.3 Hz, 1H), 6.23 (s, 2H), 5.11 (s, 2H), 2.11 (s, 3H), 2.04 (m, 3H), 2.03 (m, 3H). $^{13}$C NMR (125 MHz, CDCl$_3$): δ 187.3, 185.5, 154.4, 149.7, 145.6, 143.3, 141.4, 141.4, 141.0, 141.0, 138.4, 138.2, 137.1, 135.6, 133.8, 131.0, 128.6, 120.5, 117.1, 92.5, 61.1, 12.8, 12.7, 12.6. HRMS (ESI): calc. for C$_{24}$H$_{18}$Br$_2$ClN$_2$O$_6$ [M+H]$^+$: 624.9195, found: 624.9190. MP: 179-181° C.

Synthesis of ((2,4-dibromophenazin-1-yl)oxy) methyl (2-(2-(2-(2-hydroxyethoxy)ethoxy)ethoxy) ethyl)carbonate (82A)

To a stirring solution of 81A (25.8 mg, 0.03 mmol) at 0° C. in 6 mL of anhydrous tetrahydrofuran was added 34 µL of a 1 M solution of tetrabutylammonium fluoride (0.03 mmol). The reaction mixture was allowed to stir for 6 hours, slowly reaching ambient temperature. The reaction was then quenched with water and transferred to a separatory funnel containing ethyl acetate and brine. The organic layer was sequentially washed with brine before the organic layer was collected. The organic layer was dried with anhydrous sodium sulfate, filtered, and concentrated in vacuo. The crude solid was purified via flash column chromatography using ethyl acetate to elute pure 82A as a yellow oily residue (60% yield, 11.0 mg). $^1$H NMR (400 MHz, CDCl$_3$): δ 8.37 (m, 1H), 8.32 (s, 1H), 8.28 (m, 1H), 7.97-7.89 (m, 2H), 6.26 (s, 2H), 4.39-4.23 (m, 2H), 3.73-3.68 (m, 4H), 3.68-3.54 (m, 10H). $^{13}$C NMR (100 MHz, CDCl$_3$): δ 154.7, 149.7, 143.5, 143.0, 140.7, 138.4, 136.5, 132.3, 132.0, 130.2, 129.8, 120.5, 116.7, 92.4, 72.7, 70.9, 70.9, 70.7, 70.5, 69.0, 67.7, 62.0. HRMS (ESI): calc. for C$_{22}$H$_{25}$Br$_2$N$_2$O$_8$ [M+H]$^+$: 604.9954, found: 604.9951.

Construction of the Halogenated Phenazine (HP) Scaffold

Figure 24A:
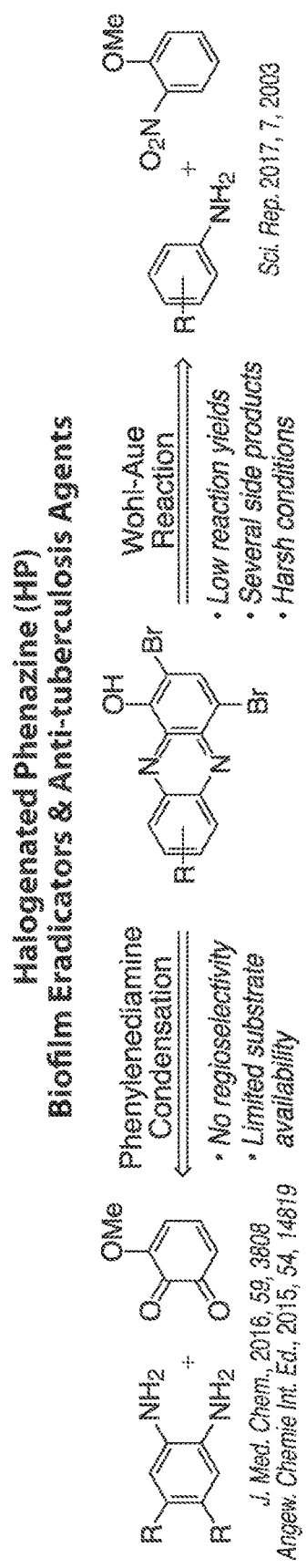
FIGS. 24A and 24B.

Although the previous HP analogues show great promise as antibacterial and biofilm-eradicating agents, a major hindrance in the rapid assembly of HP libraries was the inherently poor means of synthesizing the phenazine heterocycle. The reported phenazine syntheses by which the aforementioned halogenated phenazines were generated are not without shortcomings (FIG. 24A). The phenylenediamine-quinone condensation used previously suffers from a lack of regioselectivity with regard to substituents at the 6-, 7-, 8-, and 9-positions of the phenazine heterocycle.[52,53] This leads to complications when structural fine-tuning is necessary for optimization of SAR profiles. The regioisomers obtained from the condensation of an ortho-quinone and a mono-substituted phenylenediamine yields a mixture of products that are often not easily separable. Furthermore, structural characterization of the two resulting methoxyphenazine isomers is no trivial task. The Wohl-Aue reaction, at present, also leaves much to be desired in terms of synthetic efficiency to afford halogenated phenazine compounds.[54] The yields for phenazines synthesized from the Wohl-Aue reaction are often low, owing to the formation of diphenylamine and nitroso compounds as the major products.[55-57] Additionally, the conditions by which cyclization occurs in the Wohl-Aue reaction are very harsh (e.g. refluxing in a highly alkaline chemical environment).

There are a handful of remaining phenazine syntheses reported in literature; however, most either utilize homo-coupling or offer little to no regioselectivity for asymmetric phenazines.[58-60] Perhaps the most elegant phenazine synthesis, reported by the Ellman group, incorporated a rhodium(III)-catalyzed [3+3] annulation by C—H amination with aromatic azides and diazobenzenes.[61] Using this route, phenazines with asymmetric substitution can be obtained in good yield but for the present purposes, the synthesis would necessitate the preparation of either a diazobenzene or aryl azide diversity-incorporating coupling partner for each analogue. Consequently, improved methods by which halogenated phenazines can be rapidly synthesized needed to be developed. A primary goal of this work was to develop a modular methodology such that phenazine scaffolds could be generated using readily available materials (e.g. anilines, aryl halides), permitting a high degree of diversity with no additional synthetic steps.

Figure 24B:
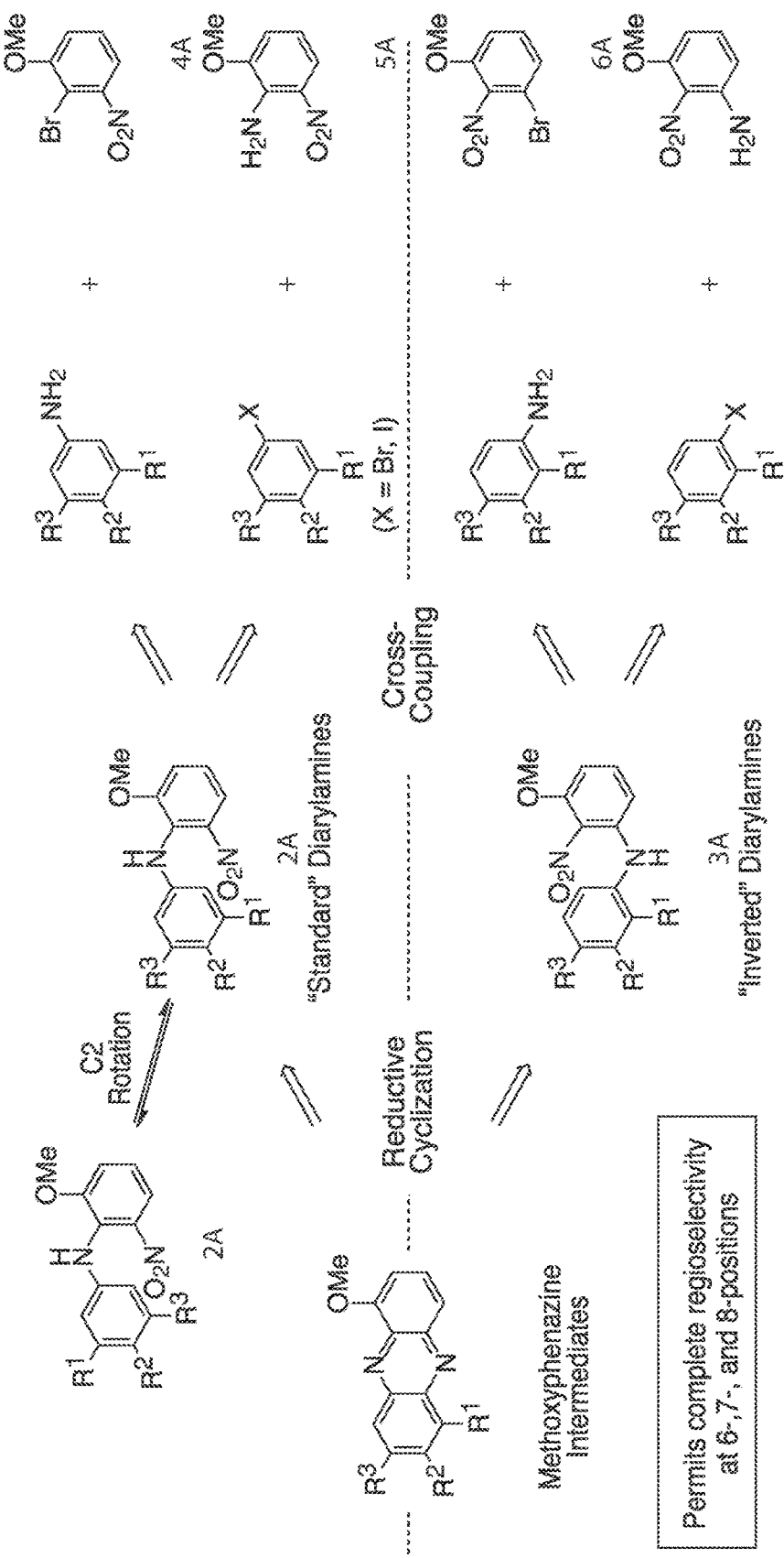

One of the few synthetic methods known to regioselectively afford phenazine compounds is the reductive cyclization of 4-amino-2-nitrodiphenylamines under basic conditions using sodium borohydride.[62-64] This protocol has the potential to incorporate a multitude of commercially available anilines, nitrobenzenes, and aryl halides into the synthesis of the diarylamine intermediate via one of several well-described methods (e.g. Buchwald-Hartwig amination, Jourdan-Ullman coupling, nucleophilic aromatic substitution).[65-71] Thus, reductive cyclization was selected for the synthesis of halogenated phenazines to accommodate diverse substitution at the 6-, 7-, 8-, and 9-positions. It was envisioned that 1-methoxyphenazine intermediates could be obtained via reductive cyclization through two orientations of diarylamine intermediates: 2A and 3A (FIG. 24B). In addition to expanding the scope of this synthesis, the use of two orientations of diarylamine intermediates can ostensibly remedy one caveat with the synthesis: C2 rotation of the phenyl moiety housing the $R^1$ through $R^3$ substituents of intermediate 2A inverts the orientation of the $R^1$ and $R^3$ substituents such that two regioisomers can form in the reductive cyclization. In the case of singly ortho-substituted anilines, cyclization can only occur through one position (the remaining ortho position), which makes these substrates a non-issue for the proposed reactions. However, in the case where a meta-substituted aniline is used as the diversity-housing coupling partner, two regioisomers can form following reductive cyclization of the diarylamine intermediate (6- and 8-substituted phenazines). Fortunately, the use of both "standard" and "inverted" diarylamines as shown in FIG. 24B paired with careful selection of coupling partners can, in theory, provide complete regioselectivity at the 6-through 9-positions.

The synthesis commenced with investigation into coupling conditions for the generation of diarylamine intermediates. A copper-catalyzed Ullmann coupling, although frequently used to couple anilines to aryl halides, yielded no desired product in the reaction between anilines and 2-bromo-1-methoxy-3-nitrobenzene (4A, FIG. 25A).[67-69] With this shortcoming in mind, attention was then turned toward a palladium-catalyzed Buchwald-Hartwig (BH) amination reaction as this chemistry has been very useful due to typical high yields and a broad substrate scope of coupling partners.[65,66] Initially, a BH cross-coupling was attempted between iodobenzene and 2-amino-1-methoxy-3-nitrobenzene (5A), but observed no product formation (FIG. 25B). It is suspected that this result is due to the electron-poor nature of the aniline coupling partner when positioned ortho to the nitro group on substrate 5A, although others have reported success with similar BH couplings using electron-poor anilines.[72,73] It was also sought to design the synthesis such that a TBS-protected hydroxyphenazine could be generated from the reductive cyclization. Since the necessity for demethylation of every successfully cyclized phenazine was anticipated, this strategy would allow for far simpler deprotections en route to the corresponding HP target structures. However, the attempt to couple anilines to (2-bromo-3-nitrophenoxy)(tert-butyl)dimethylsilane (8A) were also met with failure (FIG. 25C).

Figure 26:
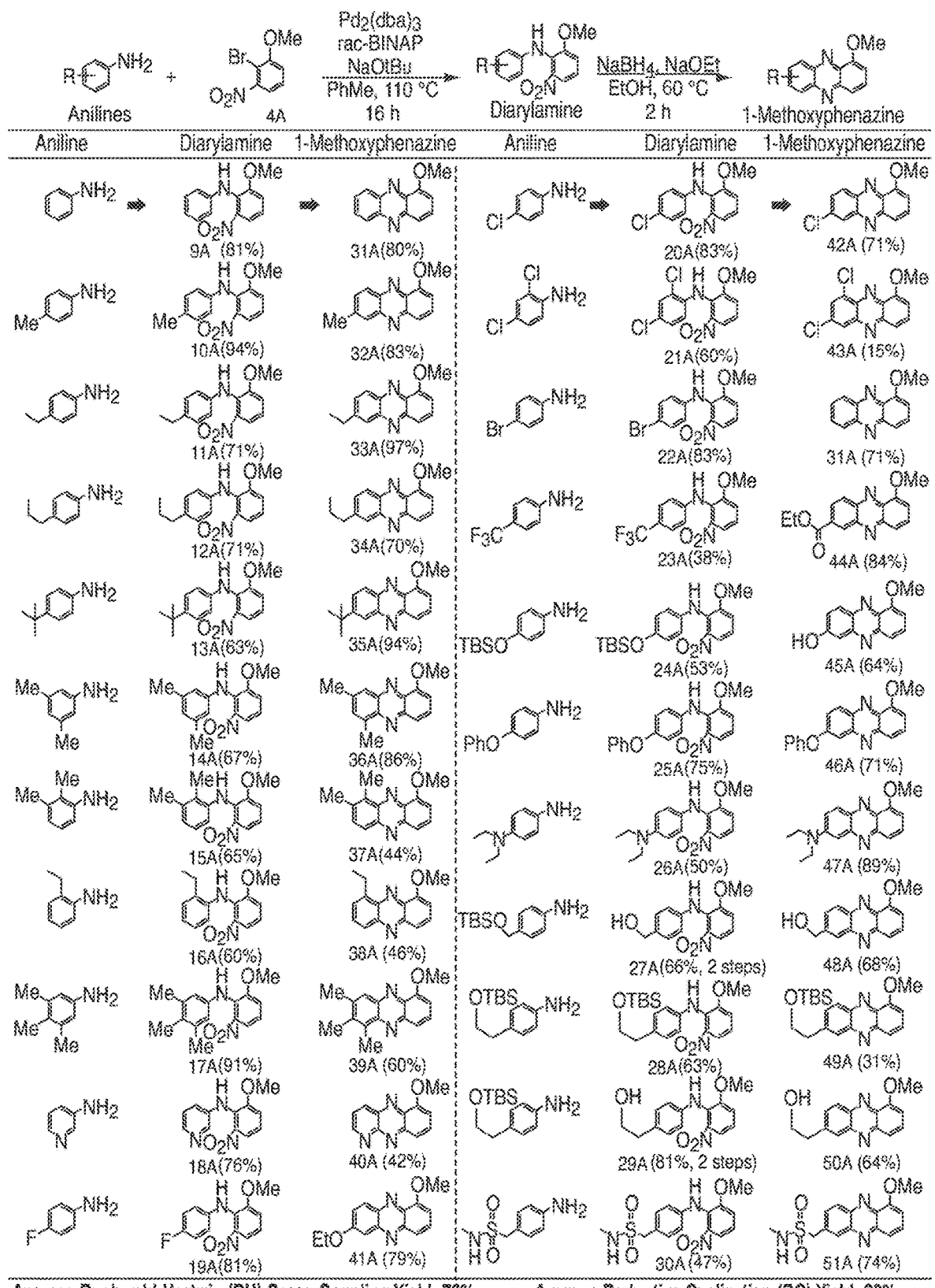
FIG. 26. 1-Methoxyphenazine syntheses starting from key building block 4A and indicated anilines with each intermediate diarylamine shown.

Simple inversion of the anilinic and aryl halide coupling partners from the example shown in FIG. 25B (e.g., from 5A and aryl halides to 4A and anilines) cleanly afforded both orientations of desired diarylamine intermediates in good yield (2A and 3A, FIGS. 25D and 25E). Anilines were coupled to 2-bromo-1-methoxy-3-nitrobenzene (4A) using 6 mol % tris(dibenzylideneacetone)dipalladium(0) with 18 mol % (±)-2,2'-bis(diphenylphosphino)-1,1'-binaphthalene (rac-BINAP) as a ligand to afford 2-series diarylamines in 71% average yield and inverted 3A-series diarylamine intermediates in 25% average yield. With diarylamine intermediates in hand, the reductive cyclization (RC) reactions were conducted using a procedure adapted from previously reported syntheses.[24] Using six equivalents of sodium borohydride in ethanolic solutions of 2 N sodium ethoxide, the reductive cyclizations proceeded smoothly for the 2A-series diarylamines, affording 1-methoxyphenazines in 70% average yield (22 examples; FIG. 26). Interestingly, the 3A-series diarylamines yielded no desired 1-methoxyphenazine products from reductive cyclization. This is likely due to electron donation from the ortho-positioned anisole oxygen, rendering the nitro group nitrogen atom much less electrophilic.

Nonetheless, the successful formation of 17 1-methoxyphenazine scaffolds was achieved as planned (FIG. 26). In several cases, unexpected 1-methoxyphenazine products (31A, 41A, 44A, 45A) were obtained following reductive cyclization of the corresponding diarylamines (19A, 22A, 23A, 24A). From these examples, it is apparent that select halogenated anilines are subject to substitution or over-reduction during cyclization and, as such, may not be ideal substrates for BH-RC. This result was initially surprising as analogous reductive ring closures have been previously reported to yield halogen-bearing phenazine products.[63,64] However, there is also literature precedence for the selective displacement of fluorine atoms during reductive ring closures en route to phenazine scaffolds.[74] Although initially discouraging, it is likely that this fluorine displacement could be utilized in future studies for regioselective cyclization from asymmetrical anilines or the introduction of nucleophilic groups during cyclization, as observed in the formation of 7-ethoxy-1-methoxyphenazine (41A). In the case of the trifluoromethylated diarylamine 23A, formation of an orthoester was observed during reductive cyclization, which could be isolated under basic workup conditions. Although acid-promoted hydrolysis of this orthoester afforded the corresponding ethyl 6-methoxyphenazine-2-carboxylate (44A) in quantitative yield, it was found that direct conversion from diarylamine 23A to this ethyl ester analogue via standard reductive cyclization conditions followed by acidic workup afforded 44A in an improved 84% yield following column chromatography. However, despite these synthetic challenges related to halogenated aniline substrates, 7-chloro-1-methoxyphenazine 42A and 7,9-dichloro-1-methoxyphenazine 43A were successfully synthesized using this BH-RC route.

It was also noted, however, that silyl ethers were unstable toward these reductive cyclization conditions. Ring closure of diarylamine intermediate 24A afforded 1-methoxyphenazine 45A with loss of the silyl protecting group as the sole product in 64% yield. Anticipating the difficulty in selectively brominating the demethylated 1,7-diol counterpart of this analogue, its advancement was discontinued.

Although desired TBS-protected products could be obtained in low yield (e.g. 49A was obtained from 28A in 31% yield), it was found that removal of the TBS group prior to reductive cyclization allowed for substantial improvements in 1-methoxyphenazine yields (e.g. a 31% to 64% yield improvement for 50A versus 49A).

Shortcomings notwithstanding, this two-step Buchwald-Hartwig/reductive cyclization (BH-RC) protocol yielded 21 discrete 1-methoxyphenazines with an average coupling yield of 70% and an average reductive cyclization yield of 68%. With this collection of 1-methoxyphenazines in hand, analogues were advanced toward HP final products for biological evaluation. Of the 21 novel 1-methoxyphenazines generated, 13 were demethylated using boron tribromide to afford 1-hydroxyphenazines in 89% average yield (FIG. 27). Several 1-methoxyphenazines presented difficulty with this demethylation reaction, resulting in decomposition (40A, 51A) or formation of unexpected products (48A, 50A). Surprisingly, demethylation of 1-methoxyphenazines 48A and 50A resulted in concomitant bromide displacement of the primary alcohol or silyl ether to afford alkyl bromides 70A and 71A in 87% and 53% yield, respectively (FIG. 28). Initially, this result was discouraging as the intention was to utilize the desired primary alcohol products for late-stage derivatization. These transformations, however, were perhaps fortuitous as reactions of the primary bromides with nucleophiles are likely preferable to attempting to selectively react the primary alcohols without undesired side reactions at the 1-position phenol.

Dibromination reactions of 1-hydroxyphenazines were conducted using 2.2 equivalents of N-bromosuccinimide in dichloromethane to afford HP target structures in 69% average yield (FIG. 27A; analogues 52A-65A). It should be noted that attempts to dibrominate the 1-hydroxyphenazine obtained from 47A at only the 2- and 4-positions were unsuccessful, as reactions using NBS or bromine in acetic acid both yielded 2,4,6-tribrominated HP 64A (and to a lesser extent, dealkylated side products). Despite this complication, the tribrominated analogue 64A was advanced to biological studies.

Figure 27B:
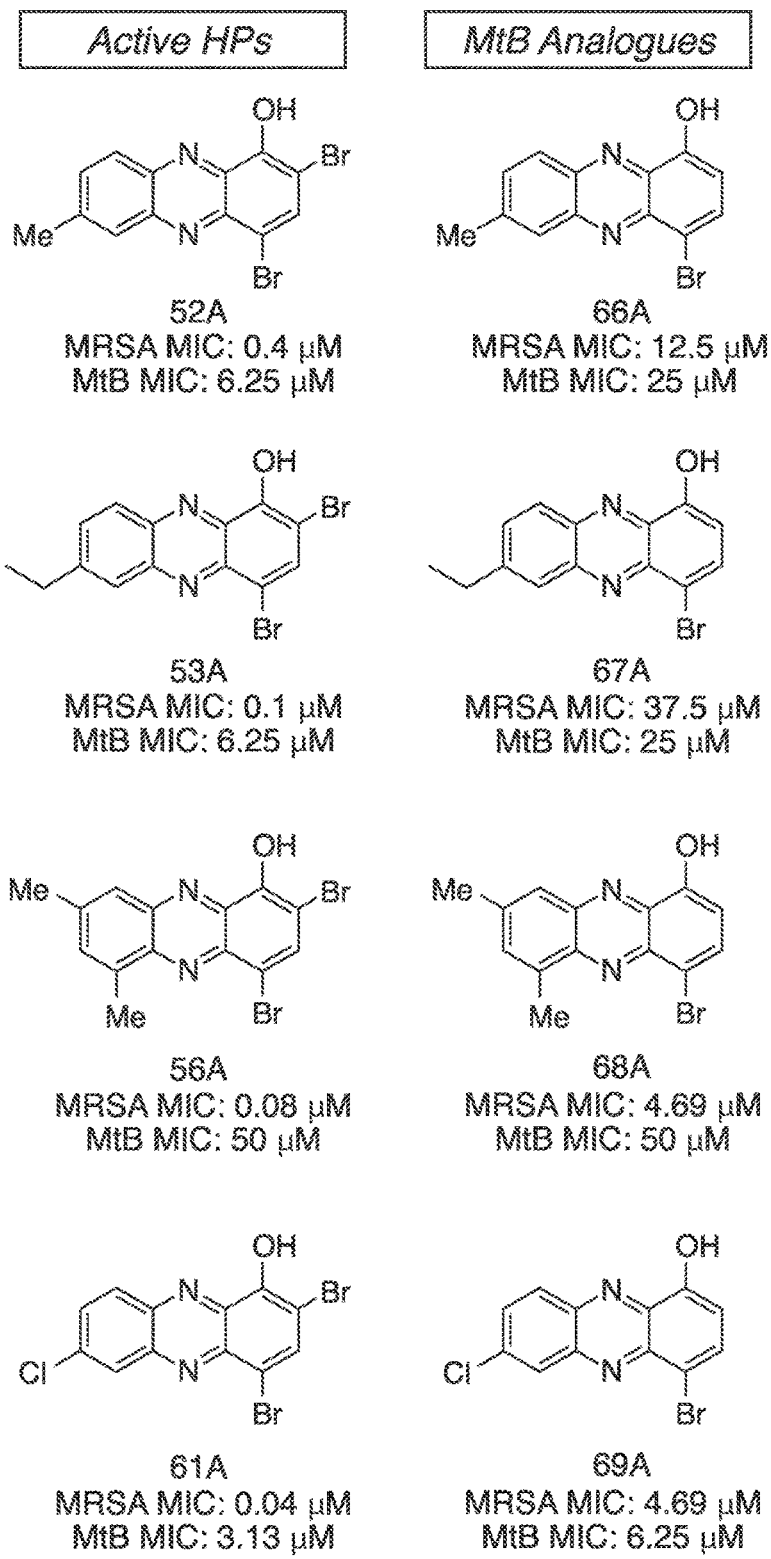
Figure 28:
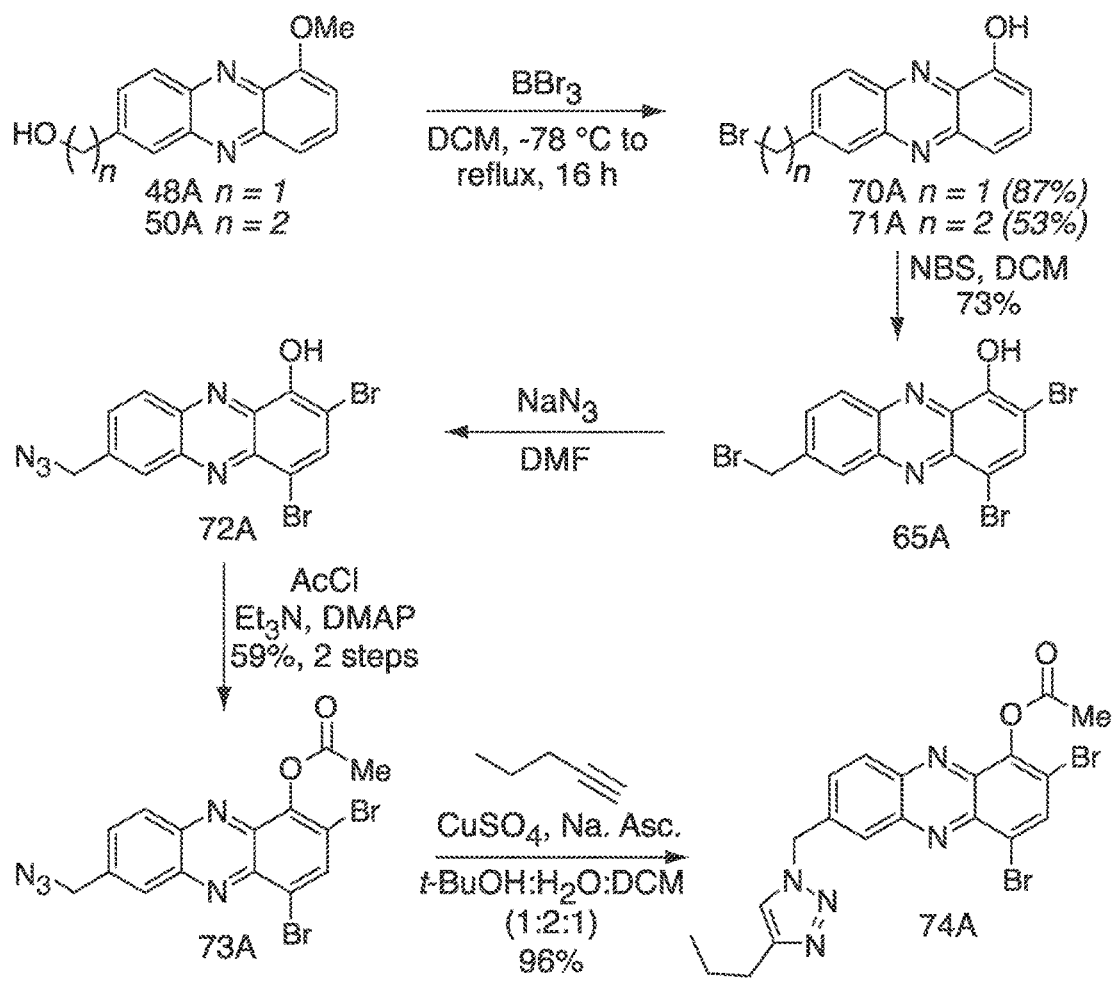
FIG. 28. Chemical synthesis of triazole-HP 74A from 1-methoxyphenazine 48A.

In previous work, 4-position halogenated HPs (i.e. without 2-position halogenation) were disclosed to demonstrate excellent antibacterial activities against *Mycobacterium tuberculosis*.[52,53] These findings motivated the synthesis of a small sub-set of HPs for investigations into novel anti-MtB agents (66A-69A, FIG. 27B). These four target analogues were chosen on the basis of the highly potent MIC activity (versus *S. aureus*) of the corresponding 2,4-dibrominated counterparts 52A, 53A, 56A, and 61A (vide infra). The chosen 1-methoxyphenazines were selectively brominated at the 4-position using N-bromosuccinimide in refluxing dichloromethane to afford 4-bromo-1-methoxyphenazines which subsequently underwent boron tribromide demethylation to afford 4-bromo-1-hydroxyphenazine anti-MtB designed analogues 66A-69A in 72% average yield over two steps.

Initially, the structure-activity relationships of this new BH-RC HP series (antibacterial activity discussed in Example 3) suggested that structural modifications could be made to select positions of the phenazine scaffold (particularly the 7-position) that would result in activity gains against bacterial pathogens. This BH-RC synthetic route grants the opportunity to introduce functional groups to the phenazine scaffold, which can be used as handles for late-stage derivatization and development (e.g. 70A and 71A). To this end, alkyl bromide compounds 70A and 71A were sought to be utilized for analogue synthesis with the goal of using functionalized 2,4-dibrominated HPs as starting materials. A last-step copper-catalyzed click reaction was chosen as the derivatization step due to generally high reaction yields and broad range of viable alkyne substrates.[75,76]

Although 7-(2-bromoethyl)phenazin-1-ol (71A) was prone to elimination of HBr (likely owing to favorable conjugation of the resulting olefin with the phenazine heterocycle), 70A proved to be an robust analogue to functionalize. A reaction of sodium azide with 70A in N,N-dimethylformamide afforded a primary azide in quantitative yield. However, subsequent 2,4-dibromination of this product proved troublesome, yielding the desired product in only 31% yield (best of three attempts). To circumvent this issue, 70A was first brominated at the 2- and 4-positions, generating HP 65A in 73% yield. This dibrominated product was then subjected to azide displacement, yielding the crude azidophenazine 72A. To avoid complications arising from undesired hydroxyphenazine-copper chelation during the last-step click reaction, the phenol of crude 72A was protected using acetyl chloride and a catalytic amount of DMAP in dichloromethane to afford the acylated azidophenazine 73A in 59% yield over two steps (FIG. 28). The final click reaction proceeded smoothly, reacting azidophenazine 73A with 1-pentyne, copper(II) sulfate, and sodium ascorbate in tert-butanol:water:dichloromethane (1:2:1) to afford triazole-HP 74A in 96% yield.

Example 2

Biological Assays of the Compounds

HP Complex Formation with Fe(II).

The rates of phenazine-iron(II) complex formation were independently evaluated via UV-vis spectrometry following addition of 0.5 equivalents ammonium iron(II) sulfate hexahydrate to stirring solutions of HP 57A, 58A, 61A, or 86A (5 mM, 5 mL) in dimethyl sulfoxide. Aliquots (20 µL) were removed from each stirring solution and added to 980 µL dimethyl sulfoxide in a cuvette. Spectral scanning was performed from 300 to 700 nm in 2 nm increments. The $\lambda_{max}$ value was determined to be 374 nm for all HP analogues tested herein. A loss of absorbance at 374 nm corresponds to a loss of free hydroxyphenazine and apparent formation of a phenazine-iron(II) complex.

Spectrophotometric Determination of Prodrug Stability in LB Media.

Into 1.5 mL Eppendorf tubes was added 750 µL of LB at 37° C. To this solution was added 7.5 µL of test compound (10 mM DMSO stock). Tubes were briefly vortexed, then incubated for up to 48 hours. At the indicated time points, 750 µL ethyl acetate was added to the LB solution and the tubes were vigorously vortexed. From the organic layer was drawn 500 µL, which was added to 1.5 mL of 1.33 mM triethylamine in ethyl acetate in a quartz cuvette (due to overlapping absorbance spectra for prodrugs and the respective HP, triethylamine was added as a reporter to generate the HP anions, which fortunately presented spectra distinct from those of the prodrugs). Spectral scans were taken from 200 to 700 nm at 2 nm increments. Results were plotted using GraphPad Prism.

Antibiotic Susceptibility Tests (MIC Assay Protocol)

Figure 6:
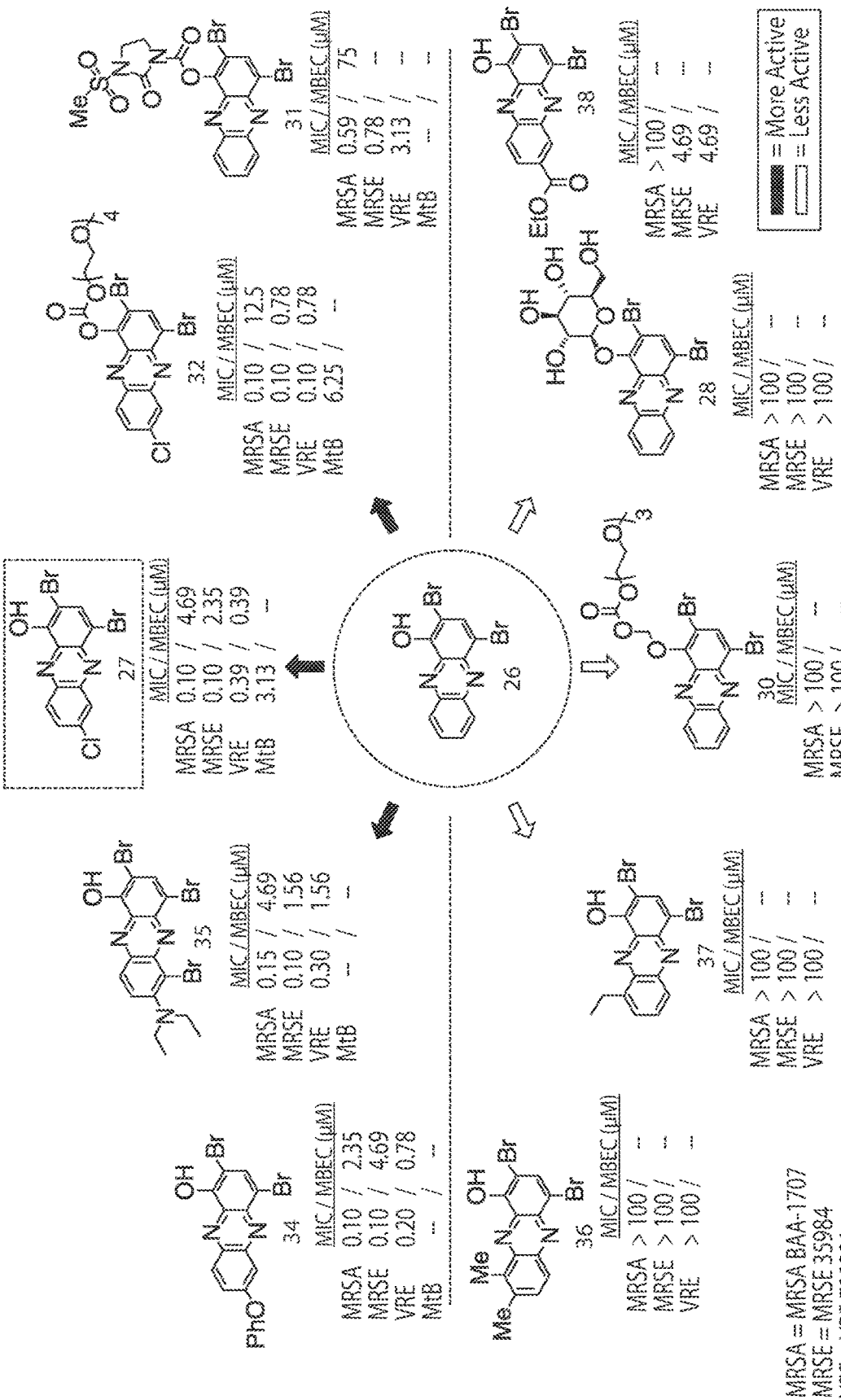
FIG. 6 shows the antibacterial profiles for various compounds of Formula (I).

The minimum inhibitory concentration (MIC) for each compound described herein was determined by the broth microdilution method as recommended by the Clinical and Laboratory Standards Institute (CLSI) (Clinical and Laboratory Standards Institute. 2009. Methods for dilution antimicrobial susceptibility tests for bacteria that grow aerobically; approved standard, eighth edition (M7-A8)). In a 96-well plate, eleven two-fold serial dilutions of each compound were made in a final volume of 100 µL Luria Broth (one column served as a blank; see the MIC assay described herein). Each well was inoculated with $10^5$ bacterial cells at the initial time of incubation, prepared from a fresh log phase culture ($OD_{600}$ of 0.5 to 1.0 depending on bacterial strain). The MIC was defined as the lowest concentration of a compound that prevented bacterial growth after incubating of 16 to 18 hours at 37° C. (MIC values were supported by spectrophotometric readings at $OD_{600}$). The concentration range tested for each compound during this study was 0.10 to 100 µM. DMSO served as the vehicle and negative control in each microdilution MIC assay. DMSO was serially diluted at the same concentration as the compounds with a top concentration of 1% v/v. Bacterial strains used included methicillin-resistant *Staphylococcus aureus* (MRSA) (Clinical Isolates from Shands Hospital in Gainesville, Fla.: MRSA-2, MRSA-1), methicillin-resistant *Staphylococcus epidermidis* (MRSE strain ATCC 35984; methicillin-sensitive strain ATCC 12228), vancomycin-resistant *Enterococcus faecium* (VRE; ATCC 700221). Exemplary results are shown in Table 2 and FIG. 6. Additionally, the compounds of Table 2 demonstrate no hemolytic or cytotoxic activities.

Minimum Inhibitory Concentration (MIC) Susceptibility Assay (In 96-Well Plate).

The minimum inhibitory concentration (MIC) for each phenazine analogue was determined by the broth microdilution method as recommended by the Clinical and Laboratory Standards Institute (CLSI). In a 96-well plate, eleven two-fold serial dilutions of each compound were made in a final volume of 100 µL Lysogeny Broth. Each well was inoculated with $10^5$ bacterial cells at the initial time of incubation, prepared from a fresh log phase culture ($OD_{600}$ of 0.5 to 1.0 depending on bacterial strain). The MIC was defined as the lowest concentration of compound that prevented bacterial growth after incubating 16 to 18 hours at 37° C. (MIC values were supported by spectrophotometric readings at $OD_{600}$). The concentration range tested for each phenazine analogue/antibacterial during this study was 0.10 to 100 µM. DMSO served as the vehicle and negative control in each microdilution MIC assay. DMSO was serially diluted with a top concentration of 1% v/v. All compounds were tested in three independent experiments.

TABLE 2

Minimum inhibitory concentrations (MICs, in µM) of select compounds of the invention against select microorganisms

| Compound | MRSA BAA-1707 | MSRE ATCC-35984 | VRE ATCC-700221 |
|---|---|---|---|
| 27 | 0.1 | 0.1 | 0.39 |
| 28 | >100 | >100 | >100 |
| 30 | >100 | >100 | >100 |
| 31 | 0.59 | 0.78 | 3.13 |
| 32 | 0.1 | 0.1 | 0.1 |
| 34 | 0.1 | 0.1 | 0.2 |
| 35 | 0.15 | 0.1 | 0.30 |
| 36 | >100 | >100 | >100 |
| 37 | >100 | >100 | >100 |
| 38 | >100 | 4.69 | 4.69 |

Biofilm Inhibition Protocol

A serial two-fold dilution of 2× compound concentration was made in 100 µL tryptic soy broth (TSB) medium with 0.5% glucose were delivered into 0.1% gelatin (Millipore) coated 96-well tissue culture plates. The same volume of DMSO (vehicle control), was used as a negative control and did not go over 1% v/v in biofilm inhibition assays. To each well, 100 µL of TSB with 0.5% glucose containing $2\times10^6$ CFU/mL methicillin resistant *Staphylococcus aureus* (MRSA), *Staphylococcus epidermidis* (ATCC 35984), or *Enterococcus faecium* (ATCC 700221) cells, prepared from fresh culture ($OD_{600}$ of 0.8), was added. The plates were incubated at 37° C. for 24 hours. The wells were gently rinsed by submerging the entire plates in a tub of cold, running tap water. The wells were then fixed with 200 µL methanol for 15 minutes. After the plates were air dried, the biofilms were stained with 100 µL of 1% crystal violet for 10 minutes. The plates were again rinsed with running water. After drying in air, quantitative assessment of biofilm formation was obtained by extracting the crystal violet associated with the remaining biofilm with 100 µL per well of the following bleaching solution (methanol:glacial acetic acid: water (v/v/v)=4:1:5). This bleaching solution dissolved the bound crystal violet and produced a violet-colored solution in each well. The intensity of coloration was determined by measuring the absorbance at 540 nm. Exemplary results are shown in Table 3 and FIG. 6.

TABLE 3

Minimum biofilm eradication concentrations (MBECs, in µM) of select compounds of the invention against select microorganisms

| Compound | MRSA BAA-1707 | MSRE ATCC-35984 | VRE ATCC-700221 |
|---|---|---|---|
| 27 | 4.69 | 2.35 | 0.39 |
| 31 | 75 | NT | NT |
| 32 | 12.5 | 0.78 | 0.78 |
| 34 | 2.35 | 4.69 | 0.78 |
| 35 | 4.69 | 1.56 | 1.56 |

*Mycobacterium Tuberculosis* (*M. Tuberculosis*) MIC Assay

*M. tuberculosis* H37Ra (ATCC 25177) was inoculated in 10 ml Middlebrook 7H9 medium and allowed to grow for two weeks. The culture was then diluted with fresh medium until an $OD_{600}$ of 0.01 was reached. Aliquots of 200 µl were then added to each well of a 96-well plate starting from the second column. Test compounds were dissolved in DMSO at final concentration of 10 mM. 7.5 µl of each compound solution along with DMSO (negative control) and streptomycin (positive control-40 mg/ml stock solution) were added to 1.5 ml of the *Mycobacterium* diluted cultures, resulting in 50 µM final concentration of each halogenated phenazine analogues and 340 µM for streptomycin. The final DMSO concentration was maintained at 0.5%. Aliquots of 400 µl were added to wells of the first column of the 96-well plate and serially diluted two-fold (200 µl) per well across the plate to obtain final concentrations that ranges from 0.024 to 50 µM for the test compounds and 0.16 to 340 µM for streptomycin. Three rows were reserved for each compound. The plates were then incubated at 37° C. for seven days. Minimum inhibitory concentrations (Mtb MICs) were reported as the lowest concentration at which no bacterial growth was observed. $OD_{600}$ absorbance was recorded using SPECTRAMAX M5 (Molecular Devices). Data obtained from three independent experiments were analyzed using Excel. Exemplary results are shown in Table 4 and FIG. 6.

MIC Assay for *Mycobacterium Tuberculosis*.

*M. tuberculosis* H37Ra (ATCC 25177) was inoculated in 10 mL Middlebrook 7H9 medium and allowed to grow for two weeks. The culture was then diluted with fresh medium until an $OD_{600}$ of 0.01 was reached. Aliquots of 200 µL were then added to each well of a 96-well plate starting from the second column. Test compounds were dissolved in DMSO at final concentration of 10 mM. 7.5 µL of each compound along with DMSO (negative control) and streptomycin (positive control-40 mg/ml stock solution) were added to 1.5 mL of the *Mycobacterium* diluted cultures, resulting in 50 µM final concentration of each halogenated phenazine analogues and 340 µM for streptomycin. The final DMSO concentration was maintained at 0.5%. Aliquots of 400 µl were added to wells of the first column of the 96-well plate and serially diluted two-fold (200 µl) per well across the plate to obtain final concentrations that ranges from 0.024 to 50 µM for the test compounds and 0.16 to 340 µM for streptomycin. Three rows were reserved for each compound. The plates were then incubated at 37° C. for seven days. Minimum inhibitory concentrations are reported as the lowest concentration at which no bacterial growth was observed. $OD_{600}$ absorbance was recorded using Spectra-Max M5 (Molecular Devices). Data obtained from three independent experiments were analyzed using Excel.

TABLE 4

Minimum inhibitory concentrations (MICs, in µM) of select compounds of the invention against *Mycobacterium tuberculosis* (*M. tuberculosis*)

| Compound | *M. tuberculosis* ATCC 25177 |
|---|---|
| 27 | 3.13 |
| 32 | 6.25 |

Calgary Biofilm Device (CBD) Assays

Figure 9:
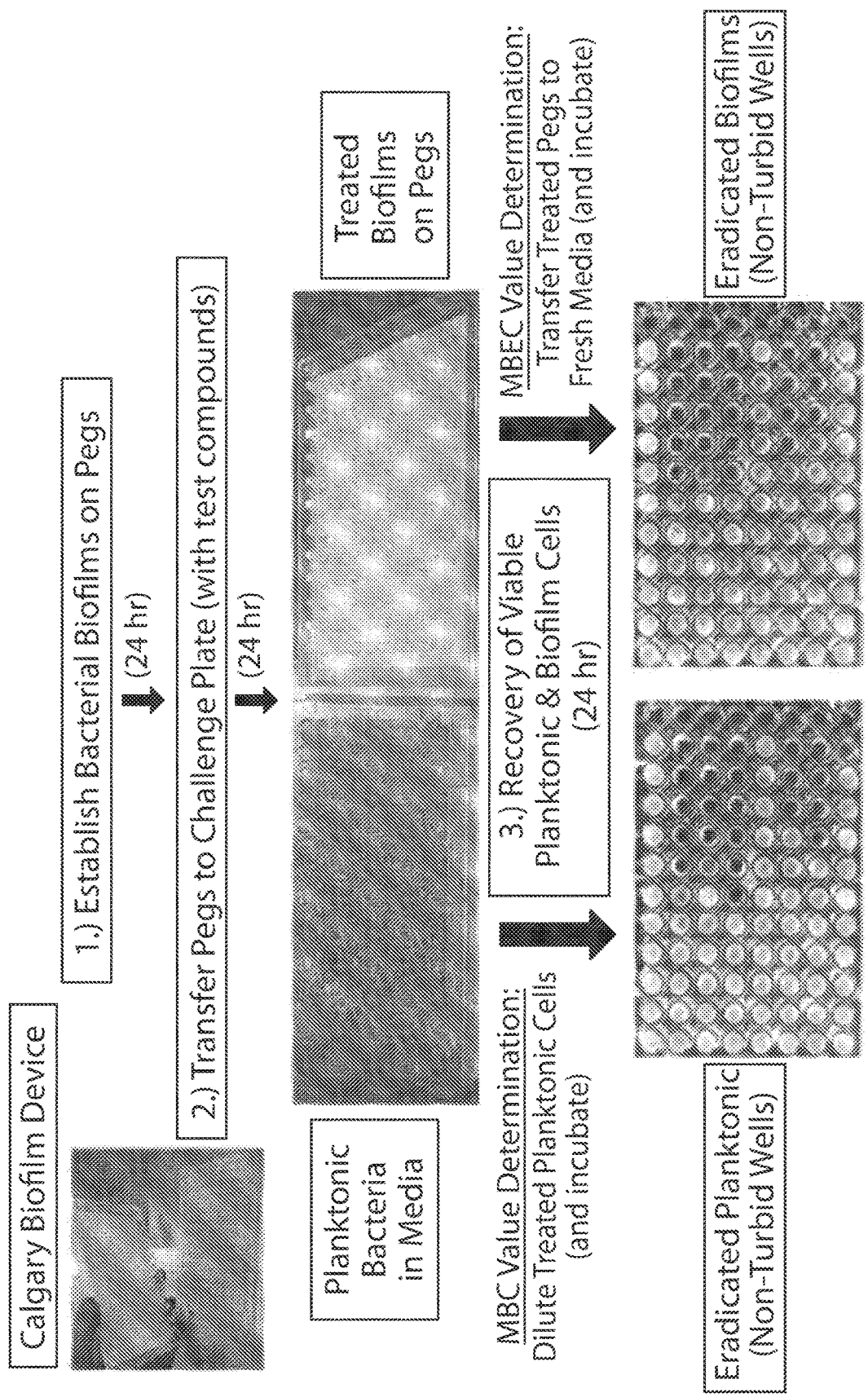
FIG. 9 shows a flowchart illustrating a Calgary Biofilm Device (CBD) assay.

HP analogues, vancomycin, and control compounds were evaluated for bacterial biofilm eradication activity against MRSA-2 using the Calgary Biofilm Device (CBD),[20] which allows biofilms to be established on pegs that are submerged in inoculated media in 96-well plates (FIG. 9). Pegs with established biofilms are then transferred to a second 96-well plate containing serial dilutions of test compounds (e.g., the HPs) for biofilm eradication. Following compound treatment, pegs are transferred to fresh media to allow viable biofilms to recover (grow and disperse) resulting in turbid wells. During these investigations, it was found that CBD assays were superior to biofilm eradication assays that regrow biofilms on the inside of microtiter wells.[17] The CBD allows for the determination of biofilm (MBEC) and planktonic (minimum bactericidal concentration or MBC) killing dynamics from a single experiment. Typically, MBEC and MIC values were compared using different assays [10,20] (e.g., bacterial density, media, incubation times), which had an impact on these values.

The Calgary device (96-well plate with lid containing pegs to establish biofilms on) was inoculated with 125 µL of a mid-log phase culture diluted 1,000-fold in tryptic soy broth with 0.5% glucose (TSBG) to establish bacterial biofilms after incubation at 37° C. for 24 hours. The lid of the Calgary device was then removed, washed and transferred to another 96-well plate containing 2-fold serial dilutions of the test compounds (the "challenge plate"). The total volume of media with compound in each well in the challenge plate is 150 µL. The Calgary device was then incubated at 37° C. for 24 hours. The lid was then removed from the challenge plate and MBC/MBEC values were determined using different experimental pathways.

Pulse experiments followed a normal CBD assay protocol, except that the compound treatment phase (the "challenge plate") consisted of two sequential 24 hour compound treatment plates before the final recovery plate. Following this, CBD pegs were removed from the lid, sonicated for 30 minutes in PBS and plated out to determine biofilm cell killing in colony forming units per milliliter (CFU/mL).

To determine MBC values, 20 µL of the challenge plate was transferred into a fresh 96-well plate containing 180 µL TSBG and incubated overnight at 37° C. The MBC values were determined as the concentration giving a lack of visible bacterial growth (i.e., turbidity).

Figure 10:
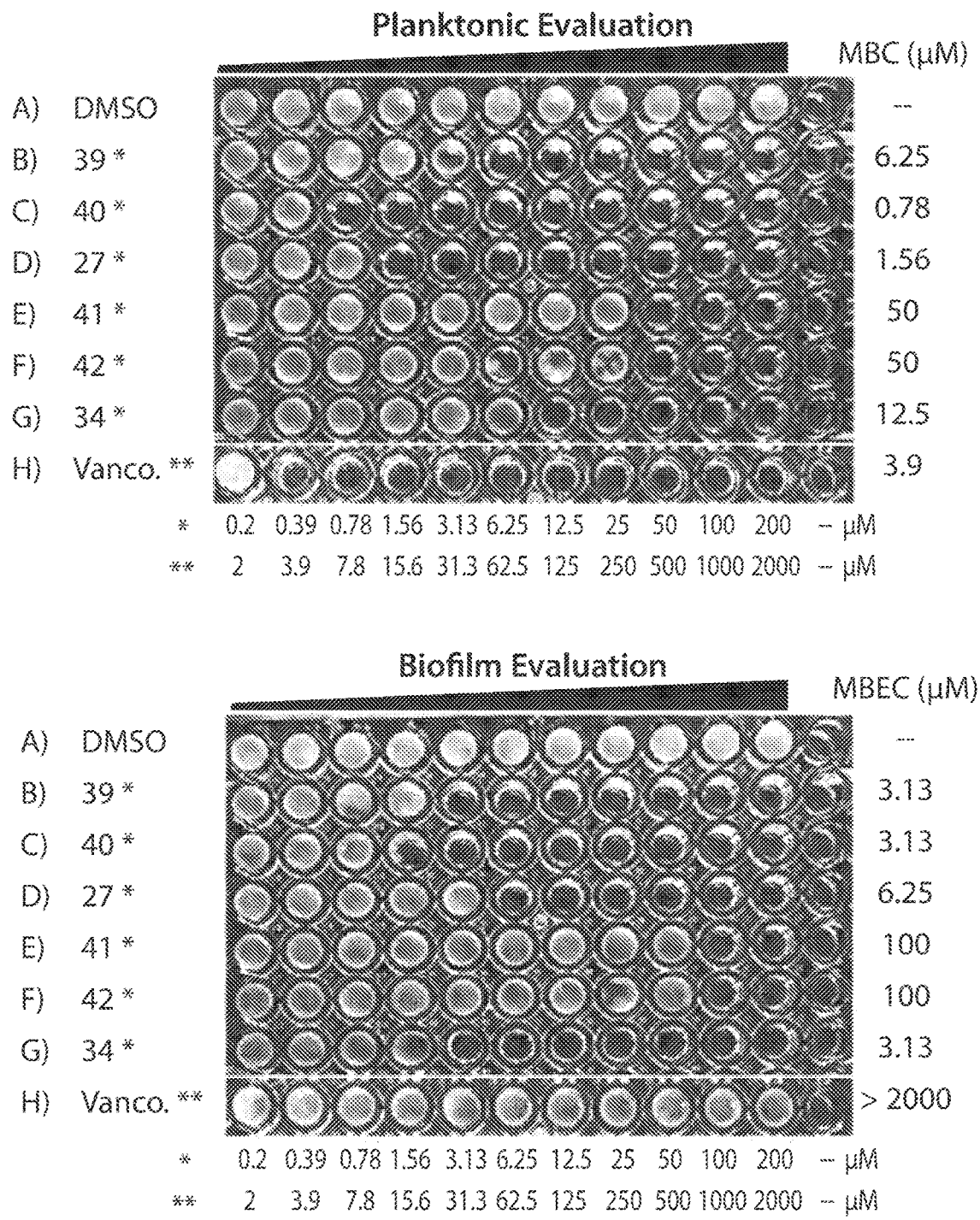
FIG. 10 shows Calgary Biofilm Device assays to quantify planktonic (MBC) and biofilm (MBEC) killing efficiencies against a methicillin-resistant strain of *Staphylococcus aureus* (MRSA, BAA-1707).
Figure 18:
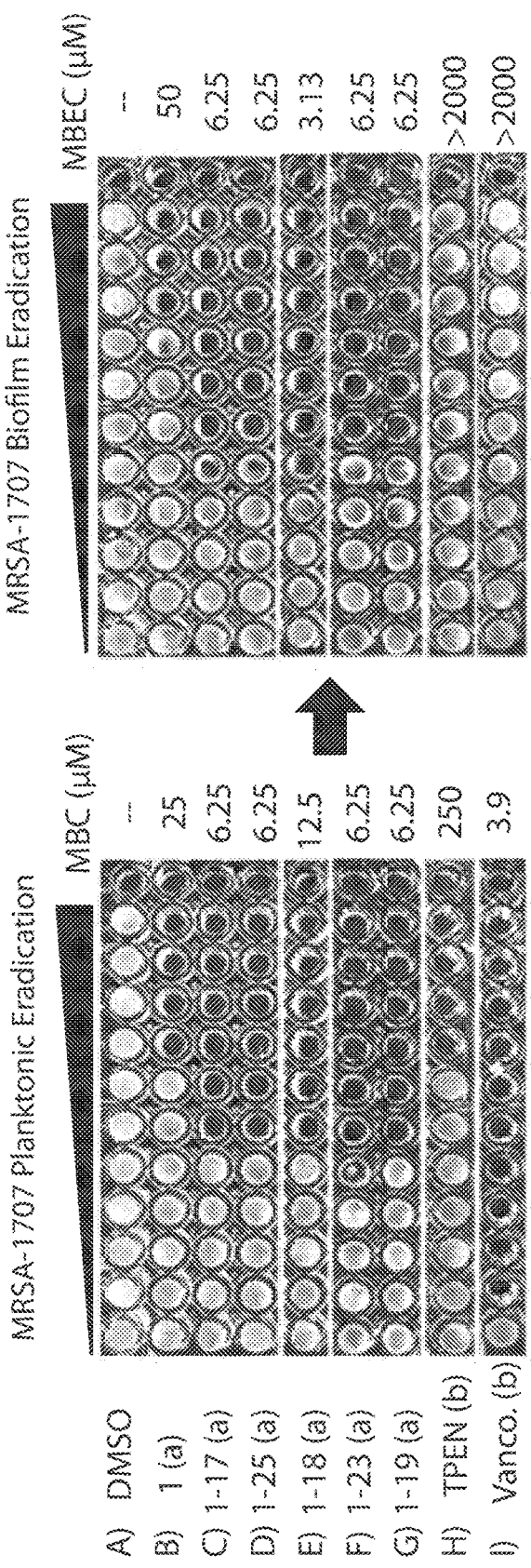
FIG. 18 shows the Calgary biofilm device (CBD) assay results for a panel of HPs, N,N,N',N'-tetrakis(2-pyridylmethyl)ethane-1,2-diamine (TPEN), and vancomycin against MRSA-1707 demonstrating the potent and unique biofilm eradication activities of HP small molecules.

To determine MBEC values, the Calgary device lid (with attached pegs/treated biofilms) was transferred to a new 96-well plate containing 150 µL of fresh TSBG media in each well and incubated for 24 hours at 37° C. to allow viable biofilms to grow and disperse resulting in turbidity after the incubation period. MBEC values were determined as the lowest test concentration that resulted in eradicated biofilm (e.g., wells that had no turbidity after final incubation period). Results are shown in FIGS. 10 and 18.

Calgary Biofilm Device (CBD) Experiments.

Biofilm eradication experiments were performed using the Calgary Biofilm Device to determine MBC/MBEC values for various compounds of interest (Innovotech, product code: 19111). The Calgary device (96-well plate with lid containing pegs to establish biofilms on) was inoculated with 125 µL of a mid-log phase culture diluted 1,000-fold in tryptic soy broth with 0.5% glucose (TSBG) to establish bacterial biofilms after incubation at 37° C. for 24 hours. The lid of the Calgary device was then removed, washed and transferred to another 96-well plate containing 2-fold serial dilutions of the test compounds (the "challenge plate"). The total volume of media with compound in each well in the challenge plate is 150 µL. The Calgary device was then incubated at 37° C. for 24 hours. The lid was then removed from the challenge plate and MBC/MBEC values were determined using different final assays. To determine MBC values, 20 µL of the challenge plate was transferred into a fresh 96-well plate containing 180 µL TSBG and incubated overnight at 37° C. The MBC values were determined as the concentration giving a lack of visible bacterial growth (i.e., turbidity). For determination of MBEC values, the Calgary device lid (with attached pegs/treated biofilms) was transferred to a new 96-well plate containing 150 µL of fresh TSBG media in each well and incubated for 24 hours at 37° C. to allow viable biofilms to grow and disperse resulting in turbidity after the incubation period. MBEC values were determined as the lowest test concentration that resulted in eradicated biofilm (i.e., wells that had no turbidity after final incubation period). All compounds were tested in three independent experiments.

Live/Dead Staining (Fluorescence Microscopy) of HP-Treated MRSA-2 Biofilms

Figure 7:
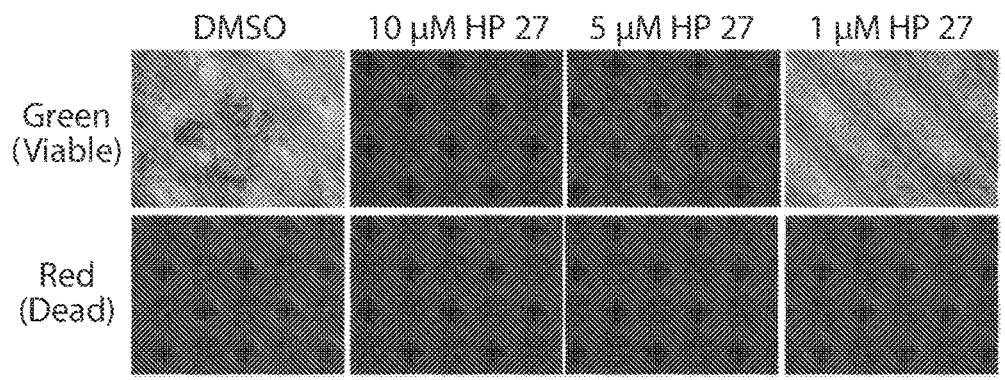
FIG. 7 shows Live/Dead staining of MRSA-2 biofilms following treatment with Compound 27.

To support the CBD assay findings, LIVE/DEAD experiments were performed with potent Compound 27 (FIG. 7). A mid-log culture of MRSA-2 was diluted 1:1,000-fold and 500 µL was transferred to each compartment of a 4 compartment CELLVIEW dish (Greiner Bio-One 627871). The dish was then incubated for 24 hours at 37° C. After this time, the cultures were removed and the plate was washed with 0.9% saline. The dish was then treated with the compounds in fresh media at various concentrations. DMSO was used as the negative control in this assay. The dish was incubated with the compound for 24 hours at 37° C. After this time, the cultures were removed and the dish was washed with 0.9% saline for 2 minutes. Saline was then removed and 500 µL of the stain (Live/Dead BacLight Viability Kit, Invitrogen) were added for 15 minutes and left in the dark. After this time, the stain was removed, and the dish was washed twice with 0.9% saline. Then the dish was fixed with 500 µL 4% paraformaldehyde in PBS for 30 minutes. Images of remaining MRSA-2 biofilms were then taken with a fluorescence microscope. All data were analyzed using Image J software.

Live/Dead Staining (Fluorescence Microscopy) of MRSE 35984 Biofilms

A mid-log culture of MRSE 35894 was diluted 1:1,000-fold and 500 µL was transferred to each compartment of a 4 compartment CELLview dish (Greiner Bio-One 627871). The dish was then incubated for 24 hours at 37° C. After this time, the cultures were removed and the plate was washed with 0.9% saline. The dish was then treated with the compounds in fresh media at various concentrations. DMSO was used as the negative control in this assay. The dish was incubated with the compound for 24 hours at 37° C. After this time, the cultures were removed and the dish was washed with 0.9% saline for 2 minutes. Saline was then removed and 500 µL of the stain (Live/Dead BacLight Viability Kit, Invitrogen) were added for 15 minutes and left in the dark. After this time, the stain was removed and the dish was washed twice with 0.9% saline. Then the dish was fixed with 500 µL 4% paraformaldehyde in PBS for 30 minutes. Images of remaining MRSE biofilms were then taken with a fluorescence microscope. All data were analyzed using Image J software from three independent experiments.

HPs 26 Complex Formation with Fe(II)

Figure 8:
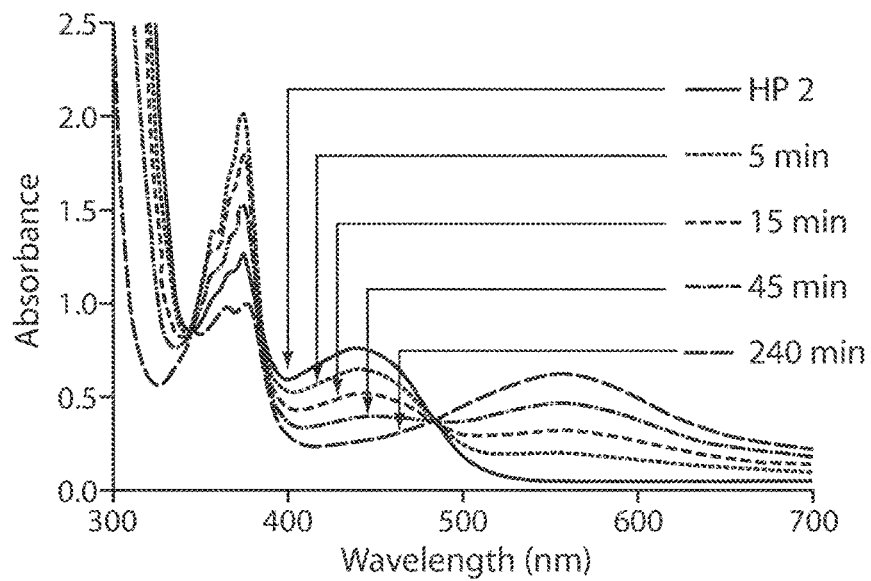
FIG. 8 shows UV-Vis analysis of metal chelation with Compound 26.

The rates of phenazine-metal(II) complex formation was evaluated via UV-vis spectrometry following addition of 0.5 equivalents\ammonium iron(II) sulfate hexahydrate to stirring solutions of HP 26 (10 mM, 20 mL) in dimethyl sulfoxide. Spectral scanning was performed from 200 to 900 nm in 2 nm increments. The λmax values are illustrated in FIG. 8. The disappearance of the complex was observed over the indicated time points.

Hemolysis Assay with Red Blood Cells

Freshly drawn human red blood cells (hRBC with ethylenediaminetetraacetic acid (EDTA) as an anticoagulant) were washed with Tris-buffered saline (0.01M Tris-base, 0.155 M sodium chloride (NaCl), pH 7.2) and centrifuged for 5 minutes at 3,500 rpm. The washing was repeated three times with the buffer. In a 96-well plate, test compounds were added to the buffer from DMSO stocks. Then 2% hRBCs (50 µL) in buffer were added to the test compounds to give a final concentration of 200 µM. The plate was then incubated for 1 hour at 37° C. After incubation, the plate was centrifuged for 5 minutes at 3,500 rpm. Then 80 µL of the supernatant was transferred to another 96-well plate and the optical density (OD) was read at 405 nm. DMSO served as the negative control (0% hemolysis) while Triton X served as the positive control (100% hemolysis). The percent of hemolysis was calculated as ($OD_{405}$ of the compound–$OD_{405}$ DMSO)/($OD_{405}$ Triton X–$OD_{405}$ buffer) from three independent experiments.

LDH Release Assay for HeLa Cytotoxicity Assessment

HeLa cytotoxicity was assessed using the LDH release assay described by CytoTox96 (Promega G1780). HeLa cells were grown in Dulbecco's Modified Eagle Medium (DMEM; Gibco) supplemented with 10% Fetal Bovine Serum (FBS) at 37° C. with 5% $CO_2$. When the HeLa cultures exhibited 70-80% confluence, halogenated phenazines were then diluted by DMEM (10% FBS) at concentrations of 25, 50 and 100 µM and added to HeLa cells. Triton X-100 (at 2% v/v) was used as the positive control for maximum lactate dehydrogenate (LDH) activity in this assay (i.e., complete cell death) while "medium only" lanes served as negative control lanes (i.e., no cell death). DMSO was used as the vehicle control. HeLa cells were treated with compounds for 24 hours and then 50 µL of the supernatant was transferred into a fresh 96-well plate where 50 µL of the reaction mixture was added to the 96-well plate and incubated at room temperature for 30 minutes. Finally, Stop Solution (50 µL) was added to the incubating plates and the absorbance was measured at 490 nm. Results are from three independent experiments.

Macromolecular Synthesis Inhibition Assay

Macromolecular synthesis experiments were carried out in methicillin-resistant *Staphylococcus aureus* BAA-1707. An overnight culture (100 µL) of *S. aureus* BAA-1707 was sub-cultured into 10 mL of fresh TSBG media, which was allowed to grow to exponential phase ($OD_{600}$=0.2–0.3) before transferring 500 µL to each well in a 24 well-plate. The test compounds and vehicle control (DMSO) were added to achieve the desired concentrations relative to their MIC values against *S. aureus* BAA-1707. Treated cultures were then incubated at 37° C. for 30 minutes before radioactive precursors for DNA ([$^3$H] thymidine (0.5 µCi)), RNA ([$^3$H] uridine (0.5 µCi)) and protein ([$^3$H] leucine (1 µCi)) were added. The following antibiotics with known modes of action were used as positive controls in these experiments: ciprofloxacin (DNA inhibition), rifampicin (RNA inhibition) and linezolid (protein inhibition). DMSO served as the negative control. DNA and RNA radiolabeled cultures were then incubated in 37° C. for 15 minutes before being stopped by adding 60 µL of cold 5% trichloroacetic acid (TCA). The protein synthesis experiment was stopped after 40 minutes by adding 60 µL cold TCA. These mixtures were then incubated at 2° C. for at least 30 minutes before the contents of the plates were transferred onto glass microfiber filters (24 mm) and washed 5 times with 1 mL of 5% TCA. The filters are allowed to dry overnight before 3.5 mL of the scintillation fluid was added to the scintillation vials containing the filters and the radiation counts were measured using liquid scintillation LS 6500.

UV-Vis Experiments to Demonstrate Direct Metal(II) Binding

Figure 17:
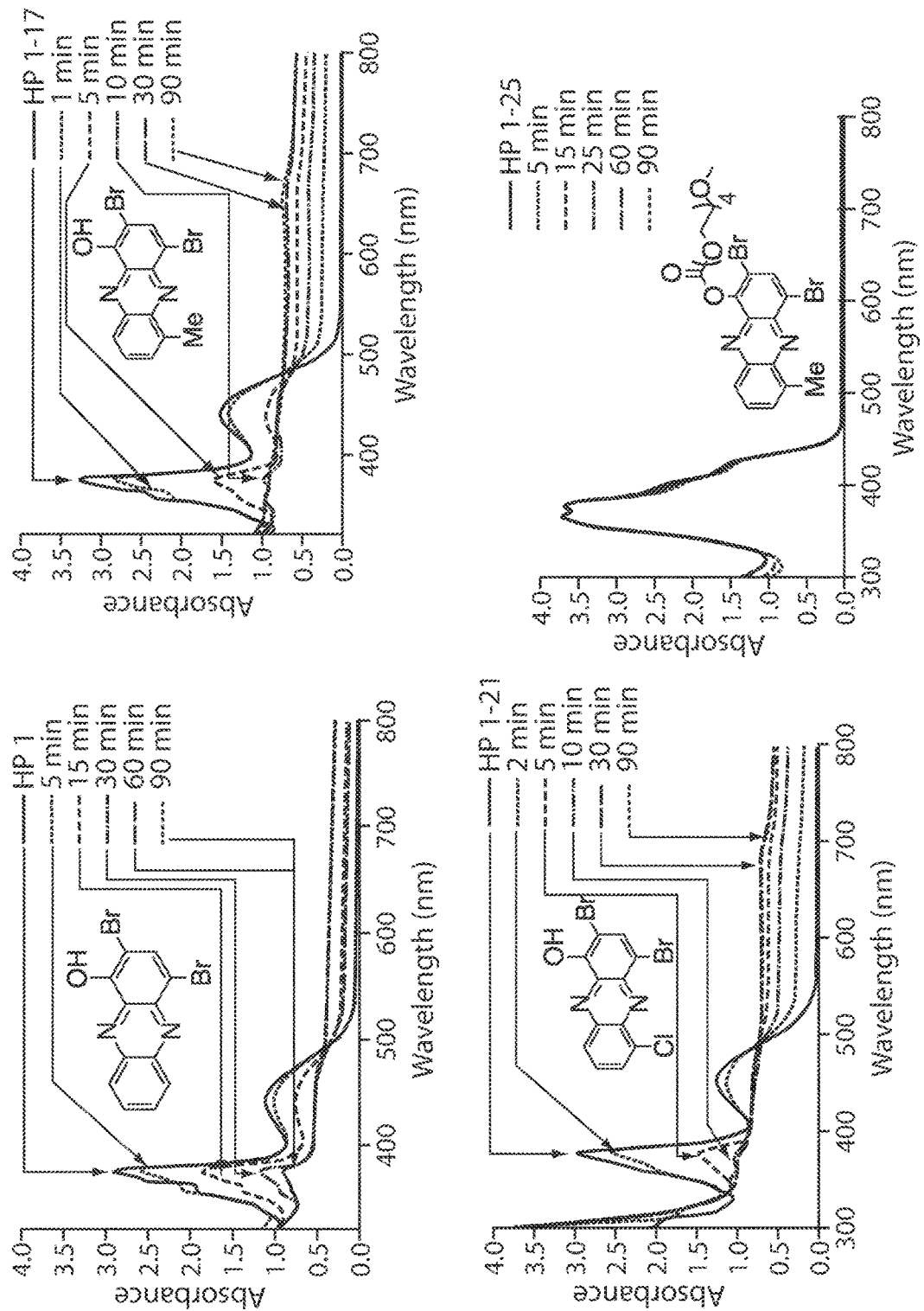
FIG. 17 shows the UV-Vis analysis of copper(II) binding by various halogenated phenazines. The HP:copper(II) complex is insoluble and precipitates out of solution, thus the disappearance of HP peaks is clear while there is not a strong appearance of HP:copper(II) complex in the UV-Vis spectrum.
Figure 22:
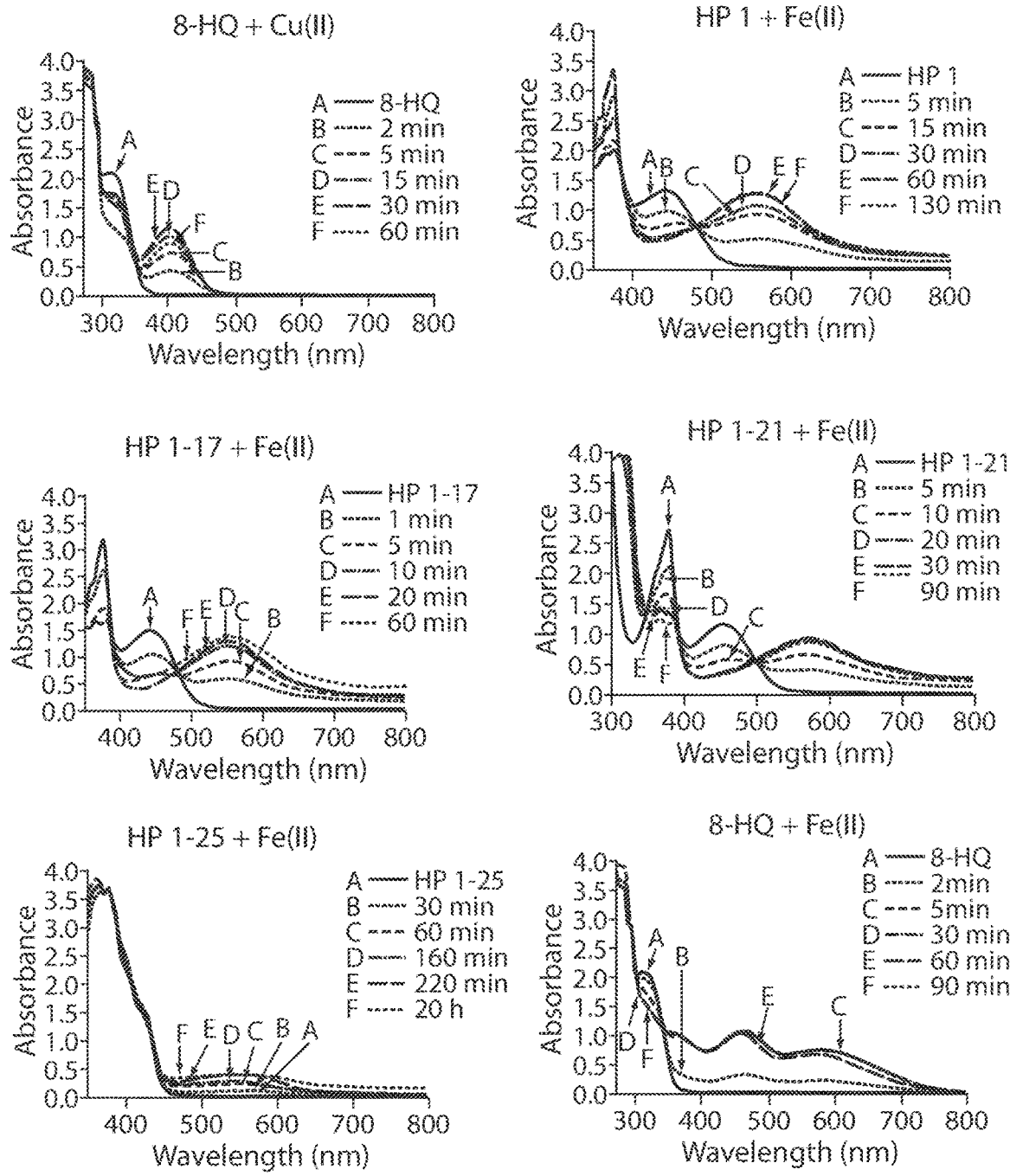
FIG. 22 shows rates of halogenated phenazine-copper(II) complex formation.
Figure 22:
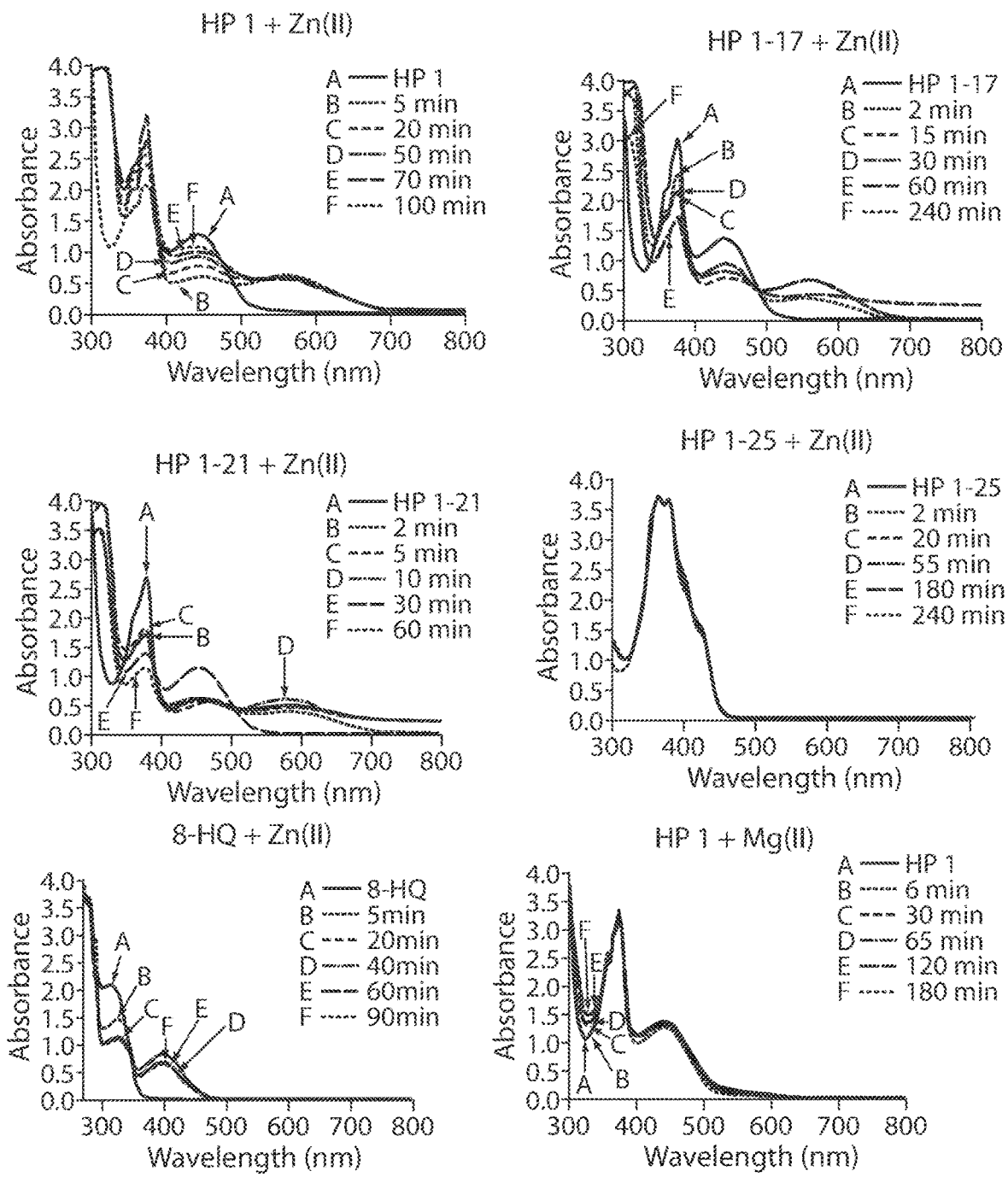
Figure 22:
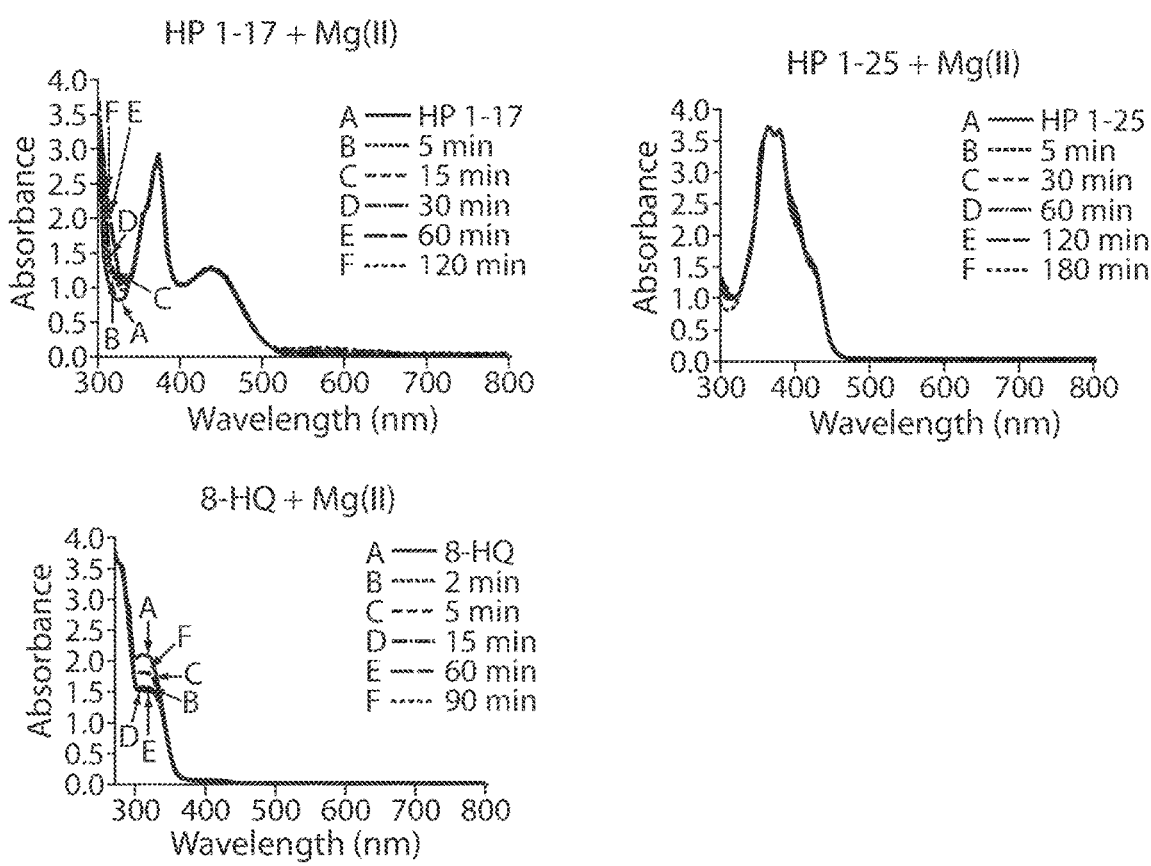
Figure 23:
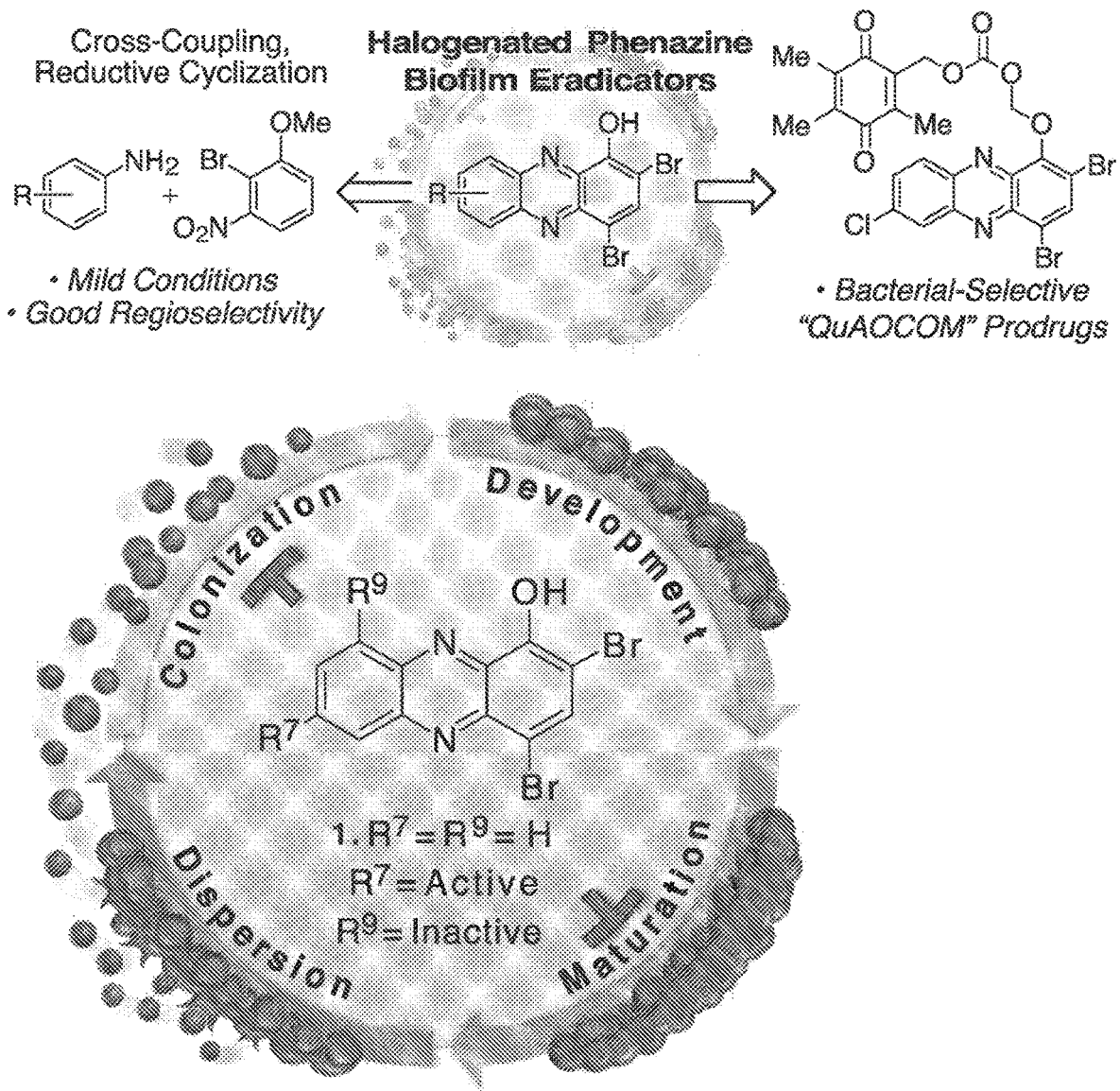
FIG. 23. Halogenated phenazine analogues exhibit antibacterial activity against antibiotic-susceptible planktonic cells and eradication activity against antibiotic-tolerant bacteria within mature biofilms.

The rates of halogenated phenazine-copper(II) complex formation were independently evaluated via UV-Vis spectrometry following addition of 0.5 equivalents copper(II) sulfate to stirring solutions of HPs (10 mM, 4 mL) in dimethyl sulfoxide. Spectral scanning was performed from 200 to 800 nm in 2 nm increments. The disappearance of HPs 1, 1-17, and 1-22 was observed over the indicated time points. The halogenated phenazine-copper(II) complex formation yielded a loss in absorbance due to precipitation. No change of the UV-Vis spectra was observed for 1-25 as a result of no metal(II) binding. 8-Hydroxyquinoline (8-HQ) was also tested as a positive control. Results are shown in FIGS. 17 and 22.

Prodrug Serum Stability Assay

In vitro serum stability assays were performed according to previously reported procedures with minor modifications.[77] First, human serum was temperature-equilibrated at 37° C. and then 200 µL of the serum solution was allocated into 1.5 mL Eppendorf tubes. To each tube was added 7.5 µL of the prodrug analyte (from 10 mM DMSO stocks) and 7.5 µL of internal standard. The serum analyte solutions were vortex-mixed for 5 seconds and then incubated for 1 minute to 60 minutes. At the end of each incubation interval, 400 µL of acetonitrile (0.5% formic acid) was added to precipitate serum proteins. The tubes were then centrifuged for 5 minutes at 1500 rcf and the supernatant was removed and evaporated to dryness under reduced pressure. Samples were reconstituted in 400 µL acetonitrile (0.5% formic acid) and analyzed via LC-MS using a Shimadzu Prominence HPLC system, AB Sciex 3200 QTRAP spectrometer and a Kinetex C18 column (50 mm×2.1 mm×2.6 μm) with a 35-minute linear gradient from 10-65% acetonitrile in 0.5% formic acid at a flow rate of 0.25 mL/min. Formation of active HPs from prodrugs was quantified by comparison of observed ratios of HPs to internal standard with previously generated standard curves.

Agar Diffusion Assay

Agar diffusion assays for prodrug evaluation were performed according to the standard Kirby-Bauer disk diffusion susceptibility test protocol with some minor modifications.[78] First, 100 μL of MRSA BAA-1707 ($OD_{600}$=0.7, ~$10^8$ CFU) was spread on lysogeny broth (LB) agar plates. The plates were dried for 10 min, and 20 μL of test compound from 10 mM DMSO stocks was gently pipetted onto the plate. The plates were incubated at 37° C. for 16 h, images were taken, and zones of bacterial clearance were measured using ImageJ software (NIH).

Example 3

Bacterial MIC Results

Figure 13:
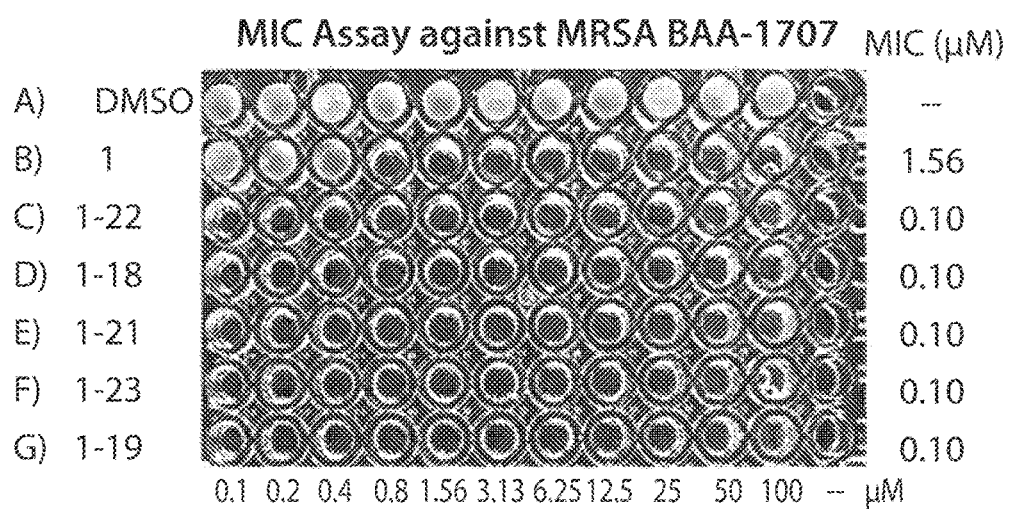
FIG. 13 shows minimum inhibitory concentration (MIC) assay results of various compounds of Formula (I) (e.g., Formulae (II)-(XIX)) against MRSA BAA-1707.

HPs 1-15 through 1-23, in addition to vancomycin, EDTA, TPEN, and QAC-10, were profiled in MIC assays against MRSA BAA-1707. The results are captured in Table 5 and FIG. 13. HPs 1-17, 1-18, 1-21, and 1-23, which are substituted at the 6-position with either a methyl-, ethyl-, chloro- or bromo-groups, demonstrated potent antibacterial activities against MRSA BAA-1707 (MIC=0.05-0.30 μM), which is 4- to 16-fold more potent than parent HP 1 (FIG. 13). Additionally, HPs 1-17, 1-18, 1-21, 1-22, and 1-23 proved to be highly potent (MIC=0.05-0.59 μM) against a panel of four MRSA isolates (Table 5).

In addition to MRSA isolates, several HPs demonstrated potent antibacterial activities against MRSE and VRE strains (Table 5). For example, 2,4-dibrominated HP analogues, 1-17, 1-18, 1-21, and 1-23, demonstrated potent antibacterial activities against MRSE 35984 (MIC=0.10-0.78 μM) and VRE 700221 (MIC=0.15-1.56 μM). HP 1-18 demonstrated the most potent antibacterial activities against *S. epidermidis* (MIC=0.10-0.30 μM) and *E. faecium* (MIC=0.15 μM), while 1-17 (6-methyl HP) gave a similar profile with a slight reduction in antibacterial potency (*S. epidermidis* MIC=0.30-0.39 μM; *E. faecium* MIC=0.59 μM). All of the HPs demonstrated improved antibacterial activities against MRSE and VRE compared to HP 1 (MRSE MIC=2.35 μM; VRE MIC=4.69 μM).

*M. tuberculosis* (MtB) is the largest bacterial threat to humans worldwide killing over 1.5 million humans around the globe each year.[35,36] MtB is a slow-growing or non-replicating pathogen that requires prolonged antibiotic treatments (i.e., ≥6 months), often with multiple drug combinations due to problems with drug-resistance.[37-39] To further compound these problems, currently there is an inadequate antibiotic pipeline for new MtB drugs.[38] With active HPs targeting both rapidly-dividing planktonic and persistent biofilm cells of Gram-positive pathogens, HPs were profiled for antibacterial activity against MtB H37Ra. Most HPs reported moderate antibacterial activities against MtB H37Ra (MIC=12.5-50 μM); however, HP 1-22 (MIC=6.25 μM, 2.4 μg/mL) demonstrated the most potent antibacterial activity from this series against MtB H37Ra.

Following the chemical synthesis of the new series of halogenated phenazine small molecules, antibacterial investigations were begun using standard minimum inhibitory concentration (MIC) assays to determine the growth-inhibitory activities against planktonic bacteria. MIC assays are operationally simple and provide a rapid approach to generating antibacterial profiles of HPs that allow for the identification of compounds to select for further investigation. This has been found to be a useful approach as HPs that demonstrate potent antibacterial activities in MIC assays typically perform well at eradicating biofilms using Calgary Biofilm Device (CBD) assays (discussed in later section).

The 17 novel HP analogues obtained from these BH-RC studies were first evaluated for antibacterial activities against several drug-resistant strains of major bacterial pathogens (Table 8). This library of HPs hosts several analogues which demonstrate improved MIC activity from that of previous lead HPs.[53,54] Halogenated phenazines 61A and 63A, particularly, report MIC activity of <0.1 μM against methicillin-resistant *Staphylococcus aureus* (0.038 μM and 0.075 μM, respectively against MRSA BAA-1707) while also demonstrating potent activity against methicillin-resistant *S. epidermidis* (MRSE 35984; MIC 0.1 μM for 61A and 63A, lowest concentration tested) and vancomycin-resistant *Enterococcus faecium* (VRE 700221; MIC 0.39 μM and 0.2 μM for 61A and 63A, respectively).

From previous investigations into a possible mechanism of action for HP analogues, it was suspected that functionalization of the 9-position of the phenazine heterocycle would not be well tolerated in terms of antibacterial activities due to interference with chelating metal(II)-cations (e.g. iron(II) cations). Expectedly, 9-alkylated HP analogues 57A and 58A were completely inactive against MRSA, MRSE, and VRE (MICs>100 μM). To further evaluate the nature of metal interaction observed from these inactive HPs, UV-vis determination of chelation kinetics was conducted. Therein, little to no loss of absorbance at the $\lambda_{max}$ wavelength for HPs 57A and 58A was observed following addition of ammonium iron(II) sulfate hexahydrate. In contrast, addition of iron(II) to active HP 61A presents a distinct loss of absorbance at the $\lambda_{max}$. To supplement kinetic chelation experiments, UV-vis evaluation of HP:metal(II) stoichiometry was conducted, wherein it was found that inactive HP 58A exhibited no chelation to copper(II) in contrast to active HP 61A, which chelates copper(II) in a manner representative of expected 2:1 HP:metal(II) stoichiometry. Thus, it was concluded that inactive analogues 57A and 58A could not form HP:metal(II) complexes due to 9-position steric bulk perturbing the metal-binding site of the HP scaffold, whereas active analogue 61A efficiently chelated iron(II) and copper (II) at rates analogous to those observed with previously reported active HPs.[54,57]

Surprisingly, mono-halogenated HPs 66A-69A reported only good to moderate activity (MICs of 6.25-50 μM; FIG. 27B) against MtB, suggesting this new series did not conform to the previously established predictive method for MtB activities (i.e. active dibrominated HPs against MRSA would correlate to active mono-halogenated counterparts against MtB). Fortunately, dihalogenated HP 61 (lead agent versus MRSA in MIC assays) reported excellent MIC activity against MtB (3.13 μM), proving to be equipotent to the previously reported anti-MtB lead.[53]

It was also discovered that triazole-HP 74 showed very poor activity against all bacterial pathogens, with the most potent MIC being 18.8 μM against MRSE (Table 8). The analogue was tested as the acetylated HP as previous reports have shown good activity from acetylated HP 1A as well as structurally-related halogenated quinolines.[66,79,80] These MIC results precluded further analogue synthesis from the HP click chemistry protocol.

TABLE 5

Minimum inhibitory concentrations (MICs, in μM) of select compounds of the invention against various bacterial pathogens

| Compound | MRSA BAA-1707 | MRSA BAA-44 | MRSA-1 | MRSA-2 | MRSE 35984 | S. epi 12228 | VRE 700221 | MtB H37Ra | HeLa Cytotox. IC$_{50}$ |
|---|---|---|---|---|---|---|---|---|---|
| 1 | 1.17$^a$ | 1.56 | 0.78 | 2.35$^a$ | 2.35$^a$ | 2.35$^a$ | 4.69$^a$ | 25 | ~100 |
| 1-15 | >50 | — | >50 | >50 | >50 | — | >50 | — | — |
| 1-16 | 9.38$^a$ | 18.8$^a$ | 25 | 18.8$^a$ | 9.38$^a$ | 18.8$^a$ | 2.35$^a$ | — | — |
| 1-17 | 0.30$^a$ | 0.39 | 0.10$^b$ | 0.30$^a$ | 0.30$^a$ | 0.39 | 0.59$^a$ | 25 | >100 |
| 1-18 | 0.10$^b$ | 0.59$^a$ | 0.15$^a$ | 0.39 | 0.10$^b$ | 0.30$^a$ | 0.15$^a$ | 25 | >100 |
| 1-19 | 0.15$^a$ | 9.38$^a$ | 4.69$^a$ | 4.69$^a$ | 0.30$^a$ | 6.25 | 0.15$^a$ | — | >100 |
| 1-20 | 2.35$^a$ | 3.13 | 18.8$^a$ | 2.35$^a$ | 6.25 | 9.38$^a$ | 2.35$^a$ | — | — |
| 1-21 | 0.08$^a$ | 0.59$^a$ | 0.10$^b$ | 0.39 | 0.30$^a$ | 0.39 | 1.56 | 50 | >100 |
| 1-22 | 0.15$^a$ | 0.30$^a$ | 0.15$^a$ | 0.59$^a$ | 18.8$^a$ | 12.5 | 1.56 | 6.25 | >100 |
| 1-23 | 0.05 | 0.59$^a$ | 0.10$^b$ | 0.30$^a$ | 0.78 | 0.30$^a$ | 1.17$^a$ | 25 | >100 |
| 1-24 | 0.59$^a$ | 1.56 | 1.17$^a$ | 2.35$^a$ | 1.56 | 0.78 | 6.25 | 25 | >100 |
| 1-25 | 0.003 | 0.013 | 0.10$^b$ | 0.10$^b$ | 0.15$^a$ | 0.10$^b$ | 0.59$^a$ | 12.5 | >100 |
| EDTA | 25 | — | 12.5 | — | — | — | — | — | — |
| TPEN | 46.9$^a$ | — | 75$^a$ | 50 | 12.5 | — | — | — | — |
| QAC-10 | 4.69$^a$ | — | 4.69$^a$ | 3.13 | 2.35$^a$ | — | 2.35$^a$ | — | — |
| BAC-16 | 1.56 | — | — | — | 1.56 | — | 3.13 | — | — |
| vancomycin | 0.39 | 0.39 | 0.39 | 0.59$^a$ | 0.78 | 1.17$^a$ | >100 | — | — |
| daptomycin | 3.13 | 18.8$^a$ | — | 4.69$^a$ | 12.5 | 6.25 | 125 | — | — |
| linezolid | 12.5 | 1.56 | 4.69$^a$ | 3.13 | 3.13 | 1.56 | 3.13 | — | — |
| streptomyci | — | — | — | — | — | — | — | 1.32 | — |

$^a$Midpoint for a 2-fold range in observed values.
$^b$Lowest concentration tested. All biological results were generated from three independent experiments.

Example 4

Macromolecular Synthesis Inhibition Results

To characterize the antibacterial mechanism of action for HP small molecules, the effects of HP 1 were investigated against MRSA BAA-1707 on global biosynthetic pathways in rapidly-dividing (exponentially-growing) planktonic cells through quantifying the incorporation of various [$^3$H]-labeled precursors into their corresponding macromolecules.[40]

Figure 14:
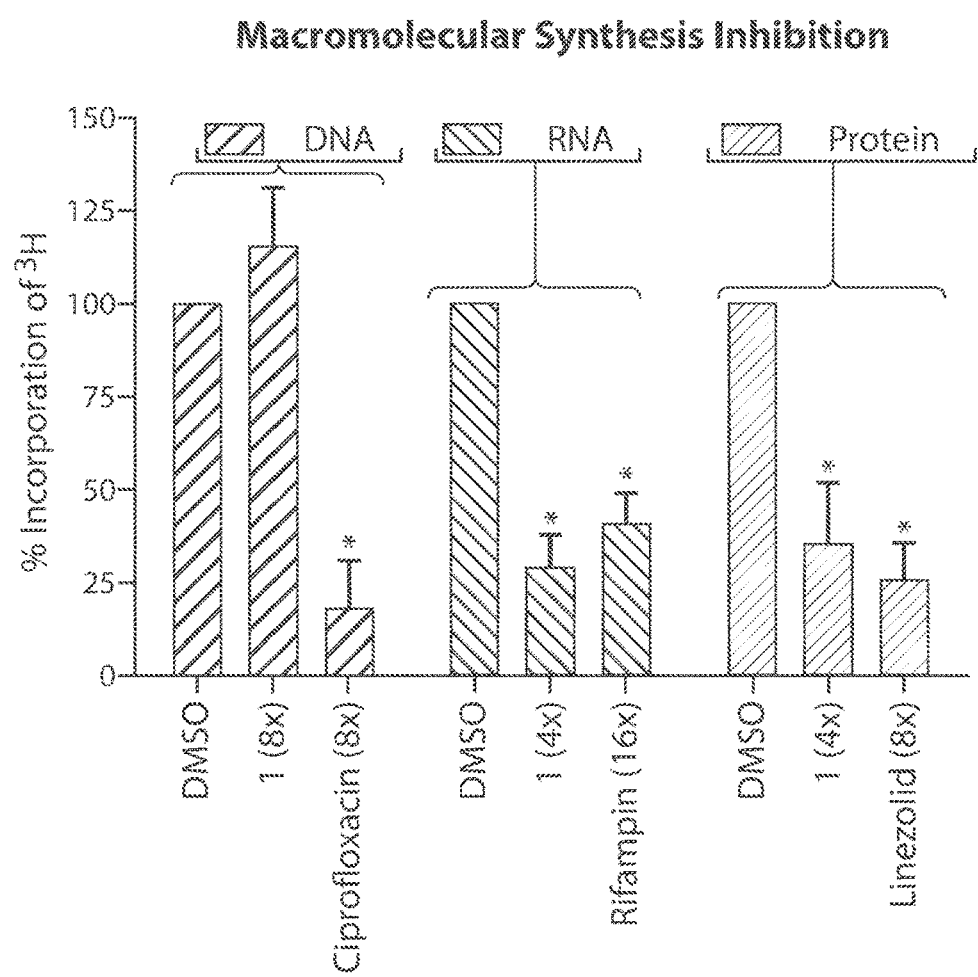
FIG. 14 shows the results of 2,4-dibromophenazin-1-ol (HP 1) against MRSA BAA-1707 in macromolecular synthesis inhibition experiments with [$^3$H]-labeled precursors (generated from three or more, independent experiments).

For these experiments, MRSA-1707 cultures were treated with [$^3$H]-thymidine (DNA biosynthesis), [$^3$H]-uridine (RNA biosynthesis) and [$^3$H]-leucine (protein biosynthesis) in the presence of HP 1 and antibiotic controls (4-16×MIC). From these initial experiments, it was discovered that HP 1 does not inhibit DNA biosynthesis at 8×MIC; however, at 4×MIC, HP 1 inhibits both RNA and protein biosynthesis in MRSA-1707 (FIG. 14).

Example 5

Mammalian Cytoxicity Results

HPs 1-17, 1-18, 1-19, 1-21, 1-22, and 1-23, which displayed potent antibacterial activities against MRSA, MRSE and VRE, were evaluated against HeLa cells to determine mammalian cell cytotoxicity in lactate dehydrogenase (LDH) release assays[41] at 25, 50 and 100 μM. During these investigations, HP 1 was found to have an IC$_{50}$ value 100 μM while the remaining HP analogues recorded IC$_{50}$ values >100 μM (Table 5). When comparing the HeLa cytotoxicity (IC$_{50}$) to the antibacterial activities (MIC) of MRSA BAA-1707, several HPs demonstrated selectivity indexes of >330- to >2,000-fold against MRSA BAA-1707 cells. For example, HP 1-23 reported an IC$_{50}$>100 μM against HeLa cells while reporting potent antibacterial activities with an MIC=0.05 μM against MRSA BAA-1707, resulting in a selective index of >2,000-fold towards inhibiting MRSA planktonic cells. This promising bacterial selectivity profile is an important consideration for translating HP antibacterial agents into viable therapeutic options.

Several HPs that demonstrated potent antibacterial activities against MRSA BAA-1707, or proved to have anti-MtB activities, were evaluated for mammalian cytotoxicity against HeLa cells in LDH-release assays (Table 8). Mammalian cytotoxicity data generated from these assays were used to provide selectivity indexes (SI) for these HPs to quantify the targeting of bacterial cells over mammalian cells, which is an important criterion in developing antibacterial agents for clinical purposes. This series of HPs demonstrated excellent cytotoxicity profiles. Despite HPs 53A and 54A reporting cytotoxicity against HeLa cells at 100 μM (highest concentration tested; IC$_{50}$>50 μM), the remaining 11 HP analogues tested (52A, 55A, 56A, 59A, 61A, 63A, 64A, 66A, 67A-69A) reported minimal, if any, cytotoxicity against HeLa cells (IC$_{50}$>100 μM). Using these results, selectivity indices were generated (HeLa cell IC$_{50}$ divided by MRSA BAA-1707 MIC) for these HPs to quantify their high degree of selectivity and bacterial targeting relative to mammalian cells (SI>169 to >2,632 for HPs active against MRSA BAA-1707; Table 8).

Example 6

PEG-Carbonate-HP Results

Figure 15:
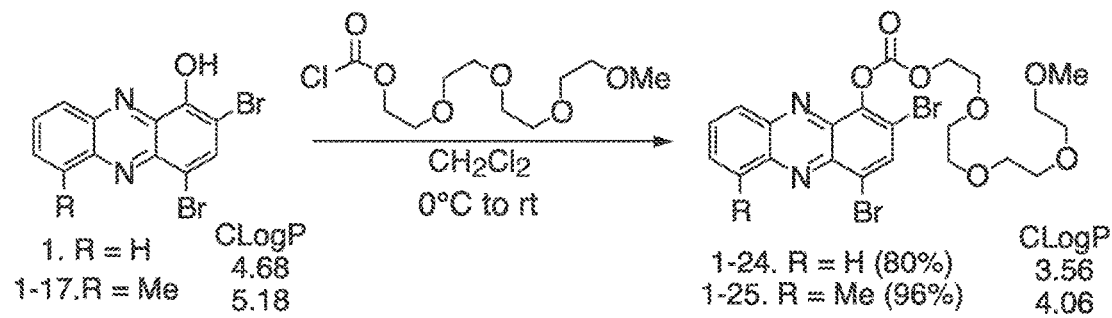
FIG. 15 shows the chemical synthesis of PEG-carbonate HPs 1-24 and 1-25.
Figure 16:
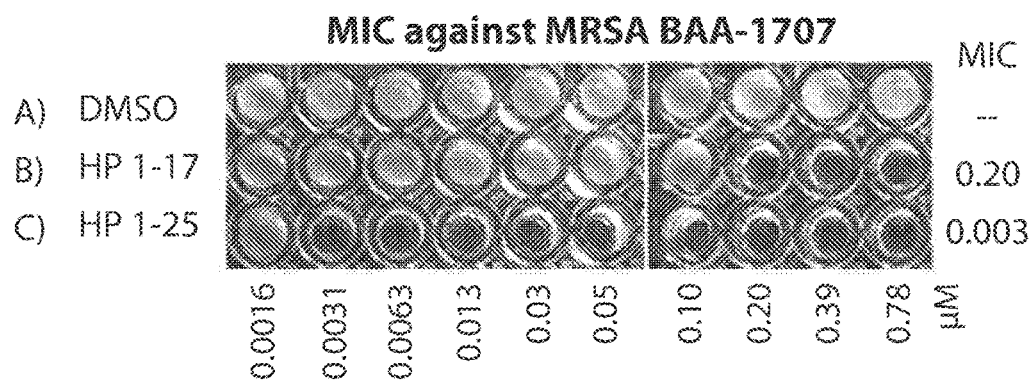
FIG. 16 shows the antibacterial assay results of PEG-carbonate HP 1-25 alongside the corresponding non-carbonate version HP 1-17 demonstrating enhanced antibacterial activities against MRSA.

Two polyethylene glycol (PEG) carbonates were synthesized and investigated in an attempt to: (1) improve water solubility through the installation of a PEG group, (2) enhance bacterial penetration and release of HPs through possible bacterial esterase processing resulting in active HPs, carbon dioxide and non-toxic PEG, and (3) mitigate the metal-binding moiety required for the antibacterial activities of HPs, which may be important in the development of HPs in more advanced preclinical studies. PEG carbonate-HPs 1-24 and 1-25 were prepared via condensation of triphosgene with tetraethyleneglycol monomethyl ether to generate a PEGylated chloroformate intermediate (not shown), which was immediately condensed with 1 to give 1-24 in 80% yield, and 1-17 to give 1-25 in 96% yield (FIG. 15). Both PEG carbonate-HPs have reduced CLogP values with 1-24 having a CLogP of 3.56 while 1-25 has a CLogP of 4.06. These carbonates do not directly bind metal(II) cations in UV-Vis experiments and are chemically stable in aqueous formulations for >1 month at room temperature. PEG carbonate-HPs 1-24 and 1-25 exhibit maintained or enhanced antibacterial and biofilm eradication activities compared to their phenolic precursors, 1 and 1-17, suggesting improved bacterial cell entry and possible involvement of bacterial esterase enzymes for cleavage of the carbonate group to deliver the active HPs once inside bacteria. To support this model, 1-25 reported MICs of 0.003 and 0.013 μM against MRSA-1707 and MRSA-44, respectively, while corresponding HP 1-17 reported MICs of 0.30 and 0.39 against the same strains correlating to an impressive 100- and 30-fold enhancement of antibacterial activities for HP carbonate 1-25 compared to (non-carbonate) 1-17 (FIG. 16). Similar to non-carbonate HPs, 1-24 and 1-25 showed no HeLa cell cytotoxicity at 100 μM.

Example 7

Metal(II) Binding (UV-Vis) and Co-Treatment in Antibacterial Assays with MRSA-170

It was previously reported that HPs directly binds copper (II) and iron(II) cations in UV-Vis experiments resulting in loss of antibacterial activities when co-treated with these metal(II) cations in antibacterial assays against MRSA-2 (clinical isolate; Shands Hospital; Gainesville, Fla.).[42] HPs bind metal(II) cations through a chelation event involving the oxygen atom of the 1-hydroxyl group and the adjacent nitrogen at the 10-position of the HP scaffold to form a stable 2:1 HP:metal(II) complex. During these investigations, the ability of HPs 1, 1-17, and 1-21 were demonstrated to bind copper(II), iron(II) and zinc(II), but not magnesium(II) cations. Based on the kinetics of UV-Vis experiments, HP 1-17 (6-methyl HP) and 1-21 (6-chloro HP) chelated copper (II) at a faster rate than HP 1 (FIG. 17), which may be one explanation as to the enhanced antibacterial activities of 1-17 and 1-21 compared to HP 1. Interestingly, HP 1-25 does not bind any of the metal(II) cations directly as the carbonate functionality blocks direct metal-chelation.

Co-treatment of HPs with metal(II) cations at 200 μM in MIC assays against MRSA BAA-1707 led to reduced antibacterial activities (i.e., 4- to >20,000-fold elevated MIC values with copper(II) cation co-treatment; Table 6) for 1, 1-17, and 1-25 with copper(II) and iron(II). However, it is interesting to note that co-treatment with zinc(II) increased antibacterial activities (reduced MICs; Table 6) of HPs and no changes were observed in the antibacterial activities when HPs were co-treated with magnesium(II). HP 1-21 showed reduced antibacterial activities against MRSA BAA-1707 in the presence of copper(II) and iron(II). However, no changes in antibacterial activities were observed when 1-21 was co-treated with zinc(II) or magnesium(II). PEG-carbonate HP 1-25 gives the most dramatic antibacterial response to co-treatment with metal(II) cations (>20,000-fold elevated MIC against MRSA with copper(II) and 67-fold reduction in MIC against MRSA with zinc(II), yet does not directly bind either metal(II) cation directly) further supporting that PEG-carbonate 1-25 enters MRSA at a high efficiency, then is converted to the active, metal-chelating HP 1-17 which elicits a potent antibacterial response. Interestingly, structurally related non-halogenated comparators, 1-hydroxyphenazine (1-OHP) and 8-hydroxyquinoline (8-OHQ), demonstrated drastically different metal(II) cation profiles compared to HPs 1, 1-17, 1-21 and 1-25.

The metal-chelating agents, EDTA and TPEN, a membrane-permeable metal-chelating agent, were used as comparators in metal(II) cation co-treatment assays. EDTA showed only slight reductions in antibacterial assays (MIC values elevated 2-fold) when co-treated with each metal(II) cation. TPEN showed more dramatic reductions in antibacterial activities (MIC values elevated 3- to 11-fold) with copper(II), iron(II) and zinc(II). However, there was not a significant change in MIC values when TPEN was co-treated with magnesium(II). Doxycycline, a tetracycline antibiotic that chelates a magnesium(II) ion in the bacterial ribosome during protein synthesis inhibition[43], was also tested in these metal(II) cation co-treatment assays against MRSA BAA-1707. Only iron(II) and zinc(II) modulated antibacterial activities with 4-fold elevated MIC values and 2-fold reduced MIC values, respectively. These studies demonstrate unique antibacterial profiles for HP small molecules with the enhancement of zinc(II) cations being of particular interest.

TABLE 6

UV-Vis and metal(II)-cation co-treatment MIC assays summary for HPs against MRSA BAA-1707
MRSA BAA-1707 (concentration in μM)

| Test Cpd. | MIC | Copper(II) Binding Y/N | MIC w/ $Cu^{2+}$ | Iron(II) Binding Y/N | MIC w/ $Fe^{2+}$ | Zinc(II) Binding Y/N | MIC w/ $Zn^{2+}$ | Magnesium(II) Binding Y/N | MIC w/ $Mg^{2+}$ |
|---|---|---|---|---|---|---|---|---|---|
| 1 | 1.17[a] | Y | 4.69[a] | Y | 2.35[a] | Y | 0.39 | N | 1.17[a] |
| 1-17 | 0.30[a] | Y | 75[a] | Y | 12.5 | Y | 0.05 | N | 0.30[a] |
| 1-21 | 0.10[b] | Y | 6.25 | Y | 0.59[a] | Y | 0.15[a] | N | 0.15[a] |
| 1-25 | 0.0047[a] | N | >100 | N | 25 | N | 0.0000 | N | 0.0047[a] |
| 8-OHQ | 9.38 | Y | 4.69[a] | Y | 12.5 | Y | 12.5 | N | 6.25 |
| 1-OHP | 250 | — | 75 | — | 250 | — | >500 | — | 250 |
| TPEN | 46.9[a] | — | 500 | — | 125 | — | 250 | — | 62.5 |
| EDTA | 25 | — | 50 | — | 50 | — | 50 | — | 50 |
| Doxy. | 0.78 | — | 0.78 | — | 3.13 | — | 0.39 | — | 0.78 |

Note:
[a]Midpoint for a 2-fold range in observed values.
[b]MIC for 21 in these experiments was 0.1 μM. UV-Vis results are reported as "Binding Y/N" for HPs. Each metal(II) cation was tested at 200 μM in co-treatment MIC assays. 8-OHQ (8-hydroxyquinoline) and 1-OHP (1-hydroxyphenazine) were used as positive controls and have metal-binding moieties related to HPs.

Example 8

Biofilm Eradication Study Results

HP analogues were profiled in biofilm eradication assays using Calgary Biofilm Devices (CBD) containing specialized 96-well plates with a lid containing 96 pegs anchored to the lid to provide a surface for biofilms to form and be treated (one peg per microtiter well). Unlike MIC assays which are used to determine the inhibition of rapidly-dividing planktonic bacteria, CDB assays have three phases to test for biofilm eradication, including: (1) biofilm-attachment/establishment to the CBD peg surface (24 hours, media and bacteria only), (2) treating established biofilms on CBD pegs with test compounds (24 hours, media and test compounds only), and (3) recovery, growth, dispersion and planktonic proliferation of viable biofilms (24 hours, media only). At the end of biofilm eradication assays, turbid microtiter wells in 96-well plates result from pegs that have viable biofilms whereas microtiter wells that results in non-turbid microtiter wells result from pegs containing eradicated biofilms. Using the CBD assay is operationally simple as lid pegs that have attached biofilms are rapidly washed and transferred to new 96-well plates (containing media, with or without test compound) as one moves through each of the three assay phases. Upon completion of biofilm eradication assays, minimum biofilm eradication concentration (MBEC) values are determined as the lowest concentration at which biofilms are completely eradicated. Using the CBD, planktonic-killing activities can also be determined and enable the assessment of planktonic-biofilm killing dynamics in the same assay using a single culture.

HP analogues 1-17, 1-18, 1-19, 1-21, 1-22, 1-23, 1-24, and 1-25 were investigated in biofilm eradication assays against MRSA BAA-1707. HP 1-17, 1-18, 1-19, 1-22, 1-23, and 1-25 exhibited potent minimum biofilm eradication concentrations (MBEC) between 4.69 and 37.5 µM (Table 7). Halogenated phenazines, 1-18 (MBEC=4.69 µM), 1-17 (MBEC=6.25 µM), 1-19 (MBEC=9.38 µM), 1-23 (MBEC=9.38 µM), and PEG-carbonate 1-25 (MBEC=9.38 µM) proved to be the most potent MRSA biofilm-eradicating HPs from this series (FIG. 18). Similar to the MIC analysis, HP analogues 1-17, 1-18, 1-19, and 1-23 possess either a methyl group, ethyl group or bromine atom at the 6-position of the HP scaffold and performed with high potency in biofilm eradication assays.

Various non-HP comparators were also profiled in biofilm eradication assays against MRSA BAA-1707 (Table 7), including membrane-lysing agents (quaternary ammonium cation-10, QAC-10, and a reported biofilm eradicating agent, BAC-16), metal-chelating agents (EDTA, TPEN), and conventional antibiotics used in MRSA treatments (i.e., vancomycin, linezolid, daptomycin). During these studies, HPs 1-17, 1-18, and 1-19 were found to be 10- to 21-fold more potent than QAC-10 (MBEC=93.8 µM) against MRSA BAA-1707 biofilms. Interestingly, the metal-chelating agents, EDTA and TPEN, were both found to be inactive (MBEC>2,000 µM; FIG. 18) in biofilm eradication assays against MRSA BAA-1707 when tested alongside HP small molecules. Without wishing to be bound by any particular theory, it is thought that the lack of biofilm eradication activity by EDTA and TPEN may speak to the unique mechanism that leads to HP-induced biofilm killing as HP 1-18 proves to be >425-fold more potent than EDTA or TPEN in CBD assays. Vancomycin, daptomycin and linezolid are front-running MRSA therapies[44,45] and are unable to eradicate MRSA BAA-1707 biofilms (MBEC>2,000 µM) despite being active against planktonic cells in CBD assays (i.e., vancomycin, MBC=3.9 µM). These findings are illustrative of the abilities of MRSA biofilms to tolerate and thrive in the presence of high concentrations of current antibiotic therapies.

Figure 19:
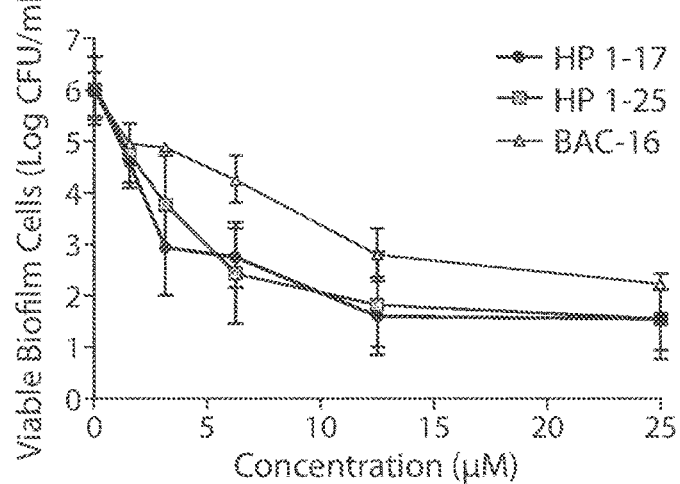
FIG. 19 shows the dose-response curve of biofilm eradication for HP 1-17 (MBEC=4.69 µM), HP 1-25 (MBEC=9.38 µM), and BAC-16 (MBEC=25 µM) against MRSA-1707 (pulse treatment).

HPs 1-17 and 1-25 were tested alongside BAC-16, a membrane-lysing comparator, in pulse experiments (i.e., two subsequent 24 hour compound treatment phases) where after the 24-hour compound treatment phase, CBD lids were transferred to a second 96-well plate (extending phase 2 of the biofilm eradication assay) with the same test compound concentrations to treat MRSA biofilms for an additional 24 hours before transferring to the recovery plate (phase 3). The results from the pulse biofilm eradication experiments showed slight improvements in biofilm eradication activities for HP 1-17 (MBEC=4.69 µM) while HP 1-25 reported the same potency as in standard CBD assay conditions (MBEC=9.38 µM) against MRSA-1707. BAC-16 reported an MBEC of 25 µM in pulse experiments against MRSA-1707. Following the completion of the pulse experiments, the treated and untreated pegs were removed from the CBD to determine viable biofilm cell counts following sonication and plating to generate the dose-response curve in FIG. 19. At 6.25 µM, 1-17 and 1-25 reduced viable MRSA-1707 biofilm cells by 3-logs (99.9% biofilm eradication) whereas at 25 µM these HPs reduced viable MRSA-1707 biofilm cells by >4-logs (>99.99% biofilm eradication).

The HP compounds also demonstrated impressive biofilm eradication activities against methicillin-resistant *S. epidermidis* (MRSE ATCC 35984) and vancomycin-resistant *Enterococcus faecium* (VRE ATCC 700221) biofilms in CBD assays. HP 1-18 demonstrated the most potent biofilm eradication activities against MRSE biofilms (MBEC=2.35 µM) and VRE biofilms (MBEC=0.59 µM). Similar biofilm eradication profiles were observed for HPs 1-17 and 1-19 as both HPs reported MBECs=4.69 µM against MRSE and MBECs=0.59 µM against VRE (Table 7). In addition, HPs were found to be more active against VRE biofilms (MBEC=0.59-9.38 µM) than MRSE biofilms (MBEC=2.35-75 µM), and HPs out-performed all conventional antibiotics (e.g., vancomycin), metal-chelating agents (e.g., EDTA), and membrane-lysing agents (e.g., QAC-10, BAC-16).

Figure 30A:
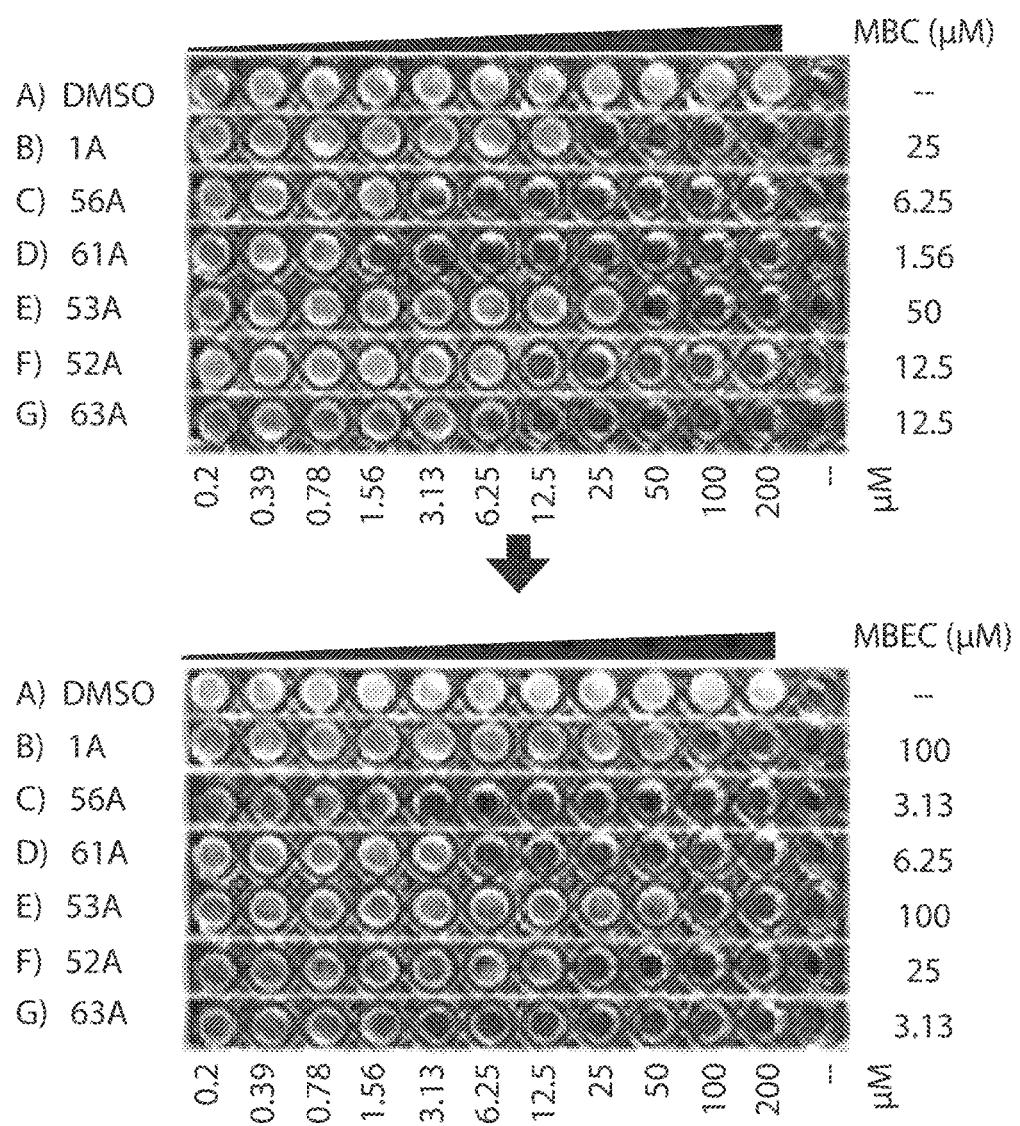
FIGS. 30A to 30D.

Nine potent HPs (52A-56A, 59A, 61A, 63A, 64A; Table 9) were identified during initial MIC studies and advanced to biofilm eradication assays against MRSA, MRSE and VRE using Calgary Biofilm Devices (CBD). CBDs are specialized 96-well plates that have lids containing pegs designed to sit down in microtiter wells (one peg per microtiter well) and provide bacteria with a surface for biofilm formation.[81,82] Biofilm eradication assays have three distinct phases, which include: 1) biofilm establishment (media and bacteria only, biofilms are established on CBD pegs), 2) compound treatment (compounds in media; test compounds have the chance to eradicate biofilms during this phase), and 3) growth and dispersion of viable biofilms (media only). Each of these phases involves static incubation (24 hours at 37° C.), a wash of the CBD pegs containing biofilms with subsequent lid transfer to new 96-well plate at the end of phases one and two; however, at the end of the final phase, the microtiter wells are evaluated for bacterial growth (turbidity). Upon completion of the assay, microtiter wells that are turbid from bacterial growth correspond to wells that contained viable biofilms that dispersed bacteria into the media followed by bacterial growth during phase 3. Microtiter wells without bacterial growth, or turbidity, at the end of the CBD assay corresponds to wells that contained eradicated biofilms that were unable to grow and disperse viable bacteria during phase 3 (see FIG. 30A for CBD plate images with assay results). HPs and control compounds were tested in 2-fold serial dilution and the lowest test concentration of a compound that is required to eradicate biofilms is known as the minimum biofilm eradication concentration (MBEC) value. The Calgary Biofilm Device also allows for planktonic toxicity (determination of minimum bactericidal concentration or MBC values) to be evaluated alongside the biofilm eradication activity, providing ideal information regarding planktonic and biofilm killing dynamics (MBC:MBEC ratios) from a single bacterial culture under the same experimental conditions.

Figure 29:
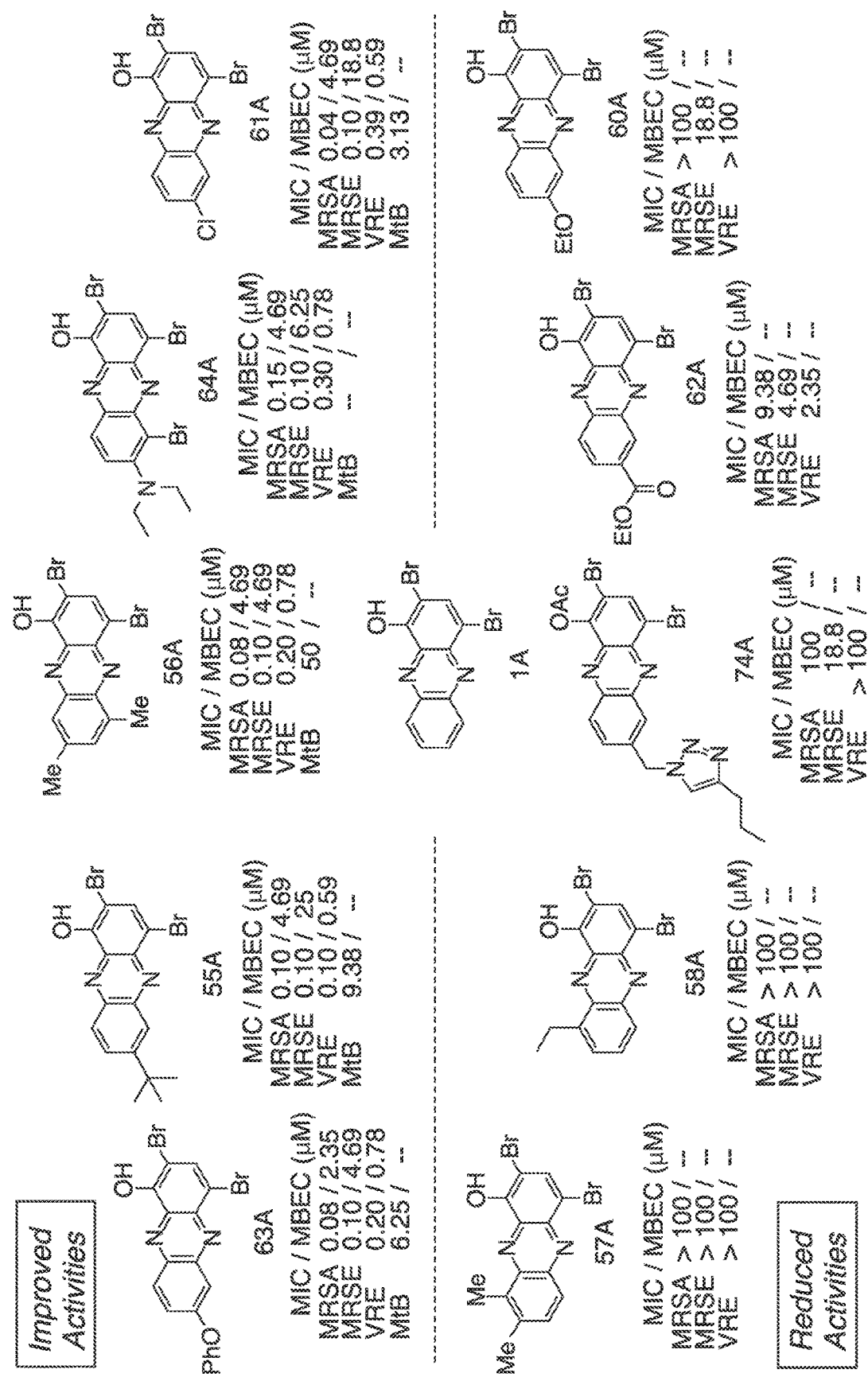
FIG. 29. Activity profiles for select HP analogues relative to parent HP 1A. Note: The MRSA data in this figure is from the MRSA BAA-1707 results.

During these investigations, several new HPs were identified with potent biofilm eradication activities against MRSA, MRSE and VRE biofilms (Table 9). Against MRSA-1707 biofilms, 7-substituted HPs 55A (MBEC=4.69 µM; 7-tert-butyl-HP), 61A (MBEC=4.69 µM; 7-chloro-HP), 63A (MBEC=2.35 µM; 7-phenoxy-HP) and 64A (MBEC=4.69 µM; 7-diethylamine-6-bromo-HP) demonstrated potent killing activities (FIG. 29, structures with activity profiles). In addition, 6,8-dimethyl-HP 56A demonstrated potent MRSA BAA-1707 biofilm eradication (MBEC=4.69 µM). Several HPs demonstrated excellent biofilm eradication activities against MRSA-2 (e.g., HP 55A; MBEC=3.13 µM) and MRSA BAA-44 (e.g., HP 55A; MBEC=9.38 µM). Multiple front-running MRSA antibiotics, including vancomycin, daptomycin and linezolid, demonstrated no biofilm eradication activities against MRSA biofilms at 2,000 µM (highest concentration tested) when tested alongside this series of halogenated phenazine small molecules. Against MRSE 35984 biofilms, HPs 56A (MBEC=4.69 µM) and 63A (MBEC=4.69 µM) demonstrated highly potent eradication activities; however, several analogues reported MBEC values ≤25 µM against MRSE 35984 biofilms. In addition, several HPs from this series demonstrated potent, sub-micromolar MBEC activities against VRE 700221 biofilms with 55A, 61A (MBEC=0.59 µM), 56A, 63A and 64A (MBEC=0.78 µM) proving to be the most active agents against this pathogen.

In addition to select antibiotic comparators, various biofilm eradication controls (e.g. QAC-10, CCCP) along with metal-chelating agents (e.g. EDTA, TPEN) were assayed alongside new halogenated phenazines. These comparator agents proved to be significantly less active, or inactive, in their ability to eradicate established biofilms in CBD assays when compared to these HPs. These data collectively point to the unique mechanism and biofilm-killing potency displayed by these HP small molecules. Similar to previous studies, the planktonic killing (MBC) to biofilm killing (MBEC) ratios generated from these Calgary Biofilm Device assays demonstrated that HPs have near equipotent killing activities against planktonic and biofilm bacteria (MBC:MBEC ratios 1-3; see Table 9), a profile that conventional antibiotic therapies do not possess.

Figure 30B:
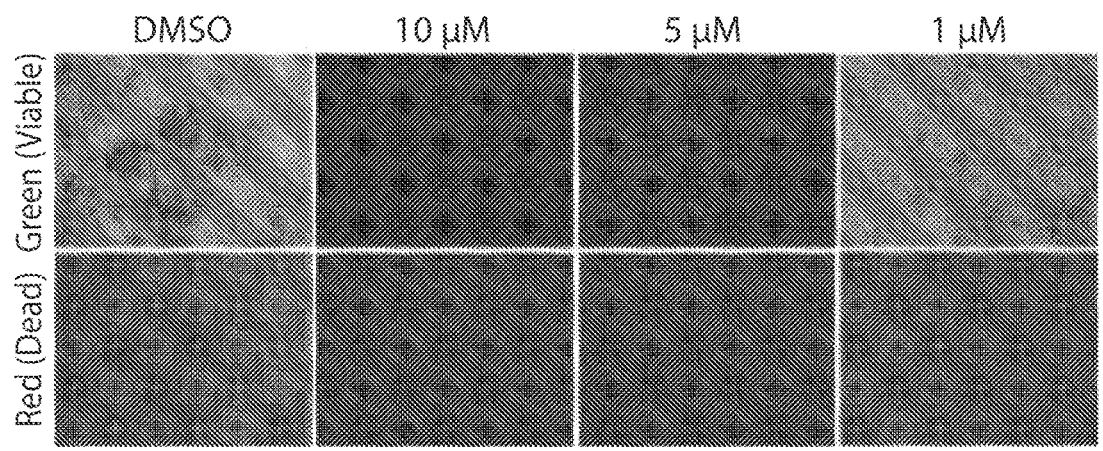

Following biofilm eradication investigations in CBD assays, lead HP 61A was tested against biofilms of MRSE 35984 in live/dead staining experiments (FIG. 30B). After a 24-hour biofilm establishment, HP 61A was added at 0.1, 5, and 10 µM then left to incubate against MRSE 35984 biofilms for an additional 24 hours at 37° C. Images were then taken of treated and untreated biofilms using fluorescence microscopy to further demonstrate the highly potent eradication and clearance of MRSE 35984 biofilms with HP 61A.

TABLE 7

Summary of biofilm eradication and hemolysis studies with halogenated phenazines

| Compound | MRSA BAA-1707 MIC | MRSA BAA-1707 MBC/MBEC | MRSE 35984 MIC | MRSE 35984 MBC/MBEC | VRE 700221 MIC | VRE 700221 MBC/MBEC | Hemolysis at 200 µM (%) |
|---|---|---|---|---|---|---|---|
| 1 | 1.17$^a$ | 50$^b$/75$^a$ | 2.35$^a$ | 23.5$^a$/250 | 4.69$^a$ | 18.8$^a$/9.38$^a$ | ≤1 |
| 1-4 | 3.13 | 46.9$^a$/93.8$^a$ | 2.35$^a$ | 150$^a$/>200 | 3.13 | 12.5$^b$/4.69$^a$ | ≤1 |
| 1-9 | 1.17$^a$ | >200/>200 | 0.39 | 12.5$^b$/>200 | 2.35$^a$ | 12.5/9.38$^a$ | ≤1 |
| 1-17 | 0.30$^a$ | 6.25/6.25 | 0.30$^a$ | 9.38$^b$/4.69$^a$ | 0.59$^a$ | 1.56$^b$/0.59$^a$ | 6.7 |
| 1-18 | 0.10$^c$ | 6.25/4.69$^a$ | 0.10$^c$ | 9.38$^a$/2.35$^a$ | 0.15$^a$ | 3.13$^b$/0.59$^a$ | 1.7 |
| 1-19 | 0.15$^a$ | 4.69$^a$/9.38$^a$ | 0.30$^a$ | 6.25/4.69$^a$ | 0.15$^a$ | 1.56$^b$/0.59$^b$ | 5.3 |
| 1-21 | 0.08$^a$ | 6.25/75$^a$ | 0.30$^a$ | 18.8$^a$/75$^a$ | 1.56 | 25/25 | ≤1 |
| 1-22 | 0.15$^a$ | 18.8$^a$/37.5$^a$ | 18.8$^a$ | 50/37.5$^a$ | 1.56 | 9.38$^a$/2.35$^a$ | ≤1 |
| 1-23 | 0.05 | 4.69$^a$/9.38$^a$ | 0.78 | 4.69$^a$/12.5 | 1.17$^a$ | 9.38$^a$/9.38$^a$ | 5.1 |
| 1-24 | 0.59$^a$ | 75$^a$/100 | 1.56 | 75$^b$/100 | 6.25 | 9.38$^a$/4.69$^a$ | 2.4 |
| 1-25 | 0.003 | 9.38$^a$/9.38$^a$ | 0.15$^a$ | 9.38$^a$/4.69$^a$ | 0.59$^a$ | 1.56$^b$/0.59$^a$ | ≤1 |
| QAC-10 | 4.69$^a$ | 93.8$^a$/93.8$^a$ | 2.35$^a$ | 31.3/31.3 | 2.35$^a$ | 3.0$^a$/3.0$^a$ | >99 |
| BAC-16 | 1.56 | 31.3$^b$/15.6 | 1.56 | — | 3.13 | 5.9$^a$/3.0$^a$ | — |
| TPEN | 46.9$^a$ | 375$^a$/>2000 | 12.5 | 250/>2000 | — | — | ≤1 |
| EDTA | 25 | >2000/>2000 | — | 1000/ | — | >2000/ | ≤1 |
| Vancomycin | 0.39 | 3.9/>2000 | 0.78 | 3.0$^b$/>2000 | >100 | >200/150$^a$ | — |
| Daptomycin | 3.13 | 125/>2000 | 12.5 | — | 125 | 375/93.8$^a$ | — |
| Linezolid | 12.5 | 31.3/>2000 | 3.13 | — | 3.13 | 4.69$^b$/1.56 | — |

Notes:
$^a$Midpoint for a 2-fold range in observed values.
$^b$Midpoint value of a 4-fold range in values.
$^c$Lowest concentration tested. All biological results summarized in this table were generated from three independent experiments.

Example 9

Live/Dead Staining Study Results

Figure 20:
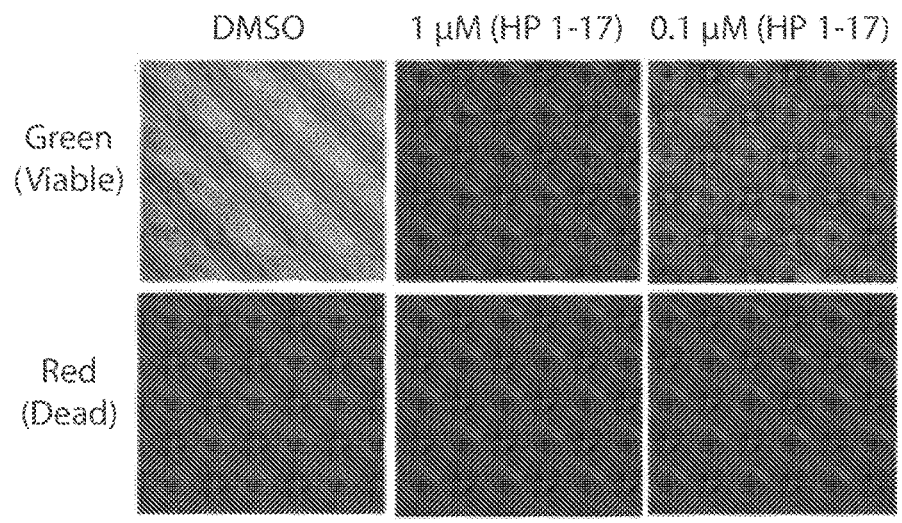
FIG. 20 shows Live/Dead staining (fluorescence images) of established MRSA-1707 biofilms treated with HP 1-17 after 24 hours.

HP 1-17 was tested against MRSA-1707 biofilms in live/dead staining experiments. Following a 24-hour MRSA-1707 biofilm establishment phase, HP 1-17 was added at 0.1, 1 and 5 µM, and then allowed to incubate at 37° C. for 24 hours. After this time, images of the treated and untreated MRSA-1707 biofilms were obtained using fluorescence microscopy (FIG. 20). HP 1-17 demonstrated a potent biofilm eradication and clearance response towards MRSA-1707 biofilms, even at the lowest concentration tested of 0.1 µM.

Example 10

Red Blood Cell Hemolysis Results

HPs were assayed for hemolysis activity against red blood cells (RBCs) at a single high concentration (200 µM). Antimicrobial peptides and mimics thereof (i.e., quaternary ammonium cationic compounds) eradicate biofilm cells through membrane lysis. However, identifying potent membrane-lysing agents that target bacterial membranes over mammalian membranes has proven challenging.[46-48] HPs demonstrated little, if any, hemolytic activity against RBCs at 200 µM (≤1 to ≤7% hemolysis, Table 7). HP 1-18, the most potent biofilm-eradicating agent from this collection, demonstrated 1.7% hemolysis at 200 µM while completely eradicating biofilms at 85- to 339-fold lower concentrations (MBEC=0.59-2.35 µM) compared to membrane-lysing agent, QAC-10 (MBEC=93.8 µM), that demonstrated >99% lysis of RBCs at 200 µM when tested alongside HPs. The potent biofilm eradication activities of HPs together with the lack of RBC lysis and HeLa cytotoxicity demonstrate a unique targeting ability of these HP small molecules which could lead to significant breakthroughs in the treatment of persistent, biofilm-associated bacterial infections in the clinic.

Hemolysis assays were conducted with human red blood cells (RBCs). No HP analogue exceeded 3% hemolysis at 200 µM (Table 9). Most importantly, this finding (in addition to demonstrating a favorable safety profile) suggests that the new HP analogues act through a mechanism that does not involve membrane lysis. QAC-10 is a known membrane-lysing agent that demonstrates antibacterial activities in addition to biofilm eradication. When tested alongside with the HP small molecules, QAC-10 served as a positive-control and demonstrated >99% hemolysis of RBCs at 200 µM.

Example 11

Structure-Activity Relationship

Substitutions at the 6-position were shown to enhance antibacterial activities of the HP scaffold as 6-methyl (1-17), 6,7-dimethyl (1-19), 6-ethyl (1-18), 6-chloro (1-21), and 6-bromo (1-23) analogs all demonstrated potent antibacterial and biofilm eradication activities compared to HP 1 (FIGS. 18-21). Both 8-phenoxyether HP (1-16) and 8-methyl HP (1-20) analogs demonstrated a 2- to 24-fold loss in antibacterial activities against staphylococcal pathogens (MRSA, MRSE) compared to HP 1. However, both 1-16 and 1-18 reported a 2-fold increase in antibacterial activities against VRE. Interestingly, 8-chloro HP, 1-22, demonstrated a 5- to 8-fold increase in antibacterial activities against four MRSA isolates (Table 5) while losing 5- to 8-fold in antibacterial activities against both S. epidermidis strains compared to HP 1. In addition, HP 1-22 demonstrated improved biofilm eradication activities against MRSA, MRSE and VRE biofilms compared to HP 1. Similar to the antibacterial profiles of HP 1-16 and 1-18, HP 1-22 showed an increased potency against VRE (4-fold) compared to HP 1.

The phenolic hydroxyl group was demonstrated to tolerate a PEG-carbonate and show enhanced antibacterial activities towards multiple MRSA isolates and maintain biofilm eradication activities against MRSA-1707 compared to their non-carbonate analogues. In previous studies, some ester groups were well-tolerated while ether- or amine-group substitution of the phenolic hydroxyl group leads to a complete loss of antibacterial activities.[49] The structural requirement for a 1-hydroxyl group (or masked ester/carbonate) on the HP scaffold, coupled with the results from UV-Vis experiments and metal(II) co-treatment MIC profiles, suggest that non-metal(II) binding carbonates, 1-24 and 1-25, are prodrugs that release metal(II)-chelators, HP 1 and 1-17, which bind metal(II)-cations and eradicate planktonic and biofilm cells against susceptible, Gram-positive human pathogens.

Example 12

HP-Prodrug Strategy and Synthesis

Due to the inherently high CLogP values and potential for off-target metal-chelating events of lead HP analogues, it was sought to preemptively address these concerns through the development of phenolic-based prodrug strategies. Although there was initial excitement about the incorporation of water-soluble moieties at the 6-through 8-positions attainable by way of BH-RC (the 9-position was not considered due to metal chelation interference), the lack of activity observed with triazole-HP 74A discouraged this endeavor. In lieu of 6-through 8-position modifications, prodrug strategies were sought wherein conjugation of water-soluble groups to the reactive 1-position phenol would afford HP analogues with reduced CLogP values. Although the phenolic prodrug approach was initially devised to attain improved water solubility, it was realized that the proposed functionalization strategy could ostensibly be used to impart bacterial selectivity onto the HP series. To this end, a library of bacterial-selective prodrugs (FIG. 31F-I; HP-prodrugs synthesized using various alkylation reactions) was assembled. This phenolic prodrug approach has additional benefits, including reduced susceptibility of HP analogues to phase II conjugative metabolism and, more importantly, attenuation of host metal homeostasis dysregulation. Thus, a library of diverse, CLogP-guided prodrugs was synthesized from active HP scaffolds (FIG. 31A-E; HP-prodrugs synthesized using acylation, alkylation and sugar-based syntheses).

Example 13

Biological Evaluation of HP-Prodrugs

The biological evaluation of this HP-prodrug library was initiated with MIC and MBEC assays against MRSA, MRSE, and VRE (Table 10). Among the CLogP-guided analogues, HP prodrugs 75A, 76A, 77A, and 78A were found to be active in MIC assays, reporting MICs between 0.0005 to 3.13 µM and MBECs of 0.78 to 75 µM against all strains (Table 10). Surprisingly, carbonate prodrugs 77A and 78A reported MICs of 0.0005 µM and 0.1 µM respectively against MRSA BAA-1707 (up to ~76-fold increase in potency relative to the corresponding HPs). As prodrug activity is not expected to exceed that of the active agent to which it is metabolized, it is suspected that the carbonate prodrugs temporarily protect HPs from ionization (phenolic pKa=~6.7[53]), allowing for improved membrane permeability prior to intracellular activation of the prodrug. Although these intriguing activities may warrant further investigation, the apparent susceptibility of prodrugs 75A-78A to rapidly undergo enzymatic or chemical hydrolysis (implied by their highly potent antibacterial activities) may limit their utility in vivo in future endeavors.

Interestingly, the HP-glycoconjugate (79A, FIG. 31D) and HP-alkyloxycarbonyloxymethyl (AOCOM) prodrugs 80A and 82A (FIG. 31E) demonstrated no activity in MIC assays. It is suspected that differences in carbonate stability of the AOCOM series relative to HP-carbonates 77A and 78A are likely responsible for this activity disparity. Fortunately, human serum stability assays for HPs 80A and 82A reveal favorable serum half-lives ($t_{1/2}$) of 15.8 minutes and 7.3 minutes, respectively, which are in line with reported half-lives for structurally related prodrugs.[83] These data suggest the HP-AOCOM prodrugs could have potential for further in vivo experiments wherein host-dependent prodrug cleavage could occur.

In an effort to develop more stable HP prodrugs, ether-based prodrug moieties were investigated. The synthesis of boron-based ether 83A and beta-lactam 84A was targeted. Each of these HP-prodrugs were designed to target different host response/bacterial features relevant to infection. Pinacol boron-HP 83A was designed to undergo a host inflammation-induced oxidation of boron, followed by the liberation of an active HP compound at the site of bacterial infection.[84,85] Beta-lactam 84A was designed to target penicillin-binding proteins/beta-lactamases for an initial beta-lactam cleavage, followed by the liberation of the active HP compound.[86,87] Although ether-linked prodrugs 83A and 84A (FIG. 31F, 31G) were able to be isolated, they were found to be unstable and, thus, further investigations of these analogues were discontinued.

Figure 30C:
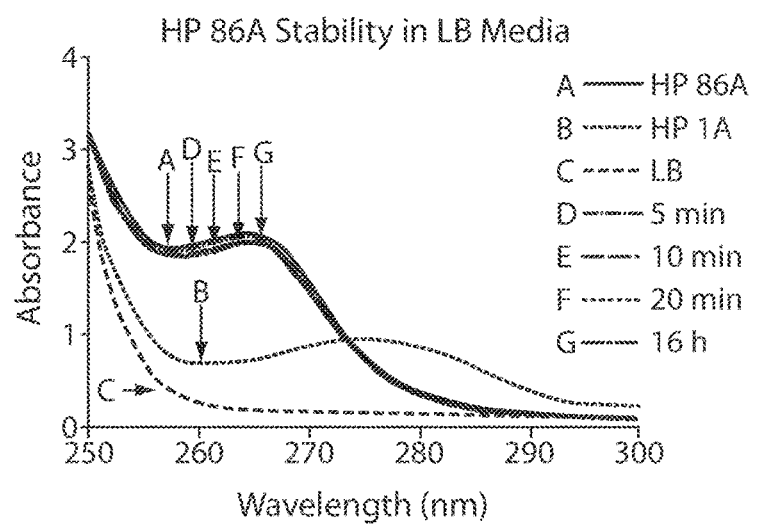
Figure 30D:
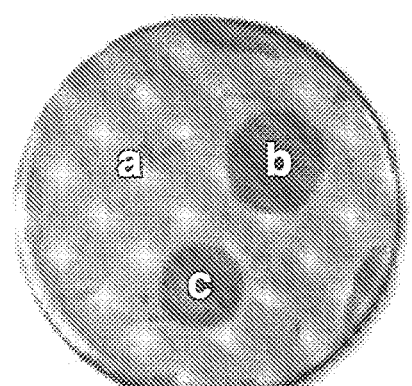
Figure 31:
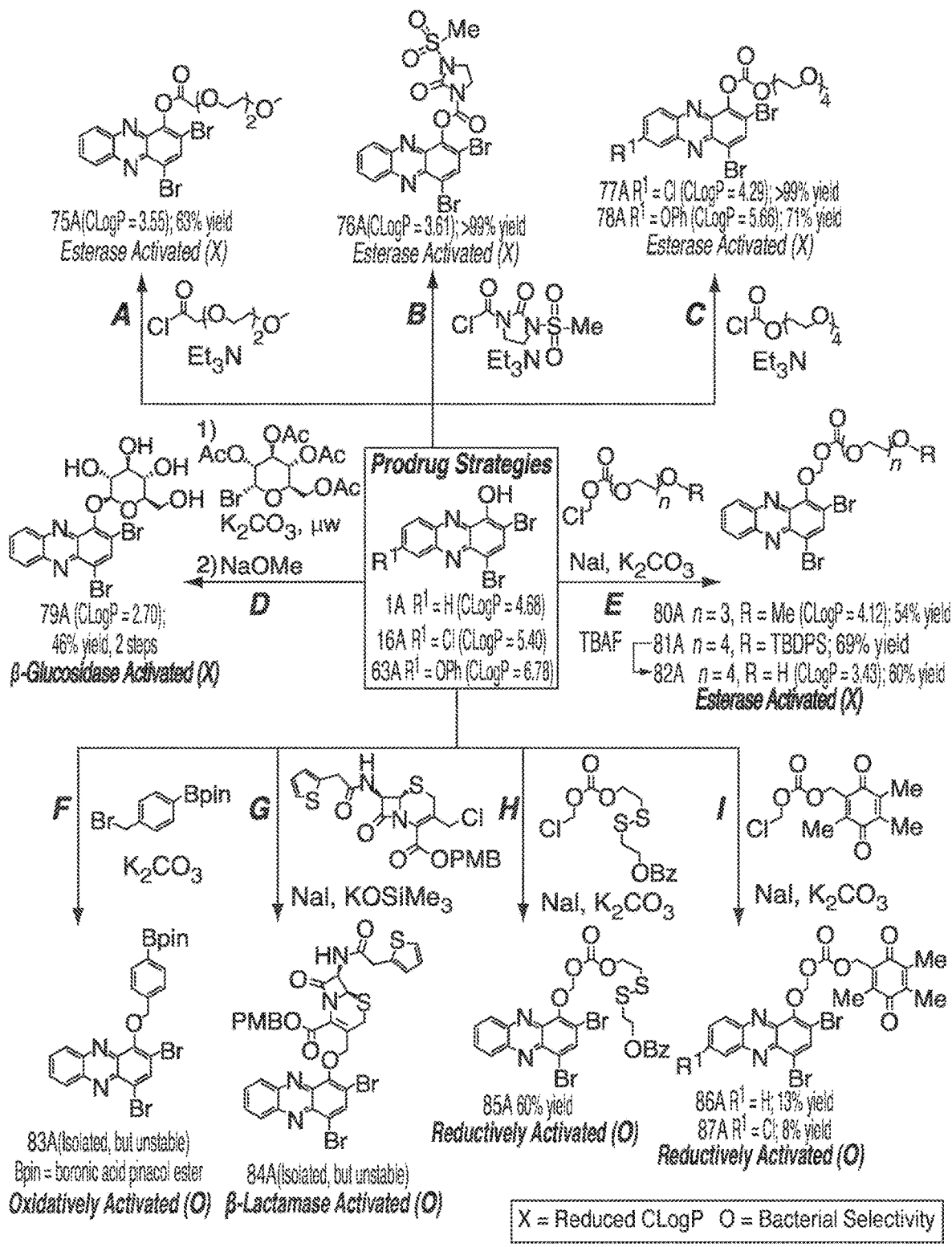
FIG. 31. Summary of phenolic prodrug strategies used to attain improved water solubility or bacterial selectivity and proposed mechanisms of prodrug activation (CLogP values determined by ChemDraw).

The bacterial cytoplasm was then exploited for the intracellular release of active Hps.[88,89] The bacterial cytoplasm is a reductive environment and inspiration was drawn from the natural product mitomycin C, a potent antibacterial agent and cytotoxin, that requires bioreductive activation of its quinone moiety before it can carry out its mode of action (DNA crosslinking).[88] Interestingly, reductively activated HP-disulfide prodrug 85A (FIG. 31H) reported no antibacterial activity against any pathogen tested. Two quinone-AOCOM (QuAOCOM) prodrugs 86A and 87A (FIG. 31I) were then designed and these agents were found to demonstrate antibacterial activities which were near equipotent to the corresponding HP counterparts with MICs=2.35 µM and 0.15 µM, respectively, versus MRSA BAA-1707. The exceptional antibacterial activity of QuAOCOM 87A was confirmed via agar diffusion assay, wherein this prodrug reported activity near that of the parent HP 61A (FIG. 30D). Additionally, the QuAOCOM prodrugs exhibited good to potent biofilm eradication activities against MRSA BAA-1707 (MBECs=75 µM and 12.5 µM for 86A and 87A, respectively). To ensure this activity was not a result of prodrug activation in the assay medium, stability experiments were conducted in lysogeny broth (LB), wherein no loss of the prodrug moiety was observed at up to 16 hours at 37° C. (FIG. 30C). Additionally, serum stability assays for QuAOCOM prodrugs revealed half-lives of 6.3±3.3 minutes and 11.4±2.8 minutes for 86A and 87A, respectively (Table 10). Finally, QuAOCOM 87A proved to have an outstanding cytotoxicity ($IC_{50}$>100 µM against HeLa cells; SI>667) and hemolysis (2.7% hemolysis of RBCs at 200 µM) profile, similar to parent HPs identified during these studies. Based on the stability assays for this prodrug class along with the well-understood reductive conditions of the bacterial cytoplasm, it can be concluded that the QuAOCOM prodrugs exhibit activities due to a bacterial-selective release mechanism. The initial activity profiles of these HP-QuAOCOM prodrugs are very encouraging and the reductive trigger of the quinone moiety in conjunction with the AOCOM linker is believed to be an ideal platform for future developments regarding HP-based biofilm therapies.

Example 14

Tables 8, 9, and 10

The biological evaluation of this HP-prodrug library was initiated with MIC and MBEC assays against MRSA, MRSE, and VRE (Table 10). Among the CLogP-guided analogues, HP prodrugs 75A, 76A, 77A, and 78A were found to be active in MIC assays, reporting MICs between 0.0005 to 3.13 µM and MBECs of 0.78 to 75 µM against all strains (Table 10). Surprisingly, carbonate prodrugs 77A and 78A reported MICs of 0.0005 µM and 0.1 µM respectively against MRSA BAA-1707 (up to ~76-fold increase in potency relative to the corresponding HPs). As prodrug activity is not expected to exceed that of the active agent to which it is metabolized, it is suspected that the carbonate prodrugs temporarily protect HPs from ionization (phenolic pKa=~6.7[53]), allowing for improved membrane permeability prior to intracellular activation of the prodrug. Although these intriguing activities may warrant further investigation, the apparent susceptibility of prodrugs 75A-78A to rapidly undergo enzymatic or chemical hydrolysis (implied by their highly potent antibacterial activities) may limit their utility in vivo in future endeavors.

TABLE 8

Summary of Gram-positive antibacterial activities (MIC values reported) and HeLa cell cytotoxicity of HP analogues and comparator compounds, including several antibiotics. All biological results are reported in micromolar (µM) concentrations.

| Compound | MRSA-1707 MIC | MRSA-2 MIC | MRSE 35984 MIC | VRE 700221 MIC | MtB H37Ra MIC | HeLa cell Cytotoxicity $IC_{50}$ | Selectivity Index |
|---|---|---|---|---|---|---|---|
| 1A | 1.17[a] | 1.56 | 1.17[a] | 6.25 | 25 | >100 | >109 |
| 52A | 0.39 | — | 0.3[a] | 2.35[a] | 6.25 | >100 | >256 |
| 53A | 0.1[b] | 0.59[a] | 0.1[b] | 2.35[a] | 6.25 | >50 | >500 |
| 54A | 0.1[b] | — | 0.15[a] | 3.13 | — | >50 | >500 |
| 55A | 0.1[b] | 0.1[b] | 0.1[b] | 0.1[b] | 9.38[a] | >100 | >1,000 |
| 56A | 0.075[a] | 0.3[a] | 0.1[b] | 0.2 | 50 | >100 | >1,333 |
| 57A | >100 | — | >100 | >100 | — | — | — |
| 58A | >100 | — | >100 | >100 | — | — | — |
| 59A | 0.59[a] | — | 0.1[b] | 4.69[a] | — | >100 | >169 |
| 60A | >100 | — | 18.8[a] | >100 | — | — | — |

TABLE 8-continued

Summary of Gram-positive antibacterial activities (MIC values reported) and HeLa cell cytotoxicity of HP analogues and comparator compounds, including several antibiotics. All biological results are reported in micromolar (μM) concentrations.

| Compound | MRSA-1707 MIC | MRSA-2 MIC | MRSE 35984 MIC | VRE 700221 MIC | MtB H37Ra MIC | HeLa cell Cytotoxicity IC$_{50}$ | Selectivity Index |
|---|---|---|---|---|---|---|---|
| 61A | 0.038$^a$ | 0.1$^b$ | 0.1$^b$ | 0.39 | 3.13 | >100 | >2,632 |
| 62A | 9.38$^a$ | 18.8$^a$ | 4.69$^a$ | 2.35$^a$ | — | — | — |
| 63A | 0.075$^a$ | 0.39 | 0.1$^b$ | 0.2 | 6.25 | >100 | >1,333 |
| 64A | 0.15$^a$ | 0.3$^a$ | 0.1$^b$ | 0.3$^a$ | — | >100 | >667 |
| 66A | 12.5 | — | 12.5 | 25 | 25 | >100 | >8 |
| 67A | 37.5$^a$ | — | 9.38$^a$ | 12.5 | 25 | >100 | >3 |
| 68A | 4.69$^a$ | — | 2.35$^a$ | 9.38$^a$ | 50 | >100 | >21 |
| 69A | 4.69$^a$ | — | 18.8$^a$ | 25 | 6.25 | >100 | >21 |
| 74A | 100 | — | 18.8$^a$ | >100 | — | — | — |
| QAC-10 | 4.69$^a$ | 3.13 | 2.35$^a$ | 2.35$^a$ | — | — | — |
| EDTA | 375$^a$ | — | — | — | — | — | — |
| TPEN | 50 | — | — | — | — | — | — |
| Vancomycin | 0.39 | 0.59$^a$ | 0.78 | >100 | — | — | — |
| Daptomycin | 3.13 | 4.69$^a$ | — | — | — | — | — |
| Linezolid | 12.5 | 3.13 | — | — | — | — | — |
| Rifampin | — | 0.1$^b$ | 0.1$^b$ | — | — | — | — |
| Streptomycin | — | — | — | — | 1.32 | — | — |

Note:
$^a$Midpoint value for independent experiments that yielded a 2-fold range.
$^b$Corresponds to the lowest concentration tested. MIC values were obtained from a minimum of three independent experiments. HPs were tested against HeLa cells at 25, 50 and 100 μM in three independent experiments. Selectivity Index was calculated by dividing the cytotoxicity IC$_{50}$ by the MIC against MRSA-1707.

TABLE 9

Summary of biofilm eradication studies against MRSA, MRSE and VRE biofilms. All biological results are reported in micromolar (μM) concentrations.

| Compound | MRSA-1707 MBC/MBEC | MRSA-2 MBC/MBEC | MRSA BAA-44 MBC/MBEC | MRSE 35984 MBC/MBEC | VRE 700221 MBC/MBEC | % Hemolysis at 200 μM |
|---|---|---|---|---|---|---|
| 1A | 37.5$^a$/150$^a$ | 50/100 | 375$^a$/150$^a$ | 50$^b$/100$^b$ | 23.5$^a$/9.38$^a$ | ≤1 |
| 52A | 18.8$^a$/37.5$^a$ | — | — | 18.8$^a$/37.5$^a$ | 12.5/3.13 | ≤1 |
| 53A | 75$^a$/150$^a$ | 75$^a$/150$^a$ | 75$^a$/75$^a$ | 50$^b$/75$^a$ | 50$^b$/2.35$^a$ | 3.0 |
| 54A | 37.5$^a$/75$^a$ | — | — | 25/37.5$^a$ | 2.5$^b$/18.8$^a$ | 2.1 |
| 55A | 4.69$^a$/4.69$^a$ | 3.13/3.13 | 18.8$^a$/9.38$^a$ | 18.8$^a$ | 1.56$^a$/0.59$^a$ | ≤1 |
| 56A | 9.38$^a$/4.69$^a$ | 9.38$^a$/37.5$^a$ | 37.5$^a$/37.5$^a$ | 4.69$^a$/4.69$^a$ | 1.17/0.78 | 2.2 |
| 59A | 150$^b$/75$^a$ | — | — | 25/5$^b$ | 4.69$^a$/1.17$^a$ | 1.3 |
| 61A | 1.17$^a$/4.69$^a$ | 6.25/25 | 6.25$^a$/18.8$^a$ | 2.35$^a$/18.8$^a$ | 1.56$^a$/0.59$^a$ | ≤1 |
| 63A | 9.38$^a$/2.35$^a$ | 4.69$^a$/4.69$^a$ | 25/18.8$^a$ | 9.38$^a$/4.69$^a$ | 2.35$^a$/0.78 | ≤1 |
| 64A | 9.38$^a$/4.69$^a$ | — | — | 9.38$^a$/6.25$^b$ | 2.35$^a$/0.78 | ≤1 |
| CCCP | — | 31.3$^b$/1000 | — | 31.3/93.8$^a$ | — | — |
| NAC | — | >2000/>2000 | — | >2000/>2000 | >2000/>2000 | — |
| QAC-10 | 93.8$^a$/93.8$^a$ | 31.3$^b$/125 | — | 31.3/31.3 | 3.0$^a$/3.0$^a$ | >99 |
| Pyrazinamide | — | >2000/>2000 | — | — | — | — |
| Vancomycin | 3.9/>2000 | 3.0$^a$/>2000 | 7.8/>2000 | 3.0$^a$/>2000 | >200/150$^a$ | ≤1 |
| Daptomycin | 125/>2000 | 62.5$^b$/>2000 | — | — | — | 1.7 |
| Linezolid | 31.3/>2000 | 15.6/>2000 | — | — | 4.69$^b$/1.56 | ≤1 |
| Doxycycline | — | 2.0/46.9$^a$ | — | — | — | — |
| Rifampin | — | 2.0/46.9$^a$ | — | 3.0$^a$/15.6$^b$ | — | — |
| EDTA | >2000/>2000 | 2000/>2000 | — | 1000/>2000 | — | 3.0 |
| TPEN | 250/>2000 | — | — | — | 188$^a$/>2000 | ≤1 |

Note:
$^a$Midpoint value for independent experiments that yielded a 2-fold range.
$^b$Corresponds to a 4-fold range in independent experiments. MBC/MBEC values were obtained from three to six independent experiments.

TABLE 10

Summary of biological investigations with HP prodrugs (entries for HPs 1A, 61A and 63A are included, all prodrugs were synthesized from these three parent HPs). All biological results are reported in micromolar (μM) concentrations.

| Compound | MRSA BAA-1707 MIC | MRSA BAA-1707 MBC/MBEC | MRSE 35984 MIC | MRSE 35984 MBC/MBEC | VRE 700221 MIC | VRE 700221 MBC/MBEC | HeLa $IC_{50}$ | % Hemo. at 200 μM | Serum Stability $t_{1/2}$ (min) |
|---|---|---|---|---|---|---|---|---|---|
| 1A | $1.17^a$ | $18.8/150^a$ | 1.17 | $50^c/100^c$ | 6.25 | $23.5^a/9.38^a$ | >100 | ≤1 | n.a. |
| 61A | 0.038 | $1.17^a/4.69^a$ | $0.1^b$ | $2.35^a/18.8^a$ | 0.39 | $1.56^c/0.59^a$ | >100 | ≤1 | n.a. |
| 63A | 0.075 | $9.38^a/2.35^a$ | $0.1^b$ | $9.38^a/4.69^a$ | 0.2 | $2.35^a/0.78$ | >100 | ≤1 | n.a. |
| 75A | $0.59^a$ | $18.8^a/75^a$ | $0.59^a$ | $9.38^a/37.5^a$ | 3.13 | $6.25/4.69^a$ | >100 | 1.2 | <1 |
| 76A | $0.59^a$ | $37.5^a/75^a$ | 1.56 | $18.8^a/37.5^a$ | 3.13 | $9.38^a/9.38^a$ | >100 | ≤1 | <1 |
| 77A | $0.0005^a$ | $6.25^c/9.38^a$ | $0.1^b$ | $9.38^a/18.8^a$ | $0.1^b$ | $1.17^a/0.59^a$ | >100 | 1.1 | <1 |
| 78A | $0.1^b$ | $18.8^a/4.69^a$ | $0.1^b$ | $9.38^a/1.56$ | $0.3^a$ | $0.78/1.17^a$ | — | ≤1 | <1 |
| 79A | >100 | — | >100 | — | >100 | — | — | ≤1 | >260 |
| 80A | >100 | — | >100 | — | >100 | — | — | 1.4 | 15.8 ± 0.9 |
| 82A | >100 | — | >100 | — | >100 | — | >100 | 2.7 | 7.3 ± 3.6 |
| 85A | >100 | — | >100 | — | >100 | — | >100 | 1.3 | — |
| 86A | $2.35^a$ | $25/75^a$ | $2.35^a$ | $37.5^a/150^a$ | $9.38^a$ | $12.5/9.38^a$ | — | ≤1 | 6.3 ± 3.3 |
| 87A | $0.15^a$ | 6.25/12.5 | 0.39 | 12.5/25 | 1.56 | $3.13^c/3.13^c$ | >100 | 2.7 | 11.4 ± 2.8 |
| Vanco. | 0.39 | 3.9/>2000 | 0.78 | $3.0^a$/>2000 | >100 | $>200/150^a$ | — | ≤1 | — |

Note:
[a] Midpoint value for independent experiments that yielded a 2-fold range.
[b] Corresponds to the lowest concentration tested.
[c] Midpoint value for independent experiments that yielded a 4-fold range. "n.a." not applicable due to compound being a non-prodrug HP (comparator).
"—" HP prodrug not tested. All values were obtained from three to six independent experiments (e.g., MIC, MBEC, HeLa cytotoxicity, RBC hemolysis, serum half-lives).

REFERENCES

[1] K. Lewis, *Annu. Rev. Microbiol. B* 2010, 64, 357-372.
[2] N. Q. Balaban, J. Merrin, R. Chait, L. Kowalik, S. Leibler, *Science* 2004, 305, 1622-1625.
[3] B. P. Conlon, *Bioessays* 2014, 36, 991-996.
[4] M. Kostakioti, M. Hadjifrangiskou, S. J. Hultgren, *Cold Spring Harb. Perspect. Med.* 2013, 3, a010306.
[5] T. Bjarnsholt, *APMIS* 2013, 121 (Suppl. 136), 1-54.
[6] K. Lewis, *Nat. Rev. Microbiol.* 2007, 5, 48-56.
[7] (a) M. H. Fletcher, M. C. Jennings, W. M. Wuest, *Tetrahedron* 2014, 70, 6373-6383; (b) R. J. Worthington, J. R. Richards, C. Melander, *Org. Biomol. Chem.* 2012, 10, 7457-7474.
[8] G. H. De Zoysa, A. J. Cameron, V. V. Hegde, S. Raghothama, V. Sarojini, *J. Med. Chem.* 2015, 58, 625-639.
[9] J. Hogue, M. M. Konai, S. Gonuguntla, G. B. Manjunath, S. Samaddar, V. Yarlagadda, J. Haldar, *J. Med. Chem.* 2015, 58, 5486-5500.
[10] M. C. Jennings, L. E. Ator, T. J. Paniak, K. P. C. Minbiole, W. M. Wuest, *ChemBioChem* 2014, 15, 2211-2215.
[11] C. C. Hughes, W. Fenical, *Chem. Eur. J.* 2010, 16, 12512-12525.
[12] W. L. Ng, B. L. Bassler, *Annu. Rev. Genet.* 2009, 43, 197-222.
[13] M. Hentzer, H. Wu, J. B. Anderson, K. Riedel, T. B. Rasmussen, N. Bagge, N. Kumar, M. A. Schembri, Z. Song, P. Kristoffersen, M. Manefield, J. W. Costerton, S. Molin, L. Eberl, P. Stienberg, S. Kjelleberg, N. Høiby, M. Givskov, *EMBO J.* 2003, 22, 3803-3815.
[14] H. Wu, Z. Song, M. Hentzer, J. B. Anderson, S. Molin, M. Givskov, N. Høiby, *J. Antimicrob. Chemother.* 2004, 53, 1054-1061.
[15] J. C. Kwan, T. Meickle, D. Ladwa, M. Teplitski, V. J. Paul, H. Luesch *Mol. BioSyst.* 2011, 7, 1205-1216.
[16] G. Navarro, A. T. Cheng, K. C. Peach, W. M. Bray, V. S. Bernan, F. H. Yildiz, R. G. Linington, *Antimicrob. Agents Chemother.* 2014, 58, 1092-1099.
[17] A. T. Garrison, F. Bai, Y. Abouelhassan, N. G. Paciaroni, S. Jin, R. W. Huigens III, *RSC Adv.* 2015, 5, 1120-1124.
[18] A. Price-Whelan, L. E. P. Dietrich, D. K. Newman, *Nat. Chem. Biol.* 2006, 2, 71-78.
[19] M. Conda-Sheridan, L. Marler, E. J. Park, T. P. Kondratyuk, K. Jermihov, A. D. Mesecar, J. M. Pezzuto, R. N. Asolkar, W. Fenical, M. Cushman, *J. Med. Chem.* 2010, 53, 8688-8699.
[20] H. Ceri, M. E. Olson, C. Stremick, R. R. Read, D. Morck, A. Buret, *J. Clin. Microbiol.* 1999, 37, 1771-1776.
[21] Taiwo, F. A. *Spectroscopy,* 2008, 22, 491-498.
[22] Y. J. Eun, M. H. Foss, D. Kiekebusch, D. A. Pauw, W. M. Westler, M. Thanbichler, D. B. Weibel, *J. Am. Chem. Soc.* 2012, 134, 11322-11325.
[23] I. Keren, N. Kaldalu, A. Spoering, Y. Wang, K. Lewis, *FEMS Microbiol. Lett.* 2004, 230, 13-18.
[24] S. Lechner, K. Lewis, R. Bertram, *J. Mol. Microbiol. Biotechnol.* 2012, 22, 235-244.
[25] D. B. Young, M. D. Perkins, K. Duncan, C. E. Barry, *J. Clin. Invest.* 2008, 118, 1255-1265.
[26] D. Zhang, Y. Liu, C. Zhang, H. Zhang, B. Wang, J. Xu, L. Fu, D. Yin, C. B. Cooper, Z. Ma, Y. Lu, H. Huang, *Molecules* 2014, 19, 4380-4394.
[27] L. Marler, M. Conda-Sheridan, M. A. Cinelli, A. E. Morrell, M. Cushman, L. Chen, K. Huang, R. Van Breemen, J. M. Pezzuto, *Anticancer Res.* 2010, 30, 4873-4882.
[28] Conda-Sheridan, M.; Marler, L.; Park, E. J.; Kondratyuk, T. P.; Jermihov, K.; Mesecar, A. D.; Pezzuto, J. M.; Asolkar, R. N.; Fenical, W.; Cushman, M. *J. Med. Chem.* 2010, 53, 8688-8699.
[29] Emmanuvel, L.; Shukla, R. K.; Sudalai, A.; Gurunath, S.; Sivaram, S. *Tetrahedron Lett.* 2006, 47, 4793-4796.
[30] Clinical and Laboratory Standards Institute. 2009. *Methods for dilution antimicrobial susceptibility tests for bacteria that grow aerobically; approved standard, 8th edition (M7-M8),* Clinical and Laboratory Standard, Wayne, Pa., 2009.
[31] Abouelhassan, Y.; Garrison, A. T.; Bal, F.; Norwood I V, V. M.; Nguyen, M. T.; Jin, S.; Huigens III, R. W. *ChemMedChem,* 2015, 10, 1157-1162.

[32] Stringer, J. R.; Bowman, M. D.; Weisblum, B.; Blackwell, H. *ACS Comb. Sci.* 2011, 13, 175-180.

[33] Wohl, A. & Aue, W. Ueber die Einwirkung von Nitrobenzol auf Anilin bei Gegenward von Alkali. *Chem. Ber.* 34, 2442-2450 (1901).

[34] Pachter, I. J. & Kloetzel, M. C. The Wohl-Aue reaction. I. Structure of benzo [a] phenazine oxides and synthesis of 1,6-dimethylphenazine and 1,6-dichlorophenazine. *J. Am. Chem. Soc.* 73, 4958-4961 (1951).

[35] Young, D. B., Perkins, M. D., Duncan, K. & Barry, C. E. Confronting the scientific obstacles to global control of tuberculosis. *J. Clin. Invest.* 118, 1255-1265 (2008).

[36] Evangelopoulos, D. & McHugh, T. D. Improving the tuberculosis drug development pipeline. *Chem. Biol. Drug Des.* 86, 951-960 (2015).

[37] Pérez-Lago, L. et al. Persistent infection by a *Mycobacterium tuberculosis* strain that was theorized to have advantageous properties, as it was responsible for a massive outbreak. *J. Clin. Microbiol.* 53, 3423-3429 (2015).

[38] Chetty, S., Ramesh, M., Singh-Pillay, A. & Soliman, M. E. S. Recent advancements in the development of anti-tuberculosis drugs. *Bioorg. Med. Chem. Lett.* 27, 370-386 (2017).

[39] Mullowney, M. W. et al. Diaza-anthracene antibiotics from freshwater-derived actinomycete with selective antibacterial activities toward *Mycobacterium tuberculosis. ACS Infect. Dis.* 1, 168-174 (2015).

[40] Thangamani, S., Younis, W. & Seleem, M. N. Repurposing ebselen for treatment of multidrug-resistant staphylococcal infections. *Sci. Rep.* 5, 1-13 (2015).

[41] Weidmann, E. et al. Lactate dehydrogenase assay: a reliable, nonradioactive technique for analysis of cytotoxic lymphocyte-mediated lytic activity against blasts from acute myelocytic leukemia. *Ann. Hematol.* 70, 153-158 (1995).

[42] Garrison, A. T. et al. Structure-activity relationships of a diverse class of halogenated phenazines that targets persistent, antibiotic-tolerant bacterial biofilms and *Mycobacterium tuberculosis. J. Med. Chem.* 59, 3808-3825 (2016).

[43] Brodersen, D. E. et al. The structural basis for the action of the antibiotics tetracycline, pactamycin, and hygromycin B on the 30S ribosomal subunit. *Cell* 103, 1143-1154 (2000).

[44] Leonard, S. N., Cheung, C. M. & Rybak, M. J. Activities of ceftobiprole, linezolid, vancomycin, and daptomycin against community-associated and hospital-associated methicillin-resistant *Staphylococcus aureus. Antimicrob. Agents Chemother.* 52, 2974-2976 (2008).

[45] Mélard, A. et al. Activity of ceftaroline against extracellular (broth) and intracellular (THP-1 monocytes) forms of methicillin-resistant *Staphylococcus aureus*: comparison with vancomycin, linezolid and daptomycin. *J. Antimicrob. Chemother.* 68, 648-658 (2013).

[46] Jennings, M. C., Ator, L. E., Paniak, T. J., Minbiole, K. P. C. & Wuest, W. M. Biofilm-eradicating properties of quaternary ammonium amphiphiles: simple mimics of antimicrobial peptides. *ChemBioChem* 15, 2211-2215 (2014).

[47] Hogue, J. et al. Membrane active small molecules show selective broad spectrum antibacterial activity with no detectable resistance and eradicate biofilms. *J. Med. Chem.* 58, 5486-5500 (2015).

[48] De Zoysa, G. H., Cameron, A. J., Hegde, V. V., Raghothama, S. & Sarojini, V. Antimicrobial peptides with potential for biofilm eradication: synthesis and structure activity relationship studies of battacin peptides. *J. Med. Chem.* 58, 625-639 (2015).

[49] Borrero, N. V. et al. Phenazine antibiotic inspired discovery of potent bromophenazine antibacterial agents against *Staphylococcus aureus* and *Staphylococcus epidermidis. Org. Biomol. Chem.* 12, 881-886 (2014).

[50] Serebryanyi, S. B.; Yufa, P. A. 1-Hydroxyphenazines. VI. Halogen Substituted 1-hydroxyphenazines. *Ukr. Khemichnii Zhurnal* 1956, 22, 512-513.

[51] Dicus, C.; Nantz, M. Synthesis of a Heterobifunctional PEG Spacer Terminated with Aminooxy and Bromide Functionality. *Synlett* 2006, 17, 2821-2823.

[52] Garrison, A. T.; Abouelhassan, Y.; Kallifidas, D.; Bai, F.; Ukhanova, M.; Mai, V.; Jin, S.; Luesch, H.; Huigens III, R. W. Halogenated Phenazines That Potently Eradicate Biofilms, MRSA Persister Cells in Non-Biofilm Cultures, and *Mycobacterium tuberculosis. Angew. Chemie Int. Ed.* 2015, 54, 14819-14823.

[53] Garrison, A. T.; Abouelhassan, Y.; Norwood I V, V. M.; Kallifidas, D.; Bai, F.; Thu Nguyen, M.; Rolfe, M.; Burch, G. M.; Jin, S.; Luesch, H.; Huigens III, R. W. Structure-Activity Relationships of a Diverse Class of Halogenated Phenazines That Targets Persistent, Antibiotic-Tolerant Bacterial Biofilms and *Mycobacterium tuberculosis. J. Med. Chem.* 2016, 59, 3808-3825.

[54] Yang, H.; Abouelhassan, Y.; Burch, G. M.; Kallifidas, D.; Huang, G.; Yousaf, H.; Jin, S.; Luesch, H.; Huigens, R. W. A Highly Potent Class of Halogenated Phenazine Antibacterial and Biofilm-Eradicating Agents Accessed Through a Modular Wohl-Aue Synthesis. *Sci. Rep.* 2017, 7, 2003.

[55] Pachter, I. J.; Kloetzel, M. C. The Wohl-Aue Reaction. I. Structure of Benzo [a] Phenazine Oxides and Syntheses of 1,6-Dimethoxyphenazine and 1,6-Dichlorophenazine1. *J. Am. Chem. Soc.* 1951, 73, 4958-4961.

[56] Kwast, A.; Stachowska, K.; Trawczyński, A.; Wróbel, Z. N-Aryl-2-Nitrosoanilines as Intermediates in the Synthesis of Substituted Phenazines from Nitroarenes. *Tetrahedron Lett.* 2011, 52, 6484-6488.

[57] Cross, B.; Williams, P. J.; Woodall, R. E. The Preparation of Phenazines by the Cyclisation of 2-Nitrodiphenylamines. *J. Chem. Soc. C Org.* 1971, 11, 2085-2090.

[58] Laha, J. K.; Tummalapalli, K. S. S.; Gupta, A. Palladium-Catalyzed Domino Double N-Arylations (Inter- and Intramolecular) of 1,2-Diamino(hetero)arenes with O,O'-Dihalo(hetero)arenes for the Synthesis of Phenazines and Pyridoquinoxalines. *European J. Org. Chem.* 2013, 2013, 8330-8335.

[59] Yu, L.; Zhou, X.; Wu, D.; Xiang, H. Synthesis of Phenazines by Cu-Catalyzed Homocoupling of 2-Halogen Anilines in Water. *J. Organomet. Chem.* 2012, 705, 75-78.

[60] Seth, K.; Raha Roy, S.; Chakraborti, A. K.; Meyer, F. M.; Gaunt, M. J.; Baran, P. S.; Himmel, H. J.; Bunz, U. H. F. Synchronous Double C—N Bond Formation via C—H Activation for a Novel Synthetic Route to Phenazine. *Chem. Commun.* 2016, 52, 922-925.

[61] Lian, Y.; Hummel, J. R.; Bergman, R. G.; Ellman, J. A. Facile Synthesis of Unsymmetrical Acridines and Phenazines by a Rh(III)-Catalyzed Amination/Cyclization/Aromatization Cascade. *J. Am. Chem. Soc.* 2013, 135, 12548-12551.

[62] Challand, S. R.; Herbert, R. B.; Holliman, F. G. A New Phenazine Synthesis. The Synthesis of Griseoluteic Acid, Griseolutein A, and Methyl Diacetylgriseolutein B. *J. Chem. Soc. D Chem. Commun.* 1970, 21, 1423-1425.

[63] Borrero, N. V; Bal, F.; Pérez, C.; Duong, B. Q.; Rocca, J. R.; Jin, S.; Huigens III, R. W. Phenazine Antibiotic Inspired Discovery of Potent Bromophenazine Antibacterial Agents against *Staphylococcus aureus* and *Staphylococcus epidermidis*. *Org. Biomol. Chem.* 2014, 12, 881-886.

[64] Paciaroni, N. G.; Borrero, N. V; Rocca, J. R.; Huigens III, R. W. Rapid Synthesis of Phenazine-1-Carboxylic Acid Derived SmallMolecules from Diverse Anilines: Privileged Structures for Discovery. *Res. Rev. J. Med. Org. Chem.* 2015, 2, 67-76.

[65] Ruiz-Castillo, P.; Buchwald, S. L. Applications of Palladium-Catalyzed C—N Cross-Coupling Reactions. *Chem. Rev.* 2016, 116, 12564-12649.

[66] Enthaler, S.; Company, A. Cross Coupling Reactions in Organic Synthesis Themed Issue Palladium-Catalysed Hydroxylation and Alkoxylationw. *Chem. Soc. Rev. Chem. Soc. Rev* 2011, 40, 4912-4924.

[67] Zheng, Z.; Dian, L.; Yuan, Y.; Zhang-Negrerie, D.; Du, Y.; Zhao, K. PhI(OAc) 2-Mediated Intramolecular Oxidative Aryl-Aldehyde C Sp 2 C-Sp 2 Bond Formation: Metal-Free Synthesis of Acridone Derivatives. *J. Org. Chem.* 2014, 79, 7451-7458.

[68] Shiu, Y. J.; Cheng, Y. C.; Tsai, W. L.; Wu, C. C.; Chao, C. T.; Lu, C. W.; Chi, Y.; Chen, Y. T.; Liu, S. H.; Chou, P. T. Pyridyl Pyrrolide Boron Complexes: The Facile Generation of Thermally Activated Delayed Fluorescence and Preparation of Organic Light-Emitting Diodes. *Angew. Chemie Int. Ed.* 2016, 55, 3017-3021.

[69] Safaei-Ghomi, J.; Akbarzadeh, Z.; Khojastehbakht-Koopaei, B.; Li, L.; Zhang, H.; Stranks, S. D.; Bharti, V.; Chand, S.; Gaur, J.; Mohanty, D. C—N Cross-Coupling Reaction Catalysed by Reusable $CuCr_2O_4$ Nanoparticles under Ligand-Free Conditions: A Highly Efficient Synthesis of Triarylamines. *RSC Adv.* 2015, 5, 28879-28884.

[70] Blaziak, K.; Danikiewicz, W.; Mąkosza, M. How Does Nucleophilic Aromatic Substitution Really Proceed in Nitroarenes? Computational Prediction and Experimental Verification. *J. Am. Chem. Soc.* 2016, 138, 7276-7281.

[71] Bunnett, J. F.; Zahler, R. E. Aromatic Nucleophilic Substitution Reactions. *Chem. Rev.* 1951, 49, 273-412.

[72] Chen, Z.; Zeng, H.; Gong, H.; Wang, H.; Li, C. J. Palladium-Catalyzed Reductive Coupling of Phenols with Anilines and Amines: Efficient Conversion of Phenolic Lignin Model Monomers and Analogues to Cyclohexylamines. *Chem. Sci.* 2015, 6, 4174-4178

[73] Fischer, C.; Koenig, B. Palladium- and Copper-Mediated N-Aryl Bond Formation Reactions for the Synthesis of Biological Active Compounds. *Beilstein J. Org. Chem* 2011, 7, 59-74.

[74] Rewcastle, G. W.; Denny, W. A. Unequivocal Synthesis of Phenazine-1-Carboxylic Acids: Selective Displacement of Fluorine During Alkaline Borohydride Reduction of N-(2-Fluorophenyl)-3-Nitro anthranilic Acids. *Synth. Commun.* 1987, 17, 1171-1179.

[75] Kolb, H. C.; Finn, M. G.; Sharpless, K. B. Click Chemistry: Diverse Chemical Function from a Few Good Reactions. Angew. *Chemie Int. Ed.* 2001, 40, 2004-2021.

[76] Moses, J. E.; Moorhouse, A. D.; Mocharla, V. P.; Lin, R. J.; Phelps, M. E.; Kolb, H. C.; Tseng, H. R.; Finn, M. G.; Sharpless, K. B.; Elder, J. H.; Fokin, V. V. The Growing Applications of Click Chemistry. *Chem. Soc. Rev.* 2007, 36, 1249-1262.

[77] Chen, Q. Y.; Liu, Y.; Cai, W.; Luesch, H. Improved Total Synthesis and Biological Evaluation of Potent Apratoxin S4 Based Anticancer Agents with Differential Stability and Further Enhanced Activity. *J. Med. Chem.* 2014, 57, 3011-3029.

[78] Furtado, G. L.; Medeiros, A. A. Single-Disk Diffusion Testing (Kirby-Bauer) of Susceptibility of Proteus mirabilis to Chloramphenicol: Significance of the Intermediate Category. *J. Clin. Microbiol.* 1980, 12, 550-553.

[79] Garrison, A. T.; Bai, F.; Abouelhassan, Y.; Paciaroni, N. G.; Jin, S.; Huigens III, R. W. Bromophenazine Derivatives with Potent Inhibition, Dispersion and Eradication Activities against *Staphylococcus aureus* Biofilms. *RSC Adv.* 2014, 5, 1120-1124.

[80] Abouelhassan, Y.; Garrison, A. T.; Burch, G. M.; Wong, W.; Norwood I V, V. M.; Huigens III, R. W. Discovery of Quinoline Small Molecules with Potent Dispersal Activity against Methicillin-Resistant *Staphylococcus aureus* and *Staphylococcus epidermidis* Biofilms Using a Scaffold Hopping Strategy. *Bioorganic Med. Chem. Lett.* 2014, 24, 5076-5080.

[81] Ceri, H.; Olson, M. E.; Stremick, C.; Read, R. R.; Morck, D.; Buret, A. The Calgary Biofilm Device: New Technology for Rapid Determination of Antibiotic Susceptibilities of Bacterial Biofilms. *J. Clin. Microbiol.* 1999, 37, 1771-1776.

[82] Harrison, J. J.; Stremick, C. A.; Turner, R. J.; Allan, N. D.; Olson, M. E.; Ceri, H. Microtiter Susceptibility Testing of Microbes Growing on Peg Lids: A Miniaturized Biofilm Model for High-Throughput Screening. *Nat. Protoc.* 2010, 5, 1236-1254.

[83] Teitelbaum, A. M.; Meissner, A.; Harding, R. A.; Wong, C. A.; Aldrich, C. C.; Remmel, R. P. Synthesis, pH-Dependent, and Plasma Stability of Meropenem Prodrugs for Potential Use against Drug-Resistant Tuberculosis. *Bioorg. Med. Chem.* 2013, 21, 5605-5617.

[84] Festa, R. A.; Helsel, M. E.; Franz, K. J.; Thiele, D. J. Exploiting Innate Immune Cell Activation of a Copper-Dependent Antimicrobial Agent during Infection. *Chem. Biol.* 2014, 21, 977-987.

[85] Sandford, C.; Aggarwal, V. K. Stereospecific Functionalizations and Transformations of Secondary and Tertiary Boronic Esters. *Chem. Commun.* 2017, 53, 5481-5494.

[86] Gao, W.; Xing, B.; Tsien, R. Y.; Rao, J. Novel Fluorogenic Substrates for Imaging β-Lactamase Gene Expression. *J. Am. Chem. Soc.* 2003, 125, 11146-11147.

[87] Phelan, R. M.; Ostermeier, M.; Townsend, C. A. Design and Synthesis of a β-Lactamase Activated 5-Fluorouracil Prodrug. *Bioorg. Med. Chem. Lett.* 2009, 19, 1261-1263.

[88] Kwan, B. W.; Chowdhury, N.; Wood, T. K. Combatting Bacterial Infections by Killing Persister Cells with Mitomycin C. *Environ. Microbiol.* 2015, 17, 4406-4414.

[89] Arts, I. S.; Gennaris, A.; Collet, J. F. Reducing Systems Protecting the Bacterial Cell Envelope from Oxidative Damage. *FEBS Lett.* 2015, 589, 1559-1568.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

This application encompasses compounds described and illustrated in the above Description, appended claims, and Figures.

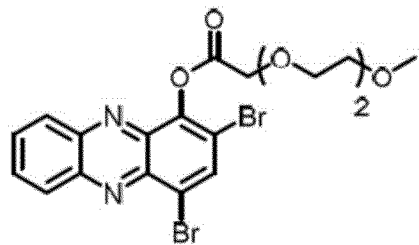

What is claimed is:
1. A compound of Formula (I):

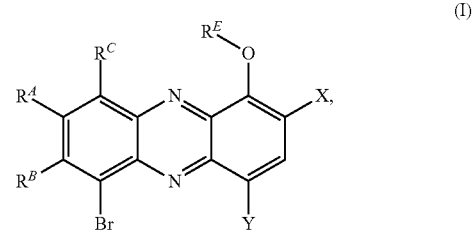

or a pharmaceutically acceptable salt, solvate, hydrate, polymorph, co-crystal, tautomer, stereoisomer, isotopically labeled derivative, or prodrug thereof, wherein:

X is hydrogen or halogen;

Y is halogen;

Z is N or $CR^D$;

$R^A$ is hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^1$, —$N(R^1)_2$, —$SR^1$, —CN, —SCN, —C(=$NR^1$)$R^1$, —C(=$NR^1$)$OR^1$, —C(=$NR^1$)$N(R^1)_2$, —C(=O)$R^1$, —C(=O)$OR^1$, —C(=O)$N(R^1)_2$, —$NO_2$, —$NR^1$C(=O)$R^1$, —$NR^1$C(=O)$OR^1$, —$NR^1$C(=O)$N(R^1)_2$, —OC(=O)$R^1$, —OC(=O)$OR^1$, or —OC(=O)$N(R^1)_2$, wherein each instance of $R^1$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^1$ are joined to form a substituted or unsubstituted heterocyclic or substituted or unsubstituted heteroaryl ring;

$R^B$ is hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^2$, —$N(R^2)_2$, —$SR^2$, —CN, —SCN, —C(=$NR^2$)$R^2$, —C(=$NR^2$)$OR^2$, —C(=$NR^2$)$N(R^2)_2$, —C(=O)$R^2$, —C(=O)$OR^2$, —C(=O)$N(R^2)_2$, —$NO_2$, —$NR^2$C(=O)$R^2$, —$NR^2$C(=O)$OR^2$, —$NR^2$C(=O)$N(R^2)_2$, —OC(=O)$R^2$, —OC(=O)$OR^2$, or —OC(=O)$N(R^2)_2$, wherein each instance of $R^2$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^2$ are joined to form a substituted or unsubstituted heterocyclic or substituted or unsubstituted heteroaryl ring;

$R^C$ is hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^3$, $-N(R^3)_2$, $-SR^3$, $-CN$, $-SCN$, $-C(=NR^3)R^3$, $-C(=NR^3)OR^3$, $-C(=NR^3)N(R^3)_2$, $-C(=O)R^3$, $-C(=O)OR^3$, $-C(=O)N(R^3)_2$, $-NO_2$, $-NR^3C(=O)R^3$, $-NR^3C(=O)OR^3$, $-NR^3C(=O)N(R^3)_2$, $-OC(=O)R^3$, $-OC(=O)OR^3$, or $-OC(=O)N(R^3)_2$, wherein each instance of $R^3$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^3$ are joined to form a substituted or unsubstituted heterocyclic or substituted or unsubstituted heteroaryl ring;

$R^D$ is hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^4$, $-N(R^4)_2$, $-SR^4$, $-CN$, $-SCN$, $-C(=NR^4)R^4$, $-C(=NR^4)OR^4$, $-C(=NR^4)N(R^4)_2$, $-C(=O)R^4$, $-C(=O)OR^4$, $-C(=O)N(R^4)_2$, $-NO_2$, $-NR^4C(=O)R^4$, $-NR^4C(=O)OR^4$, $-NR^4C(=O)N(R^4)_2$, $-OC(=O)R^4$, $-OC(=O)OR^4$, or $-OC(=O)N(R^4)_2$, wherein each instance of $R^4$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^4$ are joined to form a substituted or unsubstituted heterocyclic or substituted or unsubstituted heteroaryl ring;

$R^E$ is hydrogen, unsubstituted $C_{2-20}$ alkyl, unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-C(=NR^5)R^5$, $-C(=NR^5)OR^5$, or $-C(=NR^5)N(R^5)_2$;

or $R^E$ is hydrogen, an oxygen protecting group, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-C(=NR^5)R^5$, $-C(=NR^5)OR^5$, $-C(=NR^5)N(R^5)_2$, $-C(=O)R^5$, $-C(=O)OR^5$, or $-C(=O)N(R^5)_2$; provided that $R^A$ is not hydrogen, and/or $R^B$ is not hydrogen; and each instance of $R^5$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom, or two instances of $R^5$ are joined to form a substituted or unsubstituted heterocyclic or substituted or unsubstituted heteroaryl ring;

provided that when $R^C$ and $R^E$ are both hydrogen, Z is $CR^D$, and $R^D$ is hydrogen, then $R^A$ and $R^B$ are not the same.

2. The compound of claim 1, or a pharmaceutically acceptable salt, solvate, hydrate, polymorph, co-crystal, tautomer, stereoisomer, isotopically labeled derivative, or prodrug thereof, wherein Z is $CR^D$.

3. The compound of claim 1, or a pharmaceutically acceptable salt, solvate, hydrate, polymorph, co-crystal, tautomer, stereoisomer, isotopically labeled derivative, or prodrug thereof, wherein both X and Y are halogen.

4. The compound of claim 1, or a pharmaceutically acceptable salt, solvate, hydrate, polymorph, co-crystal, tautomer, stereoisomer, isotopically labeled derivative, or prodrug thereof, wherein each of X and Y is bromo.

5. The compound of claim 1, or a pharmaceutically acceptable salt, solvate, hydrate, polymorph, co-crystal, tautomer, stereoisomer, isotopically labeled derivative, or prodrug thereof, wherein:

$R^A$ is hydrogen, substituted or unsubstituted acyl, substituted or unsubstituted alkyl, halogen, $-OR^1$, $-N(R^1)_2$, $-C(=O)R^1$, $-C(=O)N(R^1)_2$, or $-C(=O)OR^1$;

$R^B$ is hydrogen, substituted or unsubstituted acyl, substituted or unsubstituted alkyl, halogen, $-OR^2$, $-N(R^1)_2$, $-C(=O)R^1$, $-C(=O)N(R^1)_2$, or $-C(=O)OR^1$;

$R^C$ is hydrogen, substituted or unsubstituted acyl, substituted or unsubstituted alkyl, halogen, $-OR^3$, $-N(R^3)_2$, $-C(=O)R^3$, $-C(=O)N(R^3)_2$, or $-C(=O)OR^3$; and $R^D$ is hydrogen, substituted or unsubstituted acyl, substituted or unsubstituted alkyl, halogen, $-OR^4$, $-N(R^4)_2$, $-C(=O)R^4$, $-C(=O)N(R^4)_2$, or $-C(=O)OR^4$.

6. The compound of claim 1, or a pharmaceutically acceptable salt, solvate, hydrate, polymorph, co-crystal, tautomer, stereoisomer, isotopically labeled derivative, or prodrug thereof, wherein $R^E$ is hydrogen.

7. The compound of claim 1, or a pharmaceutically acceptable salt, solvate, hydrate, polymorph, co-crystal, tautomer, stereoisomer, isotopically labeled derivative, or prodrug thereof, wherein $R^E$ is substituted or unsubstituted $C_{1-6}$ alkyl, provided that $R^A$ is not hydrogen, and/or $R^B$ is not hydrogen.

8. The compound of claim 1, wherein the compound is of the formula:

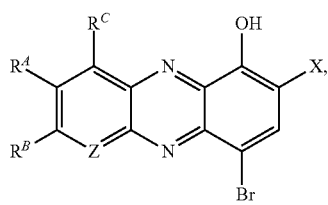

or a pharmaceutically acceptable salt, solvate, hydrate, polymorph, co-crystal, tautomer, stereoisomer, isotopically labeled derivative, or prodrug thereof.

9. The compound of claim 1, wherein the compound is of the formula:

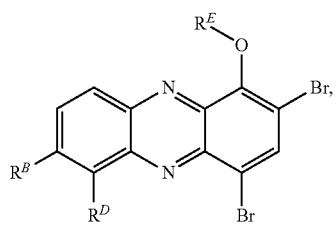

or a pharmaceutically acceptable salt, solvate, hydrate, polymorph, co-crystal, tautomer, stereoisomer, isotopically labeled derivative, or prodrug thereof.

10. The compound of claim 1, wherein the compound is of the formula:

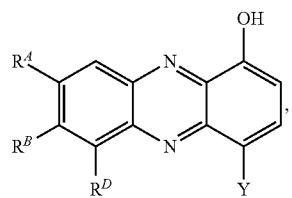

or a pharmaceutically acceptable salt, solvate, hydrate, polymorph, co-crystal, tautomer, stereoisomer, isotopically labeled derivative, or prodrug thereof.

11. The compound of claim 1, wherein the compound is of the formula:

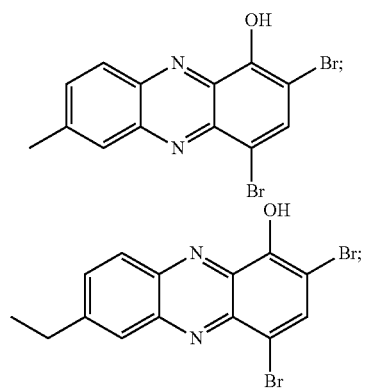

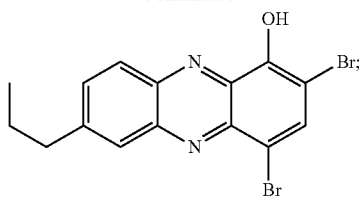

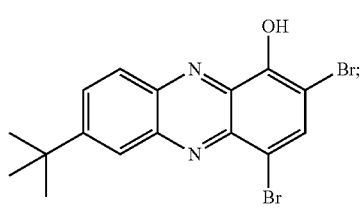

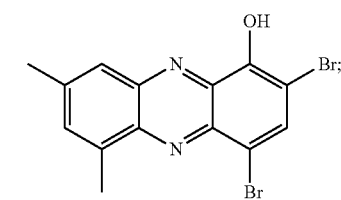

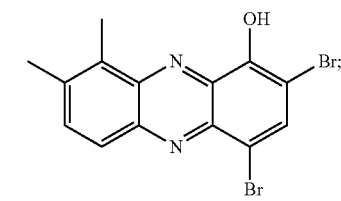

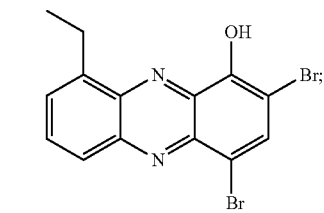

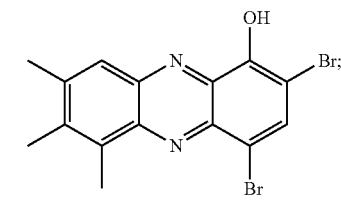

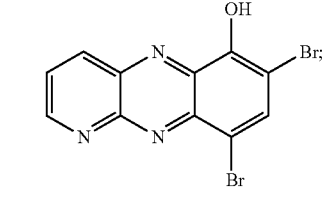

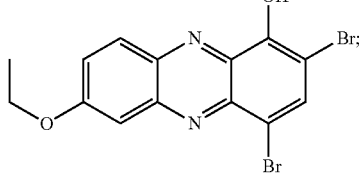

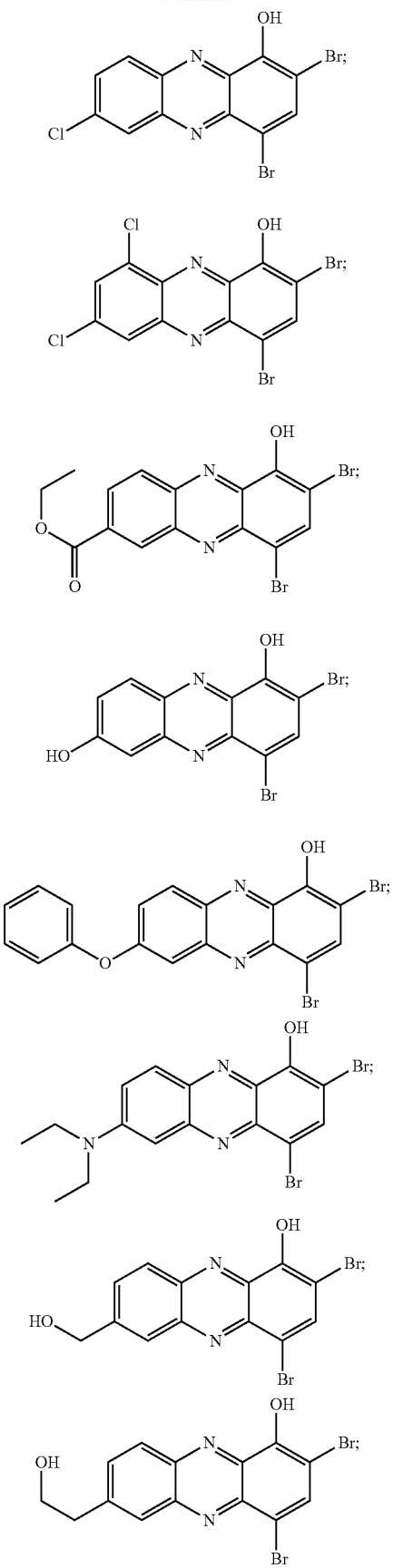
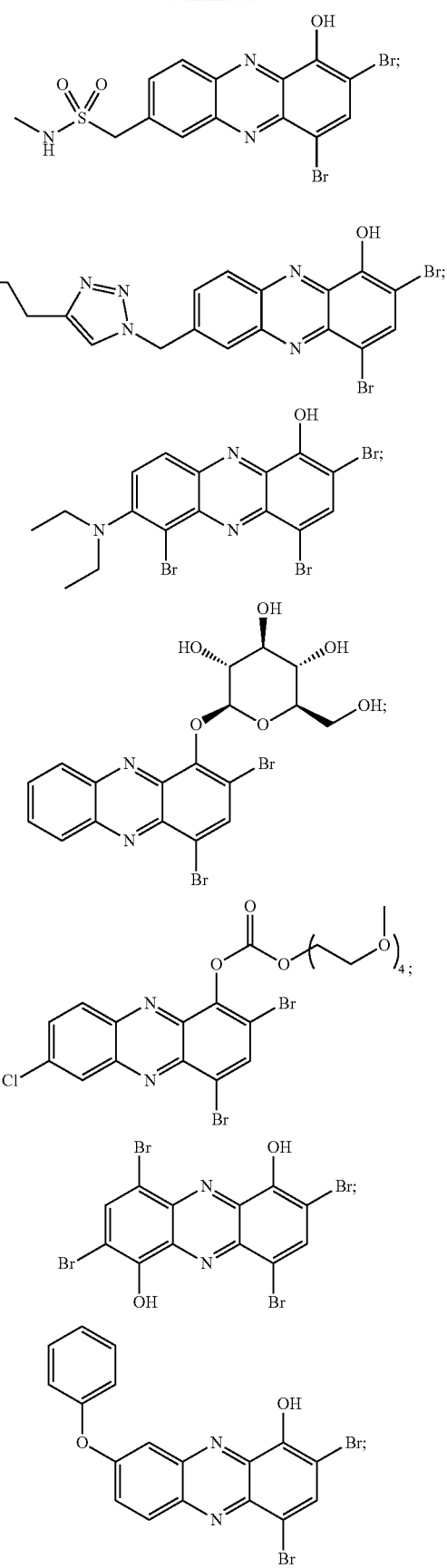

-continued

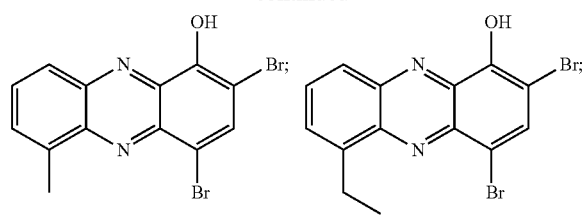

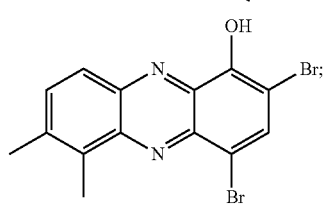

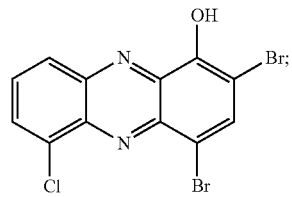

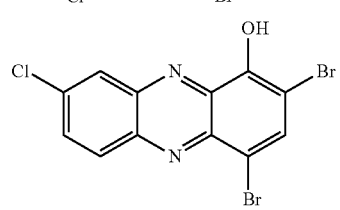

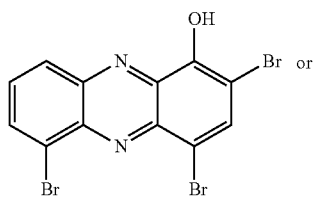

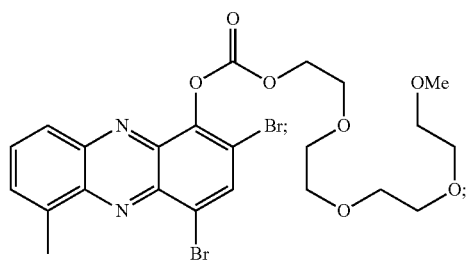 [SMILES: COCCOCCOCCOCCOC(=O)Oc1c(Br)cc(Br)c2nc3c(C)cccc3nc12]

or a pharmaceutically acceptable salt, solvate, hydrate, polymorph, co-crystal, tautomer, stereoisomer, isotopically labeled derivative, or prodrug thereof.

12. The compound of claim 1, wherein the compound is of the formula:

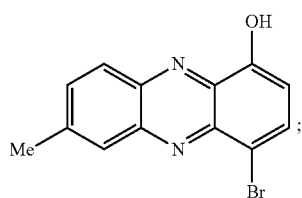

-continued

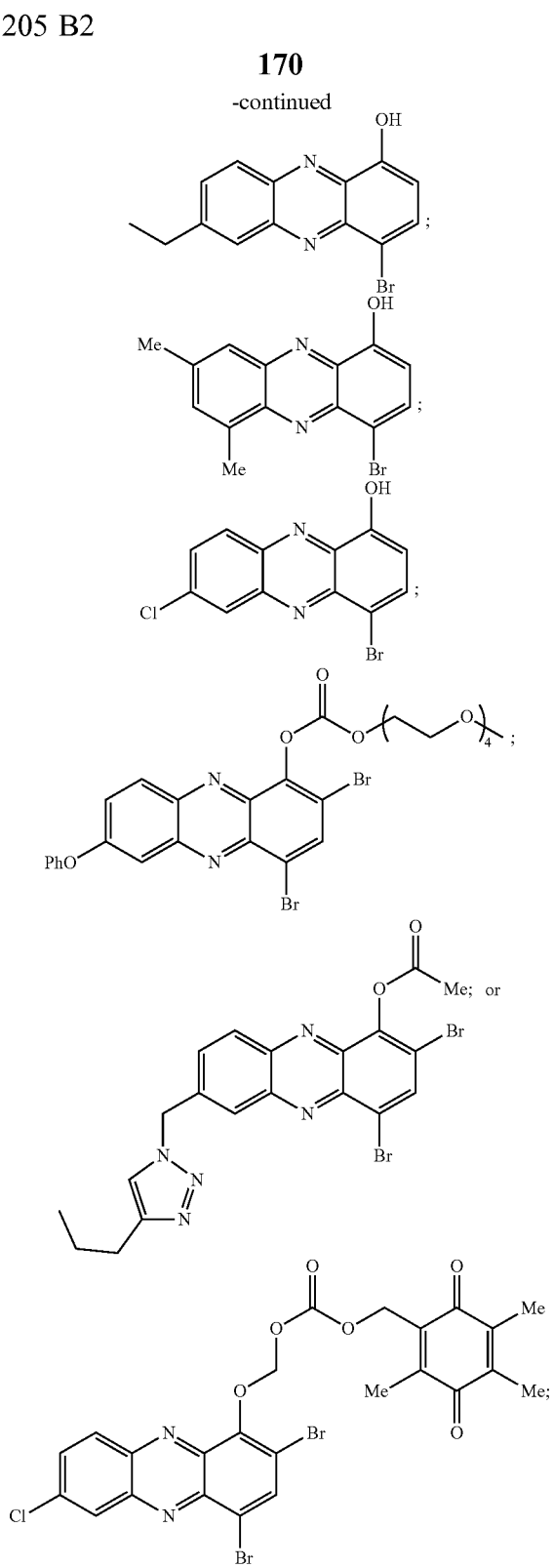

or a pharmaceutically acceptable salt, solvate, hydrate, polymorph, co-crystal, tautomer, stereoisomer, isotopically labeled derivative, or prodrug thereof.

13. A pharmaceutical composition comprising a compound of claim 1, or a pharmaceutically acceptable salt, solvate, hydrate, polymorph, co-crystal, tautomer, stereoisomer, isotopically labeled derivative, or prodrug thereof, and optionally a pharmaceutically acceptable excipient.

14. A method of treating a microbial infection in a subject in need thereof, the method comprising administering to the subject an effective amount of a compound of claim 1, or a pharmaceutically acceptable salt, solvate, hydrate, polymorph, co-crystal, tautomer, stereoisomer, isotopically labeled derivative, or prodrug thereof.

15. A method of killing a microorganism, the method comprising contacting the microorganism with an effective amount of a compound of claim 1, or a pharmaceutically acceptable salt, solvate, hydrate, polymorph, co-crystal, tautomer, stereoisomer, isotopically labeled derivative, or prodrug thereof.

16. A method of inhibiting the formation or growth of a biofilm, the method comprising contacting the biofilm with an effective amount of a compound of claim 1, or a pharmaceutically acceptable salt, solvate, hydrate, polymorph, co-crystal, tautomer, stereoisomer, isotopically labeled derivative, or prodrug thereof.

17. A method of reducing or clearing a biofilm, the method comprising contacting the biofilm with an effective amount of a compound of claim 1, or a pharmaceutically acceptable salt, solvate, hydrate, polymorph, co-crystal, tautomer, stereoisomer, isotopically labeled derivative, or prodrug thereof.

18. A method of inhibiting the growth, reproduction, or viability of a microorganism, the method comprising contacting the microorganism with an effective amount of a compound of claim 1, or a pharmaceutically acceptable salt, solvate, hydrate, polymorph, co-crystal, tautomer, stereoisomer, isotopically labeled derivative, or prodrug thereof.

19. A method of disinfecting a surface, the method comprising contacting the surface with an effective amount of a compound of claim 1, or a pharmaceutically acceptable salt, solvate, hydrate, polymorph, co-crystal, tautomer, stereoisomer, isotopically labeled derivative, or prodrug thereof.

20. The compound of claim 1, or a pharmaceutically acceptable salt, solvate, hydrate, polymorph, co-crystal, tautomer, stereoisomer, isotopically labeled derivative, or prodrug thereof, wherein $R^A$ is hydrogen.

21. The compound of claim 1, or a pharmaceutically acceptable salt, solvate, hydrate, polymorph, co-crystal, tautomer, stereoisomer, isotopically labeled derivative, or prodrug thereof, wherein $R^A$ is halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^1$, —N(R$^1$)$_2$, —SR$^1$, —CN, —SCN, —C(=NR$^1$)R$^1$, —C(=NR$^1$)OR$^1$, —C(=NR$^1$)N(R$^1$)$_2$, —C(=O)R$^1$, —C(=O)OR$^1$, —C(=O)N(R$^1$)$_2$, —NO$_2$, —NR$^1$C(=O)R$^1$, —NR$^1$C(=O)OR$^1$, —NR$^1$C(=O)N(R$^1$)$_2$, —OC(=O)R$^1$, —OC(=O)OR$^1$, or —OC(=O)N(R$^1$)$_2$.

22. The compound of claim 1, or a pharmaceutically acceptable salt, solvate, hydrate, polymorph, co-crystal, tautomer, stereoisomer, isotopically labeled derivative, or prodrug thereof, wherein $R^B$ is hydrogen.

23. The compound of claim 1, or a pharmaceutically acceptable salt, solvate, hydrate, polymorph, co-crystal, tautomer, stereoisomer, isotopically labeled derivative, or prodrug thereof, wherein $R^B$ is halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^2$, —N(R$^2$)$_2$, —SR$^2$, —CN, —SCN, —C(=NR$^2$)R$^2$, —C(=NR$^2$)OR$^2$, —C(=NR$^2$)N(R$^2$)$_2$, —C(=O)R$^2$, —C(=O)OR$^2$, —C(=O)N(R$^2$)$_2$, —NO$_2$, —NR$^2$C(=O)R$^2$, —NR$^2$C(=O)OR$^2$, —NR$^2$C(=O)N(R$^2$)$_2$, —OC(=O)R$^2$, —OC(=O)OR$^2$, or —OC(=O)N(R$^2$)$_2$.

24. The compound of claim 1, or a pharmaceutically acceptable salt, solvate, hydrate, polymorph, co-crystal, tautomer, stereoisomer, isotopically labeled derivative, or prodrug thereof, wherein $R^C$ is hydrogen.

25. The compound of claim 1, or a pharmaceutically acceptable salt, solvate, hydrate, polymorph, co-crystal, tautomer, stereoisomer, isotopically labeled derivative, or prodrug thereof, wherein $R^C$ is halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^3$, —N(R$^3$)$_2$, —SR$^3$, —CN, —SCN, —C(=NR$^3$)R$^3$, —C(=NR$^3$)OR$^3$, —C(=NR$^3$)N(R$^3$)$_2$, —C(=O)R$^3$, —C(=O)OR$^3$, —C(=O)N(R$^3$)$_2$, —NO$_2$, —NR$^3$C(=O)R$^3$, —NR$^3$C(=O)OR$^3$, —NR$^3$C(=O)N(R$^3$)$_2$, —OC(=O)R$^3$, —OC(=O)OR$^3$, or —OC(=O)N(R$^3$)$_2$.

26. The compound of claim 1, or a pharmaceutically acceptable salt, solvate, hydrate, polymorph, co-crystal, tautomer, stereoisomer, isotopically labeled derivative, or prodrug thereof, wherein $R^D$ is hydrogen.

27. The compound of claim 1, or a pharmaceutically acceptable salt, solvate, hydrate, polymorph, co-crystal, tautomer, stereoisomer, isotopically labeled derivative, or prodrug thereof, wherein $R^D$ is halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^4$, —N(R$^4$)$_2$, —SR$^4$, —CN, —SCN, —C(=NR$^4$)R$^4$, —C(=NR$^4$)OR$^4$, —C(=NR$^4$)N(R$^4$)$_2$, —C(=O)R$^4$, —C(=O)OR$^4$, —C(=O)N(R$^4$)$_2$, —NO$_2$, —NR$^4$C(=O)R$^4$, —NR$^4$C(=O)OR$^4$, —NR$^4$C(=O)N(R$^4$)$_2$, —OC(=O)R$^4$, —OC(=O)OR$^4$, or —OC(=O)N(R$^4$)$_2$.

28. The compound of claim 1, or a pharmaceutically acceptable salt, solvate, hydrate, polymorph, co-crystal, tautomer, stereoisomer, isotopically labeled derivative, or prodrug thereof, wherein $R^E$ is —C(=O)R$^5$, —C(=O)OR$^5$, or —C(=O)N(R$^5$)$_2$, provided that $R^A$ is not hydrogen, and/or $R^B$ is not hydrogen.

29. The compound of claim 1, or a pharmaceutically acceptable salt thereof.

30. The method of claim 14, wherein the microbial infection is a bacterial infection.

31. A compound of the formula:

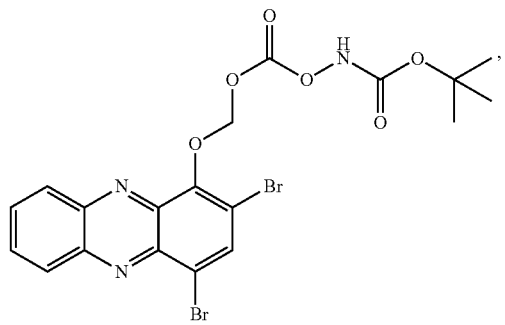

173
-continued
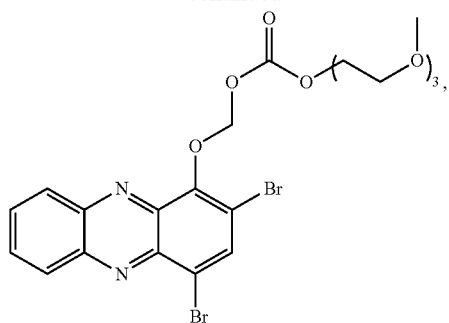
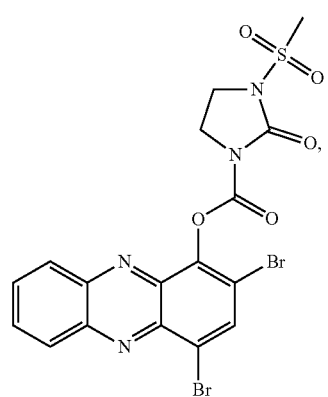
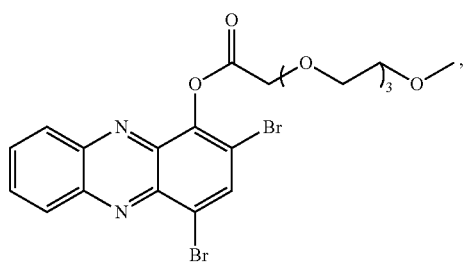
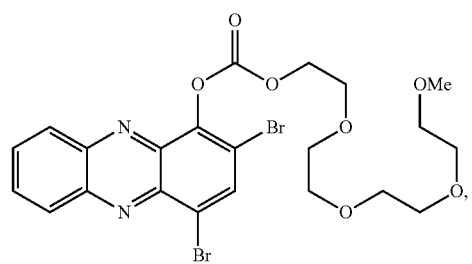
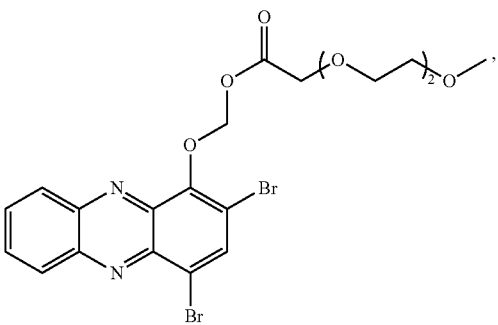
174
-continued
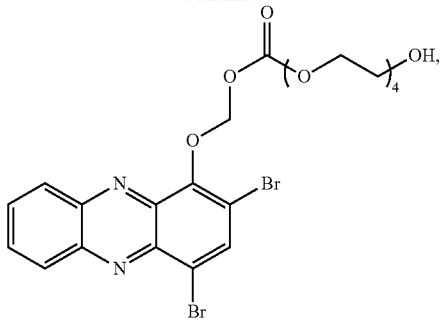
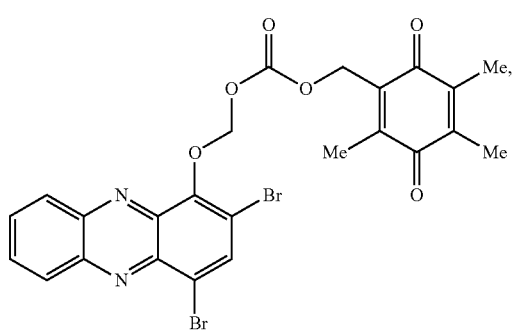
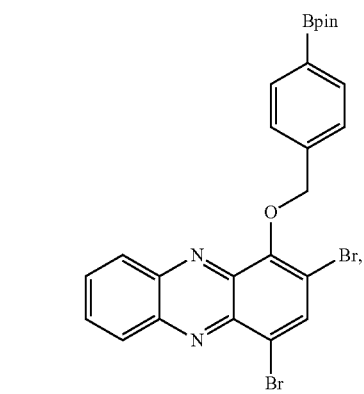
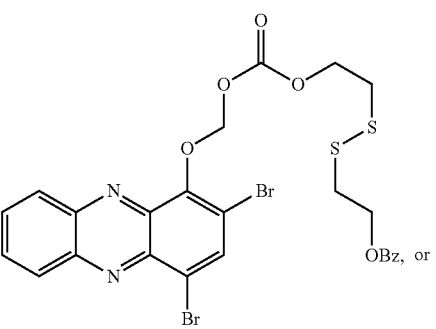

-continued

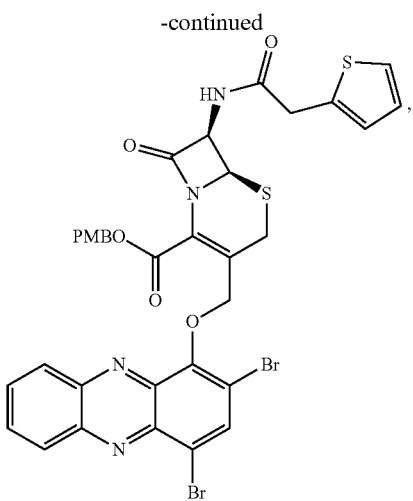

or a pharmaceutically acceptable salt, solvate, hydrate, polymorph, co-crystal, tautomer, stereoisomer, isotopically labeled derivative, or prodrug thereof.

32. A pharmaceutical composition comprising a compound of claim 31, or a pharmaceutically acceptable salt, solvate, hydrate, polymorph, co-crystal, tautomer, stereoisomer, isotopically labeled derivative, or prodrug thereof, and optionally a pharmaceutically acceptable excipient.

33. A method of treating a microbial infection in a subject in need thereof, the method comprising administering to the subject an effective amount of a compound of claim 31, or a pharmaceutically acceptable salt, solvate, hydrate, polymorph, co-crystal, tautomer, stereoisomer, isotopically labeled derivative, or prodrug thereof.

34. The method of claim 33, wherein the microbial infection is a bacterial infection.

35. A method of killing a microorganism or inhibiting the growth, reproduction, or viability of a microorganism, the method comprising contacting the microorganism with an effective amount of a compound of claim 31, or a pharmaceutically acceptable salt, solvate, hydrate, polymorph, co-crystal, tautomer, stereoisomer, isotopically labeled derivative, or prodrug thereof.

36. A method of inhibiting the formation or growth of a biofilm or reducing or clearing a biofilm, the method comprising contacting the biofilm with an effective amount of a compound of claim 31, or a pharmaceutically acceptable salt, solvate, hydrate, polymorph, co-crystal, tautomer, stereoisomer, isotopically labeled derivative, or prodrug thereof.

37. A method of disinfecting a surface, the method comprising contacting the surface with an effective amount of a compound of claim 31, or a pharmaceutically acceptable salt, solvate, hydrate, polymorph, co-crystal, tautomer, stereoisomer, isotopically labeled derivative, or prodrug thereof.

* * * * *

UNITED STATES PATENT AND TRADEMARK OFFICE
CERTIFICATE OF CORRECTION

PATENT NO. : 11,053,205 B2  
APPLICATION NO. : 16/486694  
DATED : July 6, 2021  
INVENTOR(S) : Robert William Huigens, III et al.

Page 1 of 2

It is certified that error appears in the above-identified patent and that said Letters Patent is hereby corrected as shown below:

In the Claims

In Claim 1, at Column 162, Lines 6-14, the formula: 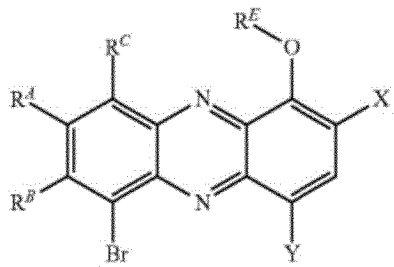 should be replaced with the formula: 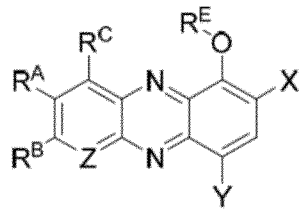 .

Signed and Sealed this  
Tenth Day of August, 2021

Drew Hirshfeld  
*Performing the Functions and Duties of the  
Under Secretary of Commerce for Intellectual Property and  
Director of the United States Patent and Trademark Office*

CERTIFICATE OF CORRECTION (continued)
U.S. Pat. No. 11,053,205 B2

In Claim 31, at Column 173, Lines 55-66, the formula:

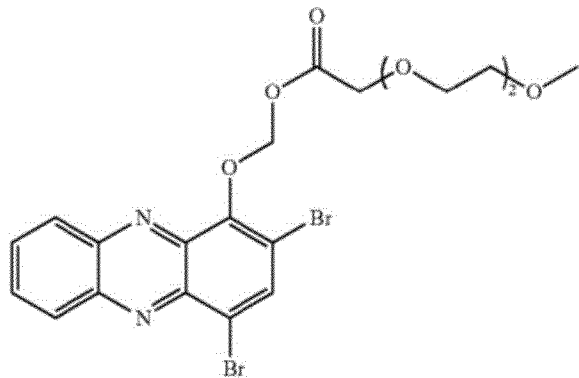

should be replaced with the formula: